US008383400B2

(12) United States Patent
Satchell

(10) Patent No.: US 8,383,400 B2
(45) Date of Patent: Feb. 26, 2013

(54) KITS FOR PRODUCING RECOMBINANT POLYPEPTIDES VIA CYSTEINE PROTEASE AUTOPROCESSING OF FUSION PROTEINS

(75) Inventor: Karla J. F. Satchell, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/563,171

(22) Filed: Jul. 31, 2012

(65) Prior Publication Data

US 2012/0295305 A1    Nov. 22, 2012

Related U.S. Application Data

(63) Continuation of application No. 13/183,071, filed on Jul. 14, 2011, now Pat. No. 8,257,946, and a continuation of application No. 12/630,603, filed on Dec. 3, 2009, now abandoned.

(60) Provisional application No. 61/119,489, filed on Dec. 3, 2008.

(51) Int. Cl.
*C12N 15/00* (2006.01)
*C07F 9/02* (2006.01)

(52) U.S. Cl. ...................... 435/320.1; 554/79

(58) Field of Classification Search ............... None
See application file for complete search history.

(56) References Cited

U.S. PATENT DOCUMENTS

| 7,045,677 | B2 | 5/2006 | Cottingham et al. |
| 7,176,287 | B2 | 2/2007 | Hamilton et al. |
| 7,276,355 | B2 | 10/2007 | Furutani et al. |
| 7,378,512 | B2 | 5/2008 | Rumenapf et al. |
| 7,396,664 | B2 | 7/2008 | Daly et al. |

OTHER PUBLICATIONS

Altschul et al., "Basic local alignment search tool", Journal of Molecular Biology, Oct. 5, 1990, 215(3):403-410.
Boardman et al., "Vibrio cholerae Strains with Mutations in an Atypical Type I Secretion System Accumulate RTX Toxin Intracellularly", Journal of Bacteriology, Dec. 2004, 186(23):8137-8143.
Cordero et al., "RTX Toxin Actin Cross-Linking Activity in clinical and Environmental Isolates of *Vibrio cholerae*", Journal of Clinical Microbiology, Jul. 2007, 45(7):2289-2292.
Cordero et al., "The Actin Cross-Linking Domain of the *Vibrio cholerae* RTX Toxin Directly Catalyzes the Covalent Cross-Linking of Actin", Journal of Biological Chemistry, Oct. 27, 2006, 281(43)32366-32374.
Deutscher et al., "Section VII: Purification Procedures: Chromatographic Methods", Methods in Enzymology: Guide to Protein Purification, 1990, 182:309-392.
Egerer et al., "Auto-catalytic Cleavage of *Clostridium difficile* Toxins A and B Depends on Cysteine Protease Activity", Journal of Biological Chemistry, Aug. 31, 2007, 282(35):25314-25321.

Fullner et al., "Genetic Characterization of a New Type IV-A Pilus Gene Cluster Found in Both Classical and El Tor Biotypes of *Vibrio cholerae*", Infection and Immunity, Mar. 1999, 67(3):1393-1404.
Fullner et al., "In vivo covalent cross-linking of cellular actin by the *Vibrio cholerae* RTX toxin", EMBO Journal, 2000, 19(20):5315-5323.
Fullner-Satchell, "MiniReview: MARTX, Multifunctional Autoprocessing Repeats-in-Toxin Toxins", Infection and Immunity, Nov. 2007, 75(11):5079-5084.
Fullner et al., "The Contribution of Accessory Toxins of *Vibrio cholerae* O1 El Tor to the Proinflammatory Response in a Murine Pulmonary Cholera Model", Journal of Experimental Medicine, Jun. 3, 2002, 195(11):1455-1462.
Fullner et al., "*Vibrio cholerae*-Induced Cellular Responses of Polarized T84 Intestinal Epithelial Cells Are Dependent on Production of Cholera Toxin and the RTX Toxin", Infection and Immunity, Oct. 2001, 69 (10):6310-6317.
Haines et al., "Role of Toll-Like Receptor 4 in the Proinflammatory Response to *Vibrio cholerae* O1 El Tor Strains Deficient in Production of Cholera Toxin and Accessory Toxins", Infection and Immunity, Sep. 2005, 73 (9):6157-6164.
Kudryashov et al., "Characterization of the Enzymatic Activity of the Actin Cross-Linking Domain from the *Vibrio cholerae* MARTXvc Toxin", Journal of Biological Chemistry, Jan. 4, 2008, 283(1):445-452.
Kudryashov et al., "Connecting actin monomers by iso-peptide bond is a toxicity mechanism of the *Vibrio cholerae* MARTX toxin", PNAS, Nov. 25, 2008, 105(47):18537-18542.
Lin et al., "Identification of a *Vibrio cholerae* RTX toxin gene cluster that is tightly linked to the cholera toxin prophage", PNAS, Feb. 1999, 96:1071-1076.
Mel et al., "Association of Protease Activity in *Vibrio cholerae* Vaccine Strains with Decreases in Transcellular Epithelial Resistance of Polarized T84 Intestinal Epithelial Cells", Infection and Immunity, Nov. 2000, 68 (11):6487-6492.
Olivier et al., "Hemolysin and the Multifunctional Autoprocessing RTX Toxin Are Virulence Factors during Intestinal Infection of Mice with *Vibrio cholerae* El Tor O1 Strains", Infection and Immunity, Oct. 2007(b), 75(10):5035-5042.
Olivier et al., "Prolonged Colonization of Mice by *Vibrio cholerae* El Tor O1 Depends on Accessory Toxins", Infection and Immunity, Oct. 2007(a), 75(10):5043-5051.
Olivier et al., "Successful Small Intestine Colonization of Adult Mice by *Vibrio cholerae* Requires Ketamine Anesthesia and Accessory Toxins", Public Library of Science, Oct. 2009, 4(10):1-6.
Osickova et al., "An Amphipathic alpha-Helix Including Glutamates 509 and 516 Is Crucial for Membrane Translocation of Adenylate Cyclase Toxin and Modulates Formation and Cation Selectivity of Its Membrane Channels", Journal of Biological Chemistry, Dec. 31, 1999, 274(53):37644-37650.
Prochazkova et al., "Structure-Function Analysis of Inositol Hexakisphosphate-induced Autoprocessing of the *Vibrio cholerae* Multifunctional Autoprocessing RTX Toxin", Journal of Biological Chemistry, Aug. 29, 2008, 283 (35):23656-23664.

(Continued)

*Primary Examiner* — Nashaat Nashed
(74) *Attorney, Agent, or Firm* — Andrus, Sceales, Starke & Sawall, LLP

(57) ABSTRACT

Disclosed are fusion proteins, polynucleotides that encode the disclosed fusion proteins, and methods for expressing and autoprocessing of the disclosed fusion proteins to obtain a target protein. The disclosed fusion proteins include an autoproteolytic cysteine protease fused to a heterologous polypeptide, which may be isolated as the target protein. Preferably, the protease activity of the cysteine protease is inducible. Suitable autoproteolytic cysteine proteases for the fusion proteins include the cysteine protease of the *Vibrio cholerae* RTX toxin.

12 Claims, 7 Drawing Sheets

OTHER PUBLICATIONS

Pfeifer et al., "Cellular Uptake of *Clostridium difficile* Toxin B", Journal of Biological Chemistry, Nov. 7, 2003, 278(45):44535-44541.

Reineke et al., "Autocatalytic cleavage of *Clostridium difficile* toxin B", Nature, Mar. 22, 2007, 446:415-419.

Rupnik et al., "Characterization of the cleavage site and function of resulting cleavage fragments after limited proteolysis of *Clostridium difficile* toxin B (TcdB) by host cells", Microbiology, 2005, 151:199-208.

Sheahan et al., "Autoprocessing of the *Vibrio cholerae* RTX toxin by the cysteine protease domain", EMBO Journal, 2007, 26(10):2552-2561.

Sheahan et al., "Inactivation of small Rho GTPases by the multifunctional RTX toxin from *Vibrio cholerae*", Cellular Microbiology, May 2007, 9(5):1324-1335.

Sheahan et al., "Identification of a domain within the multifunctional *Vibrio cholerae* RTX toxin that covalently cross-links links actin", PNAS, Jun. 29, 2004, 101(26):9798-9803.

Shen et al., "Simplified, Enhanced Protein Purification Using an Inducible, Autoprocessing Enzyme Tag", Public Library of Science, Dec. 2009, 4(12):1-11.

Stols et al., "A New Vector for High-Throughput, Ligation-Independent Cloning Encoding a Tobacco Etch Virus Protease Cleavage Site", Protein Expression and Purification, 2002, 25:8-15.

Tatusova et al., "BLAST 2 sequences, a new tool for comparing protein and nucleotide sequences", FEMS Microbiology Letters, May 15, 1999, 174(2):247-250.

Watnick et al., "A Role for the Mannose-Sensitive Hemagglutinin in Biofilm Formation by *Vibrio cholerae* El Tor", Journal of Bacteriology, Jun. 1999, 181(11):3606-3609.

SEQUENCE LISTING

```
<160> NUMBER OF SEQ ID NOS: 18

<210> SEQ ID NO 1
<211> LENGTH: 4545
<212> TYPE: PRT
<213> ORGANISM: Vibrio cholerae
<220> FEATURE:
<221> NAME/KEY: misc_feature
<222> LOCATION: (1555)..(1555)
<223> OTHER INFORMATION: Xaa can be any naturally occurring amino acid
<220> FEATURE:
<221> NAME/KEY: misc_feature
<222> LOCATION: (4440)..(4440)
<223> OTHER INFORMATION: Xaa can be any naturally occurring amino acid

<400> SEQUENCE: 1

Met Gly Lys Pro Phe Trp Arg Ser Val Glu Tyr Phe Phe Thr Gly Asn
1               5                   10                  15

Tyr Ser Ala Asp Asp Gly Asn Asn Asn Ile Val Ala Ile Gly Phe Gly
                20                  25                  30

Gly Gln Ile His Ala Tyr Gly Gly Asp His Val Thr Val Gly Ser
            35                  40                  45

Ile Gly Ala Thr Val Tyr Thr Gly Ser Gly Asn Asp Thr Val Val Gly
        50                  55                  60

Gly Ser Ala Tyr Leu Lys Val Glu Asp Ser Thr Gly His Leu Ile Val
65                  70                  75                  80

Lys Gly Ala Ala Gly Tyr Ala Asp Ile Asn Lys Ser Gly Asp Gly Asn
                85                  90                  95

Val Ser Phe Ala Gly Ala Ala Gly Val Ser Ile Asp His Leu Gly
                100                 105                 110

Asn His Gly Asp Val Ser Tyr Gly Gly Ala Ala Ala Tyr Asn Gly Ile
            115                 120                 125

Thr Arg Lys Gly Leu Ser Gly Asn Val Thr Phe Ala Gly Ala Gly Gly
        130                 135                 140

Tyr Asn Ala Leu Trp His Glu Thr Asn Gln Gly Asn Leu Ser Phe Thr
145                 150                 155                 160

Gly Ala Gly Ala Gly Asn Lys Leu Asp Arg Thr Trp Ser Asn Arg Tyr
                165                 170                 175

Gln Gly Ser His Gly Asp Val Thr Phe Asp Gly Ala Gly Ala Ala Asn
            180                 185                 190

Ser Ile Ser Ser Arg Val Glu Thr Gly Asn Ile Thr Phe Arg Gly Ala
```

```
                195                 200                 205
Gly Ala Asp Asn His Leu Val Arg Lys Gly Lys Val Gly Asp Ile Thr
210                 215                 220
Leu Gln Gly Ala Gly Ala Ser Asn Arg Ile Glu Arg Thr His Gln Ala
225                 230                 235                 240
Glu Asp Val Tyr Thr Gln Thr Arg Gly Asn Ile Arg Phe Glu Gly Val
                245                 250                 255
Gly Gly Tyr Asn Ser Leu Tyr Ser Asp Val Ala His Gly Asp Ile His
            260                 265                 270
Phe Ser Gly Gly Ala Tyr Asn Thr Ile Ile Arg Lys Gly Ser Gly
        275                 280                 285
Asn Asp Phe Ala Lys Glu Gly Met Thr Asn Ala Lys Ala Asp Glu Ile
290                 295                 300
Val Leu Thr Lys Ala Val Met Ser Gly Ser Trp Ile Gly Gln Asp His
305                 310                 315                 320
His Val Thr Ala Val Lys Ser Ala Ser Glu Pro Asn Thr Tyr Leu Phe
                325                 330                 335
Ala Phe Ala Asp Ser Thr Tyr Thr Lys Ile Asn Lys Val Gln Leu Arg
            340                 345                 350
Asn Asp Pro Gln Thr Gly Glu Leu Lys Tyr Tyr Ser Thr Ala Trp Tyr
        355                 360                 365
Lys Glu Val Asn His Leu Ser Asn Leu Ala Asn Gln Asp Ile Ser Asp
    370                 375                 380
Asn Gly Gly Phe Thr Ala Val Asn Ile Asn Gly Ala Tyr Thr Leu Ser
385                 390                 395                 400
Asp Leu Lys Val Glu His Gln Gln Ser Val Thr Val His Ala Val Glu
                405                 410                 415
Lys Ser Leu Thr Glu Tyr Glu Trp Val Thr Tyr Ala Asn Gly Ala Val
            420                 425                 430
Ile Asp Ala Lys Glu Val Ser Leu Ser Asp Ala Lys Met Gly Gly His
        435                 440                 445
Ala Ile Tyr Ala Asp Gly Thr Lys Val Asp Val Lys Ala Val Lys Ser
    450                 455                 460
Asn Arg Gln Pro Asn Thr Tyr Ile Tyr Ala Lys Val Leu Gly Pro Tyr
465                 470                 475                 480
Thr Lys Ile Val Val Val Glu Leu Ala Asn Asp Pro Glu Thr Gly Ala
                485                 490                 495
Leu Lys Tyr Gln Ala Arg Ser Trp Tyr Lys Glu Gly Asp His Thr Ala
            500                 505                 510
Asn Ile Ala Asn Gln Asp Ile Ser Ser Ala Thr Gly Tyr Asn Pro Met
        515                 520                 525
Gly Lys Gly Gly Tyr Ser Leu Ser Asp Leu His Tyr Ser Val Asn Ala
    530                 535                 540
Val Arg Ser Thr Ser Glu Thr Val Ala Asp Ile Glu Glu Tyr Thr Asp
545                 550                 555                 560
Gln Thr Leu Phe Lys Pro Ala Asn Asp Ser Gly Glu Ser Ser Gly Asp
                565                 570                 575
Val Arg Phe Asn Gly Ala Gly Gly Asn Val Ile Lys Ser Asn Val
            580                 585                 590
Thr Arg Gly Asn Val His Phe Asn Gly Gly Ile Ala Asn Val Ile
        595                 600                 605
Leu His Ser Ser Gln Phe Gly Asn Thr Glu Phe Asn Gly Gly Ala
    610                 615                 620
```

-continued

Ala Asn Val Ile Val Lys Ser Gly Glu Glu Gly Asp Leu Thr Phe Arg
625                 630                 635                 640

Gly Ala Gly Leu Ala Asn Val Leu Val His Gln Ser Glu Gln Gly Lys
            645                 650                 655

Met Asp Val Tyr Ala Gly Gly Ala Val Asn Val Leu Val Arg Leu Gly
        660                 665                 670

Asp Gly Gln Tyr Leu Ala His Leu Leu Ala Tyr Gly Asn Ile Ser Val
    675                 680                 685

Gln Lys Gly Ser Gly Asp Ser Arg Val Val Met Leu Gly Gly Tyr Asn
690                 695                 700

Thr His Thr Gln Ile Gly Ser Gly Asn Gly Leu Trp Leu Ala Ala Gly
705                 710                 715                 720

Gly Phe Asn Val Met Thr Gln Val Gly Lys Gly Asp Val Ala Ala Val
            725                 730                 735

Leu Ala Gly Gly Ala Asn Val Leu Thr Lys Met Gly Glu Gly Glu Leu
        740                 745                 750

Thr Ser Gly Met Leu Gly Gly Ala Asn Val Ile Thr His Ile Ser Asn
    755                 760                 765

Asp Asp Gln Leu Ser Asn Thr Thr Ala Val Ala Leu Gly Gly Ala Asn
770                 775                 780

Ile Leu Thr Lys Lys Gly Lys Gly Asn Thr Leu Ala Val Met Gly Gly
785                 790                 795                 800

Gly Ala Asn Val Leu Thr His Val Gly Asp Gly Thr Thr Thr Gly Val
            805                 810                 815

Met Val Gly Gly Ala Asn Ile Leu Thr Lys Val Gly Asn Gly Asp Thr
        820                 825                 830

Thr Gly Ile Leu Leu Gly Val Gly Asn Val Leu Thr His Val Gly Asp
    835                 840                 845

Gly Gln Thr Leu Gly Val Met Gly Ala Ala Gly Asn Ile Phe Thr Lys
850                 855                 860

Val Gly Asp Gly Thr Ser Ile Ala Val Met Ile Gly Ala Gly Asn Ile
865                 870                 875                 880

Phe Thr His Val Gly Glu Gly Asn Ala Trp Ala Leu Met Gly Gly Leu
            885                 890                 895

Gly Asn Val Phe Thr Lys Val Gly Asn Gly Asp Ala Leu Ala Leu Met
        900                 905                 910

Val Ala Glu Ala Asn Val Phe Thr His Ile Gly Asp Gly Met Ser Val
    915                 920                 925

Ala Leu Met Leu Ala Lys Gly Asn Val Ala Thr Lys Val Gly Asn Gly
930                 935                 940

Thr Thr Leu Ala Ala Met Val Gly Asn Val Asn Ile Phe Thr His Ile
945                 950                 955                 960

Gly His Gly Ser Thr Phe Ala Ala Met Ile Gly Gln Ala Asn Ile Met
            965                 970                 975

Thr Lys Val Gly Asn Asp Leu Thr Ala Ala Leu Met Val Gly Lys Ala
        980                 985                 990

Asn Ile Met Thr His Val Gly Asp Gly Thr Ser Leu Gly Leu Phe Ala
    995                 1000                1005

Gly Glu Val Asn Val Met Thr Lys Val Gly Asn Gly Thr Thr Leu
    1010                1015                1020

Ala Ala Met Phe Gly Lys Ala Asn Ile Met Thr His Val Gly Asp
    1025                1030                1035

Gly Leu Thr Gly Val Leu Ala Leu Gly Glu Ala Asn Ile Val Thr
    1040                1045                1050

```
Lys Leu Gly Asp Asp Phe Met Gly Val Val Ala Ala Ala Lys Ala
    1055                1060                1065

Asn Val Val Thr His Val Gly Asp Ala Thr Thr Ala Ala Val Leu
    1070                1075                1080

Ala Gly Lys Gly Asn Ile Leu Thr Lys Val Gly Glu Gly Thr Thr
    1085                1090                1095

Val Gly Leu Leu Ile Ser Asp Val Gly Asn Val Met Thr His Val
    1100                1105                1110

Gly Asp Gly Thr Thr Ile Gly Ile Ala Lys Gly Lys Ala Asn Leu
    1115                1120                1125

Ile Thr Lys Val Gly Asp Gly Leu Gly Val Asn Val Thr Trp Gly
    1130                1135                1140

Gln Ala Asn Val Phe Thr Gln Val Gly Asp Gly Asp Arg Tyr Asn
    1145                1150                1155

Phe Ala Lys Gly Glu Ala Asn Leu Ile Thr Lys Val Gly Asp Gly
    1160                1165                1170

Gln Glu Val Ser Val Val Gln Gly Glu Ala Asn Ile Ile Thr His
    1175                1180                1185

Val Gly Asn Gly Asp Asp Tyr Thr Gly Ala Trp Gly Lys Ala Asn
    1190                1195                1200

Val Ile Thr Lys Val Gly His Gly Gln Asn Val Val Leu Ala Lys
    1205                1210                1215

Gly Glu Ala Asn Ile Val Thr Gln Val Gly Asp Gly Asp Ser Phe
    1220                1225                1230

Asn Ala Leu Trp Ser Lys Gly Asn Ile Val Thr Lys Val Gly Asp
    1235                1240                1245

Gly Met Gln Val Thr Ala Ala Lys Gly Gln Ala Asn Ile Thr Thr
    1250                1255                1260

Thr Val Gly Asn Gly Leu Asn Val Thr Ala Ala Tyr Gly Asp Ala
    1265                1270                1275

Asn Ile Asn Thr Lys Val Gly Asp Gly Val Ser Val Asn Val Ala
    1280                1285                1290

Trp Gly Lys Tyr Asn Ile Asn Thr Lys Val Gly Asp Gly Leu Asn
    1295                1300                1305

Val Ala Val Met Lys Gly Lys Ala Asn Ala Asn Ile His Val Gly
    1310                1315                1320

Asp Gly Leu Asn Ile Asn Ala Ser Tyr Ala Gln Asn Asn Val Ala
    1325                1330                1335

Ile Lys Val Gly Asn Gly Asp Phe Tyr Ser Leu Ala Val Ala Ser
    1340                1345                1350

Ser Asn Thr Ser Ser Asn Lys Leu Ser Ala Leu Phe Asp Asn Ile
    1355                1360                1365

Lys Gln Thr Val Leu Gly Val Gly Gly Ser Gln Ala Ile Asn Tyr
    1370                1375                1380

Leu Val Gln Gly Asp Glu Ala Ser Ser Ser Gly Thr His Lys Gly
    1385                1390                1395

Arg Gly Ala Ile Ala Thr Pro Glu Ile Thr Lys Leu Asp Gly Phe
    1400                1405                1410

Gln Met Asp Ala Ile Lys Glu Val Ser Ser Asp Leu Gly Asp Ser
    1415                1420                1425

Leu Thr Gly Ser Val Thr Lys Val Asp Thr Pro Asp Leu Asn Lys
    1430                1435                1440

Met Gln His Ala Leu Asn Val Asp Asp Ser Ser Val Gln Ala Pro
```

-continued

```
            1445                1450                1455

Asn Leu Ile Val Asn Gly Asp Phe Glu Leu Gly Glu His Gly Trp
    1460                1465                1470

Gln Ser Thr His Gly Val Glu Ala Ser Tyr Ala Gly Ser Val Tyr
    1475                1480                1485

Gly Val Glu Gly Glu Gly His Gly Ala Arg Val Thr Glu Leu Asp
    1490                1495                1500

Thr Tyr Thr Asn Thr Ser Leu Tyr Gln Asp Leu Ala Asn Leu Ala
    1505                1510                1515

Gln Gly Glu Val Ile Ala Val Ser Phe Asp Phe Ala Lys Arg Ala
    1520                1525                1530

Gly Leu Ser Asn Asn Glu Gly Ile Glu Val Leu Trp Asn Gly Glu
    1535                1540                1545

Val Val Phe Ser Ser Ser Xaa Asp Glu Ser Ala Trp Gln Gln Lys
    1550                1555                1560

Asn Leu Lys Leu Thr Ala Gln Ala Gly Ser Asn Arg Ile Glu Phe
    1565                1570                1575

Lys Gly Thr Gly His Asn Asp Gly Leu Gly Tyr Ile Leu Asp Asn
    1580                1585                1590

Val Val Ala Thr Ser Glu Ser Ser Gln Ala Asn Ala Ile Arg
    1595                1600                1605

Glu His Ala Thr Gln Asn Pro Ala Ala Gln Asn Ala Leu Ser Asp
    1610                1615                1620

Lys Glu Arg Ala Glu Ala Asp Arg Gln Arg Leu Glu Gln Glu Lys
    1625                1630                1635

Gln Lys Gln Leu Asp Ala Val Ala Gly Ser Gln Ser Gln Leu Glu
    1640                1645                1650

Ser Thr Asp Gln Gln Ala Leu Glu Asn Asn Gly Gln Ala Gln Arg
    1655                1660                1665

Asp Ala Val Lys Glu Glu Ser Glu Ala Val Thr Ala Glu Leu Ala
    1670                1675                1680

Lys Leu Ala Gln Gly Leu Asp Val Leu Asp Gly Gln Ala Thr His
    1685                1690                1695

Thr Gly Glu Ser Gly Asp Gln Trp Arg Asn Asp Phe Ala Gly Gly
    1700                1705                1710

Leu Leu Asp Gly Val Gln Ser Gln Leu Asp Asp Ala Lys Gln Leu
    1715                1720                1725

Ala Asn Asp Lys Ile Ala Ala Ala Lys Gln Thr Leu Ser Asp Asn
    1730                1735                1740

Asn Ser Lys Val Lys Glu Ser Val Ala Lys Ser Glu Ala Gly Val
    1745                1750                1755

Ala Gln Gly Glu Gln Asn Arg Ala Gly Val Glu Gln Asp Ile Ala
    1760                1765                1770

Asp Ala Gln Ala Asp Ala Glu Lys Arg Lys Ala Asp Ala Leu Ala
    1775                1780                1785

Lys Gly Lys Asp Ala Gln Gln Ala Glu Ser Asp Ala His His Ala
    1790                1795                1800

Val Asn Asn Ala Gln Ser Arg Gly Asp Arg Asp Val Gln Leu Ala
    1805                1810                1815

Glu Asn Lys Ala Asn Gln Ala Gln Ala Asp Ala Gln Gly Ala Lys
    1820                1825                1830

Gln Asn Glu Gly Asp Arg Pro Asp Arg Gln Gly Val Thr Gly Ser
    1835                1840                1845
```

-continued

Gly Leu Ser Gly Asn Ala His Ser Val Glu Gly Ala Gly Glu Thr
1850                1855                1860

Asp Ser His Val Asn Thr Asp Ser Gln Thr Asn Ala Asp Gly Arg
1865                1870                1875

Phe Ser Glu Gly Leu Thr Glu Gln Glu Gln Glu Ala Leu Glu Gly
1880                1885                1890

Ala Thr Asn Ala Val Asn Arg Leu Gln Ile Asn Ala Gly Ile Arg
1895                1900                1905

Ala Lys Asn Ser Val Ser Ser Met Thr Ser Met Phe Ser Glu Thr
1910                1915                1920

Asn Ser Lys Ser Ile Val Val Pro Thr Lys Val Ser Pro Glu Pro
1925                1930                1935

Glu Arg Gln Glu Val Thr Arg Arg Asp Val Arg Ile Ser Gly Val
1940                1945                1950

Asn Leu Glu Ser Leu Ser Ala Val Gln Gly Ser Gln Pro Thr Gly
1955                1960                1965

Gln Leu Ala Ser Lys Ser Val Pro Gly Phe Lys Ser His Phe Ala
1970                1975                1980

Ser Thr Ser Ile Gly Ile Glu Asn Glu Leu Ser Gly Leu Val Val
1985                1990                1995

Val Leu Pro Lys Asn Ser Ala Gln Thr Phe Gly Tyr Val His Asp
2000                2005                2010

Ser Gln Gly Asn Pro Leu Phe Met Leu Thr Lys Asp Met Asn Gln
2015                2020                2025

Gly Gly Tyr Ser Asn Pro Val Gly Ile Asn Asp Ile Gln Gly Val
2030                2035                2040

Asn Asn Trp Gln Thr His Thr Ile Glu Leu Val Thr Tyr Pro Ser
2045                2050                2055

Glu Ile Ser Asp Thr Ala Ala Val Glu Ser Arg Lys Glu Ala Met
2060                2065                2070

Leu Trp Leu Ala Lys Glu Phe Thr Asp His Ile Asn Gln Ser Asn
2075                2080                2085

His Gln Ser Leu Pro His Leu Val Ser Asp Asp Gly Arg Phe Thr
2090                2095                2100

Leu Val Ile Ser Asn Ser Lys His Leu Ile Ala Ala Gly Asn Gly
2105                2110                2115

Thr Ser Ile Asp Ala Gln Gly Lys Thr Ile Gly Met Thr Pro Ser
2120                2125                2130

Gly Gln Gln Ala Thr Met Ala Ile Ser Ala Lys Glu Phe Gly Thr
2135                2140                2145

Ser Ser Ser Pro Glu Val Arg Leu Leu Glu Ser Ala Pro Trp Tyr
2150                2155                2160

Gln Ala Gly Leu Arg Asp Glu Phe Leu Ala Asn Ala Lys Asn Thr
2165                2170                2175

Thr Leu Asp Asp Pro Ala Thr Ala Gln Asn Val Tyr Ala Tyr Leu
2180                2185                2190

Thr Ser Val Tyr Ser Lys Thr Ala Asp Leu Ala Lys Glu Tyr Gly
2195                2200                2205

Ile Tyr Ile Asn Asp Trp Asp Pro Ala Ser Glu Gly Phe Ser Pro
2210                2215                2220

Asn Ala Gln Gly Leu Thr Asp Pro Lys Val Lys Asn Ala Trp Ser
2225                2230                2235

Ile Leu Pro Arg Thr Lys Pro Val Arg Met Leu Glu Leu Leu Ser
2240                2245                2250

```
Ala Glu Asp Ser Arg Tyr Val Arg Gln Gln Ile Ala Glu Lys Leu
2255                2260                2265

Lys Gly Thr Tyr Ser Glu Ser Leu Ala Lys Asn Val Phe Glu Tyr
2270                2275                2280

Phe Gln Tyr Gly Gly Glu Val Ala Gly His Gly Ile Asn Asn Ala
2285                2290                2295

Thr Thr Gly Ser Val Gln Gln Pro Glu Pro Ala Ile Leu Phe Glu
2300                2305                2310

Phe Arg Ser Val Pro Ser Ala Leu Ser Asp Phe Val Pro Lys Thr
2315                2320                2325

Ala Ser Thr Val Lys Val Asp Val Lys Ala Leu Asp His Phe Asp
2330                2335                2340

Ser Ala Ser Arg Lys Ala Ile Ile Thr Glu Val Asn Ala Leu Val
2345                2350                2355

Ser Gly Ser Glu Asp Phe Asp Ala Trp Tyr Gln Glu Tyr Arg Ala
2360                2365                2370

Ser Lys Gly Gln Pro Pro Val Lys Asn Pro Lys Ser Ser Ala Ser
2375                2380                2385

Ala Asn His Lys Ala Glu Trp Leu Met Thr Gln His Ala Glu Gln
2390                2395                2400

Trp Ala Lys Ile Thr Ala Pro Tyr Thr Asp Asn His Glu Thr Leu
2405                2410                2415

Thr Ser Thr Lys Leu Ala Ser Asn Asp Lys Glu Leu His Ala
2420                2425                2430

Leu Gly Glu Thr Ser Asn Leu Glu Asn Asn Lys Gln Gln Glu Asn
2435                2440                2445

Val Ala Ser Ile Ile Asn Thr Met Leu Asn Asp Met Leu Pro Phe
2450                2455                2460

Tyr Ala Leu Arg Thr Glu Arg Asn Leu Leu Val Gln Glu Gly Asp
2465                2470                2475

Glu Gly Phe Glu Val Arg Ala Trp Pro Gly Thr Glu Asp Lys Ser
2480                2485                2490

Lys Thr Ile Ile Leu Glu Asp Pro Glu Asp Ala Ala Gln His Lys
2495                2500                2505

Ala Ile Glu Arg Phe Ile Leu Ala Asn Phe Asp Asn Phe Glu Gln
2510                2515                2520

Met Pro Asp Glu Leu Phe Leu Val Asp Asn Lys Val Ile Ser His
2525                2530                2535

His Glu Gly Arg Thr His Val Leu Ala Gln Lys Val Asp Gly Ala
2540                2545                2550

Trp Gln Tyr Asn Ala Thr Val Glu Leu Met Ser Val Thr Glu Leu
2555                2560                2565

Leu Asp Ala Ala Asn Val Thr Gly Lys Ile Arg Gly Glu Ser Tyr
2570                2575                2580

Gln Gln Val Ile Asp Ala Leu Thr Asp Tyr His Ala Ser Ile Thr
2585                2590                2595

Glu His Ala Asp Tyr Glu Pro Glu Ser Val Glu Lys Leu Leu Asn
2600                2605                2610

Leu Arg Lys Lys Ile Glu Gly Tyr Val Leu Gly His Pro Asp Ser
2615                2620                2625

Gly Arg Val Glu Ala Met Asn Ser Leu Leu Asn Gln Val Asn Thr
2630                2635                2640

Arg Leu Asp Glu Val Ser Leu Leu Ser Val Ala Glu Gln Thr Ile
```

```
                2645                2650                2655

Gln Ala Gln Asn Ser Phe Ser Arg Leu Tyr Asp Gln Leu Glu Ala
            2660                2665                2670

Ala Asn Leu Lys Glu Ser Lys His Leu Tyr Leu Asp Gln Asn Gly
            2675                2680                2685

Asp Phe Val Thr Lys Gly Lys Gly Asn Leu Ala Asn Ile Asp Leu
            2690                2695                2700

Leu Gly Ser Arg Glu Ala Val Leu Glu Lys Val Lys Leu Thr Val
            2705                2710                2715

Ser Asn Glu Tyr Gly Gln Thr Val Ala Asp Thr Ile Phe Ala Gly
            2720                2725                2730

Leu Ser Ala Lys Asp Leu Ala Lys Asp Gly Lys Gly Val Asp Ile
            2735                2740                2745

Ala Gly Leu Asn Lys Val His Gln Ala Ile Glu Gln His Leu Ser
            2750                2755                2760

Pro Val Ser Ala Thr Leu Tyr Ile Trp Lys Pro Ser Asp His Ser
            2765                2770                2775

Ala Leu Gly His Ala Ala Leu Gln Ile Gly Gln Gly Arg Thr Gln
            2780                2785                2790

Leu Glu Gly Gln Ala Ala Ala Asp Phe Asn Gln Gln Asn Tyr Val
            2795                2800                2805

Ser Trp Trp Pro Leu Gly Ser Lys Ser Ser Asn Ile Ser Asn Ile
            2810                2815                2820

Leu Asn Val Ala Thr Lys Asp Gln Pro Asp Leu Lys Leu Arg Trp
            2825                2830                2835

Ser Asp Phe Ser Gln Pro Ala His Gln Asn Asp Thr Leu Glu His
            2840                2845                2850

Asp Val Ala Ser Glu Glu Asn Asp Gly Phe Gly Leu His Asp Gly
            2855                2860                2865

Asp Ile Lys Leu Lys Arg Phe Ile Glu Lys Leu Asn Ala Ala Lys
            2870                2875                2880

Gly Ile Asp Ala Ser Phe Lys Glu Ala Ser Glu Gly Tyr Ala Ser
            2885                2890                2895

Val Leu Leu Gly Asn Pro Asp Met Leu Glu Thr Thr Ser Ile Pro
            2900                2905                2910

Ala His Val Phe Gln Pro Phe Val Glu Gln Trp Asn Asp Thr Ser
            2915                2920                2925

Tyr Asp Met Met Asp Val Ala His Arg Phe Ala Gln Glu Leu Arg
            2930                2935                2940

Leu Gln Ala Gln Arg Ser Asp Pro Glu Leu Leu Glu Lys Arg
            2945                2950                2955

Ile Gly Asn Val Ile Arg Gln Phe Ala Glu Arg Ala Leu Glu Glu
            2960                2965                2970

Ile Glu Thr Phe Lys Ala Ser Gln Ala Asp Gln Gly Arg Val Phe
            2975                2980                2985

Arg Ile Asn Leu Glu Gly Leu Asp Val Ala Ala Met Gln Ala Glu
            2990                2995                3000

Trp His Arg Leu Ser Asn Asp Pro Asp Ala Arg Tyr Gln Leu Leu
            3005                3010                3015

Thr Lys Asn Cys Ser Ser Thr Val Ala Lys Val Leu Lys Ala Gly
            3020                3025                3030

Gly Ala Asp Lys Leu Ile Gly His Thr Trp Leu Pro Lys Phe Gly
            3035                3040                3045
```

-continued

```
Val Trp Thr Pro Thr Glu Leu Phe Asn Phe Gly Gln Ala Leu Gln
3050                3055                3060

Glu Ala Gln Leu Glu Ile Ala Ala Lys Lys Gln Ser His Gln Val
3065                3070                3075

Thr Asp Val Leu Asp Ala Leu Ser Gly Asn Glu Lys Pro Lys Glu
3080                3085                3090

Asn Val Ala Ile Glu Asn Asp Gly Thr Pro Pro Arg Asp Lys Glu
3095                3100                3105

Ser Leu Ser Pro Leu Thr Arg Phe Leu Asn Asn Glu Leu Tyr Gly
3110                3115                3120

Asp Lys Glu Ala Arg Arg Lys Ile Gly Glu Ile Thr Gln Thr Leu
3125                3130                3135

Leu Asp His Ala Val Glu Lys Gly Glu Ser Gln Lys Ile Thr Leu
3140                3145                3150

Gln Gly Glu Ala Gly Arg Leu Thr Gly Tyr Tyr His Gln Gly Thr
3155                3160                3165

Ala Pro Ser Glu Gly Glu Thr Ser Ser Pro Ser Gly Lys Val Val
3170                3175                3180

Leu Phe Leu His Gly Ser Gly Ser Ser Ala Glu Glu Gln Ala Ser
3185                3190                3195

Ala Ile Arg Asn His Tyr Gln Lys Gln Gly Ile Asp Met Leu Ala
3200                3205                3210

Val Asn Leu Arg Gly Tyr Gly Glu Ser Asp Gly Gly Pro Ser Glu
3215                3220                3225

Lys Gly Leu Tyr Gln Asp Ala Arg Thr Met Phe Asn Tyr Leu Val
3230                3235                3240

Asn Asp Lys Gly Ile Asp Pro Ser Asn Ile Ile Ile His Gly Tyr
3245                3250                3255

Ser Met Gly Gly Pro Ile Ala Ala Asp Leu Ala Arg Tyr Ala Ala
3260                3265                3270

Gln Asn Gly Gln Ala Val Ser Gly Leu Leu Leu Asp Arg Pro Met
3275                3280                3285

Pro Ser Met Thr Lys Ala Ile Thr Ala His Glu Val Ala Asn Pro
3290                3295                3300

Ala Gly Ile Val Gly Ala Ile Ala Lys Ala Val Asn Gly Gln Phe
3305                3310                3315

Ser Val Glu Lys Asn Leu Glu Gly Leu Pro Lys Glu Thr Ser Ile
3320                3325                3330

Leu Leu Leu Thr Asp Asn Glu Gly Leu Gly Asn Glu Gly Glu Lys
3335                3340                3345

Leu Arg Thr Lys Leu Thr Ala Ser Gly Tyr Asn Val Thr Gly Glu
3350                3355                3360

Gln Thr Phe Tyr Gly His Glu Ala Ser Asn Arg Leu Met Ser Gln
3365                3370                3375

Tyr Ala Asp Gln Ile Val Ser Gly Leu Ser Ser Ser Ala Ser Val
3380                3385                3390

Asp Glu Asp Leu Asp Gln Gln Gly Leu Asp Thr Thr Ser Thr Lys
3395                3400                3405

Asp Gln Gly Ile Ser Asn Lys Asn Asp His Leu Gln Val Val Asp
3410                3415                3420

Ser Lys Glu Ala Leu Ala Asp Gly Lys Ile Leu His Asn Gln Asn
3425                3430                3435

Val Asn Ser Trp Gly Pro Ile Thr Val Thr Pro Thr Thr Asp Gly
3440                3445                3450
```

-continued

```
Gly Glu Thr Arg Phe Asp Gly Gln Ile Ile Val Gln Met Glu Asn
    3455            3460                3465
Asp Pro Val Val Ala Lys Ala Ala Asn Leu Ala Gly Lys His
    3470            3475                3480
Ala Glu Ser Ser Val Val Val Gln Leu Asp Ser Asp Gly Asn Tyr
    3485            3490                3495
Arg Val Val Tyr Gly Asp Pro Ser Lys Leu Asp Gly Lys Leu Arg
    3500            3505                3510
Trp Gln Leu Val Gly His Gly Arg Asp His Ser Glu Thr Asn Asn
    3515            3520                3525
Thr Arg Leu Ser Gly Tyr Ser Ala Asp Glu Leu Ala Val Lys Leu
    3530            3535                3540
Ala Lys Phe Gln Gln Ser Phe Asn Gln Ala Glu Asn Ile Asn Asn
    3545            3550                3555
Lys Pro Asp His Ile Ser Ile Val Gly Cys Ser Leu Val Ser Asp
    3560            3565                3570
Asp Lys Gln Lys Gly Phe Gly His Gln Phe Ile Asn Ala Met Asp
    3575            3580                3585
Ala Asn Gly Leu Arg Val Asp Val Ser Val Arg Ser Ser Glu Leu
    3590            3595                3600
Ala Val Asp Glu Ala Gly Arg Lys His Thr Lys Asp Ala Asn Gly
    3605            3610                3615
Asp Trp Val Gln Lys Ala Glu Asn Asn Lys Val Ser Leu Ser Trp
    3620            3625                3630
Asp Ala Gln Gly Glu Val Val Ala Lys Asp Glu Arg Ile Arg Asn
    3635            3640                3645
Gly Ile Ala Glu Gly Asp Ile Asp Leu Ser Arg Ile Gly Val Asn
    3650            3655                3660
Asn Val Asp Glu Pro Ala Arg Gly Ala Ile Gly Asp Asn Asn Asp
    3665            3670                3675
Val Phe Asp Ala Pro Glu Lys Arg Lys Pro Glu Thr Glu Val Ile
    3680            3685                3690
Ala Asn Ser Ser Ser Ser Asn Gln Phe Ser Tyr Ser Gly Asn Ile
    3695            3700                3705
Gln Val Asn Val Gly Glu Gly Glu Phe Thr Ala Val Asn Trp Gly
    3710            3715                3720
Thr Ser Asn Val Gly Ile Lys Val Gly Thr Gly Gly Phe Lys Ser
    3725            3730                3735
Leu Ala Phe Gly Asp Asn Asn Val Met Val His Ile Gly Asp Gly
    3740            3745                3750
Glu Ser Lys His Ser Val Asp Ile Gly Gly Tyr Gln Ala Leu Glu
    3755            3760                3765
Gly Ala Gln Met Phe Leu Gly Asn Arg Asn Val Ser Phe Asn Phe
    3770            3775                3780
Gly His Ser Asn Asp Leu Ile Leu Met Met Asp Lys Ser Ile Pro
    3785            3790                3795
Thr Pro Pro Leu Val Asn Pro Phe Asp Gly Ala Ala Arg Ile Ser
    3800            3805                3810
Gly Val Leu Gln Gly Ile Ala Thr Ser Gly Glu Gly Glu Asp Trp
    3815            3820                3825
Leu Ala Ala Gln Glu Gln Gln Trp Thr Leu Ser Gly Ala Lys Lys
    3830            3835                3840
Phe Val Lys Asp Met Ser Gly Leu Asp Gln Ser Ser Ser Val Asp
```

```
                3845                3850                3855

Tyr Thr Thr Leu Val Glu Leu Asp Ser Gln Asn Glu Arg Asp Ser
        3860                3865                3870

Arg Gly Leu Lys His Asp Ala Glu Ala Thr Leu Asn Lys Gln Tyr
        3875                3880                3885

Asn Gln Trp Leu Ser Gly Asn Gly Asn Ser Gly Thr Ser Gln Leu
        3890                3895                3900

Ser Arg Ala Asp Lys Leu Arg Gln Ala Asn Glu Lys Leu Ala Phe
        3905                3910                3915

Asn Phe Ala Val Gly Gly Gln Gly Ala Asp Ile Gln Val Thr Thr
        3920                3925                3930

Gly Asn Trp Asn Phe Met Phe Gly Asp Asn Ile Gln Ser Ile Leu
        3935                3940                3945

Asp Thr Asn Leu Gly Ser Leu Phe Gly Leu Met Thr Gln Gln Phe
        3950                3955                3960

Thr Ala Thr Gly Gln Ala Lys Thr Thr Phe Thr Tyr Thr Pro Gln
        3965                3970                3975

Asp Leu Pro Arg Gln Leu Lys Asn Lys Leu Leu Gly Gln Leu Ala
        3980                3985                3990

Gly Val Gly Ala Glu Thr Thr Leu Ala Asp Ile Phe Gly Val Asp
        3995                4000                4005

Tyr Thr Ala Ser Gly Gln Ile Val Ser Arg Asn Gly Gln Ala Val
        4010                4015                4020

Asp Gly Val Ala Ile Leu Lys Glu Met Leu Glu Val Ile Gly Glu
        4025                4030                4035

Phe Ser Gly Asp Gln Leu Gln Ala Phe Val Asp Pro Ala Lys Leu
        4040                4045                4050

Leu Asp Ser Leu Lys Ala Gly Ile Asp Met Gly Ala Asp Gly Ile
        4055                4060                4065

Lys Ser Phe Ala Glu Thr His Gly Leu Lys Glu Lys Ala Pro Glu
        4070                4075                4080

Glu Glu Lys Asp Asn Ser Ser Val Ser Val Asn Gly Ala Asn Val
        4085                4090                4095

Asn Ser Ala Gln Gly Ala Thr Val Ala Asp Gly Asn Thr Glu Thr
        4100                4105                4110

Ala Glu Thr Gln Asp Arg Ala Phe Gly Phe Asn Ser Leu Asn Leu
        4115                4120                4125

Pro Asn Leu Phe Ala Thr Ile Phe Ser Gln Asp Lys Gln Lys Glu
        4130                4135                4140

Met Lys Ser Leu Val Glu Asn Leu Lys Gln Asn Leu Thr Ala Asp
        4145                4150                4155

Leu Leu Asn Met Lys Glu Lys Thr Phe Asp Phe Leu Arg Asn Ser
        4160                4165                4170

Gly His Leu Gln Gly Asp Gly Asp Ile Asn Ile Ser Leu Gly Asn
        4175                4180                4185

Tyr Asn Phe Asn Trp Gly Gly Asp Gly Lys Asp Leu Gly Ala Tyr
        4190                4195                4200

Leu Gly Asp Asn Asn Asn Phe Trp Gly Gly Arg Gly Asp Asp Val
        4205                4210                4215

Phe Tyr Ala Thr Gly Lys Ser Asn Ile Phe Thr Gly Gly Glu Gly
        4220                4225                4230

Asn Asp Met Gly Val Leu Met Gly Arg Glu Asn Met Met Phe Gly
        4235                4240                4245
```

-continued

Gly Asp Gly Asn Asp Thr Ala Val Val Ala Gly Arg Ile Asn His
4250                4255                4260

Val Phe Leu Gly Ala Gly Asp Asp Gln Ser Phe Val Phe Gly Glu
    4265                4270                4275

Gly Gly Glu Ile Asp Thr Gly Ser Gly Arg Asp Tyr Val Val Thr
        4280                4285                4290

Ser Gly Asn Phe Asn Arg Val Asp Thr Gly Asp Gln Asp Tyr
    4295                4300                4305

Ser Val Thr Ile Gly Asn Asn Gln Val Glu Leu Gly Ala Gly
    4310                4315                4320

Asn Asp Phe Ala Asn Ile Phe Gly Asn Tyr Asn Arg Ile Asn Ala
    4325                4330                4335

Gly Ala Gly Asn Asp Val Val Lys Leu Met Gly Tyr His Ala Val
    4340                4345                4350

Leu Asn Gly Gly Asp Gly Asp Asp His Leu Ile Ala Thr Ala Ile
    4355                4360                4365

Ser Lys Phe Ser Gln Phe Asn Gly Gly Glu Gly Arg Asp Leu Met
    4370                4375                4380

Val Leu Gly Gly Tyr Gln Asn Thr Phe Lys Gly Gly Thr Asp Val
    4385                4390                4395

Asp Ser Phe Val Val Ser Gly Asp Val Ile Asp Asn Leu Val Glu
    4400                4405                4410

Asp Ile Arg Ser Glu Asp Asn Ile Val Phe Asn Gly Ile Asp Trp
    4415                4420                4425

Gln Lys Leu Trp Phe Glu Arg Ser Gly Tyr Asp Xaa Lys Leu Ser
    4430                4435                4440

Ile Leu Arg Asp Pro Ser Asn Asp Ser Asp Gln Ser Lys Phe Glu
    4445                4450                4455

His Ile Gly Ser Val Thr Phe Ser Asp Tyr Phe Asn Gly Asn Arg
    4460                4465                4470

Ala Gln Val Val Ile Gly Met Ser Glu Lys Asp Leu Ser Gly Glu
    4475                4480                4485

Arg Glu Tyr Thr Met Leu Ser Asp Ser Ala Ile Asp Ala Leu Val
    4490                4495                4500

Gln Ala Met Ser Gly Phe Glu Pro Gln Ala Gly Asp Asn Gly Phe
    4505                4510                4515

Ile Asp Ser Leu Glu Ser Lys Ser Gln Ala Ala Ile Ser Met Ala
    4520                4525                4530

Trp Ser Asp Val Val His Lys Lys Gly Leu Met Val
    4535                4540                4545

<210> SEQ ID NO 2
<211> LENGTH: 5206
<212> TYPE: PRT
<213> ORGANISM: Vibrio vulnificus

<400> SEQUENCE: 2

Met Gly Lys Pro Phe Trp Arg Ser Val Glu Tyr Phe Phe Thr Gly Asn
1               5                   10                  15

Tyr Ser Ala Asp Asp Gly Asn Asn Ser Ile Val Ala Ile Gly Phe Gly
            20                  25                  30

Gly Glu Ile His Ala Tyr Gly Gly Asp Asp His Val Thr Val Gly Ser
        35                  40                  45

Ile Gly Ala Thr Val Tyr Thr Gly Ser Gly Asn Asp Thr Val Val Gly
    50                  55                  60

```
Gly Ser Ala Tyr Leu Arg Val Glu Asp Thr Thr Gly His Leu Ser Val
 65                  70                  75                  80

Lys Gly Ala Ala Gly Tyr Ala Asp Ile Asn Lys Ser Gly Asp Gly Asn
                 85                  90                  95

Val Ser Phe Ala Gly Ala Gly Gly Val Ser Ile Asp His Leu Gly
            100                 105                 110

Asn His Gly Asp Val Ser Tyr Gly Ala Ala Ala Tyr Asn Gly Ile
        115                 120                 125

Thr Arg Lys Gly Leu Ser Gly Asn Val Thr Phe Lys Gly Ala Gly Gly
    130                 135                 140

Tyr Asn Ala Leu Trp His Glu Thr Asn Gln Gly Asn Leu Ser Phe Ala
145                 150                 155                 160

Gly Ala Gly Ala Gly Asn Lys Leu Asp Arg Thr Trp Phe Asn Arg Tyr
                165                 170                 175

Gln Gly Ser Arg Gly Asp Val Thr Phe Asp Gly Ala Gly Ala Ala Asn
            180                 185                 190

Ser Ile Ser Ser Arg Val Glu Thr Gly Asn Ile Thr Phe Arg Gly Ala
            195                 200                 205

Gly Ala Asp Asn His Leu Val Arg Lys Gly Lys Val Gly Asp Ile Thr
210                 215                 220

Leu Gln Gly Ala Gly Ala Ser Asn Arg Ile Glu Arg Thr Arg Gln Ala
225                 230                 235                 240

Glu Asp Val Tyr Ala Gln Thr Arg Gly Asn Ile Arg Phe Glu Gly Val
            245                 250                 255

Gly Gly Tyr Asn Ser Leu Tyr Ser Asp Val Ala His Gly Asp Ile His
            260                 265                 270

Phe Ser Gly Gly Ala Tyr Asn Thr Ile Thr Arg Lys Gly Ser Gly
    275                 280                 285

Ser Ser Phe Asp Ala Gln Gly Met Glu Tyr Ala Lys Ala Glu Asp Ile
    290                 295                 300

Val Leu Thr Ala Ala Gln Met His Gly Leu Ser Ile Asp Asn Gly Asn
305                 310                 315                 320

Lys Phe His Ala Val Thr Ala Val Lys Ser Glu Arg Glu Pro Asn Thr
                325                 330                 335

Tyr Leu Phe Ala Ile Ala Asp Gly Thr Tyr Thr Lys Ile Asn Lys Val
            340                 345                 350

Arg Leu Tyr Asn Asp Pro Glu Thr Gly Lys Leu Lys Tyr Tyr Ser Glu
            355                 360                 365

Ala Trp Phe Lys Arg Gly Asn His Leu Ala Glu Leu Ala Arg Ser Asp
    370                 375                 380

Val Ser Ala Gly Gly Phe Glu Val Asn Pro Ile Asn Gly Gly Tyr
385                 390                 395                 400

Thr Leu Ser Asn Ile Ala Val Glu His Gln Gln Ser Leu Thr Val His
            405                 410                 415

Ala Val Glu Lys Asp Leu Thr Glu Tyr Glu Trp Val Thr Tyr Ala Asn
                420                 425                 430

Gly Ala Leu Ile Asp Ala Lys Asp Val Ala Leu Ser Glu Ala Lys Met
            435                 440                 445

Gly Gly His Ala Ile Ser Thr Asp Gly Thr Thr Val Asp Val Gln Ala
        450                 455                 460

Val Lys Ser Asn Arg Lys Pro Asn Thr Tyr Val Tyr Ala Lys Val Leu
465                 470                 475                 480

Gly Pro Tyr Thr Lys Ile Val Val Val Glu Leu Ala Asn Asp Pro Lys
                485                 490                 495
```

```
Thr Gly Ala Leu Lys Tyr Gln Ala Arg Ser Trp Tyr Lys Glu Gly Asn
            500                 505                 510
His Thr Ala Asn Leu Ala Asn Glu Asp Ile Ser Ser Ala Asn Gly Tyr
        515                 520                 525
His Ser Met Gly Lys Gly Tyr Ser Leu Ser Asp Leu His Tyr Ser
    530                 535                 540
Val Asn Ala Val Arg Ser Thr Ser Glu Thr Val Ala Asp Ile Asp Glu
545                 550                 555                 560
Tyr Thr Asp Gln Thr Leu Phe Lys Pro Ala Thr Asp Ser Gly Glu Ser
                565                 570                 575
Ser Gly Asp Val Arg Phe Asn Gly Ala Gly Gly Asn Val Ile Lys
            580                 585                 590
Ser Asn Val Thr Arg Gly Asn Val Tyr Phe Asn Gly Gly Ile Ala
            595                 600                 605
Asn Val Ile Leu His Ser Ser Gln Phe Gly His Thr Glu Phe Asn Gly
        610                 615                 620
Gly Gly Ala Ala Asn Val Ile Val Lys Ser Gly Glu Glu Gly Asp Leu
625                 630                 635                 640
Thr Phe Arg Gly Ala Gly Leu Ala Asn Val Leu Val His Gln Ser Lys
                645                 650                 655
Gln Gly Lys Met Asp Val Tyr Ala Gly Gly Ala Val Asn Val Leu Val
            660                 665                 670
Arg Ile Gly Asp Gly Gln Tyr Leu Ala His Leu Leu Ala Tyr Gly Asn
            675                 680                 685
Ile Ser Val His Lys Gly Asn Gly Asn Ser Arg Val Val Met Leu Gly
        690                 695                 700
Gly Tyr Asn Thr His Thr Gln Ile Gly Ser Gly Asn Gly Leu Trp Leu
705                 710                 715                 720
Ala Ala Gly Gly Phe Asn Val Met Thr Gln Val Gly Lys Gly Asp Val
                725                 730                 735
Ala Ser Val Leu Ala Gly Gly Ala Asn Val Leu Thr Lys Val Gly Asp
            740                 745                 750
Gly Asp Leu Thr Ala Gly Met Leu Gly Gly Ala Asn Val Ile Thr His
        755                 760                 765
Ile Ser Gly Asp Asn Glu Thr Ser Asn Thr Thr Ala Val Ala Leu Gly
        770                 775                 780
Gly Ala Asn Ile Leu Thr Lys Lys Gly Lys Gly Asn Thr Leu Ala Val
785                 790                 795                 800
Met Gly Gly Gly Ala Asn Val Leu Thr His Val Gly Asp Gly Thr Thr
                805                 810                 815
Thr Gly Val Met Val Gly Gly Ala Asn Ile Leu Thr Lys Val Gly Asn
            820                 825                 830
Gly Asp Thr Thr Gly Ile Met Leu Gly Val Gly Asn Val Leu Thr His
        835                 840                 845
Val Gly Asp Gly Gln Thr Leu Gly Val Met Gly Ala Ala Gly Asn Ile
        850                 855                 860
Phe Thr Lys Val Gly Asp Gly Thr Ser Ile Ala Val Met Ile Gly Ala
865                 870                 875                 880
Gly Asn Ile Phe Thr His Val Gly Glu Gly Asn Ala Trp Ala Leu Met
                885                 890                 895
Gly Gly Leu Gly Asn Val Phe Thr Lys Val Gly Asn Gly Asp Ala Leu
            900                 905                 910
Ala Leu Met Val Ala Glu Ala Asn Val Phe Thr His Ile Gly Asp Gly
```

-continued

```
            915                 920                 925
Met Ser Val Ala Leu Met Leu Ala Lys Gly Asn Val Ala Thr Lys Val
            930                 935                 940
Gly Asn Gly Thr Thr Leu Ala Ala Met Val Gly Asn Ala Asn Ile Phe
945                 950                 955                 960
Thr His Val Gly Ser Gly Ser Thr Phe Ala Ala Met Ile Gly Gln Ala
                965                 970                 975
Asn Ile Met Thr Lys Val Gly Asn Asp Leu Thr Ala Ala Leu Met Val
            980                 985                 990
Gly Lys Ala Asn Ile Tyr Thr His Val Gly Asp Gly Thr Ser Leu Gly
            995                 1000                1005
Ile Phe Ala Gly Glu Val Asn Val Ile Thr Lys Val Gly Asn Gly
    1010                1015                1020
Thr Thr Leu Ala Ala Met Phe Gly Lys Ala Asn Ile Met Thr His
    1025                1030                1035
Val Gly Asp Gly Leu Thr Gly Val Leu Ala Leu Gly Glu Ala Asn
    1040                1045                1050
Ile Val Thr Lys Val Gly Asp Asp Phe Met Gly Val Val Ala Ala
    1055                1060                1065
Ala Lys Ala Asn Val Val Thr His Val Gly Asp Ala Thr Thr Ala
    1070                1075                1080
Ala Val Leu Ala Gly Lys Gly Asn Ile Leu Thr Lys Val Gly Glu
    1085                1090                1095
Gly Thr Thr Val Gly Leu Leu Ile Ser Asp Ile Gly Asn Val Met
    1100                1105                1110
Thr His Val Gly Asp Gly Thr Ile Gly Ile Ala Lys Gly Lys
    1115                1120                1125
Ala Asn Ile Ile Thr Lys Val Gly Asp Gly Leu Gly Val Asn Val
    1130                1135                1140
Ala Trp Gly Gln Ala Asn Val Phe Thr Gln Val Gly Asp Gly Asp
    1145                1150                1155
Arg Tyr Asn Phe Ala Lys Gly Glu Ala Asn Ile Ile Thr Lys Val
    1160                1165                1170
Gly Asp Gly Gln Glu Val Ser Val Val Gln Gly Lys Ala Asn Ile
    1175                1180                1185
Ile Thr His Val Gly Asn Gly Asp Asp Tyr Thr Gly Ala Trp Gly
    1190                1195                1200
Lys Ala Asn Val Ile Thr Lys Val Gly Asn Gly Arg Asn Val Val
    1205                1210                1215
Leu Ala Lys Gly Glu Ala Asn Ile Val Thr Gln Val Gly Asp Gly
    1220                1225                1230
Asp Ser Phe Asn Ala Leu Trp Ser Lys Gly Asn Ile Val Thr Lys
    1235                1240                1245
Val Gly Asp Gly Met Gln Val Thr Ala Ala Lys Gly Lys Ala Asn
    1250                1255                1260
Ile Thr Thr Thr Val Gly Asp Gly Leu Ser Val Thr Ala Ala Tyr
    1265                1270                1275
Gly Asp Ala Asn Ile Asn Thr Lys Val Gly Asp Gly Val Ser Val
    1280                1285                1290
Asn Val Ala Trp Gly Lys Tyr Asn Ile Asn Thr Lys Val Gly Asp
    1295                1300                1305
Gly Leu Asn Val Ala Val Met Lys Gly Lys Ala Asn Ala Asn Ile
    1310                1315                1320
```

-continued

His Val Gly Asp Gly Leu Asn Ile Asn Ala Ser Tyr Ala Gln Asn
1325                     1330                1335

Asn Val Ala Ile Lys Val Gly Asn Gly Asp Phe Tyr Ser Leu Ala
1340                     1345                1350

Val Ala Ser Ser Asn Thr Ser Ser Asn Lys Leu Ser Ala Leu Phe
1355                     1360                1365

Asp Asn Ile Lys Gln Thr Leu Leu Gly Val Gly Ser Gln Ala
1370                     1375                1380

Ile Asn Tyr Leu Val Gln Gly Asp Glu Ala Ser Ser Gly Thr
1385                     1390                1395

Gln Lys Gly Arg Gly Ala Ile Ala Thr Pro Glu Ile Thr Lys Leu
1400                     1405                1410

Asp Gly Phe Gln Met Glu Ala Ile Glu Glu Val Gly Ser Asp Leu
1415                     1420                1425

Gly Asp Ser Leu Thr Gly Ser Val Thr Lys Val Asp Thr Pro Asp
1430                     1435                1440

Leu Asn Lys Met Gln Asn Ala Leu Asp Val Asp Gly Ser Ala Asp
1445                     1450                1455

Gln Thr Gln Ala Pro Asn Leu Ile Val Asn Gly Asp Phe Glu Gln
1460                     1465                1470

Gly Asp Arg Gly Trp Lys Ser Thr His Gly Val Glu Ala Ser Tyr
1475                     1480                1485

Ser Gly Asn Val Tyr Gly Val Asn Gly Glu Gly His Gly Ala Arg
1490                     1495                1500

Val Thr Glu Leu Asp Thr Tyr Thr Asn Thr Ser Leu Tyr Gln Asp
1505                     1510                1515

Leu Thr Asp Leu Thr Glu Gly Glu Val Ile Ala Val Ser Phe Asp
1520                     1525                1530

Phe Ala Lys Arg Ala Gly Leu Ser Asn Asn Glu Gly Ile Glu Val
1535                     1540                1545

Leu Trp Asn Gly Glu Val Val Phe Ser Ser Gly Asp Ala Ser
1550                     1555                1560

Ala Trp Gln Gln Lys Thr Leu Lys Leu Thr Ala His Ala Gly Ser
1565                     1570                1575

Asn Arg Ile Glu Phe Lys Gly Thr Gly His Asn Asp Gly Leu Gly
1580                     1585                1590

Tyr Ile Leu Asp Asn Val Val Ala Lys Ser Glu Ser Ser Gln Gln
1595                     1600                1605

Ala Asn Ala Val Ser Glu His Ala Thr Gln Asn Gln Ala Ser Gln
1610                     1615                1620

Asn Ala Leu Ser Asp Lys Glu Cys Ala Glu Ala Asp Arg Gln Arg
1625                     1630                1635

Leu Glu Gln Glu Lys Gln Lys Gln Leu Asp Ala Val Ala Gly Ser
1640                     1645                1650

Gln Ser Gln Leu Glu Ser Thr Asp Gln Ala Leu Glu Asn Asn
1655                     1660                1665

Gly Gln Ala Gln Arg Asp Ala Val Lys Glu Glu Ser Glu Ala Val
1670                     1675                1680

Thr Ala Glu Leu Thr Lys Leu Ala Gln Gly Leu Asp Val Leu Asp
1685                     1690                1695

Gly Gln Ala Thr His Thr Gly Glu Ser Gly Asp Gln Trp Arg Asn
1700                     1705                1710

Asp Phe Ala Gly Gly Leu Leu Asp Gly Val Gln Ser Gln Leu Asp
1715                     1720                1725

```
Asp Ala Lys Gln Leu Ala Asn Asp Lys Ile Ala Ala Ala Lys Gln
    1730                1735                1740

Thr Gln Ser Asp Asn Asn Ser Lys Val Lys Glu Ser Val Ala Lys
    1745                1750                1755

Ser Glu Ala Gly Val Ala Lys Gly Glu Gln Asn Arg Ala Gly Ala
    1760                1765                1770

Glu Gln Asp Ile Ala Glu Ala Lys Ala Asp Ala Glu Thr Arg Lys
    1775                1780                1785

Ala Asp Ala Val Ala Lys Ser Asn Asp Ala Lys Gln Ala Glu Ser
    1790                1795                1800

Asp Ala His Ser Ala Ala Asn Asp Ala Gln Ser Arg Gly Asp Arg
    1805                1810                1815

Asp Ala Met Asn Ala Glu Asn Lys Ala Asn Gln Ala Gln Asn Asp
    1820                1825                1830

Ala Lys Gly Thr Lys Gln Asn Glu Gly Asp Arg Pro Asp Arg Glu
    1835                1840                1845

Gly Val Ala Gly Ser Gly Leu Ser Gly Asn Ala His Ser Val Glu
    1850                1855                1860

Gly Ala Gly Glu Thr Gly Ser His Val Asn Thr Asp Ser Pro Thr
    1865                1870                1875

Asn Ala Asp Gly Arg Phe Ser Glu Gly Leu Ser Glu Gln Glu Gln
    1880                1885                1890

Glu Ala Leu Glu Gly Ala Thr Asn Ala Val Asn Arg Leu Gln Ile
    1895                1900                1905

Asn Ala Gly Ile Arg Gly Lys Asn Ser Gly Ser Thr Ile Thr Ser
    1910                1915                1920

Met Phe Thr Glu Thr Asn Ser Asp Ser Ile Val Val Pro Thr Thr
    1925                1930                1935

Ala Ser Gln Asp Val Val Arg Gln Glu Ile Arg Ile Ser Gly Val
    1940                1945                1950

Asn Leu Glu Gly Leu Gly Glu Thr Ser His Asp Ser Ala Glu Ser
    1955                1960                1965

Leu Val Ala Ala Arg Ala Glu Lys Val Ala Asn Leu Tyr Arg Trp
    1970                1975                1980

Leu Asp Thr Asp Asn Asp Val Ala Thr Asp Lys Tyr Val Pro Val
    1985                1990                1995

Pro Gly Phe Glu Arg Val Asp Ala Asp Val Ser Asp Glu Val Lys
    2000                2005                2010

Gln Arg Met Ile Gln Ser Met Ser Gly Tyr Ile Glu His Thr Asp
    2015                2020                2025

Asn Gln Val Pro Lys Asp Gln Ala Glu Ala Leu Ala Thr Leu Phe
    2030                2035                2040

Val Glu Ser Thr Leu Asp Tyr Asp Trp Asp Lys Arg Val Glu Phe
    2045                2050                2055

Leu Thr Lys Leu Glu Ser Tyr Gly Tyr Ser Phe Glu Ala Pro His
    2060                2065                2070

Ala Glu Lys Ser Ile Val Ser Phe Trp Ser Gly Lys Asn Phe Lys
    2075                2080                2085

Gln Tyr Arg Asp Val Leu Asp Asn Ala Gln Thr Asp Gly Lys Lys
    2090                2095                2100

Val Val Tyr Asp Ile Asp Val Lys Gly Asn Ala Phe Ala Ile Asp
    2105                2110                2115

Leu Asn Lys His Leu Met Arg Trp Gly Gly Leu Phe Leu Asp Pro
```

```
              2120                2125                2130

Asp Asn Ala Glu Gln Asn Gln Leu Lys Ser Ser Ile Asp Ala Ala
    2135                2140                2145

Thr Phe Ser Asn Thr Gly Phe Trp Ser Ser Val Tyr Ala Thr Gly
    2150                2155                2160

Ala Gln Asn Asp Val Tyr Val Ile Ala Glu Gly Gly Val Arg Leu
    2165                2170                2175

Gly Asn Tyr Phe Trp Asn Val Glu Leu Pro Ala Leu Arg Gln Leu
    2180                2185                2190

Gln Arg Glu Gly Leu Val Gly Glu Ile Arg Leu Leu Asp Lys Pro
    2195                2200                2205

Val Ser Glu Tyr Lys Asp Leu Pro Ala Asp Gln Ile Gly Arg Arg
    2210                2215                2220

Leu Thr Asp Ala Gly Val Ala Val Lys Val Arg Phe Asp Ala Leu
    2225                2230                2235

Ser His Glu Arg Gln Ala Glu Leu Leu Ala Asp Asn Pro Asp Gly
    2240                2245                2250

Tyr Lys Ala Asp Thr Leu Val Glu Leu Asp Val Lys Leu Ser Ala
    2255                2260                2265

Ile Asp Ser Met Leu Arg Glu Ser Leu Pro Phe Tyr Ser Leu Arg
    2270                2275                2280

Thr Glu Arg Asn Leu Leu Val Gln Glu Gly Glu Glu Gly Phe Glu
    2285                2290                2295

Val Arg Ser Trp Pro Gly Ile Asp Gly Lys Ser Lys Thr Ile Leu
    2300                2305                2310

Leu Asp Asn Pro Glu Asp Ala Ala Gln Gln Lys Ser Ile Glu Arg
    2315                2320                2325

Phe Ile Leu Ala Asn Phe Asp Asn Phe Glu Gln Met Pro Asp Glu
    2330                2335                2340

Leu Phe Leu Val Asp Asn Lys Val Leu Ser His His Asp Gly Arg
    2345                2350                2355

Thr Arg Ile Ile Ala Gln Lys Glu Asp Gly Ala Trp Thr Tyr Asn
    2360                2365                2370

Thr Asn Val Glu Leu Met Ser Val Thr Glu Leu Leu Asp Ala Ala
    2375                2380                2385

His Val Asn Gly Lys Val Arg Gly Asp Ser Tyr Gln Gln Val Ile
    2390                2395                2400

Asp Ala Leu Thr Glu Tyr His Ala Ser Thr Val Glu His Ala Asp
    2405                2410                2415

Tyr Glu Leu Glu Ser Val Glu Lys Leu Leu Asn Leu Arg Lys Gln
    2420                2425                2430

Ile Glu Gly Tyr Val Leu Gly His Pro Asp Ser Gly Arg Val Glu
    2435                2440                2445

Ala Met Asn Ser Leu Leu Asn Gln Val Asn Ser Arg Leu Glu Glu
    2450                2455                2460

Val Ser Val Leu Ala Val Ser Glu Gln Ser Ile Lys Ala His Asp
    2465                2470                2475

Ser Phe Ser Arg Leu Tyr Asp Gln Leu Asp Asn Ala Asn Leu Lys
    2480                2485                2490

Glu Ser Lys His Leu Tyr Leu Asp Gly Asn Gly Asp Phe Val Thr
    2495                2500                2505

Lys Gly Lys Gly Asn Leu Ala Thr Ile Asp Gln Leu Gly Gly Ser
    2510                2515                2520
```

-continued

| | | | | | | | | | | | |
|---|---|---|---|---|---|---|---|---|---|---|---|
| Asp | Ala | Val | Leu | Glu | Lys | Val | Lys | Ala | Ala | Val | Thr | His | Glu | Tyr |
| 2525 | | | | 2530 | | | | | 2535 | | | | | |
| Gly | Gln | Val | Val | Ala | Asp | Thr | Ile | Phe | Ala | Gly | Leu | Ser | Ala | Asn |
| 2540 | | | | | 2545 | | | | | 2550 | | | | |
| Asp | Leu | Ala | Lys | Asp | Gly | Lys | Gly | Ile | Asp | Ile | Ala | Gly | Leu | Asn |
| 2555 | | | | | 2560 | | | | | 2565 | | | | |
| Lys | Val | His | Gln | Ala | Ile | Glu | Gln | His | Met | Ser | Pro | Val | Ser | Ala |
| 2570 | | | | | 2575 | | | | | 2580 | | | | |
| Thr | Met | Tyr | Ile | Trp | Lys | Pro | Ser | Asp | His | Ser | Ala | Leu | Gly | His |
| 2585 | | | | | 2590 | | | | | 2595 | | | | |
| Ala | Ala | Leu | Gln | Ile | Gly | Gln | Gly | Arg | Thr | Gln | Leu | Glu | Gly | Gln |
| 2600 | | | | | 2605 | | | | | 2610 | | | | |
| Ala | Ala | Ala | Asp | Phe | Asn | Lys | Gln | Asn | Tyr | Val | Ser | Trp | Trp | Pro |
| 2615 | | | | | 2620 | | | | | 2625 | | | | |
| Leu | Gly | Ser | Lys | Ser | Ser | Asn | Ile | Arg | Asn | Ile | Phe | Asn | Val | Ala |
| 2630 | | | | | 2635 | | | | | 2640 | | | | |
| Thr | Glu | Asp | Gln | Pro | Asp | Leu | Lys | Leu | Arg | Trp | Ser | Asp | Phe | Ser |
| 2645 | | | | | 2650 | | | | | 2655 | | | | |
| Gln | Pro | Ala | His | Gln | Asn | Asp | Thr | Leu | Glu | His | Asp | Met | Ala | Ser |
| 2660 | | | | | 2665 | | | | | 2670 | | | | |
| Glu | Glu | Asn | Asp | Gly | Phe | Gly | Leu | Lys | Asp | Gly | Glu | Thr | Lys | Leu |
| 2675 | | | | | 2680 | | | | | 2685 | | | | |
| Lys | Arg | Phe | Ile | Glu | Lys | Leu | Asn | Ala | Ala | Lys | Gly | Ile | Asp | Ala |
| 2690 | | | | | 2695 | | | | | 2700 | | | | |
| Ser | Tyr | Lys | Asp | Ala | Ser | Glu | Gly | Tyr | Ala | Ser | Val | Leu | Leu | Gly |
| 2705 | | | | | 2710 | | | | | 2715 | | | | |
| Asn | Pro | Asp | Met | Leu | Ala | Ser | Thr | Gly | Ile | Pro | Ala | His | Val | Phe |
| 2720 | | | | | 2725 | | | | | 2730 | | | | |
| Gln | Pro | Phe | Val | Asp | Gln | Trp | Asn | Asp | Thr | Ser | Tyr | Asp | Met | Met |
| 2735 | | | | | 2740 | | | | | 2745 | | | | |
| Asp | Val | Ala | Asn | Arg | Phe | Ala | Glu | Glu | Leu | Gln | Lys | Gln | Ala | Gln |
| 2750 | | | | | 2755 | | | | | 2760 | | | | |
| Ala | Ser | Gly | Asp | Pro | Ala | Leu | Val | Glu | Lys | Arg | Ile | Asp | Asn | Val |
| 2765 | | | | | 2770 | | | | | 2775 | | | | |
| Val | Arg | Leu | Phe | Ala | Glu | Arg | Ala | Leu | Glu | Glu | Ile | Glu | Ala | Phe |
| 2780 | | | | | 2785 | | | | | 2790 | | | | |
| Lys | Ala | Ser | Gln | Ala | Asp | Glu | Gly | Arg | Val | Phe | Arg | Ile | Asn | Leu |
| 2795 | | | | | 2800 | | | | | 2805 | | | | |
| Glu | Gly | Leu | Asp | Val | Ala | Ala | Met | Gln | Ala | Glu | Trp | Asn | Arg | Leu |
| 2810 | | | | | 2815 | | | | | 2820 | | | | |
| Ser | Asn | Asp | Pro | Asp | Ala | Arg | Tyr | Gln | Leu | Leu | Thr | Lys | Asn | Cys |
| 2825 | | | | | 2830 | | | | | 2835 | | | | |
| Ser | Ser | Thr | Val | Ala | Lys | Val | Leu | Lys | Ala | Gly | Ala | Asp | Lys |
| 2840 | | | | | 2845 | | | | | 2850 | | | | |
| Leu | Ile | Gly | His | Thr | Trp | Arg | Pro | Lys | Phe | Gly | Val | Trp | Thr | Pro |
| 2855 | | | | | 2860 | | | | | 2865 | | | | |
| Thr | Glu | Leu | Phe | Asn | Phe | Gly | Gln | Ala | Leu | Gln | Glu | Ala | Gln | Leu |
| 2870 | | | | | 2875 | | | | | 2880 | | | | |
| Glu | Ile | Ala | Ala | Lys | Lys | Gln | Ser | His | Gln | Val | Thr | Asp | Val | Leu |
| 2885 | | | | | 2890 | | | | | 2895 | | | | |
| Asp | Ala | Leu | Ser | Gly | Asn | Glu | Lys | His | Lys | Glu | Asn | Val | Ala | Ile |
| 2900 | | | | | 2905 | | | | | 2910 | | | | |
| Glu | Asn | Asp | Gly | Thr | Pro | Pro | Arg | Asp | Lys | Glu | Ser | Leu | Ser | Pro |
| 2915 | | | | | 2920 | | | | | 2925 | | | | |

```
Leu Thr Arg Phe Leu Asn Asn Glu Leu Tyr Gly Glu Lys Asp Ala
    2930                2935                2940

Arg Arg Lys Ile Gly Glu Ile Thr Gln Thr Leu Leu Asp His Ala
    2945                2950                2955

Val Glu Asn Gly Glu Ser Gln Lys Val Thr Leu Lys Gly Glu Val
    2960                2965                2970

Gly Arg Leu Thr Gly Tyr Tyr His Gln Gly Ala Ala Ser Ser Glu
    2975                2980                2985

Gly Glu Thr Ser Ala Thr Ser Gly Lys Val Val Leu Phe Leu His
    2990                2995                3000

Gly Ser Gly Ser Ser Ala Glu Glu Gln Ala Ser Glu Ile Arg Asn
    3005                3010                3015

His Tyr Gln Lys Gln Gly Ile Asp Met Leu Ala Val Asn Leu Arg
    3020                3025                3030

Gly Tyr Gly Glu Ser Asp Gly Pro Ser Glu Lys Gly Leu Tyr
    3035                3040                3045

Gln Asp Ala Arg Thr Met Phe Asn Tyr Leu Val Asn Asp Lys Gly
    3050                3055                3060

Ile Asp Pro Ser Asn Ile Ile Ile His Gly Tyr Ser Met Gly Gly
    3065                3070                3075

Pro Ile Ala Ala Asp Leu Ala Arg Tyr Ala Ala Gln Asn Gly Gln
    3080                3085                3090

Ala Val Ser Gly Leu Leu Leu Asp Arg Pro Met Pro Ser Met Thr
    3095                3100                3105

Lys Ala Ile Thr Ala His Glu Met Ala Asn Pro Ala Gly Ile Val
    3110                3115                3120

Gly Ala Ile Ala Lys Ala Val Asn Gly Gln Phe Ser Val Glu Lys
    3125                3130                3135

Asn Leu Lys Gly Leu Pro Lys Glu Thr Pro Ile Leu Leu Leu Thr
    3140                3145                3150

Asp Asn Glu Gly Leu Gly Glu Glu Gly Glu Lys Leu Arg Ala Lys
    3155                3160                3165

Leu Ala Ile Ala Gly Tyr Asn Val Thr Gly Glu Gln Thr Phe Tyr
    3170                3175                3180

Gly His Glu Ala Ser Asn Arg Leu Met Gly Gln Tyr Ala Asp Gln
    3185                3190                3195

Ile Val Ser Gly Leu Phe Asn Ala Glu Gln Ala Ala Val Glu Ala
    3200                3205                3210

Gly Glu Val Leu Lys Gly Leu Glu Lys Asp Phe Lys Arg Tyr Gly
    3215                3220                3225

Asp Ala Leu Lys Pro Asp Thr Ser Val Pro Gly Lys Ser Lys Asp
    3230                3235                3240

Ile Arg Thr Thr Lys Asp Phe Leu Asn Gly Tyr Lys Asn Asp His
    3245                3250                3255

Ala Lys Glu Ile Val Asp Gly Phe Arg Ser Asp Met Ser Ile Lys
    3260                3265                3270

Gln Leu Val Asp Leu Phe Val Lys Gly Asn Trp Ser Ala Glu Gln
    3275                3280                3285

Lys Gly Ala Leu Ala Trp Glu Ile Glu Ser Arg Ala Leu Lys Val
    3290                3295                3300

Thr Phe Gln Asn Lys Ser Glu Lys Tyr Asn Arg Leu Phe Arg Glu
    3305                3310                3315

Ile Ala Ser Ala Gly Val Val Asp Ala Lys Ala Thr Glu Gln Leu
```

|     |     |     |     |     |     |     |     |     |     |
|---|---|---|---|---|---|---|---|---|---|
|     |     | 3320 |     |     | 3325 |     |     | 3330 |     |
| Ala | Pro 3335 | Gln | Leu | Met | Leu 3340 | Asn | Leu | Ser | Asn Asp 3345 | Gly | Phe | Gly |
| Gly | Arg 3350 | Cys | Asp | Pro | Leu 3355 | Ser | Lys | Leu | Val Leu 3360 | Ala | Lys | Gln |
| Leu | Glu 3365 | Asn | Asp | Gly | Gln 3370 | Val | Gly | Val | Ala Arg 3375 | Gln | Leu | Leu | Glu |
| Lys | Met 3380 | Tyr | Ser | Ala | Ala 3385 | Ala | Val | Leu | Ser Asn 3390 | Pro | Thr | Leu | Tyr |
| Ser | Asp 3395 | Ser | Glu | Lys | Ala 3400 | Asn | Ala | Ser | Lys Leu 3405 | Leu | Ser | Ser | Leu |
| Ala | Ala 3410 | Ile | His | Ala | Lys 3415 | Asn | Pro | Met | His Asp 3420 | Thr | Ser | Met | Lys |
| Val | Trp 3425 | Gln | Glu | Lys | Leu 3430 | Glu | Gly | Lys | Gln Ala 3435 | Leu | Thr | Val | Asn |
| Gly | Val 3440 | Val | Glu | Lys | Ile 3445 | Thr | Asp | Ala | Ser Ala 3450 | Asn | Gly | Lys | Pro |
| Val | Leu 3455 | Leu | Glu | Leu | Asp 3460 | Ala | Pro | Gly | His Ala 3465 | Met | Ala | Ala | Trp |
| Ala | Lys 3470 | Gly | Ser | Gly | Asp 3475 | Arg | Val | Tyr | Gly Phe 3480 | Tyr | Asp | Pro |
| Asn | Ala 3485 | Gly | Ile | Val | Glu 3490 | Phe | Ser | Ser | Ala Glu 3495 | Lys | Phe | Gly | Asp |
| Tyr | Leu 3500 | Thr | Arg | Phe | Phe 3505 | Gly | Lys | Ser | Asp Leu 3510 | Asn | Met | Ala | Gln |
| Ser | Tyr 3515 | Lys | Leu | Gly | Lys 3520 | Asn | Asp | Ala | Gly Glu 3525 | Ala | Ile | Phe | Asn |
| Arg | Val 3530 | Val | Val | Met | Asp 3535 | Gly | Asn | Thr | Leu Ala 3540 | Ser | Tyr | Lys | Pro |
| Thr | Phe 3545 | Gly | Asp | Lys | Thr 3550 | Thr | Met | Gln | Gly Ile 3555 | Leu | Asp | Leu | Pro |
| Val | Phe 3560 | Asp | Ala | Thr | Pro 3565 | Ile | Lys | Lys | Pro Thr 3570 | Gly | Gly | Val | Ala |
| Ser | Asp 3575 | Leu | Glu | Ala | Leu 3580 | Gly | Asp | Lys | Thr Lys 3585 | Val | Val | Val | Asp |
| Leu | Ala 3590 | Gln | Ile | Phe | Thr 3595 | Val | Gln | Glu | Leu Lys 3600 | Glu | Arg | Ala | Lys |
| Val | Phe 3605 | Ala | Lys | Pro | Ile 3610 | Gly | Ala | Ser | Tyr Gln 3615 | Gly | Ile | Leu | Asp |
| Gln | Leu 3620 | Asp | Leu | Val | His 3625 | Gln | Ala | Lys | Gly Arg 3630 | Asp | Gln | Ile | Ala |
| Ala | Ser 3635 | Phe | Glu | Leu | Asn 3640 | Lys | Lys | Ile | Asn Asp 3645 | Tyr | Ile | Ala | Glu |
| His | Pro 3650 | Thr | Ser | Gly | Arg 3655 | Asn | Gln | Ala | Leu Thr 3660 | Gln | Leu | Lys | Lys |
| Gln | Val 3665 | Thr | Asn | Ala | Leu 3670 | Phe | Ile | Gly | Lys Met 3675 | Gln | Val | Ala | Gln |
| Ala | Gly 3680 | Ile | Asp | Ala | Ile 3685 | Ala | Gln | Thr | Arg Pro 3690 | Glu | Leu | Ala | Ala |
| Arg | Ile 3695 | Phe | Met | Val | Ala 3700 | Ile | Glu | Glu | Ala Asn 3705 | Gly | Lys | His | Val |
| Gly | Leu 3710 | Thr | Asp | Met | Met 3715 | Val | Arg | Trp | Ala Asn 3720 | Glu | Asp | Pro | Tyr |

-continued

Leu Ala Pro Lys His Gly Tyr Lys Gly Glu Thr Pro Ser Asp Leu
3725            3730                3735

Gly Phe Asp Ala Lys Tyr His Val Asp Leu Gly Glu His Tyr Ala
3740            3745                3750

Asp Phe Lys Gln Trp Leu Glu Thr Ser Gln Ser Asn Gly Leu Leu
3755            3760                3765

Ser Lys Ala Thr Leu Asp Glu Ser Thr Lys Thr Val His Leu Gly
3770            3775                3780

Tyr Ser Tyr Gln Glu Leu Gln Asp Leu Thr Gly Ala Glu Ser Val
3785            3790                3795

Gln Met Ala Phe Tyr Phe Leu Lys Glu Ala Ala Lys Lys Ala Asp
3800            3805                3810

Pro Ile Ser Gly Asp Ser Ala Glu Met Ile Leu Leu Lys Lys Tyr
3815            3820                3825

Ala Asp Gln Ser Tyr Leu Ser Gln Leu Asp Ser Asp Arg Met Asp
3830            3835                3840

Gln Ile Glu Gly Ile Tyr Arg Ser Ser His Glu Thr Asp Ile Asp
3845            3850                3855

Ala Trp Asp Arg Arg Tyr Ser Gly Thr Gly Tyr Asp Glu Leu Thr
3860            3865                3870

Asn Lys Leu Ala Ser Ala Thr Gly Val Asp Glu Gln Leu Ala Val
3875            3880                3885

Leu Leu Asp Asp Arg Lys Gly Leu Leu Ile Gly Glu Val His Gly
3890            3895                3900

Ser Asp Val Asn Gly Leu Arg Phe Val Asn Glu Gln Met Asp Ala
3905            3910                3915

Leu Lys Lys Gln Gly Val Thr Val Ile Gly Leu Glu His Leu Arg
3920            3925                3930

Ser Asp Leu Ala Gln Pro Leu Ile Asp Arg Tyr Leu Ala Thr Gly
3935            3940                3945

Val Met Ser Ser Glu Leu Ser Ala Met Leu Lys Thr Lys His Leu
3950            3955                3960

Asp Val Thr Leu Phe Glu Asn Ala Arg Ala Asn Gly Met Arg Ile
3965            3970                3975

Val Ala Leu Asp Ala Asn Ser Ser Ala Arg Pro Asn Val Gln Gly
3980            3985                3990

Thr Glu His Gly Leu Met Tyr Arg Ala Gly Ala Ala Asn Asn Ile
3995            4000                4005

Ala Val Glu Val Leu Gln Asn Leu Pro Asp Gly Glu Lys Phe Val
4010            4015                4020

Ala Ile Tyr Gly Lys Ala His Leu Gln Ser His Lys Gly Ile Glu
4025            4030                4035

Gly Phe Val Pro Gly Ile Thr His Arg Leu Asp Leu Pro Ala Leu
4040            4045                4050

Lys Val Ser Asp Ser Asn Glu Phe Thr Val Glu Gln Asp Asp Val
4055            4060                4065

Ser Leu Arg Val Val Tyr Asp Val Ala Asn Lys Pro Lys Ile
4070            4075                4080

Thr Phe Lys Asp Ser Leu Ser Gly Ala Asn Thr Ala Leu His Asn
4085            4090                4095

Gln Asn Val Asn Asp Trp Glu Arg Val Val Thr Pro Thr Ala
4100            4105                4110

Asp Gly Gly Glu Ser Arg Phe Asp Gly Gln Ile Ile Val Gln Met
4115            4120                4125

```
Glu Asn Asp Asp Val Val Ala Lys Ala Ala Asn Leu Ala Gly
    4130            4135                4140

Lys His Pro Glu Ser Ser Val Val Gln Ile Asp Ser Asp Gly
    4145            4150                4155

Asn Tyr Arg Val Val Tyr Gly Asp Pro Ser Lys Leu Asp Gly Lys
    4160            4165                4170

Leu Arg Trp Gln Leu Val Gly His Gly Arg Asp Asp Ser Glu Ser
    4175            4180                4185

Asn Asn Thr Arg Leu Ser Gly Tyr Ser Ala Asp Glu Leu Ala Val
    4190            4195                4200

Lys Leu Ala Lys Phe Gln Gln Ser Phe Asn Gln Ala Glu Asn Ile
    4205            4210                4215

Asn Asn Lys Pro Asp His Ile Ser Ile Val Gly Cys Ser Leu Val
    4220            4225                4230

Ser Asp Asp Lys Gln Lys Gly Phe Gly His Gln Phe Ile Asn Ala
    4235            4240                4245

Met Asp Ala Asn Gly Leu Arg Val Asp Val Ser Val Arg Ser Ser
    4250            4255                4260

Glu Leu Ala Val Asp Glu Ala Gly Arg Lys His Thr Lys Asp Ala
    4265            4270                4275

Asn Gly Asp Trp Val Gln Lys Ala Glu Asn Asn Lys Val Ser Leu
    4280            4285                4290

Ser Trp Asp Glu Gln Gly Glu Val Val Ala Lys Asp Glu Arg Ile
    4295            4300                4305

Arg Asn Gly Ile Ala Glu Gly Asp Ile Asp Leu Ser Arg Ile Gly
    4310            4315                4320

Val Ser Asp Val Asp Glu Pro Ala Arg Gly Ala Ile Gly Asp Asn
    4325            4330                4335

Asn Asp Val Phe Asp Ala Pro Glu Lys Arg Lys Ala Glu Thr Glu
    4340            4345                4350

Thr Ser Ser Ser Ser Ala Asn Asn Lys Leu Ser Tyr Ser Gly Asn
    4355            4360                4365

Ile Gln Val Asn Val Gly Asp Gly Glu Phe Thr Ala Val Asn Trp
    4370            4375                4380

Gly Thr Ser Asn Val Gly Ile Lys Val Gly Thr Gly Gly Phe Lys
    4385            4390                4395

Ser Leu Ala Phe Gly Asp Asn Asn Val Met Val His Ile Gly Asn
    4400            4405                4410

Gly Glu Ser Lys His Ser Phe Asp Ile Gly Gly Tyr Gln Ala Leu
    4415            4420                4425

Glu Gly Ala Gln Met Phe Ile Gly Asn Arg Asn Val Ser Phe Asn
    4430            4435                4440

Leu Gly Arg Ser Asn Asp Leu Ile Val Met Met Asp Lys Ser Ile
    4445            4450                4455

Pro Thr Pro Pro Leu Val Asn Pro Phe Asp Gly Ala Ala Arg Ile
    4460            4465                4470

Ser Gly Val Leu Gln Ser Ile Ala Thr Ser Gly Glu Gly Gln Asp
    4475            4480                4485

Trp Leu Ala Ala Gln Glu Gln Gln Trp Thr Leu Ser Gly Ala Lys
    4490            4495                4500

Lys Phe Val Lys Asp Met Ser Gly Leu Asp Gln Ser Ser Ser Val
    4505            4510                4515

Asp Tyr Thr Ser Leu Val Glu Leu Asp Ser Gln Asn Glu Arg Ser
```

-continued

```
                4520                4525                4530
Ser Arg Gly Leu Lys His Asp Ala Glu Ala Ala Leu Asn Lys Gln
    4535                4540                4545
Tyr Asn Gln Trp Leu Ser Gly Asn Ser Asp Ser Asp Thr Ser Lys
    4550                4555                4560
Leu Ser Arg Ala Asp Lys Leu Arg Gln Ala Asn Glu Lys Leu Ala
    4565                4570                4575
Phe Asn Phe Ala Val Gly Gly Gln Gly Ala Asp Ile Gln Val Thr
    4580                4585                4590
Thr Gly Asn Trp Asn Phe Met Phe Gly Asp Asn Ile Gln Ser Ile
    4595                4600                4605
Leu Asp Thr Asn Leu Gly Ser Leu Phe Gly Leu Met Thr Gln Gln
    4610                4615                4620
Phe Ser Ala Thr Gly Gln Ala Lys Thr Thr Phe Thr Tyr Thr Pro
    4625                4630                4635
Glu Asp Leu Pro Arg Gln Leu Lys Asn Lys Leu Leu Gly Gln Leu
    4640                4645                4650
Ala Gly Val Gly Ala Glu Thr Thr Leu Ala Asp Ile Phe Gly Val
    4655                4660                4665
Asp Tyr Thr Ala Ser Gly Gln Ile Val Ser Arg Asn Gly Glu Ala
    4670                4675                4680
Val Asp Gly Val Ala Ile Leu Lys Glu Met Leu Glu Val Ile Gly
    4685                4690                4695
Glu Phe Ser Gly Asp Gln Leu Gln Ala Phe Val Asp Pro Ala Lys
    4700                4705                4710
Leu Leu Asp Ser Leu Lys Ala Gly Ile Asn Met Gly Ala Asp Gly
    4715                4720                4725
Ile Lys Ser Phe Ala Glu Thr His Gly Leu Lys Glu Lys Ala Pro
    4730                4735                4740
Glu Glu Glu Glu Asp Asn Ser Ser Val Ser Val Asn Gly Ala Ser
    4745                4750                4755
Val Asn Ser Ala Gln Gly Ala Thr Val Ala Asp Gly Ser Thr Glu
    4760                4765                4770
Thr Ala Glu Thr Pro Asp Arg Ala Phe Gly Phe Asn Ser Leu Asn
    4775                4780                4785
Leu Pro Asn Leu Phe Ala Thr Ile Phe Ser Gln Asp Lys Gln Lys
    4790                4795                4800
Glu Met Lys Ser Leu Val Glu Asn Leu Lys Glu Asn Leu Thr Ala
    4805                4810                4815
Asp Leu Leu Asn Met Lys Glu Lys Thr Phe Asp Phe Leu Arg Asn
    4820                4825                4830
Ser Gly His Leu Gln Gly Asp Gly Asp Ile Asn Ile Ser Leu Gly
    4835                4840                4845
Asn Tyr Asn Phe Asn Trp Gly Gly Asp Gly Lys Asp Leu Gly Ala
    4850                4855                4860
Tyr Leu Gly Asp Asn Asn Phe Trp Gly Gly Arg Gly Asp Asp
    4865                4870                4875
Val Phe Tyr Ala Thr Gly Thr Ser Asn Ile Phe Thr Gly Gly Glu
    4880                4885                4890
Gly Asn Asp Met Gly Val Leu Met Gly Arg Glu Asn Met Met Phe
    4895                4900                4905
Gly Gly Asp Gly Asn Asp Thr Ala Val Val Ala Gly Arg Ile Asn
    4910                4915                4920
```

-continued

```
His Val Phe Leu Gly Ala Gly Asp Asp Gln Ser Phe Val Phe Gly
    4925            4930                4935

Glu Gly Gly Glu Ile Asp Thr Gly Ser Gly Arg Asp Tyr Val Val
    4940            4945                4950

Thr Ser Gly Asn Phe Asn Arg Val Asp Thr Gly Asp Asp Gln Asp
    4955            4960                4965

Tyr Ser Val Thr Ile Gly Asn Asn Asn Gln Val Glu Leu Gly Ala
    4970            4975                4980

Gly Asn Asp Phe Ala Asn Val Phe Gly Asn Tyr Asn Arg Ile Asn
4985            4990                4995

Ala Ser Ala Gly Asn Asp Val Val Lys Leu Met Gly Tyr His Ala
    5000            5005                5010

Val Leu Asn Gly Gly Glu Gly Glu Asp His Leu Ile Ala Ala Ala
    5015            5020                5025

Ile Ser Lys Phe Ser Gln Phe Asn Gly Gly Glu Gly Arg Asp Leu
    5030            5035                5040

Met Val Leu Gly Gly Tyr Gln Asn Thr Phe Lys Gly Gly Thr Asp
    5045            5050                5055

Val Asp Ser Phe Val Val Ser Gly Asp Val Ile Asp Asn Leu Val
    5060            5065                5070

Glu Asp Ile Arg Ser Glu Asp Asn Ile Val Phe Asn Gly Ile Asp
    5075            5080                5085

Trp Gln Lys Leu Trp Phe Glu Arg Ser Gly Tyr Asp Leu Lys Leu
    5090            5095                5100

Ser Ile Leu Arg Asp Pro Ala Ser Asp Ser Asp Gln Ala Lys Phe
    5105            5110                5115

Glu His Ile Gly Ser Val Thr Phe Ser Asp Tyr Phe Asn Gly Asn
    5120            5125                5130

Arg Ala Gln Val Ile Ile Ala Met Gly Glu Lys Asp Ala Thr Gly
    5135            5140                5145

Glu Arg Glu Tyr Thr Thr Leu Ser Glu Ser Ala Ile Asp Ala Leu
    5150            5155                5160

Val Gln Ala Met Ser Gly Phe Asp Pro Gln Ala Gly Asp Asn Gly
    5165            5170                5175

Phe Ile Asp Asn Leu Asp Ser Lys Ser Arg Val Ala Ile Thr Thr
    5180            5185                5190

Ala Trp Ala Asp Val Val His Lys Lys Gly Ile Thr Val
    5195            5200                5205

<210> SEQ ID NO 3
<211> LENGTH: 4872
<212> TYPE: PRT
<213> ORGANISM: Vibrio splendidus

<400> SEQUENCE: 3

Met Gly Lys Pro Phe Trp Arg Ser Val Glu Tyr Phe Phe Thr Gly Asn
1               5                   10                  15

Tyr Ser Ala Asp Glu Gly Asn Asn Ile Val Ala Ile Gly Phe Gly
            20                  25                  30

Gly Glu Ile His Ala Arg Gly Gly Asp Asp His Val Thr Val Gly Ser
        35                  40                  45

Ile Gly Ala Thr Val Tyr Thr Gly Ser Gly Asn Asp Thr Val Val Gly
    50                  55                  60

Gly Ala Ala Tyr Leu Arg Val Glu Asp Ser Val Gly Asn Leu Asn Val
65                  70                  75                  80
```

```
Lys Gly Ala Ala Gly Tyr Ala Asp Ile Asn Lys Ser Gly Asp Gly Asn
                85                  90                  95

Val Ser Phe Ala Gly Ala Ala Gly Val Ser Ile Asp His Leu Gly
            100                 105                 110

Asn Arg Gly Asp Val Asn Tyr Gly Gly Val Ala Ala Tyr Asn Gly Ile
            115                 120                 125

Thr Arg Lys Gly Leu Ser Gly Asn Val Thr Phe Gly Ala Gly Gly
            130                 135                 140

Tyr Asn Ser Leu Trp His Glu Thr Asn Gln Gly Asn Leu Ser Phe Thr
145                 150                 155                 160

Gly Ala Gly Ala Gly Asn Lys Leu Asp Arg Thr Trp Phe Asn Gln Tyr
                165                 170                 175

Gln Gly Ser Arg Gly Asn Val Thr Phe Asp Gly Val Gly Ala Ala Asn
            180                 185                 190

Ser Ile Ser Ser Arg Val Glu Thr Gly Asn Ile Thr Phe Arg Gly Ala
            195                 200                 205

Gly Ala Asp Asn His Leu Val Arg Lys Gly Lys Val Gly Asp Ile Thr
            210                 215                 220

Leu Gln Gly Ala Gly Ala Ser Asn Arg Ile Glu Arg Thr Arg Gln Ser
225                 230                 235                 240

Asp Asp Val Tyr Val Glu Thr Arg Gly Asn Ile Arg Phe Glu Gly Val
            245                 250                 255

Gly Gly Tyr Asn Ser Ile Tyr Ser Asp Val Ala His Gly Asp Ile His
            260                 265                 270

Phe Ser Gly Gly Gly Ala Tyr Asn Lys Ile Thr Arg Lys Gly Ser Gly
            275                 280                 285

Asn Asp Phe Lys Gly Glu Gly Leu Ala Asn Ala Asn Ala Asp Glu Ile
            290                 295                 300

Val Leu Thr Lys Ala Val Met Ser Gly Ser Trp Val Gly Gln Asn His
305                 310                 315                 320

Gln Val Thr Gly Ile Ser Ser Arg Glu Pro Asn Thr Tyr Leu Phe
            325                 330                 335

Ala Phe Ala Asp Asp Thr Tyr Thr Lys Ile Asn Lys Val Gln Leu Arg
            340                 345                 350

Asn Asp Pro Gln Thr Gly Leu Leu Glu Tyr Tyr Ser Thr Ala Trp Tyr
            355                 360                 365

Lys Ala Gly Asn His Leu Asp Asn Leu Ser Asp Leu Asp Ile Ser Ser
            370                 375                 380

Gln Gly Gly Phe Asn Ala Val Asn Ile Asn Gly Ala Tyr Thr Leu Ser
385                 390                 395                 400

Asp Leu Thr Val Glu His Gln Gln Pro Val Thr Val His Ala Ile Glu
            405                 410                 415

Lys Asp Leu Thr Glu Tyr Glu Trp Val Thr Tyr Ala Asn Gly Ala Leu
            420                 425                 430

Ile Asp Ala Glu Asp Val Val Leu Ala Asp Ala Lys Met Gly Gly His
            435                 440                 445

Ala Ile Ser Thr Asn Gly Thr Thr Val Asp Val Lys Gly Val Lys Ser
            450                 455                 460

Asn Arg Lys Ser Asn Thr Tyr Val Tyr Ala Lys Val Leu Gly Pro Tyr
465                 470                 475                 480

Thr Lys Ile Val Val Glu Leu Ala Asn Asp Ser Glu Thr Gly Glu
            485                 490                 495

Leu Lys Tyr Gln Ala Arg Ser Trp Tyr Lys Glu Gly Asn Tyr Thr Gly
            500                 505                 510
```

-continued

```
Asn Leu Ala Asn Glu Asp Ile Ser Ser Ala Asn Gly Tyr His Ser Met
        515                 520                 525
Gly Arg Gly Gly Tyr Ser Leu Ser Asp Leu Gln Tyr Ser Val Asn Ala
    530                 535                 540
Val Arg Ser Thr Ser Glu Thr Val Ala Asp Ile Asp Glu Tyr Asn Glu
545                 550                 555                 560
Gln Ala Leu Ile Lys Pro Ala Thr Asp Thr Gly Glu Ser Ser Gly Asp
                565                 570                 575
Val Arg Phe Asn Gly Val Gly Gly Asn Val Ile Lys Ser Asn Val
            580                 585                 590
Thr Arg Gly Asp Val His Phe Asn Gly Gly Ile Ala Asn Val Ile
        595                 600                 605
Leu His Ser Ser Lys Phe Gly Asp Thr Glu Phe Ile Gly Gly Ala
    610                 615                 620
Ala Asn Val Ile Val Lys Ser Gly Asp Glu Gly Asp Leu Thr Phe Arg
625                 630                 635                 640
Gly Ala Gly Leu Ala Asn Val Leu Val His Gln Ser Lys Gln Gly Lys
                645                 650                 655
Met Asp Val Tyr Ala Gly Gly Ala Val Asn Val Leu Val Arg Ile Gly
            660                 665                 670
Asp Gly Glu Tyr Leu Ala His Leu Leu Ala Tyr Gly Asn Ile Ser Val
        675                 680                 685
His Lys Gly Asn Gly Asn Ser Arg Leu Thr Met Leu Gly Gly Tyr Asn
    690                 695                 700
Thr His Thr Gln Ile Gly Ser Gly Asn Gly Leu Trp Leu Ala Val Gly
705                 710                 715                 720
Gly Phe Asn Val Met Thr Gln Val Gly Lys Gly Asp Ile Ala Ser Val
                725                 730                 735
Leu Val Gly Gly Ala Asn Val Met Thr Lys Val Gly Asp Gly Asp Leu
            740                 745                 750
Thr Ala Gly Met Leu Gly Gly Ala Asn Ile Ile Thr His Ile Ser Gly
        755                 760                 765
Asp Asp Thr Ala Ser Asn Thr Thr Ala Val Ala Leu Gly Gly Ala Asn
    770                 775                 780
Ile Leu Thr Lys Lys Gly Asn Gly Asn Ala Leu Ala Val Met Gly Gly
785                 790                 795                 800
Gly Ala Asn Val Leu Thr His Ile Gly Asp Gly Ser Thr Thr Gly Val
                805                 810                 815
Met Val Gly Gly Ala Asn Ile Leu Thr Lys Val Gly Asp Gly Asp Thr
            820                 825                 830
Thr Gly Ile Met Leu Gly Ile Gly Asn Val Leu Thr His Val Gly Asp
        835                 840                 845
Gly Gln Thr Ile Gly Val Met Gly Ala Ala Gly Asn Ile Phe Thr Lys
    850                 855                 860
Val Gly Asp Gly Thr Ser Ile Ala Ala Met Ile Gly Val Gly Asn Ile
865                 870                 875                 880
Phe Thr His Val Gly Glu Gly Asn Ala Trp Ala Leu Met Gly Gly Leu
                885                 890                 895
Gly Asn Val Phe Thr Lys Val Gly His Gly Asp Ala Leu Ala Leu Met
            900                 905                 910
Val Ala Glu Ala Asn Val Phe Thr His Ile Gly Asp Gly Thr Thr Val
        915                 920                 925
Ala Leu Met Val Ala Lys Gly Asn Ile Ala Thr Lys Val Gly Asn Gly
```

-continued

```
            930             935             940
Thr Ser Ile Ala Ala Met Val Gly Asn Ala Asn Ile Phe Thr Gln Val
945                     950             955             960

Gly Asn Gly Ser Thr Phe Ala Ala Met Leu Gly Gln Ala Asn Ile Met
            965             970             975

Thr Lys Val Gly Asn Asp Leu Thr Ala Ala Leu Met Ile Gly Lys Ala
            980             985             990

Asn Ile Tyr Thr His Val Gly Asp Gly Thr Ser Leu Gly Leu Phe Ala
            995             1000            1005

Gly Glu Leu Asn Val Met Thr Lys Val Gly Asn Gly Thr Thr Leu
    1010            1015            1020

Ala Ala Met Phe Gly Lys Ala Asn Ile Met Thr His Val Gly Asp
    1025            1030            1035

Gly Leu Thr Gly Val Leu Ala Leu Gly Glu Ala Asn Ile Ile Thr
    1040            1045            1050

Lys Val Gly Asp Phe Met Gly Val Val Ala Ala Ala Lys Ala
    1055            1060            1065

Asn Val Val Thr His Val Gly Asp Ala Thr Thr Ala Ala Val Leu
    1070            1075            1080

Ala Gly Lys Gly Asn Ile Leu Thr Lys Val Gly Glu Gly Thr Thr
    1085            1090            1095

Val Gly Leu Leu Ile Ser Lys Val Gly Asn Val Met Thr His Val
    1100            1105            1110

Gly Asp Gly Thr Thr Ile Gly Leu Ala Lys Gly Lys Ala Asn Ile
    1115            1120            1125

Ile Thr Lys Val Gly Asp Gly Leu Gly Val Asn Val Ala Trp Gly
    1130            1135            1140

Gln Ala Asn Ile Phe Thr His Val Gly Asp Gly Asp Arg Tyr Asn
    1145            1150            1155

Phe Ala Lys Gly Glu Ala Asn Ile Ile Thr Lys Val Gly Asp Gly
    1160            1165            1170

Gln Glu Val Ser Val Val Gln Gly Lys Ala Asn Val Ile Thr His
    1175            1180            1185

Val Gly Asn Gly Asp Asp Tyr Thr Gly Ala Trp Gly Lys Ala Asn
    1190            1195            1200

Ile Ile Thr Lys Val Gly Asp Gly Arg Asn Val Val Leu Ala Lys
    1205            1210            1215

Gly Glu Ala Asn Ile Ile Thr Gln Val Gly Asp Gly Asp Ser Phe
    1220            1225            1230

Asn Ala Leu Trp Ser Lys Gly Asn Ile Val Thr Lys Val Gly Asp
    1235            1240            1245

Gly Met Gln Val Thr Ala Ala Lys Gly Lys Ala Asn Ile Thr Thr
    1250            1255            1260

Thr Val Gly Asn Gly Leu Ser Val Thr Ala Ala Tyr Gly Asp Ala
    1265            1270            1275

Asn Ile Asn Thr Lys Ile Gly Asp Gly Ile Ser Val Asn Val Ala
    1280            1285            1290

Trp Gly Lys Tyr Asn Val Asn Thr Lys Val Gly Asp Gly Leu Asn
    1295            1300            1305

Val Ala Val Met Lys Gly Lys Ala Asn Val Asn Ile His Val Gly
    1310            1315            1320

Asp Gly Leu Gly Ile Asn Ala Ser Tyr Ala Arg Asn Asn Val Ala
    1325            1330            1335
```

```
Ile Lys Val Gly Asn Gly Asp Phe Tyr Ser Leu Ala Val Ala Ser
1340                1345                1350

Ser Asn Thr Ser Ser Asn Lys Leu Ser Ala Leu Phe Asp Asn Ile
    1355                1360                1365

Lys Gln Thr Leu Leu Gly Val Gly Gly Ser Gln Ala Ile Asn Tyr
1370                1375                1380

Leu Val Gln Gly Asp Glu Ala Ser Ser Ser Gly Ile Gln Lys Gly
1385                1390                1395

Arg Gly Ala Ile Ser Thr Pro Glu Ile Thr Lys Leu Asp Gly Phe
1400                1405                1410

Ala Leu Asp Glu Ile Glu Glu Val Gly Ser Asp Leu Gly Asp Gly
1415                1420                1425

Leu Ser Gly Ser Val Thr Asn Val Glu Thr Pro Asp Leu Ser Ser
1430                1435                1440

Met Glu Asn Glu Leu Asn Ile Glu Glu Ser Ser Asp Gln Ala Gln
1445                1450                1455

Ala Pro Asn Leu Ile Val Asn Gly Asp Phe Glu Gln Gly Gly Asp
1460                1465                1470

Gly Trp Glu Ser Thr His Gly Val Glu Ala Ser Tyr Ser Ser Ser
1475                1480                1485

Ala Tyr Gly Val Ser Gly Glu Gly His Gly Ser Arg Val Thr Glu
1490                1495                1500

Leu Asp Thr Tyr Thr Asn Thr Ser Leu Ser Gln Asp Leu Thr Asp
1505                1510                1515

Leu Ala Glu Gly Glu Val Ile Ala Val Ser Phe Asp Phe Ala Lys
1520                1525                1530

Arg Ala Gly Ile Ser Ser Asn Glu Gly Ile Glu Val Leu Trp Asn
1535                1540                1545

Gly Asp Val Val Phe Ser Thr Ser Gly Asp Glu Ala Ala Trp Gln
1550                1555                1560

Gln Lys Thr Leu Lys Leu Thr Ala Asn Ser Gly Ser Asn Arg Ile
1565                1570                1575

Glu Phe Lys Gly Thr Gly His Asn Asp Gly Leu Gly Tyr Val Leu
1580                1585                1590

Asp Asn Val Val Ala Lys Ser Glu Thr Ser His Gln Ala Asn Ala
1595                1600                1605

Val Ala Asp Asn Ala Glu Gln Asn Gln Ala Ala Lys Asn Ala Met
1610                1615                1620

Ser Asp Lys Glu Arg Ala Glu Ala Asp Arg Gln Arg Leu Glu Gln
1625                1630                1635

Glu Lys Gln Lys Gln Leu Glu Ala Val Ser Gly Ser Gln Ala Gln
1640                1645                1650

Leu Glu Ser Thr Asp Gln Glu Ala Leu Glu Ser Asn Gly Gln Ala
1655                1660                1665

Gln Arg Asp Ala Val Asn Glu Glu Ser Lys Ala Val Thr Lys Asp
1670                1675                1680

Leu Thr Ala Met Ala Gln Gly Leu Asp Val Leu Asp Asn Lys Ala
1685                1690                1695

Glu Tyr Thr Gly Val Ser Gly Asp His Trp Arg Asp Arg Phe Ala
1700                1705                1710

Gly Gly Leu Leu Lys Asp Val Gln Thr Gln Leu Asp Asn Ala Lys
1715                1720                1725

Asp Val Ser Gly Glu Gln Ile Ala Asp Ala Lys Gln Ala His Lys
1730                1735                1740
```

```
Asp Asn Gln Lys Asn Val Asn Asp Ser Val Ala Lys Ser Glu Ala
    1745                1750                1755

Gly Val Ala Lys Gly Glu Asp Asn Arg Ser Ser Ala Glu Gln Asp
    1760                1765                1770

Ile Ala Asp Ala Lys Ala Asp Ala Asp Ala Arg Lys Ala Glu Ala
    1775                1780                1785

Thr Thr Lys Thr Asn Glu Ala Lys Gln Ala Glu Ser Asn Ala Asn
    1790                1795                1800

Asn Ser Ala Arg Asp Ala Glu Glu Arg Gly Asn Ser Asp Ala Arg
    1805                1810                1815

Asn Ala Glu Asn Lys Ala His Gln Ala Gln Ala Asp Ala Lys Gly
    1820                1825                1830

Ser Lys Gln Asn Glu Ser Asp Arg Pro Asp Arg Gln Gly Ala Ser
    1835                1840                1845

Gly Ser Gly Leu Ser Asn Glu Ser His Phe Thr Gln Ser Glu Glu
    1850                1855                1860

Thr Thr Ser Ser Asp Val Asp Thr Val Asn Pro Gln Ser Ala Asp
    1865                1870                1875

Gly Arg Phe Ser Glu Gly Leu Thr Asp Gln Glu Gln Glu Ala Leu
    1880                1885                1890

Asp Gly Ala Val Gln Ala Val Asn Arg Leu Gln Ile Asn Ala Gly
    1895                1900                1905

Ile Arg Ser Lys Asn Thr Gly Ser Ser Val Thr Ser Leu Phe Thr
    1910                1915                1920

Glu Ser Asn Ala Asp Ser Ile Val Leu Pro Thr Thr His Ser Gln
    1925                1930                1935

Asp Val Ala Arg Lys Glu Ile Arg Ile Ser Gly Val Asn Leu Tyr
    1940                1945                1950

Gly Leu Gly Glu Thr Ala Asp Val Ser Ala Ser Ile Thr Lys Asn
    1955                1960                1965

Val Asp Gly Phe Lys Phe Ser Leu Leu Gly Pro Asp Asp Val Arg
    1970                1975                1980

Phe Val Asp Ser Thr Lys Arg His Leu Gly Lys Leu Ser Thr Asp
    1985                1990                1995

Leu Pro Ser Lys Glu Leu Lys Ala Val Arg Ser His Ile Gln Ser
    2000                2005                2010

Ile Gln Arg Ile Pro Ser Glu Ser Asn Leu Ala Val Leu Glu Leu
    2015                2020                2025

Ala Val Glu Gln Trp Gln Gln Asn Asn Pro Lys Glu Phe Ala Gln
    2030                2035                2040

Arg Gly Glu Met Val Lys Thr Leu Gln Phe Glu Ile Val Ser Leu
    2045                2050                2055

Gln Ser His Ile Gln Lys Asn Arg Ser Lys Asp Ala Gly Ile Phe
    2060                2065                2070

Gly Ile Ala Ile Asp Pro Lys Ser Val Glu Ala Phe Glu Ser Lys
    2075                2080                2085

Val Val Phe Asp Gly Val Gly Arg Val Ile Gly Leu Val Glu Pro
    2090                2095                2100

Leu Ala Asp Ala Gln Ile Asn Ser Leu Lys Ser Leu Glu Val Val
    2105                2110                2115

Ser Pro Thr Leu Thr Asn Ser Thr Ser Asp Arg Glu Thr Ala Lys
    2120                2125                2130

Thr Glu Ser Glu Ser Ile Val Glu Phe Ile Tyr Lys Leu Gly Gln
```

```
                2135               2140               2145
Val Glu Ser Thr Glu Thr Ser Thr Ser Glu Ile Asn Lys Leu Ala
    2150               2155               2160
Glu Gln Ala Lys Thr Leu Trp Met Ser Gly Asn Val Thr Gln Asp
    2165               2170               2175
Ser Ala Val Lys Leu Phe Thr Glu Ala Asn Asp Lys Leu Ala Ala
    2180               2185               2190
His Pro Lys Leu Gln Val Leu Ala Ser Lys Leu Leu Phe Asp Ala
    2195               2200               2205
Lys Lys Glu Lys Glu Ile Gly Gln Tyr Phe Asp Asn Leu Phe Gly
    2210               2215               2220
Arg Arg Phe Asp Ser Glu Ile Ala His Glu Leu Val Lys Thr Pro
    2225               2230               2235
Thr Asp Lys Ala Ile Asn Thr Ser Ala Gln Ile Gly Asn Ser Leu
    2240               2245               2250
Val Asn Asp Phe Asp Glu Trp Met His Ser Leu Leu Pro Asp Ala
    2255               2260               2265
Ala Asp Asp Ala Leu Arg Ala Glu Arg Ile Gln Thr Lys Met Glu
    2270               2275               2280
Glu Phe Ala Gln Ala Ile Ala Gln Asp Glu Arg Pro Trp Phe Ser
    2285               2290               2295
Arg Val Pro Thr Leu Thr Gln Phe Leu Asp Thr Pro Ser His Ala
    2300               2305               2310
Asn Phe Lys Thr Met Met Thr Gln Val Asp Asp Gly Phe Gly Val
    2315               2320               2325
Ile Lys Val Pro Phe Leu Ala Val Lys Met Ala Ile Thr Pro Gly
    2330               2335               2340
Leu Gly Met Glu Met Ala Pro Trp Lys Ala Glu Gly Asp Arg Phe
    2345               2350               2355
Tyr Gln Asn Val Ile Thr Lys Ala Arg Ser Thr Asn Thr Val Ile
    2360               2365               2370
Ser Ser Gly Val Asp Gly Glu Asn Gln Val Asn Leu Ile Glu Lys
    2375               2380               2385
Lys Thr Ser Asp Tyr Gly Thr Ala Leu His Tyr Gln Pro Lys Gly
    2390               2395               2400
Asp Thr Tyr Asp Asp Phe Lys Glu Gly Arg Ser Val Ala Asp Gly
    2405               2410               2415
Arg Ile Leu Asn Pro Gly Lys Lys Thr Thr Phe Glu Ser Asn Ala
    2420               2425               2430
Leu Asn Asn Gly Leu Ser Val Val Thr Gly Ala Ser Gly Ser Thr
    2435               2440               2445
Asn Ile Met Thr His Leu Asn Gln Tyr Ile Ala Ser Lys Asn Pro
    2450               2455               2460
Gly Phe Ser Val Asp Gln Ala Tyr Leu Asn Thr Leu Ser Phe Leu
    2465               2470               2475
Val Phe Asp Gly Gly His Ser Val Asn Glu Ser Leu Ala Val Tyr
    2480               2485               2490
Lys Ala Leu Gln Glu Thr Gly Asp Asp Arg Lys Ala Val Leu Glu
    2495               2500               2505
Ser Tyr Thr Ala Asn Tyr Gln Asp Leu Ile Asp Leu Val Asp Asp
    2510               2515               2520
Ser Ser Lys Gly Thr Val Arg Asp Ala Leu Asp Asn Ala Leu Gly
    2525               2530               2535
```

```
Lys Thr Leu Glu Phe Tyr Lys Glu His Ala Asn Ser Ala Ser Asn
2540                2545                2550

Glu Leu Glu Ala Leu Gly Gly Lys Arg Lys Pro Ile Ser Glu Arg
2555                2560                2565

Asn Lys Glu Asn Val Ala Ile Glu Asn Asp Gly Thr Pro Pro Arg
2570                2575                2580

Asp Lys Glu Ser Val Ser Pro Leu Thr Arg Phe Leu Asn Asn Glu
2585                2590                2595

Leu Phe Gly Thr Lys Asp Ala Arg Arg Lys Val Gly Asp Ile Thr
2600                2605                2610

Glu Thr Leu Leu Gly Phe Ala Val Glu Lys Gly Glu Ser Gln Lys
2615                2620                2625

Val Thr Leu Lys Gly Glu Ala Gly Arg Leu Ser Gly Tyr Phe His
2630                2635                2640

Lys Gly Ala Lys Ala Ser Glu Gly Glu Glu Ser Val Gly Asn Gly
2645                2650                2655

Lys Val Val Leu Phe Leu His Gly Ser Gly Ser Ser Ser Glu Glu
2660                2665                2670

Gln Ala Ser Ala Ile Arg Ser His Tyr His Lys Gln Asn Ile Asp
2675                2680                2685

Met Leu Ala Val Asn Met Arg Gly Tyr Gly Glu Ser Asp Gly Gly
2690                2695                2700

Pro Ser Glu Lys Gly Leu Tyr Gln Asp Ala Arg Thr Met Phe Lys
2705                2710                2715

Tyr Leu Val Asn Asp Lys Gly Ile Asp Pro Ser Asn Ile Ile Ile
2720                2725                2730

His Gly Tyr Ser Met Gly Gly Pro Ile Ala Ala Asp Leu Ala Arg
2735                2740                2745

Phe Ala Ala Gln Asn Gly Gln Ala Val Ser Gly Leu Leu Leu Asp
2750                2755                2760

Arg Pro Met Pro Ser Met Thr Lys Ala Ile Thr Ala His Glu Val
2765                2770                2775

Ala Asn Pro Ala Gly Ile Val Gly Ala Leu Ser Lys Ala Val Asn
2780                2785                2790

Gly Gln Phe Ser Val Glu Lys Asn Leu Lys Gly Leu Pro Lys Asp
2795                2800                2805

Ala Pro Ile Met Leu Leu Thr Asp Asn Glu Gly Leu Gly Gly Glu
2810                2815                2820

Gly Glu Lys Leu Arg Ala Lys Leu Ala Val Ser Gly Phe Asn Val
2825                2830                2835

Thr Gly Glu Gln Thr Phe Tyr Gly His Glu Ala Ser Asn Arg Leu
2840                2845                2850

Met Ser Gln Tyr Ala Glu Gln Ile Val Ser Gly Leu Phe Asp Ala
2855                2860                2865

Asp Arg Val Ser Ala Asp Ala Ser Asp Val Leu Lys Gly Ile Lys
2870                2875                2880

Asn Asp Leu Ser Arg Tyr Gly Glu Ala Leu Lys Pro Asp Thr Lys
2885                2890                2895

Val Pro Gly Lys Ser Lys Asp Ile Arg Thr Thr Lys Asp Phe Leu
2900                2905                2910

Asn Gly Tyr Lys Ile Asp His Ala Lys Asp Ile Val Glu Gly Phe
2915                2920                2925

Arg Pro Asp Met Asn Ile Lys Gln Leu Val Asp Leu Leu Val Glu
2930                2935                2940
```

```
Gly Asn Trp Ser Ala Glu Gln Lys Gly Ala Leu Ala Trp Glu Val
    2945                2950                2955

Glu Ser Arg Gly Leu Lys Ala Thr Phe Gln Ala Lys Ser Glu Lys
    2960                2965                2970

His Asn Arg Leu Phe Arg Asp Val Ala Ser Ser Gly Val Thr Asp
    2975                2980                2985

Ala Lys Ala Ser Glu Gln Leu Ala Pro Gln Leu Leu Leu Leu Asn
    2990                2995                3000

Leu Ser Asn Asp Gly Phe Gly Gly Arg Cys Asp Pro Leu Ser Lys
    3005                3010                3015

Leu Ile Leu Val Ala Lys Gln Leu Glu Ser Asp Gly Gln Val Gly
    3020                3025                3030

Val Ala Arg Lys Leu Leu Glu Lys Met Tyr Ser Thr Ala Ala Val
    3035                3040                3045

Leu Ser Asn Pro Thr Leu Tyr Ser Glu Thr Glu Arg Ala Asn Ala
    3050                3055                3060

Ser Lys Leu Met Asp Ser Leu Ala Ala Ile His Thr Lys Asn Pro
    3065                3070                3075

Met His Asp Thr Ser Met Lys Val Trp Gln Glu Lys Leu Glu Gly
    3080                3085                3090

Lys Lys Ala Leu Thr Val Thr Gly Val Ile Glu Lys Ile Thr Asp
    3095                3100                3105

Val Ser Val Asp Asn Lys Pro Val Leu Leu Glu Leu Asp Ala Pro
    3110                3115                3120

Gly His Ala Met Ala Ala Trp Ala Lys Gly Asp Gly Glu Asn Arg
    3125                3130                3135

Val Tyr Gly Phe Tyr Asp Pro Asn Ala Gly Val Val Glu Phe Ser
    3140                3145                3150

Ser Lys Asp Lys Phe Ser Thr Tyr Leu Thr Arg Phe Phe Gly Lys
    3155                3160                3165

Ser Asp Leu Asp Met Ala Gln Arg Tyr Arg Leu Pro Lys Asn Asp
    3170                3175                3180

Val Gly Glu Ala Ile Phe Asn Arg Val Val Met Asp Gly Asn
    3185                3190                3195

Thr Leu Ala Thr Tyr Lys Pro Thr Leu Gly Asp Lys Thr Thr Leu
    3200                3205                3210

Gln Gly Ile Leu Asp Leu Pro Val Phe Asp Ala Thr Pro Ile Lys
    3215                3220                3225

Lys Ser Thr Glu Val Lys Val Thr Asp Leu Glu Ser Leu Gly Asn
    3230                3235                3240

Lys Thr Lys Leu Val Val Asp Leu Ser Thr Ile Met Thr Lys Gln
    3245                3250                3255

Glu Leu Lys Asp Gly Gly Lys Val Phe Ala Lys Pro Ile Gly Ala
    3260                3265                3270

Ser Tyr Gln Ala Ile Leu Asp Gln Val Glu Leu Val His Ser Phe
    3275                3280                3285

Ile Gly Arg Asp Gln Val Gly Ala Ser Phe Glu Leu Asn Lys Gln
    3290                3295                3300

Ile Asn Asn Tyr Leu Ala Glu His Pro Thr Ser Gly Arg Asn Leu
    3305                3310                3315

Ala Leu Thr Thr Leu Lys Glu Gln Val Ser Thr Ala Leu Phe Ser
    3320                3325                3330

Gly Lys Met Lys Val Thr Gln Glu Ser Ile Asp Ala Ile Ala Gln
```

-continued

```
                3335                3340                3345
Thr Arg Thr Asp Val Ala Ala Arg Ile Tyr Val Val Ala Met Glu
    3350                3355                3360
Glu Ala Asn Gly Glu His Val Gly Leu Thr Asp Met Met Val Arg
    3365                3370                3375
Trp Ala Asn Glu Asp Pro Tyr Leu Ser Pro Lys Gln Gly Tyr Ala
    3380                3385                3390
Gly Glu Thr Pro Ser Asp Leu Gly Phe Asp Ala Lys Tyr His Ile
    3395                3400                3405
Glu Leu Gly Glu Gln Tyr Ser Asp Phe Lys Leu Trp Leu Glu Lys
    3410                3415                3420
Ser Gln Ser Ala Asp Leu Leu Ser Lys Ala Val Leu Asp Glu Ala
    3425                3430                3435
Thr Gln Thr Val His Leu Gly Tyr Ser Tyr Gln Glu Leu Gln Asp
    3440                3445                3450
Leu Thr Gly Val Glu Ser Val Gln Met Ala Phe Tyr Phe Leu Lys
    3455                3460                3465
Glu Ala Ala Lys Lys Ser Asp Ser Thr Thr Ser Asp Ser Ala Glu
    3470                3475                3480
Met Ile Leu Leu Lys Lys Phe Ala Asp Gln Gly Tyr Ile Ser Gln
    3485                3490                3495
Leu Glu Thr Asp Arg Met Asp His Ile Glu Gly Ile Tyr Arg Ser
    3500                3505                3510
Ser His Glu Thr Asp Val Asp Asn Trp Asp Arg Arg Tyr Ser Gly
    3515                3520                3525
Ala Gly Tyr Asp Glu Leu Ser Asp Lys Leu Ala Gly Ala Asn Gly
    3530                3535                3540
Gly Val Glu Glu Gln Leu Ser Val Leu Leu Asn Glu Arg Lys Gly
    3545                3550                3555
Leu Leu Ile Gly Glu Val His Gly Ser Asp Val Asn Gly Leu Arg
    3560                3565                3570
Phe Val Asn Glu Gln Met Asp Ala Leu Lys Lys Gln Gly Val Thr
    3575                3580                3585
Val Ile Gly Leu Glu His Leu Arg Ser Asp Leu Ala Gln Pro Leu
    3590                3595                3600
Ile Asp Asn Tyr Leu Ser Thr Gly Ile Met Ser Ser Glu Leu Ser
    3605                3610                3615
Ala Met Ile Lys Thr Lys His Leu Asp Ile Thr Leu Phe Glu Asn
    3620                3625                3630
Ala Arg Ala Asn Gly Met Arg Ile Leu Ala Leu Asp Ala Asn Ser
    3635                3640                3645
Thr Ala Arg Pro Thr Val Gln Gly Thr Glu His Gly Leu Met Tyr
    3650                3655                3660
Arg Ala Gly Ala Ala Asn Asn Val Ala Val Asp Ala Leu Gln Ala
    3665                3670                3675
Leu Pro Asp Gly Glu Lys Phe Val Ala Ile Tyr Gly Lys Ala His
    3680                3685                3690
Leu Gln Ser His Lys Gly Ile Glu Ser Phe Val Pro Gly Ile Thr
    3695                3700                3705
His Arg Leu Gly Leu Pro Ala Leu Lys Val Ser Ala Ser Asp Gln
    3710                3715                3720
Phe Val Ile Glu Gln Asp Asp Lys Thr Leu Arg Thr Val Tyr Asp
    3725                3730                3735
```

-continued

Asp Val Ala Asn Lys Pro Lys Ile Asp Phe Arg Ala Ser Leu Asn
3740              3745              3750

Gly Ser Asp Asp Thr Val Lys Asn Lys Asp Val Asn Ser Trp Glu
3755              3760              3765

Arg Leu Ile Val Ser Pro Gln Ser Asp Gly Glu Thr Arg Phe
3770              3775              3780

Asp Gly Gln Ile Ile Ile Gln Met Glu Asn Asp Ser Ser Val Ser
3785              3790              3795

Lys Ala Ala Glu Asn Leu Ala Gly Lys His Pro Asp Ser Thr Val
3800              3805              3810

Val Val Gln Leu Asp Ser Asp Gly Asn Tyr Arg Val Val Tyr Gly
3815              3820              3825

Asp Pro Ser Lys Leu Pro Lys Asp Lys Ser Thr Gly Gln Leu Arg
3830              3835              3840

Trp Gln Leu Val Gly His Gly Arg Asp Glu Ser Glu Asn Asn Asn
3845              3850              3855

Thr His Leu Ser Gly Tyr Ser Ala Asp Glu Leu Ala Val Lys Leu
3860              3865              3870

Ala Ala Phe Asn Gln Ala Phe Ser Glu Ala Glu Asn Val Lys Ala
3875              3880              3885

Ser Pro Asp Tyr Ile Ser Val Val Gly Cys Ser Leu Ile Ser Asp
3890              3895              3900

Asp Lys Gln Asn Gly Phe Gly Arg Leu Leu Ile Gln Ser Met Gly
3905              3910              3915

Asp Asn Asp Ile Arg Ser Asp Val Ser Val Arg Ser Ser Glu Val
3920              3925              3930

Ala Val Asp Ser Asn Gly Arg Lys His Thr His Asp Glu Asn Gly
3935              3940              3945

His Trp Val Gln Lys Glu Lys Ser Asn Lys Val Thr Leu Ser Trp
3950              3955              3960

Asp Glu Gln Gly Glu Val Thr Glu Lys His Glu Arg Ile Arg Asn
3965              3970              3975

Gly Ile Ala Glu Gly Asp Ile Asp Leu Ser Arg Val Gly Thr Ser
3980              3985              3990

Asp Val Asp Glu Thr Ala Arg Gly Ala Ile Ala Glu Asn Ser Asp
3995              4000              4005

Val Phe Asn Ala Pro Glu Lys Arg Lys Asn Asp Thr Glu Ser Ser
4010              4015              4020

Ser Ser Gly Ser Ser Lys Ser Lys Leu Ser Tyr Ser Gly Asn Ile
4025              4030              4035

Gln Val Asn Val Gly Asp Gly Glu Phe Thr Ala Val Asn Trp Gly
4040              4045              4050

Thr Ser Asn Val Ser Val Lys Val Gly Thr Gly Phe Lys Ser
4055              4060              4065

Leu Ala Phe Gly Asp Asn Asn Val Met Val His Val Gly Asp Gly
4070              4075              4080

Glu Ser Lys His Ser Phe Asp Ile Gly Gly Tyr Gln Ala Leu Glu
4085              4090              4095

Gly Ala Gln Met Phe Ile Gly Asn Arg Asn Val Ser Phe Asn Leu
4100              4105              4110

Gly Gln Ser Asn Asp Leu Ile Val Met Met Asp Lys Ser Ile Pro
4115              4120              4125

Thr Pro Pro Leu Val Asn Pro Phe Asp Gly Ala Ser Arg Ile Ser
4130              4135              4140

-continued

Gly Val Leu Lys Ser Ile Ala Ser Ser Gly Gly Gln Asp Trp
    4145            4150            4155

Leu Ala Ala Gln Glu Gln Gln Trp Thr Leu Ser Gly Ala Lys Lys
    4160            4165            4170

Phe Val Lys Asp Met Ser Gly Leu Asp Gln Ser Ser Ser Val Asp
    4175            4180            4185

Tyr Thr Ser Leu Val Asp Leu Asp Ser Gln Asn Glu Arg Ser Ser
    4190            4195            4200

Arg Gly Leu Lys Asn Asp Ala Glu Ala Thr Leu Asn Lys Gln Tyr
    4205            4210            4215

Asn Gln Trp Leu Gly Gly Ser Asp Asn Ser Asp Ser Ser Lys Met
    4220            4225            4230

Ser Arg Ala Asp Lys Phe Arg Gln Ala Asn Glu Lys Leu Ala Phe
    4235            4240            4245

Asn Phe Ala Val Gly Gly Gln Gly Ala Asp Ile Gln Val Thr Thr
    4250            4255            4260

Gly Asn Trp Asn Phe Met Phe Gly Asp Asn Ile Gln Ser Ile Leu
    4265            4270            4275

Asp Thr Asn Leu Gly Ser Leu Phe Gly Leu Met Thr Gln Gln Phe
    4280            4285            4290

Ser Thr Thr Gly Gln Ala Lys Thr Thr Phe Thr Tyr Ser Pro Glu
    4295            4300            4305

Asp Leu Pro Arg Gln Leu Lys Asn Lys Leu Leu Gly Gln Leu Ala
    4310            4315            4320

Gly Val Gly Ala Glu Thr Thr Leu Gly Asp Ile Phe Gly Val Asp
    4325            4330            4335

Tyr Thr Ala Ala Gly His Ile Val Ser Arg Thr Gly Glu Ser Val
    4340            4345            4350

Asp Gly Val Ala Ile Leu Lys Glu Met Leu Glu Val Val Gly Glu
    4355            4360            4365

Phe Ser Gly Asp Gln Leu Gln Ala Phe Val Asp Pro Ala Lys Leu
    4370            4375            4380

Leu Asp Ser Leu Glu Ser Gly Val Asn Met Gly Ala Asp Gly Ile
    4385            4390            4395

Lys Thr Phe Ala Glu Thr His Gly Leu Lys Glu Lys Ala Pro Glu
    4400            4405            4410

Glu Glu Glu Asp Asn Ser Ser Val Ser Val Asn Gly Thr Asn Val
    4415            4420            4425

Ala Gly Ala Gln Asp Asn Gly Asp Ala Ile Thr Ala Asp Ser Ser
    4430            4435            4440

Ala Lys Glu Asp Arg Ala Phe Gly Phe Asn Ser Leu Asn Leu Pro
    4445            4450            4455

Asn Leu Phe Ala Thr Ile Phe Ser Glu Asn Lys Gln Thr Glu Met
    4460            4465            4470

Lys Ser Leu Val Glu Asn Lys Glu Asn Leu Thr Ala Asp Leu
    4475            4480            4485

Leu Asn Met Lys Glu Lys Thr Phe Asp Phe Leu Arg Asn Ser Gly
    4490            4495            4500

His Leu Gln Gly Asp Gly Asp Ile Asn Val Ser Leu Gly Asn Tyr
    4505            4510            4515

Asn Phe Asn Trp Gly Gly Asp Gly Lys Asp Leu Gly Ala Tyr Leu
    4520            4525            4530

Gly Asp Asn Asn Asn Phe Trp Gly Gly Arg Gly Asp Asp Val Tyr

|  | 4535 | 4540 | 4545 |  |

Tyr Ala Thr Gly Thr Ser Asn Ile Phe Thr Gly Gly Glu Gly Asn
    4550              4555              4560

Asp Met Gly Val Leu Met Gly Arg Glu Asn Met Met Phe Gly Gly
    4565              4570              4575

Glu Gly Asn Asp Thr Ala Val Val Ala Gly Arg Ile Asn His Val
    4580              4585              4590

Phe Leu Gly Ala Gly Asp Asp Glu Ser Phe Val Phe Gly Glu Gly
    4595              4600              4605

Gly Glu Ile Asp Thr Gly Thr Gly Arg Asp Tyr Val Val Thr Ser
    4610              4615              4620

Gly Asn Tyr Asn Arg Val Asp Thr Gly Gly Asp Gln Asp Tyr Ser
    4625              4630              4635

Val Thr Ile Gly Asn Asn Asn Gln Val Glu Leu Gly Ala Gly Asn
    4640              4645              4650

Asp Phe Ala Asn Val Phe Gly Asn Tyr Asn Arg Ile Asn Ala Ser
    4655              4660              4665

Gly Gly Asn Asp Val Val Lys Leu Met Gly Tyr Asn Ala Val Leu
    4670              4675              4680

Asn Gly Gly Glu Gly Asp Asp His Leu Ile Ala Ala Ala Leu Ser
    4685              4690              4695

Lys Phe Ser Gln Leu Asn Gly Gly Glu Gly Ser Asp Val Met Val
    4700              4705              4710

Leu Gly Gly Phe Gln Asn Thr Phe Lys Gly Gly Thr Gly Val Asp
    4715              4720              4725

Ser Phe Val Val Ser Gly Asp Val Ile Asp Asn Leu Val Glu Asp
    4730              4735              4740

Ile Arg Ser Glu Asp Asn Ile Val Phe Asn Gly Ile Asp Trp Gln
    4745              4750              4755

Lys Leu Trp Leu Glu Arg Ser Gly Tyr Asp Leu Lys Leu Ser Ile
    4760              4765              4770

Leu Arg Asp Pro Glu Ser Asp Thr Asp Gln Ala Lys Phe Glu His
    4775              4780              4785

Ile Gly Ser Val Thr Phe Asn Asp Tyr Phe Asn Gly Asn Arg Ala
    4790              4795              4800

Gln Val Val Ala Met Gly Asp Gln Gly Thr Ser Gln Asp His
    4805              4810              4815

Thr Val Leu Ser Asn Asn Ala Val Asp Ala Leu Val Gln Ala Met
    4820              4825              4830

Ser Ala Phe Glu Pro Gln Ala Gly Asp Asn Gly Phe Ile Asp Asn
    4835              4840              4845

Leu Asp Ser Lys Ser Arg Val Ala Ile Thr Thr Ala Trp Ser Asp
    4850              4855              4860

Val Ser Lys Gly Asn Ser Val Ile Ser
    4865              4870

<210> SEQ ID NO 4
<211> LENGTH: 3672
<212> TYPE: PRT
<213> ORGANISM: Photorhabdus luminescens

<400> SEQUENCE: 4

Met Gly Lys Ser Ser Asn Arg Ser Thr Glu Tyr Ile Phe Thr Gly Lys
1               5                   10                  15

Tyr Tyr Asp Asp Asp Asp Asn Ile Asp Asn Ser Ile Thr Ala Ile Gly

```
                 20                  25                  30
Ile Gly Gly Asn Val Tyr Ala Tyr Gly Gly Asp Asp Val Thr Val
             35                  40                  45
Gly Ser Phe Lys Val Asp Val Tyr His Thr Asp Gly Asp Leu Ala Val
 50                  55                  60
Lys Gly Ala Ser Gly Tyr Thr Gly Ile His Lys Thr Gly Asn Gly Gly
 65                  70                  75                  80
Leu Ser Phe Ala Gly Ala Gly Ala Val Phe Ile Asn His Thr Gly
                 85                  90                  95
Glu Thr Gly Asn Leu Asn Tyr Ser Gly Val Ala Gly Tyr Asn Lys Leu
                100                 105                 110
Val Arg Lys Gly Leu Ser Gly Asp Ser Ser Phe Lys Gly Gly Gly Gly
             115                 120                 125
Tyr Asn Gln Leu Trp His Glu Thr Asn Arg Gly Asp Leu Asp Phe Ala
             130                 135                 140
Gly Ala Gly Ala Gly Asn Asn Ile Asp Arg Thr Trp Phe Asn Arg Tyr
145                 150                 155                 160
Gln Asp Ser Gln Gly Asn Val Ile Phe Asn Gly Ala Gly Val Thr Asn
                 165                 170                 175
Asn Ile Asn Ser Arg Val Glu Ser Gly Asp Ile Ile Leu His Gly Ile
                 180                 185                 190
Gly Thr Asp Asn His Ile Val Arg Arg Gly Arg Asn Gly Asp Ile Leu
             195                 200                 205
Leu Arg Gly Val Gly Ala Ala Asn Arg Ile Glu Arg Ile Arg His Ser
 210                 215                 220
Glu Asp Lys Tyr Gly Gln Thr Gln Gly Asp Ile Thr Leu Glu Gly Ala
225                 230                 235                 240
Gly Gly Tyr Asn Thr Leu Tyr Ser Asp Val Ala His Gly Asn Ile His
                 245                 250                 255
Phe Thr Gly Thr Gly Val Tyr Asn Lys Ile Ala Arg Val Gly Val Arg
                 260                 265                 270
Asn Glu Ile Glu Phe Ala Gln Ala Lys Asp Ile Ile Met Thr Ser Ala
             275                 280                 285
Thr Met Glu Gly Asp Gly Thr Gln Gln Ser Arg Gln Val Lys Ala Val
 290                 295                 300
Lys Ser Ala Val Glu Pro Asp Thr Tyr Leu Phe Ala Ile Ala Asn Asn
 305                 310                 315                 320
Ile Asn Thr Lys Val Val Ala Val Arg Leu Arg Asn Asn Pro Asp Thr
             325                 330                 335
Gly Lys Leu Arg Tyr Tyr Ala Thr Ser Trp Tyr Lys Gln Gly Asp His
             340                 345                 350
Leu Glu Asp Ile Ala Lys Glu Asn Ile Asn Thr Asn Asn Gly Phe Ile
             355                 360                 365
Pro Val Lys Gly Asp Asp Thr Ile Thr Leu Ala Asn Ile Asn Val Val
             370                 375                 380
Tyr Arg Gln Lys Asn Thr Ile Gln Gly Val Val Lys Ala Leu Leu Thr
385                 390                 395                 400
Asp Lys Trp Gly Asn Tyr Ala Arg Gly Ile Asn Ile Lys Ala Glu Asp
                 405                 410                 415
Val Ile Leu Ala Ser Ala Lys Ile Gly Gly Asp Thr Leu Ser Ser Asn
             420                 425                 430
Gly Leu Lys Ile Asp Val Ser Pro Val Lys Ser Asn Thr Gln Pro Asn
             435                 440                 445
```

```
Thr Tyr Val Tyr Ala Ile Phe Leu Asp Pro Tyr Thr Lys Val Val Glu
    450                 455                 460

Val Lys Leu Ala Asn Asp Ser Glu Thr Gly Arg Leu Lys Tyr Ile Ala
465                 470                 475                 480

Arg Ser Trp Tyr Lys Lys Gly Asp His Thr Gly Arg Ile Ala Asn Glu
                485                 490                 495

Thr Phe Ser Tyr Pro Tyr Gly Tyr Arg Leu Ile Arg Ala Gly Tyr Thr
                500                 505                 510

Val Ser Glu Leu His Tyr Lys Leu Asn Val Thr Asp Ile Thr Asp
            515                 520                 525

Cys Leu Thr Asp Leu Lys Ser Tyr Phe Glu Gln Asp Val Ile Lys Ser
    530                 535                 540

Ser Lys Ser Gly Gly Asp Ser Ser Gly Asn Ile Tyr Phe Ser Gly Ala
545                 550                 555                 560

Gly Gly Gly Asn Ile Ile Lys Ser Asp Val Thr Arg Gly Asp Ile Asn
                565                 570                 575

Phe Thr Gly Leu Gly Ala Ala Asn Val Ile Leu His Asp Ser Lys Phe
                580                 585                 590

Gly Asp Thr His Phe Asp Gly Ala Gly Ala Ala Asn Val Ile Val Lys
            595                 600                 605

Lys Gly Glu Lys Gly Asp Leu Thr Phe Arg Gly Thr Gly Leu Ala Asn
    610                 615                 620

Val Leu Val His Arg Gly Gln Ser Gly Lys Met Asp Val Tyr Ala Gly
625                 630                 635                 640

Gly Ala Val Asn Val Leu Val Arg Ile Gly Asp Gly Gln Tyr Leu Ala
                645                 650                 655

His Leu Leu Ala Tyr Gly Asn Ile Ser Ile His Lys Gly Asn Gly Ser
            660                 665                 670

Ser Arg Val Arg Met Leu Gly Gly Tyr Asn Thr His Thr Gln Ile Gly
    675                 680                 685

Asn Gly Asp Gly Asn Trp Ser Gly Lys Gly Gly Phe Asn Val Ile Thr
    690                 695                 700

Gln Ala Gly Lys Gly Ser Ile Ser Ser Val Leu Leu Gly Gly Ala Asn
705                 710                 715                 720

Ala Leu Thr Lys Leu Gly Ala Gly Ser Leu Val Ala Gly Met Leu Gly
                725                 730                 735

Gly Ala Asn Ile Ile Ser His Leu Ser Glu Glu Thr Glu Thr Ser Asn
            740                 745                 750

Thr Thr Ala Ile Ala Leu Gly Gly Ala Ser Ile Leu Thr Lys Lys Gly
    755                 760                 765

Thr Gly His Ala Gln Ala Val Met Gly Gly Ala Asn Val Leu Thr
    770                 775                 780

His Ile Gly Asp Gly Asn Thr Thr Gly Val Met Leu Gly Gly Ala Asn
785                 790                 795                 800

Ile Leu Thr Lys Val Gly Ser Gly Asp Ser Thr Gly Ile Met Phe Gly
                805                 810                 815

Ile Gly Asn Val Leu Thr His Val Gly Asp Gly Leu Thr Leu Gly Val
            820                 825                 830

Met Ala Ala Gly Asn Ile Phe Thr Lys Val Gly Glu Gly Thr Ser
    835                 840                 845

Ile Ala Ala Leu Thr Gly Thr Gly Asn Leu Thr His Ile Gly Lys
    850                 855                 860

Gly Asp Val Trp Ala Leu Met Gly Gly Ala Val Asn Val Phe Thr Lys
865                 870                 875                 880
```

-continued

```
Val Gly Asp Gly Asp Ala Leu Ala Leu Met Val Ala Ala Gly Asn Val
            885                 890                 895
Phe Thr His Ile Gly Asp Gly Thr Ser Val Ala Leu Met Gln Ala Glu
            900                 905                 910
Gly Asn Ile Ala Thr Lys Val Gly Asn Gly Met Thr Leu Ala Ala Met
            915                 920                 925
Ile Gly Lys Ala Asn Ile Phe Thr His Val Gly Glu Gly Asn Thr Phe
            930                 935                 940
Ala Ala Leu Ile Gly Gly Ala Asn Val Leu Thr Lys Val Gly Asn Asp
945                 950                 955                 960
Gln Thr Ala Ala Leu Met Ile Gly Lys Ala Asn Ile Tyr Ser His Val
                965                 970                 975
Gly Asn Gly Pro Ser Ile Gly Leu Phe Ala Gly Glu Leu Asn Val Met
            980                 985                 990
Thr Lys Val Gly Glu Gly Thr Thr Leu Ala Ala Met Phe Gly Arg Ala
            995                 1000                1005
Asn Ile Met Thr His Val Gly Asp Gly Leu Thr Gly Val Leu Ala
            1010                1015                1020
Leu Gly Glu Ala Asn Ile Val Thr Lys Val Gly Asn Asp Phe Met
            1025                1030                1035
Gly Val Val Ala Thr Val Lys Ala Asn Val Ile Thr His Val Gly
            1040                1045                1050
Asn Ala Val Thr Ala Ser Ile Leu Phe Gly Lys Gly Asn Ile Leu
            1055                1060                1065
Thr Lys Val Gly Asp Gly Thr Thr Val Gly Leu Leu Val Ser Asp
            1070                1075                1080
Val Gly Asn Val Met Thr His Ile Gly Glu Gly Ser Thr Val Gly
            1085                1090                1095
Phe Ala Lys Gly Lys Ala Asn Leu Ile Thr Lys Ile Gly Asp Gly
            1100                1105                1110
Ala Gly Val Asn Ala Ala Trp Gly Glu Ala Asn Ile Leu Thr Gln
            1115                1120                1125
Val Gly Asn Gly Asp Arg Tyr Asn Phe Ala Lys Gly Gln Ala Asn
            1130                1135                1140
Leu Met Thr Lys Val Gly Lys Gly Gln Glu Val Thr Val Val Gln
            1145                1150                1155
Gly Asp Ala Asn Ile Ile Thr His Val Gly Asn Gly Asp Asp Tyr
            1160                1165                1170
Thr Gly Ala Trp Gly Lys Ala Asn Val Val Thr Lys Val Gly Asp
            1175                1180                1185
Gly Arg Asn Val Val Leu Ala Lys Gly Lys Ala Asn Ile Ile Thr
            1190                1195                1200
Gln Val Gly Gln Gly Asp Ser Phe Asn Ala Leu Trp Ser Glu Gly
            1205                1210                1215
Asn Ile Val Thr Lys Val Gly Asp Gly Met Gln Val Thr Val Ala
            1220                1225                1230
Lys Gly Lys Ala Asn Val Thr Thr Val Gly Asn Gly Leu Asn
            1235                1240                1245
Val Thr Ala Ala His Gly Asp Ser Asn Ile Asn Thr His Val Gly
            1250                1255                1260
Asn Gly Val Ser Val Asn Leu Ala Trp Gly Lys His Asn Ile Asn
            1265                1270                1275
Thr Lys Val Gly Asn Gly Leu Asn Val Ala Val Met Lys Gly Gln
```

```
                1280            1285            1290

Ser Asn Ala Asn Ile Gln Val Gly His Gly Leu Ala Val Asn Ala
    1295            1300            1305

Ser Tyr Ala Arg Asn Asn Val Ala Ile Lys Ile Gly Glu Gly Asp
    1310            1315            1320

Phe Tyr Ser Leu Ala Val Ala Ala Ser Asn Thr Glu Ser Asn Lys
    1325            1330            1335

Leu Ala Ala Phe Phe Asn Asn Ile Lys Gln Thr Val Leu Gly Val
    1340            1345            1350

Met Gly Ser Gln Ala Ile Asn Tyr Leu Val Gln Gly Glu Glu Val
    1355            1360            1365

Asn Thr Phe Gly Ile His Lys Gly Arg Gly Ala Ile His Leu Ala
    1370            1375            1380

Glu Val Ser Thr Ile Asp Gly Phe Gln Met Glu Ala Ile Ala Pro
    1385            1390            1395

Val Ser Ser Asp Leu Asn Tyr Arg Leu Asn Gly Thr Val Thr Ala
    1400            1405            1410

Val Glu Thr Pro Asp Val Asp Val Ile Glu Ser Val Leu Asn Gln
    1415            1420            1425

Lys Thr Arg Ser Ile Ser Asp Gln Asn Asn Leu Ile Ile Asn
    1430            1435            1440

Gly Asp Phe Glu Gln Gly Lys Leu Gly Trp Gln Ser Thr His Gly
    1445            1450            1455

Ile Glu Ala Tyr Gly Ser Ala Ser Ala Tyr Gly Leu Val Ile Ala
    1460            1465            1470

Gly His Gly Glu Arg Val Ser Glu Leu Asp Ala Glu Arg Asn Thr
    1475            1480            1485

Thr Ile Tyr Gln Asp Leu Gln Asn Leu Ser Glu Gly Glu Val Ile
    1490            1495            1500

Ser Leu Ser Phe Asp Phe Ala His Arg Ser Asn Thr Tyr Val Ile
    1505            1510            1515

Asn Asn Gly Met Glu Val Phe Trp Asn Gly Gln Trp Val Phe Ser
    1520            1525            1530

Ala Ser Gly Asn Ala Ile Glu Trp Lys Ser Lys Thr Leu Glu Leu
    1535            1540            1545

Ile Ala Arg Ala Gly Ser Asn Arg Ile Glu Phe Lys Gly Thr Gly
    1550            1555            1560

Leu Asn Asp Gly Val Gly Tyr Val Leu Asp Asn Val Val Ala Lys
    1565            1570            1575

Ser Glu Asn Pro Leu Gln Thr Asp Val Val Thr Glu His Ala Lys
    1580            1585            1590

Gln Asp Lys Ala Ala Gln Asn Ala Leu Asn Asp Lys Glu Lys Ala
    1595            1600            1605

Glu Lys Asp Arg Gln Leu Leu Glu Gln Glu Gln Glu Lys Gln Leu
    1610            1615            1620

Ala Gly Ile Ala Lys Ser Gln Ser Gln Leu Glu Leu Thr Asp Gln
    1625            1630            1635

Ala Ala Val Ser Gln Asn Gly Leu Thr Gln Arg Asn Ala Ile Glu
    1640            1645            1650

Ala Glu Ala Gln Ala Glu Thr Gly Lys Leu Ile Ser Met Thr Gln
    1655            1660            1665

Gly Leu Ala Val Leu Asp Asn His Ala Ser Tyr Ser Gly Gln Ser
    1670            1675            1680
```

-continued

```
Gly Asp Pro Trp Arg Asn Pro Phe Ala Ala Glu Phe Leu Asn His
    1685                1690                1695

Val Gln Asn Glu Leu Tyr Tyr Val Lys Phe Ile Ala Gln Lys Lys
    1700                1705                1710

Leu Ala Asn Ala Arg Gln Ala Ile Ala Asp Asn Gln Gln Gln Val
    1715                1720                1725

Lys Lys Ala Val Ala Lys Ala Glu Ala Gly Val Ala Gln Ser Glu
    1730                1735                1740

Gln His Cys Val Ser Ala Lys Gln Asp Ile Ala Ala Ala Gln Glu
    1745                1750                1755

Lys Ala Glu Leu Arg Lys Ile Glu Ala Val Leu Gln Gln Gln Gln
    1760                1765                1770

Ala Lys Glu Ala Glu Asn Asp Ala Asn Ile Ala Tyr Gln Gly Ala
    1775                1780                1785

Glu Tyr Arg Gly Lys His Asp Ile Ala Val Ala Glu Ser Lys Ile
    1790                1795                1800

Thr Gln Val Gln Val Asp Ala Lys Val Ala Lys Gln Ser Asp Ser
    1805                1810                1815

Arg Pro Asp Arg Thr Gly Ala Gly Gly Ser Gly Leu Ser Gly Lys
    1820                1825                1830

Ala Tyr Glu Ser Thr Gly Ala Gly Glu Thr Gly Ser His Ile Asp
    1835                1840                1845

Pro Glu Leu Val Pro Glu Ala Glu Lys Lys Phe Tyr Glu Gly Leu
    1850                1855                1860

Ser Glu Glu Glu Leu Gln Ala Leu Asp Ser Val Glu Gln Leu Val
    1865                1870                1875

Asp His Leu Lys Ile Asn Ala Ser Ile His Ala Glu Asn Thr Gly
    1880                1885                1890

Val Leu Thr Ala Ser Lys Phe Ala Lys Gly Gln Ser Gly Ser Met
    1895                1900                1905

Val Met Pro Ala Ser Asn Ser Pro Gly Glu Phe Val Arg Arg Val
    1910                1915                1920

Pro Arg Ile Ser Gly Ile Asn Leu Lys Ser Leu Gly Asp Asp Ile
    1925                1930                1935

Lys Leu Gly Gln Lys Gly Asn Ser Ala Ile Phe Glu Ser Ala Lys
    1940                1945                1950

Phe Asn Leu Leu Lys Glu Gly Ser Lys Leu Phe Ile Asn Pro Asp
    1955                1960                1965

Glu Arg Thr Leu Gly Gln Lys Arg Pro Leu Ser Gln Ala Met Thr
    1970                1975                1980

Ala Val Arg Asp Ile Phe Tyr Lys Thr Met Ser His Phe Asp Glu
    1985                1990                1995

Glu His Val Leu Gln Phe Glu Gln Val Ile Ala Asp Trp Gln Gln
    2000                2005                2010

His Ser Pro Lys Glu Phe Ala Leu Arg Ala Asn Gln Val Asn Leu
    2015                2020                2025

Ile Arg Phe Arg Met Gly Arg Val Met Glu Tyr Leu Gln Ala Gln
    2030                2035                2040

Arg Ala Glu Ser Ala Lys Val Leu Gly Ile Ala Val Ser Pro Gln
    2045                2050                2055

Arg Ala Glu Gln Leu Ser Gln Arg Val Ile Phe Asp Gly Thr Gly
    2060                2065                2070

Arg Val Val Gly Leu Lys Gly Ser Val Thr Gln Asp Glu Ile Asn
    2075                2080                2085
```

His Leu Ile Glu Trp Lys Ile Thr Pro Leu Thr Arg Ala Asn Ser
2090            2095            2100

Thr Ala Glu Arg Glu Ala Pro Lys Thr Glu Ser Glu Ser Leu Ile
2105            2110            2115

Ala Phe Met Ser Arg Leu Glu Ala Ala Asn Ile Pro Glu Ala Met
2120            2125            2130

Pro Leu Ile Glu Gln Ala Arg Gly Leu Trp Leu Ile Gly Gln Val
2135            2140            2145

Thr Ser Lys Glu Thr Ile Lys Leu Phe Asn Asp Ala Ala Ser Gln
2150            2155            2160

Leu Gln Ala Tyr Pro Glu Leu Gln Ala Leu Val Leu Ser Leu Gln
2165            2170            2175

Ala Asp Ala His Lys Lys Lys Ser Thr Thr Gln Tyr Ile Asp Asn
2180            2185            2190

Leu Phe Gly Arg Arg Phe Asp Ser Glu Val Ala His Thr Leu Val
2195            2200            2205

Lys Thr Ala Ser Pro Asp Ala Ile Ala Val Ser Lys Arg Ile Gly
2210            2215            2220

Gln Phe Leu Val Gln Glu Phe Glu Leu Tyr Met Gln Asn Thr Ala
2225            2230            2235

Ser Ser Thr Ile Arg Asp Gly Gln Ile Thr Asn Gly Gln Met Ala
2240            2245            2250

Ile Arg Met His Ala Phe Ala Glu Lys Ile Lys Lys Asp Ile Arg
2255            2260            2265

Pro Trp Phe Ser Arg Val Pro Glu Leu Thr Thr Phe Leu Gln Lys
2270            2275            2280

Pro Thr Leu Asp Asn Phe Lys Ile Met Met Thr Lys Val Asp Asn
2285            2290            2295

Gly Phe Glu Met Ile Lys Ile Pro Phe Leu Ala Val Lys Met Ser
2300            2305            2310

Asn Thr Asp Gly Met Gly Leu His Leu Ser Gln Trp Lys Ala Glu
2315            2320            2325

Ala Asp Ile Phe Tyr Arg Gly Glu Ile Tyr Lys Ala Arg Ser Thr
2330            2335            2340

Ser Asn Thr Leu Thr His Arg Ala Asp Val Thr His Thr Val Glu
2345            2350            2355

Leu Ile Asp Gln Gln Thr Asn Asp Tyr Gly Ile Ala Leu Pro Tyr
2360            2365            2370

Gln Pro Ser Gly Asp Gln Tyr Asp Asp Phe Leu Ser Gly Arg Lys
2375            2380            2385

Val Ala Ala Gly Ser Val Leu Thr Pro Gly Gln Glu Thr Val Leu
2390            2395            2400

Glu Arg Asn Ala Leu Ala Gln Gly His Ser Val Val Thr Gly Ala
2405            2410            2415

Ser Gly Ser Thr Asn Ile Met Val His Leu Asn Asn Tyr Ile Ala
2420            2425            2430

Arg Gln Asp Pro Thr Phe Ser Gln Glu Gln Ala Tyr Leu Asn Thr
2435            2440            2445

Leu Ala Phe Leu Val Phe Asp Gly Gly His Ser Val Asn Glu Ser
2450            2455            2460

Leu Val Val Tyr Lys Ala Leu Gln Ala Thr Ser Asp Glu Arg Arg
2465            2470            2475

Gln Val Leu Gln His Tyr Thr Ala Ser Tyr Met Asp Leu Met Asp

```
                2480                2485                2490

Ile Ala  Gly Asp Lys Gly  Glu Arg Trp Ile  Asn Gln Ala Leu Asn
    2495             2500              2505

Ser Ala  Phe Glu Lys Thr  Leu His Phe Tyr  Arg Glu Asn Thr Pro
    2510             2515              2520

Glu Arg  Lys Arg Asn Asp  Val Pro Val Glu  Ala Leu Gln Ala Leu
    2525             2530              2535

Ser Gly  Lys Asn Gly Thr  Ser Glu Ser Leu  Phe Ile Lys Asp Gly
    2540             2545              2550

Gly Thr  Ser Pro Gln Asp  Lys Ala Ala Leu  Asn Pro Val Thr Arg
    2555             2560              2565

Phe Phe  Asn Asn Glu Leu  Tyr Gly Phe Lys  Glu Asp Lys Asn Gln
    2570             2575              2580

Asp Arg  Val Lys Asn Ser  Gln Gln Lys Asn  Asp Asn Arg Gly Thr
    2585             2590              2595

Arg Phe  Asp Gly Gln Ile  Ile Ile Gln Met  Glu Asp Asp Pro Ile
    2600             2605              2610

Val Ala  Lys Ala Ala Ile  Asn Leu Ala Gly  Lys His Pro Asp Ser
    2615             2620              2625

Ser Val  Val Val Lys Leu  Asp Ala Asp Gly  Lys Tyr His Val Ile
    2630             2635              2640

Asp Gly  Asp Pro Ala Gly  Leu Ser Gly Lys  Leu Arg Trp Gln Ile
    2645             2650              2655

Val Gly  His Gly Arg Asp  Glu Ser Thr Gln  Asn Asn Thr Arg Leu
    2660             2665              2670

Ser Gly  Tyr Arg Ala Asp  Glu Leu Ala Ile  Lys Leu Lys Gln Phe
    2675             2680              2685

Ser Gln  Asp Phe Glu Gln  Ala Gly Lys Pro  Glu Arg Ile Ser Ile
    2690             2695              2700

Val Gly  Cys Ser Leu Ile  Ser Asp Asp Lys  Gln Asn Gly Phe Ala
    2705             2710              2715

Tyr Arg  Phe Met Phe Ala  Leu Asp Lys Gln  Gly Ile Arg Ser Glu
    2720             2725              2730

Val Ser  Val Arg Arg Ser  Asp Val Ala Val  Asp Ala Thr Gly Arg
    2735             2740              2745

Lys Phe  Thr Arg Asp Lys  Asn Tyr Gln Trp  Val Asn Arg Leu Asp
    2750             2755              2760

Asp Asn  Lys Gln Val Leu  Cys Trp Asn Glu  Glu Gly Glu Leu Thr
    2765             2770              2775

Ala Thr  Thr Glu Arg Glu  Arg Cys Gly Val  Ala Glu Ser Asp Ile
    2780             2785              2790

Asn Leu  Ala Arg Val Gly  Tyr Thr Glu Ala  Asp Ser Val Thr Arg
    2795             2800              2805

Gly Ala  Ile Ala Asp Asn  His Asp Val Phe  Ile Ala Pro Arg Lys
    2810             2815              2820

Arg Lys  Asn Arg Ile Glu  Pro Gly Ser Asn  Pro Gln Ser Asp Lys
    2825             2830              2835

Pro Leu  Ser Tyr Ala Gly  Asn Ile Gln Val  Asn Val Gly Asp Gly
    2840             2845              2850

Glu Phe  Thr Ala Ile Asn  Trp Gly Thr Ser  Asn Val Gly Ile Lys
    2855             2860              2865

Val Gly  Thr Gly Gly Phe  Lys Ser Leu Ala  Phe Gly Asp Asn Asn
    2870             2875              2880
```

Val Met Ala His Ile Gly Glu Gly Asp Ser Lys His Ser Val Asn
2885                2890                2895

Leu Gly Gly Tyr Gln Ala Phe Glu Gly Ala Gln Val Phe Ile Gly
2900                2905                2910

Thr Arg Asn Ile Ser Phe Asn Gln Gly Arg Ser Asn Asp Leu Ile
2915                2920                2925

Val Met Met Asp Lys Ser Leu Ser Thr Pro Pro Leu Val Asn Pro
2930                2935                2940

Phe Asp Gly Thr Ala Arg Ile Ser Gly Val Leu Lys Ser Ile Ala
2945                2950                2955

Arg Ser Gly Glu Glu Gln Asn Trp Leu Ala Val Gln Asp Gln Gln
2960                2965                2970

Trp Thr Leu Ser Gly Ala Glu Lys Phe Val Arg Asp Met Ser Gly
2975                2980                2985

Leu Asp Gln Thr Ser Ser Val Asp Tyr Lys Thr Leu Val Asp Leu
2990                2995                3000

Asp Ala Gln His Glu Arg Ser Ser Arg Gly Leu Lys Ser Asp Thr
3005                3010                3015

Glu Thr Ala Leu Asn Lys Lys Tyr His Arg Trp Leu Ser Asp Asn
3020                3025                3030

Ser Asn Asp Ile Asp Thr Ser Lys Met Ser Arg Val Asp Lys Phe
3035                3040                3045

Arg Gln Ala Asn Glu Lys Leu Ile Phe Asn Phe Ala Val Gly Gly
3050                3055                3060

Arg Gly Ala Asp Ile Gln Val Thr Thr Gly Ser Trp Asn Phe Met
3065                3070                3075

Phe Gly Asp His Ile Gln Ser Ile Leu Asp Thr Asn Leu Gly Ser
3080                3085                3090

Leu Phe Gly Leu Met Thr Gln Gln Tyr Ser Ala Thr Gly Ile Ala
3095                3100                3105

Lys Thr Thr Phe Thr Tyr Lys Pro Gln Asp Leu Pro Arg Gln Leu
3110                3115                3120

Lys Asn Lys Leu Leu Gly Arg Leu Ala Ser Val Asn Ala Glu Thr
3125                3130                3135

Thr Leu Ala Asp Ile Phe Gly Val Asp Cys Thr Pro Glu Gly Gln
3140                3145                3150

Ile Val Ala Arg Thr Gly Glu Pro Val Asp Gly Thr Ala Ile Leu
3155                3160                3165

Arg Glu Met Leu Glu Met Ile Lys Gln Phe Gly Gly Asp Gln Phe
3170                3175                3180

Arg Val Phe Ala Asp Pro Asp Lys Trp Ile Glu Gly Leu Lys Gln
3185                3190                3195

His Ile Asp Met Gly Ala Asp Gly Ile Lys Ser Phe Leu Ile Ser
3200                3205                3210

His Gly Leu Lys Glu Lys Ala Pro Asp Glu Asn Arg Glu Glu Ser
3215                3220                3225

Val Pro Gly Val Ile Asn Ser Gly Asn Ser Gln Val Asp Asn Lys
3230                3235                3240

Pro Glu Arg Ala Leu Gly Phe His Ser Leu Asn Leu Pro Asn Leu
3245                3250                3255

Phe Ala Thr Ile Phe Asn Arg Asn Lys Gln Glu Glu Met Arg Ser
3260                3265                3270

Leu Val Thr Asn Leu Lys Glu Asn Leu Thr Ala Asp Leu Leu Asn
3275                3280                3285

-continued

```
Met Glu Gln Lys Thr Phe Asp Phe Leu Arg Asn Ser Gly His Leu
    3290                3295                3300
His Asp Asp Gly Asp Ile His Ile Ser Leu Gly Asn Tyr Asn Phe
    3305                3310                3315
Asn Trp Gly Gly Asp Gly Lys Asp Leu Gly Ala Tyr Leu Gly Asp
    3320                3325                3330
Asn Asn Asn Phe Trp Gly Gly Arg Gly Glu Asp Val Tyr Tyr Ala
    3335                3340                3345
Ile Gly Ile Ser Asn Leu Phe Thr Gly Gly Gly Asn Asp Leu
    3350                3355                3360
Gly Val Leu Met Gly Arg Glu Asn Trp Met Phe Gly Gly His Gly
    3365                3370                3375
Asp Asp Thr Ala Val Ile Ala Gly Arg Ile Asn Tyr Ala Phe Met
    3380                3385                3390
Gly Glu Gly Asn Asp Gln Thr Phe Val Phe Gly Glu Gly Gly Leu
    3395                3400                3405
Ile Asp Ala Gly Ser Gly Tyr Asp Tyr Val Val Thr Ala Gly Asn
    3410                3415                3420
Tyr Asn Arg Val Glu Thr Gly Glu Asp Gln Asp Tyr Ala Val Thr
    3425                3430                3435
Ile Gly Asn Asn Asn Trp Val Glu Leu Gly Ala Gly His Asp Phe
    3440                3445                3450
Gly Trp Val Phe Gly Asn Asp Asn Arg Ile Asp Gly Asn Thr Gly
    3455                3460                3465
Asp Asp Val Ile Lys Leu Met Gly Tyr His Ala Val Ile Asn Gly
    3470                3475                3480
Gly Glu Gly Asp Asp His Leu Ile Ala Ala Thr Ile Ser Lys Phe
    3485                3490                3495
Ser Gln Phe Asp Gly Gly Glu Gly Gln Asp Leu Leu Val Leu Gly
    3500                3505                3510
Gly Tyr Gln Asn His Phe Gln Gly Gly Ala Gly Val Asp Ser Phe
    3515                3520                3525
Val Val Ser Gly Gln Val Ile Asp Ser Gln Val Asp Asp Ile Asn
    3530                3535                3540
Ala Glu Asp Met Ile Ala Phe Asn Asp Ile Asp Trp Gln Asp Leu
    3545                3550                3555
Trp Phe Gln Arg Ser Gly Tyr Asp Leu Val Leu Ser Val Asn Arg
    3560                3565                3570
Pro Thr Gln Asp Lys Thr Ala Gln Gly Ile Phe Glu Ser Ile Gly
    3575                3580                3585
Ser Val Thr Phe Ser Asp Tyr Phe Asn Gly Asn Arg Ala Lys Leu
    3590                3595                3600
Val Met Arg Met Gly Asp Lys Asn Ala Leu Gly Glu Arg Glu Phe
    3605                3610                3615
Thr Ala Leu Ser Asp Asn Ala Val Asp Thr Leu Ile Gln Ala Met
    3620                3625                3630
Ser Ser Phe Ala Pro Thr Val Gly Asp Asn Gly Phe Ile Asp Asn
    3635                3640                3645
Leu Ala Ser Gln Ala Lys Ile Val Met Ala Thr Ala Trp Ala Asp
    3650                3655                3660
Thr Thr Glu Gly Lys Val Gln Phe Ala
    3665                3670
```

<210> SEQ ID NO 5
<211> LENGTH: 4070
<212> TYPE: PRT
<213> ORGANISM: Photorhabdus luminescens

<400> SEQUENCE: 5

```
Met Gly Lys Ser Ser Asn Arg Ser Thr Glu Tyr Phe Phe Thr Gly Lys
1               5                   10                  15

Tyr Tyr Asp Asp Asn Asp Gly Asn Ser Ile Ile Ala Ile Gly Ile Gly
            20                  25                  30

Gly Glu Val Tyr Ala Tyr Gly Asp Asp Val Thr Ile Gly Ser
        35                  40                  45

Phe Lys Val Asp Val Tyr His Thr Asn Gly Glu Leu Ser Val Lys Gly
    50                  55                  60

Ala Ser Gly Tyr Thr Gly Ile Ser Lys Thr Gly Asn Gly Gly Leu Ser
65                  70                  75                  80

Phe Ser Gly Ala Ala Gly Thr Ala Phe Ile Asp His Thr Gly Glu Thr
                85                  90                  95

Gly Asp Leu Ser Tyr Ser Gly Ala Ala Gly Tyr Asn Lys Leu Val Arg
            100                 105                 110

Lys Gly Ser Ser Gly Asp Thr Arg Phe Lys Gly Ala Gly Gly Tyr Asn
            115                 120                 125

Gln Leu Trp His Glu Thr Asp Gln Gly Asn Val Tyr Phe Ala Gly Ala
130                 135                 140

Gly Ala Ala Asn Lys Ile Asp Arg Thr Trp Ser Asn Tyr Tyr Glu Gly
145                 150                 155                 160

Thr Gln Gly Asp Val Thr Phe Asn Gly Ala Gly Ala Ala Asn Ser Ile
                165                 170                 175

Asp Ser Arg Ile Glu Ser Gly Asp Ile Thr Leu Asn Gly Val Gly Ala
            180                 185                 190

Asp Asn His Ile Val Arg Lys Gly Arg Glu Gly Asn Ile Ile Leu His
        195                 200                 205

Gly Ala Gly Ala Ala Asn Arg Ile Glu Arg Thr Arg His Ser Glu Asp
210                 215                 220

Gln Tyr Gly Gln Thr Gln Gly Asp Ile Thr Leu Glu Gly Ala Gly Gly
225                 230                 235                 240

Tyr Asn Lys Leu Tyr Ser Asp Val Ala His Gly Asn Ile His Phe Thr
                245                 250                 255

Gly Ala Gly Ala Tyr Asn Glu Ile Thr Arg Ala Gly Ala Arg Asn Glu
            260                 265                 270

Ile Glu Phe Ala Gln Ala Lys Asp Ile Val Met Thr Ser Ala Thr Met
        275                 280                 285

Glu Glu Arg Gly Ile Gln Gln Ser Gln Gln Val Lys Ala Val Lys Ser
    290                 295                 300

Glu Val Glu Pro Asp Thr Tyr Leu Phe Ala Ile Ala Asp Asn Val Asn
305                 310                 315                 320

Thr Lys Val Val Ala Val Arg Leu Gln Asn Asn Pro Asp Thr Gly Lys
                325                 330                 335

Leu Arg Tyr Tyr Ala Thr Ser Trp Tyr Lys Glu Gly Asn His Leu Lys
            340                 345                 350

Asp Ile Ala Lys Glu Asn Ile Asp Val Asn Asn Gly Phe Ile Ser Val
        355                 360                 365

Lys Gly Asp Asp Ala Ile Thr Leu Ala Asn Ile Asn Val Val Tyr Arg
    370                 375                 380

Gln Glu Thr Ile Val Gln Gly Val Glu Glu Val Leu Leu Thr Asp Lys
```

```
                385                 390                 395                 400
Trp Val Asn Tyr Ser Asp Gly Thr Asn Ile Lys Ala Lys Asn Val Thr
                    405                 410                 415

Leu Gly Ser Ala Lys Met Gly Gly Tyr Ala Ile Ser Ser Asn Gly Leu
                420                 425                 430

Lys Ile Asp Val Ser Pro Val Lys Ser Asn Gln Gln Pro Asp Thr Tyr
            435                 440                 445

Val Tyr Ala Ile Phe Leu Glu Pro Tyr Thr Lys Val Val Glu Val Lys
        450                 455                 460

Leu Ala Asn Asp Asp Glu Thr Gly Lys Leu Lys Tyr Ile Ala Arg Ser
465                 470                 475                 480

Trp Tyr Lys Lys Gly Asp His Thr Gly Arg Leu Ala Asn Glu Arg Phe
                485                 490                 495

Ser Tyr Pro Arg Gly Tyr Gln Ser Ile Gly Ala Gly Tyr Thr Leu Ser
                500                 505                 510

Gln Leu His Tyr Asp Leu Asn Val Thr Asp Glu Ile Thr Asp Cys Leu
            515                 520                 525

Thr Asp Ile Glu Gly Tyr Ser Glu Gln Asp Val Ile Lys Ser Ser Lys
        530                 535                 540

Asn Gly Gly Asp Ser Ser Gly Asn Ile Tyr Phe Ile Gly Ala Gly Gly
545                 550                 555                 560

Gly Asn Ile Ile Thr Ser Asn Val Thr His Gly Asn Ile Asn Phe Thr
                565                 570                 575

Gly Ala Gly Ala Ala Asn Ile Ile Leu His Ser Ser Thr Phe Gly Asn
                580                 585                 590

Thr Tyr Phe Glu Gly Gly Gly Ala Asn Val Ile Val Lys Asn Gly
            595                 600                 605

Glu Glu Gly Asp Leu Ser Phe Arg Gly Ala Gly Leu Ala Asn Val Leu
        610                 615                 620

Val His Gln Ser Gln Arg Gly Lys Met Asp Val Tyr Ala Gly Gly Ala
625                 630                 635                 640

Val Asn Val Leu Val Arg Val Gly Asp Gly Arg Tyr Leu Ala His Leu
                645                 650                 655

Leu Ser Tyr Gly Asn Ile Ser Ile His Lys Gly Asn Gly Asp Ser Arg
                660                 665                 670

Val Leu Met Leu Gly Gly Tyr Asn Thr His Thr Gln Ile Gly Asp Gly
            675                 680                 685

Ser Ala Asn Trp Phe Gly Ala Gly Gly Phe Asn Val Ile Thr Gln Ala
        690                 695                 700

Gly Thr Gly Asp Ile Phe Ser Val Phe Leu Gly Gly Ala Asn Val Leu
705                 710                 715                 720

Thr Lys Leu Gly Ala Gly Asp Met Val Ala Gly Met Leu Gly Gly Ala
                725                 730                 735

Asn Ile Ile Thr His Leu Ser Asp Glu Thr Glu Thr Asn Thr Thr
                740                 745                 750

Ala Ile Ala Leu Gly Gly Ala Asn Ile Phe Thr Lys Lys Gly Lys Gly
            755                 760                 765

His Thr Gln Ala Val Met Gly Gly Ala Asn Val Leu Thr His Ile
        770                 775                 780

Gly Asp Gly Asn Thr Thr Gly Val Met Leu Gly Gly Ala Asn Ile Leu
785                 790                 795                 800

Thr Lys Val Gly Lys Gly Asp Met Thr Gly Ile Met Phe Gly Val Gly
                805                 810                 815
```

-continued

Asn Val Leu Thr His Val Gly Asp Gly Leu Thr Leu Gly Val Met Ala
                820             825             830

Ala Ala Gly Asn Ile Phe Thr Lys Val Gly Glu Gly Thr Ser Ile Ala
            835             840             845

Ala Met Ile Gly Ala Gly Asn Leu Phe Thr His Val Gly Lys Gly Asp
850             855             860

Ala Trp Ala Leu Met Gly Gly Val Gly Asn Ile Phe Thr Lys Val Gly
865             870             875             880

Asp Gly Asp Ala Leu Ala Leu Met Val Ala Ala Gly Asn Val Phe Thr
                885             890             895

His Ile Gly Asp Gly Thr Ser Val Ala Leu Met Leu Ala Lys Gly Asn
            900             905             910

Ile Ala Thr Lys Val Gly Asn Gly Met Thr Leu Ala Ala Met Ile Gly
            915             920             925

Lys Ala Asn Ile Phe Thr His Val Gly Glu Gly Asn Thr Phe Ala Ala
            930             935             940

Met Ile Gly Gly Ala Asn Val Leu Thr Lys Val Gly Asn Asp Leu Thr
945             950             955             960

Ala Ala Leu Met Val Gly Lys Ala Asn Ile Tyr Ser His Val Gly Asn
            965             970             975

Gly Thr Ser Ile Gly Leu Phe Ala Gly Glu Leu Asn Val Met Thr Lys
                980             985             990

Val Gly Asn Gly Thr Thr Leu Ala Ala Met Phe Gly Lys Ala Asn Met
            995             1000            1005

Met Thr His Val Gly Asp Gly Leu Thr Gly Val Leu Ala Leu Gly
    1010            1015            1020

Glu Ala Asn Ile Val Thr Lys Val Gly Asp Asp Phe Met Gly Val
    1025            1030            1035

Val Ala Ala Ala Lys Ala Asn Val Ile Thr His Val Gly Asp Ala
    1040            1045            1050

Thr Thr Ala Ala Ile Leu Phe Gly Lys Gly Asn Ile Leu Thr Lys
    1055            1060            1065

Val Gly Asp Gly Thr Thr Val Gly Leu Leu Ile Ser Asp Val Gly
    1070            1075            1080

Asn Val Met Thr His Val Gly Glu Gly Thr Thr Val Gly Phe Ala
    1085            1090            1095

Lys Gly Lys Ala Asn Leu Ile Thr Lys Ile Gly Asp Gly Ala Gly
    1100            1105            1110

Val Asn Ala Ala Trp Gly Glu Ala Asn Ile Leu Thr Gln Val Gly
    1115            1120            1125

Asn Gly Asp Arg Tyr Asn Phe Ala Lys Gly Lys Ala Asn Leu Met
    1130            1135            1140

Thr Lys Val Gly Lys Gly Gln Glu Val Thr Val Val Gln Gly Asp
    1145            1150            1155

Ala Asn Ile Ile Thr His Val Gly Asn Gly Asp Asp Tyr Thr Gly
    1160            1165            1170

Ala Trp Gly Lys Ala Asn Val Ile Thr Lys Ile Gly Asp Gly Arg
    1175            1180            1185

Asn Val Val Leu Ala Lys Gly Lys Ala Asn Ile Val Thr Gln Val
    1190            1195            1200

Gly Gln Gly Asp Ser Phe Asn Ala Leu Trp Ser Glu Gly Asn Ile
    1205            1210            1215

Val Thr Lys Val Gly Asp Gly Met Gln Val Thr Val Ala Lys Gly
    1220            1225            1230

```
Lys Ala Asn Val Thr Thr Val Gly Asn Gly Leu Asn Val Thr
1235             1240                 1245

Ala Ala His Gly Asp Ala Asn Ile Asn Thr His Val Gly Asn Gly
1250             1255                 1260

Val Ser Val Asn Leu Ala Trp Gly Lys His Asn Ile Asn Thr Lys
1265             1270                 1275

Val Gly Asn Gly Leu Asn Val Ala Val Met Lys Gly Gln Ala Asn
1280             1285                 1290

Ala Asn Ile His Val Gly Asp Gly Leu Gly Ile Asn Ala Ser Tyr
1295             1300                 1305

Ala Arg Asn Asn Val Ala Val Lys Ile Gly Asn Gly Asp Phe Tyr
1310             1315                 1320

Ser Phe Ser Val Thr Asn Ser Asn Lys Leu Ser Ser Leu Phe Glu
1325             1330                 1335

His Ile Lys Gln Thr Thr Leu Gly Val Gly Gly Ser Gln Ala Ile
1340             1345                 1350

Asn Tyr Leu Val His Gly Glu Glu Ala Asn Thr Ser Gly Thr His
1355             1360                 1365

Lys Gly Arg Gly Ala Ile Asn Leu Ala Glu Val Ser Gly Ile Asp
1370             1375                 1380

Gly Phe Gln Met Asp Glu Ile Ala Pro Ile Ser Ser Asp Leu Asn
1385             1390                 1395

His Ser Phe Asn Gly Ala Ile Thr Ala Val Glu Thr Pro Asp Val
1400             1405                 1410

Ser Ser Ile Glu Gly Ala Leu Ser Gln Lys Thr Leu Ser Val Ser
1415             1420                 1425

Asp Gln Asp Glu Asn Leu Ile Val Asn Gly Asp Phe Glu Gln Gly
1430             1435                 1440

Glu Leu Gly Trp Gln Ser Thr His Gly Ile Glu Ala Tyr Asn Pro
1445             1450                 1455

Ala Ser Asp Tyr Gly Leu Asp Asn Thr Gly Asp Gly Glu Arg Val
1460             1465                 1470

Ser Lys Phe Asp Val Asp Lys Asn Thr Val Ile Trp Gln Glu Leu
1475             1480                 1485

Gln Asn Leu Ser Glu Gly Glu Val Val Ser Leu Thr Phe Asp Phe
1490             1495                 1500

Met Ser His Phe Glu Arg Val Asp Arg Asp Leu Ser Gly Ser Gly
1505             1510                 1515

Ile Met Val Leu Trp Asn Gly Lys Ser Val Phe Ser Thr Ser Gly
1520             1525                 1530

Pro Arg Ala Ile Trp Arg Thr Gln Lys Leu Asp Leu Met Ala Lys
1535             1540                 1545

Ala Gly Thr Asn Arg Ile Glu Phe Lys Gly Thr Gly Gln Asp Asp
1550             1555                 1560

Gly Phe Ser Tyr Ile Leu Asp Asn Ile Ile Val Lys Ser Glu Thr
1565             1570                 1575

Ser Leu Ile Val Asn Asn Asp Leu Glu Gln Gly Lys Leu Asp Trp
1580             1585                 1590

Gln Ser Thr Asn Asp Ile Ala Ala Tyr Ser Ser Val Ser Thr Asp
1595             1600                 1605

Gly Pro Asn Asn Thr Arg Tyr Gly Glu Arg Val Ser Glu Leu Asp
1610             1615                 1620

Val Asp Lys Asn Thr Thr Ile Tyr Gln Asp Leu Gln Asn Arg Ser
```

-continued

```
            1625                1630                1635

Glu Gly Glu Val Ile Ser Leu Ser Phe Asp Phe Ala Asn Arg Pro
        1640                1645                1650

Asp Ala Tyr Ser Val Asp Asn Gly Met Asp Val Phe Trp Asn Asp
        1655                1660                1665

Lys Leu Val Phe Ser Thr Phe Gly Asp Ala Ala Lys Trp Gln Asn
        1670                1675                1680

Lys Thr Leu Glu Leu Thr Ala Lys Ala Gly Ser Asn Arg Ile Glu
        1685                1690                1695

Phe Lys Gly Thr Gly Leu Ser Asp Gly Val Gly Tyr Ile Leu Asp
        1700                1705                1710

Asn Val Ile Ala Lys Ser Lys Ser Ser Gln Ala Asn Ile Ile
        1715                1720                1725

Thr Glu His Val Lys Gln Asp Lys Ala Ala Gln Asn Ala Leu Ser
        1730                1735                1740

Asp Lys Glu Lys Ala Glu Lys Asp Arg Arg Leu Leu Glu Gln Glu
        1745                1750                1755

Lys Glu Lys Gln Leu Ala Glu Ile Ala Lys Ser Gln Ser Gln Leu
        1760                1765                1770

Glu Leu Thr Asp Gln Ala Ala Val Ser Gln Asn Gly Leu Thr Gln
        1775                1780                1785

Arg Asn Ala Ile Glu Ala Glu Ala Gln Ala Glu Thr Asp Lys Leu
        1790                1795                1800

Val Ser Met Thr Gln Gly Leu Asp Ala Leu Gly Asp Tyr Ala Asn
        1805                1810                1815

Tyr Ser Gly Gln Ser Gly Asp Gln Trp Arg Asn Gln Phe Ala Ser
        1820                1825                1830

Gln Phe Leu Asp His Ala Gln Asp Lys Leu Asn Asp Ile Lys Phe
        1835                1840                1845

Ile Ala Gln Arg Lys Leu Met His Ala Arg Gln Ala Ile Thr Asp
        1850                1855                1860

Asn Gln Gln His Val Lys Glu Ala Val Lys Lys Ser Glu Val Gly
        1865                1870                1875

Val Ala Gln Ser Glu Gln His His Ala Ser Ala Lys Gln Asp Ile
        1880                1885                1890

Ala Ala Ala Gln Lys Lys Ala Glu Leu Arg Lys Glu Glu Ala Leu
        1895                1900                1905

Leu Gln Gln Arg Ala Glu Lys Ala Glu Asn Asp Ala Asn Ile
        1910                1915                1920

Ala Tyr Gln Gly Ala Glu Tyr Arg Gly Lys Arg Asp Ile Ala Ala
        1925                1930                1935

Ala Glu Asn Lys Ile Ala Gln Val Gln Glu Asp Val Arg Gly Ala
        1940                1945                1950

Lys Gln Ser Asp Ser Lys Pro Asp Arg Thr Gly Ala Gly Gly Ser
        1955                1960                1965

Gly Leu Ser Gly Asn Gly Tyr Glu Ser Thr Gly Ala Gly Glu Thr
        1970                1975                1980

Gly Ser Tyr Ile Asp Pro Glu Leu Ile Pro Glu Ala Glu Lys Lys
        1985                1990                1995

Phe Tyr Lys Gly Leu Thr Glu Glu Leu Gln Ala Leu Asp Asp
        2000                2005                2010

Ala Lys Gln Ala Val Asp Arg Leu Gln Ile Asn Ala Ser Ile Arg
        2015                2020                2025
```

```
Val Glu Asn Thr Gly Val Leu Thr Thr Ser Lys Phe Ala Lys Gly
    2030                2035                2040

Gln Ser Asp Asp Arg Val Ile Pro Thr Ser Asn Ser Ser Gly Glu
    2045                2050                2055

Arg Val Arg Arg Val Pro Arg Ile Ser Gly Ile Asn Leu Lys Ser
    2060                2065                2070

Leu Gly Asn Asp Val Lys Val Glu Gln Lys Asn Ser Ala Ile Phe
    2075                2080                2085

Glu Asn Ala Lys Phe Asn Leu Leu Lys Glu Gly Asn Lys Leu Phe
    2090                2095                2100

Ile Asn Pro Asn Val Arg Thr Leu Gly Arg Lys Arg Lys Leu Ser
    2105                2110                2115

Thr Ala Leu Ala Thr Val Arg Asp Thr Phe Tyr Lys Thr Met Ser
    2120                2125                2130

His Phe Asp Glu Glu His Ile Leu Leu Leu Glu Arg Ala Ile Ala
    2135                2140                2145

Asp Trp Gln Gln His Ser Pro Lys Glu Phe Ala Leu Arg Thr Asn
    2150                2155                2160

Gln Val Asn Leu Val Arg Phe Lys Met Gly Arg Met Ile Glu His
    2165                2170                2175

Leu Gln Ala Gln Arg Ala Glu Ser Ala Gly Val Leu Gly Ile Ala
    2180                2185                2190

Val Ala Pro Gln His Ala Glu His Leu Thr Gln Arg Val Ile Phe
    2195                2200                2205

Asp Gly Thr Gly Arg Val Val Gly Leu Lys Gly Gly Ile Thr Gln
    2210                2215                2220

Asn Glu Ile Asn Arg Leu Ile Glu Trp Gln Ile Thr Pro Leu Thr
    2225                2230                2235

Arg Thr Asn Ser Thr Ala Glu Arg Glu Ala Pro Lys Thr Glu Ser
    2240                2245                2250

Glu Ser Leu Ile Ala Phe Met Ser Arg Leu Glu Thr Ala Asn Ile
    2255                2260                2265

Pro Glu Ala Arg Phe Leu Ile Gly Arg Ala Arg Gly Leu Trp Leu
    2270                2275                2280

Thr Gly Gln Val Thr Ser Lys Glu Thr Ile Lys Leu Phe Asp Asp
    2285                2290                2295

Ala Ala Ser Gln Leu Gln Ala Tyr Pro Glu Leu His Gly Leu Val
    2300                2305                2310

Leu Ser Leu Gln Ala Asp Ala His Arg Glu Lys Ser Thr Thr Gln
    2315                2320                2325

Tyr Ile Asp Asn Leu Phe Gly Arg Arg Phe Asp Ser Glu Val Ala
    2330                2335                2340

His Thr Leu Val Lys Met Ala Ser Pro Asp Ala Leu Ala Thr Ser
    2345                2350                2355

Arg Arg Ile Gly Gln Phe Leu Val Gln Glu Phe Glu Leu Tyr Met
    2360                2365                2370

Gln Ser Thr Ala Asp Ser Pro Val Leu Asp Gly Gln Ile Asp Ile
    2375                2380                2385

Arg Met Gln Ala Phe Ala Glu Lys Ile Lys Lys Asp Ile Arg Pro
    2390                2395                2400

Trp Phe Ser Arg Val Pro Glu Leu Thr Ala Phe Leu Gln Lys Pro
    2405                2410                2415

Thr Leu Asp Asn Phe Lys Ile Met Met Thr Lys Val Asp Asn Gly
    2420                2425                2430
```

```
Phe Glu Met Ile Lys Ile Pro Phe Leu Ala Val Lys Met Ser Asn
    2435            2440                2445
Thr Asp Gly Met Gly Leu His Leu Ser Gln Trp Lys Ala Glu Ala
    2450            2455                2460
Asp Ile Phe Tyr Arg Glu Ile Tyr Lys Ala Arg Ser Thr Ser
    2465            2470                2475
Ser Lys Leu Thr Asn Met Ala Asp Val Thr Tyr Lys Val Lys Leu
    2480            2485                2490
Thr Glu Gln Gln Thr Asn Asp Tyr Gly Ile Ala Leu Pro Tyr Gln
    2495            2500                2505
Pro Ser Gly Asp Gln Tyr Gly Asp Phe Leu Tyr Gly Arg Lys Val
    2510            2515                2520
Ala Ala Gly Arg Val Leu Thr Pro Gly Gln Glu Thr Thr Leu Glu
    2525            2530                2535
Arg Asn Ala Leu Ala Gln Gly His Ser Val Val Thr Gly Ala Ser
    2540            2545                2550
Gly Ser Thr Asn Ile Met Val His Leu Asn Asn Tyr Ile Ala Ser
    2555            2560                2565
Gln Asp Pro Thr Phe Ser Gln Glu Gln Ala Tyr Leu Asn Thr Leu
    2570            2575                2580
Ala Phe Leu Val Phe Asp Gly His Ser Val Asn Glu Ser Leu
    2585            2590                2595
Val Val Tyr Lys Ala Leu Gln Met Thr Gly Asp Glu Arg Arg Gln
    2600            2605                2610
Val Leu Gln Asn Tyr Thr Ala Ser Tyr Met Asp Leu Met Asp Ile
    2615            2620                2625
Ala Gly Asp Lys Gly Lys Leu Ser Ile Asn Gln Ala Leu Asn Asn
    2630            2635                2640
Ala Phe Glu Lys Thr Gln His Leu Tyr Arg Glu Asn Thr Pro Glu
    2645            2650                2655
Arg Glu Gln Asn Asp Ser Pro Val Glu Ala Leu Gln Ala Leu Ser
    2660            2665                2670
Gly Lys Asn Gly Ala Ser Glu Ser Val Leu Ile Glu Asn Asp Asp
    2675            2680                2685
Thr Pro Pro Arg Asp Lys Asp Ser Leu Asn Pro Val Thr Arg Phe
    2690            2695                2700
Phe Asn Asn Glu Leu Tyr Gly Phe Lys Glu Asp Arg Arg His Ile
    2705            2710                2715
Ser Asp Lys Thr Gln Thr Ile Leu Asn Asp Ala Val Ala Asn Gly
    2720            2725                2730
Lys Ser Ser Lys Ile Thr Leu Lys Gly Glu Glu Gly Arg Leu Thr
    2735            2740                2745
Gly Tyr Tyr His Gln Gly Asp Ile Lys Pro Asp Asp Ile Ser Thr
    2750            2755                2760
Ala Ala Glu Lys Lys Val Val Leu Phe Leu His Gly Ser Gly Leu
    2765            2770                2775
Ser Ala Glu Glu Gln Ala His Asp Ile Gln Ser His Tyr Gln Lys
    2780            2785                2790
Gln Gly Ile Asp Ile Leu Ala Val Asn Met Arg Gly Tyr Gly Gly
    2795            2800                2805
Ser Asp Gly Ser Pro Gly Glu Gln Gly Phe Tyr Gln Asp Ala Arg
    2810            2815                2820
Thr Met Phe Arg Tyr Leu Val Gln Asp Arg Gly Ile Lys Pro Gly
```

-continued

```
                2825                2830                2835

Asn Ile Ile Leu His Gly Tyr Ser Val Gly Gly Pro Val Ala Ala
    2840                2845                2850

Asp Leu Ala Arg Tyr Ala Ser Gln Asn Asn Gln Ala Val Ser Gly
    2855                2860                2865

Leu Leu Leu Asp Arg Pro Ile Ser Ser Met Thr Lys Thr Ile Thr
    2870                2875                2880

Ala His Asp Val Pro Asn Pro Gly Gly Met Ile Gly Ala Leu Ala
    2885                2890                2895

Lys Ala Met Asn Gly Gln Phe Ser Val Glu Lys Asn Leu Lys Gly
    2900                2905                2910

Leu Pro Ile Asn Thr Pro Ile Met Leu Leu Thr Asp Asn Gln Gly
    2915                2920                2925

Leu Gly His Glu Gly Glu Lys Leu Arg Ala Arg Leu Ala Ala Ser
    2930                2935                2940

Gly Tyr Arg Val Ser Gly Glu Gln Thr Phe Tyr Gly His Val Glu
    2945                2950                2955

Ser Gly Ala Leu Met Ser Gln Tyr Thr Asp Arg Ile Val Ser Thr
    2960                2965                2970

Leu Ser Asp Phe Gln Asn Lys Asn Arg Asp Gly Val Lys Asn Ser
    2975                2980                2985

Trp Gln Lys Ser Asp Asn Arg Gly Thr Arg Phe Asp Gly Gln Ile
    2990                2995                3000

Ile Ile Gln Met Glu Asn Asp Pro Ile Val Ala Lys Ala Ala Leu
    3005                3010                3015

Asn Leu Ala Ser Lys His Arg Lys Ser Ser Val Val Lys Leu
    3020                3025                3030

Asp Ser Asn Gly Lys Tyr His Val Ile Tyr Gly Asp Pro Ala Gly
    3035                3040                3045

Leu Ser Gly Lys Leu Arg Trp Gln Ile Val Gly His Gly Arg Asn
    3050                3055                3060

Glu Ser Ala Gln Asn Asn Thr Arg Leu Ser Gly Tyr Ser Ala Asp
    3065                3070                3075

Glu Leu Ala Ile Lys Leu Lys Gln Phe Ser Gln Asn Phe Glu Gln
    3080                3085                3090

Ala Gly Lys Pro Asp Arg Ile Ser Ile Val Gly Cys Ser Leu Ile
    3095                3100                3105

Ser Asp Asp Lys Arg Asn Gly Phe Ala Tyr Arg Phe Ile Thr Ala
    3110                3115                3120

Leu Asp Lys Gln Gly Ile Arg Ser Glu Val Ser Ala Arg Arg Ser
    3125                3130                3135

Glu Val Ala Val Asp Ala Thr Gly Arg Lys Phe Thr Arg Asp Lys
    3140                3145                3150

Asn His Gln Trp Val Asn Lys Leu Asp Asp Asn Lys Leu Val Leu
    3155                3160                3165

Arg Trp Asn Glu Gln Asp Glu Leu Thr Thr Thr Glu Lys Leu
    3170                3175                3180

Arg Arg Gly Val Ala Glu Ser Asp Ile Asn Leu Ala Lys Val Gly
    3185                3190                3195

His Thr Glu Ala Asp Ser Ala Thr Arg Gly Ala Ile Ala Asp Asn
    3200                3205                3210

His Asp Val Phe Thr Ala Pro Gly Lys Arg Lys Asn Arg Val Glu
    3215                3220                3225
```

-continued

Leu Gly Ser Asn Pro Gln Ser Glu Pro Leu Tyr Ala Gly Asn
3230              3235                3240

Ile Gln Val Asn Val Gly Asp Gly Glu Phe Thr Ala Ile Asn Trp
3245              3250                3255

Gly Thr Ser Asn Val Gly Ile Lys Val Gly Thr Gly Gly Phe Lys
3260              3265                3270

Ser Leu Ala Phe Gly Asp Asn Asn Val Met Val His Ile Gly Glu
3275              3280                3285

Gly Asp Ser Lys His Ser Val Asn Leu Ala Gly Tyr Gln Ala Leu
3290              3295                3300

Glu Gly Ala Gln Met Phe Ile Gly Asn Arg Asn Val Ser Phe Asn
3305              3310                3315

Gln Gly Arg Ser Asn Asp Leu Ile Val Met Met Asp Lys Ser Ile
3320              3325                3330

Pro Thr Pro Pro Leu Val Asn Pro Phe Asp Gly Ala Ala Arg Ile
3335              3340                3345

Thr Gly Val Leu Lys Ser Ile Ala His Ser Gly Glu Glu Arg Asn
3350              3355                3360

Trp Leu Ala Ala Gln Asn Gln Gln Trp Thr Leu Ser Gly Ala Lys
3365              3370                3375

Lys Phe Val Arg Asp Met Ser Gly Leu Asp Gln Thr Ser Ser Val
3380              3385                3390

Asp Tyr Lys Thr Leu Val Asp Leu Asp Ser Gln Leu Lys Arg Ser
3395              3400                3405

Ser Arg Gly Leu Lys Ser Asp Thr Glu Ala Ala Leu Asn Lys Lys
3410              3415                3420

Tyr His Gln Trp Leu Asn Gly His Gly Asn Asn Ile Asp Thr Lys
3425              3430                3435

Lys Met Ser Arg Val Asp Lys Phe Arg Gln Ala Asn Glu Lys Leu
3440              3445                3450

Ala Phe Asn Phe Ala Val Gly Gly Gln Gly Ala Asp Ile Gln Val
3455              3460                3465

Thr Thr Gly Ser Trp Asn Phe Met Phe Gly Asp His Ile Gln Ser
3470              3475                3480

Ile Leu Asp Thr Asn Leu Gly Ser Leu Phe Gly Leu Met Thr Gln
3485              3490                3495

Gln Tyr Ser Thr Thr Gly Leu Ala Lys Thr Thr Phe Thr Tyr Asn
3500              3505                3510

Leu Gln Asp Leu Pro Arg Gln Leu Lys Asn Lys Leu Leu Gly Arg
3515              3520                3525

Leu Ala Gly Val Asn Ala Glu Thr Thr Leu Ala Asp Ile Phe Gly
3530              3535                3540

Val Asp Tyr Thr Pro Glu Gly Gln Ile Val Ala Arg Thr Gly Glu
3545              3550                3555

Pro Val Asp Gly Lys Ala Ile Leu Arg Glu Met Leu Glu Val Ile
3560              3565                3570

Lys Gln Phe Gly Gly Asp Gln Leu Ser Val Phe Thr Asp Pro Asp
3575              3580                3585

Lys Leu Ile Glu Gly Leu Lys Gln Asn Ala Asn Met Ser Ala Asp
3590              3595                3600

Gly Ile Glu Ser Phe Phe Val Ser His Gly Leu Lys Glu Lys Ala
3605              3610                3615

Pro Asp Glu Asn Arg Glu Lys Ser Val Pro Asp Ala Val Asn Ser
3620              3625                3630

-continued

Gly Lys Ser Gln Ala Asp Asp Lys Ser Glu Arg Ala Leu Gly Phe
3635                3640                3645

Asn Ser Leu Asn Leu Pro Asn Leu Phe Ala Thr Ile Phe Ser Lys
3650                3655                3660

Asp Lys Gln Gln Glu Met Lys Ser Leu Val Thr Asn Leu Lys Glu
3665                3670                3675

Asn Leu Thr Ala Asp Leu Leu Asn Met Glu Gln Lys Thr Phe Asp
3680                3685                3690

Phe Leu Arg Asn Ser Gly His Leu Gln Gly Asp Ser Asp Ile His
3695                3700                3705

Ile Ser Leu Gly Asn Tyr Asn Phe Asn Trp Gly Gly Asp Gly Lys
3710                3715                3720

Asp Leu Gly Ala Tyr Leu Gly Asp Asn Asn Asn Phe Trp Gly Gly
3725                3730                3735

Arg Gly Asp Asp Val Tyr Tyr Ser Ile Gly Thr Ser Asn Ile Phe
3740                3745                3750

Thr Gly Gly Glu Gly Asp Asp Leu Gly Val Leu Met Gly Arg Glu
3755                3760                3765

Asn Trp Met Phe Gly Gly Ser Gly Asp Asp Thr Ala Val Val Ala
3770                3775                3780

Gly Arg Ile Asn His Val Phe Met Gly Glu Gly Asn Asp Gln Thr
3785                3790                3795

Phe Val Phe Gly Glu Gly Gly Val Ile Asp Ala Gly Asn Gly Arg
3800                3805                3810

Asp Tyr Val Val Thr Ser Gly Asn Tyr Asn Gln Val Asp Thr Gly
3815                3820                3825

Glu Asp Gln Asp Tyr Ala Val Thr Ile Gly Asn Asn Asn Arg Val
3830                3835                3840

Glu Leu Gly Glu Gly Asn Asp Phe Gly Arg Val Phe Gly Asn Asp
3845                3850                3855

Asn Arg Ile Asp Gly Asn Met Gly Asn Asp Val Ile Lys Leu Met
3860                3865                3870

Gly Tyr His Ala Val Ile Asn Gly Gly Glu Gly Asp Asp His Leu
3875                3880                3885

Ile Ala Ala Thr Ile Ser Lys Phe Ser Gln Phe Asp Gly Gly Glu
3890                3895                3900

Gly Gln Asp Leu Leu Val Leu Gly Gly Tyr Gln Asn His Phe Gln
3905                3910                3915

Gly Gly Ala Gly Val Asp Ser Phe Val Val Ser Gly Lys Val Ile
3920                3925                3930

Asp Ser Gln Val Asp Asp Ile Asn Ala Glu Asp Met Ile Ala Phe
3935                3940                3945

Asn Asp Ile Asp Trp Gln Asp Leu Trp Phe Gln Arg Ser Gly Tyr
3950                3955                3960

Asp Leu Val Leu Ser Val Asn Arg Pro Thr Gln Asp Lys Thr Ala
3965                3970                3975

Gln Gly Leu Phe Glu Ser Val Gly Ser Val Thr Phe Arg Asp Tyr
3980                3985                3990

Phe Asn Gly Asn Arg Ala Lys Leu Val Thr Gln Met Gly Arg Lys
3995                4000                4005

Asp Ala Ser Gly Glu Arg Glu Phe Thr Ala Leu Ser Asp Asn Ala
4010                4015                4020

Val Asp Thr Leu Ile Gln Ala Met Ser Ser Phe Ala Pro Thr Ala

```
                        4025                4030                4035

Gly Asp Asn Gly Phe Ile Glu Ala Leu Asp Asn Arg Glu Lys Met
    4040                4045                4050

Ala Ile Thr Thr Ala Trp Ala Asp Thr Thr Ile Gly Lys Gly Lys
    4055                4060                4065

Phe Ala
    4070

<210> SEQ ID NO 6
<211> LENGTH: 3528
<212> TYPE: PRT
<213> ORGANISM: Photorhabdus luminescens

<400> SEQUENCE: 6

Met Phe Met Gly Lys Ser Ser Asn Arg Ser Ala Glu Tyr Phe Phe Thr
1               5                   10                  15

Gly Arg Tyr Tyr Asp Asp Asp Gly Asn Asn Ile Val Ala Ile Gly
            20                  25                  30

Val Gly Gly Ile Ile Tyr Ala Lys Gly Gly Asp Asp Arg Ile Thr Leu
        35                  40                  45

Gly Ser Ile Gly Ala Thr Val Tyr Ala Asp Ser Gly Asn Lys Val Val
    50                  55                  60

Asn Gly Gly Ala Gly Tyr Leu Lys Ile Val Asp Lys Glu Gly Asn Leu
65                  70                  75                  80

Ala Val His Gly Ala Ala Gly Tyr Ser Gly Ile Asp Lys Cys Gly Asn
                85                  90                  95

Gly Asn Ile Ser Phe Thr Gly Thr Ala Gly Val Ser Met Asp His
            100                 105                 110

Arg Gly Asp His Gly Asp Leu Asn Phe Ser Gly Ala Ala Ala Tyr Asn
        115                 120                 125

Gly Leu Asn Arg Gln Gly Gln Ser Gly Asn Val Thr Phe Asn Gly Val
    130                 135                 140

Gly Gly Tyr Asn Glu Leu Trp His Glu Thr Asn Gln Gly Asn Leu Asn
145                 150                 155                 160

Phe Ala Gly Ala Gly Ala Gly Asn Lys Ile Asp Arg Thr Trp Tyr Asp
                165                 170                 175

His Tyr Glu Lys Ser His Gly Asp Val Lys Phe Asp Gly Gly Gly Ala
            180                 185                 190

Ala Asn Ser Ile Ser Ser Arg Val Glu Ser Gly Asn Ile Asn Phe Thr
        195                 200                 205

Gly Val Gly Ala Asp Asn His Leu Ile Arg Lys Gly Lys Glu Gly Asn
    210                 215                 220

Ile Ile Leu His Gly Ala Gly Ala Ser Asn Arg Ile Glu Arg Leu Arg
225                 230                 235                 240

Gln Asn Gln Asp Gln Tyr Glu Gln Thr His Gly Asn Ile Glu Phe Glu
                245                 250                 255

Gly Thr Gly Gly Tyr Asn Arg Ile Tyr Ser Asp Ile Ala His Gly Asp
            260                 265                 270

Ile Thr Phe Glu Gly Ala Gly Ala Tyr Asn Glu Ile Ser Arg Ile Gly
        275                 280                 285

Glu Asp Ser Asp Ser Arg Asn Glu Ala Leu Glu Tyr Ala Lys Ala Glu
    290                 295                 300

Glu Ile Val Leu Thr Thr Ala Met Met Gly Gly Ser Trp Ile Gln Gln
305                 310                 315                 320

Ser Gln Gln Val Thr Gly Ile Lys Ser Thr Ala Glu Pro Asp Thr Tyr
```

```
                   325                 330                 335
Leu Phe Ala Phe Ala Asp Glu Met Tyr Thr Lys Ile Ser Lys Val Gln
            340                 345                 350
Leu Arg Asn Asp Pro Glu Thr Gly Lys Leu Ser Tyr Tyr Ala Thr Ser
            355                 360                 365
Trp Tyr Lys Glu Gly Asn His Leu Asn Asn Leu Ala Thr Glu Asn Ile
            370                 375                 380
Ser Ser Ser Asn Gly Phe Phe Asp Ile Arg Ser Asn Gly Gly Tyr Arg
385                 390                 395                 400
Leu Phe Asn Leu Ile Phe Glu His His His Pro Val Ile Ile Gln His
                405                 410                 415
Thr Val Glu Glu Asp Leu Gln Glu Asn Gln Trp Val Thr Tyr Ala Gly
            420                 425                 430
Gly Thr Asn Ala Arg Ala Glu Asn Val Met Leu Thr Asn Ala Lys Met
            435                 440                 445
His Gly Asn Ala Ile His Ser Gly Gly Leu Ile Leu Asp Val Ser Ala
            450                 455                 460
Val Lys Ser Asn Arg Gln Ala Asn Thr Tyr Ile Tyr Ala Lys Tyr Val
465                 470                 475                 480
Glu Ser Tyr Thr Lys Val Val Met Val Glu Leu Arg Asn Asp Ala Lys
                485                 490                 495
Thr Gly Ala Leu Gln Tyr Tyr Ala Ser Ala Trp Tyr Lys Ala Gly Asp
            500                 505                 510
His Thr Ser Asn Leu Ala Ala Glu Lys Val Ser Pro Gln Asn Gly Tyr
            515                 520                 525
Arg Ser Met Asp Ile Gly Gly Tyr Ser Leu Thr Asn Leu Gln Tyr Gln
            530                 535                 540
Val Asn Thr Val Arg Arg Val Ser Glu His Leu Ala Gln Thr Glu Glu
545                 550                 555                 560
Tyr Ser His Gln Glu Leu Val Lys Ser Ser Ala Asp Met Gly Asp Ser
                565                 570                 575
Ser Gly Asp Ile Asn Phe Lys Gly Met Gly Gly Gly Asn Val Ile Thr
            580                 585                 590
Ser Ser Val Thr Arg Gly Asn Ile Asn Phe Glu Gly Ala Gly Ala Ala
            595                 600                 605
Asn Val Ile Val Lys Lys Gly Glu Gln Gly Asp Leu Thr Phe Arg Gly
            610                 615                 620
Ala Gly Leu Ala Asn Val Leu His Gln Gly Gln Arg Gly Glu Met
625                 630                 635                 640
Asp Val Tyr Ala Gly Gly Ala Ala Asn Val Leu Val Arg Ile Gly Asp
                645                 650                 655
Gly Arg Tyr Leu Ala Arg Leu Leu Ala Ile Gly Asn Ile Ser Ile His
            660                 665                 670
Gln Gly Asn Gly Asp Ser Arg Val Ser Met Phe Gly Gly Tyr Asn Thr
            675                 680                 685
His Ser Gln Ile Gly Asn Gly Asn Ala Asn Trp Leu Gly Ala Gly Gly
            690                 695                 700
Phe Asn Val Met Thr Gln Thr Gly Lys Gly Lys Val Ser Ser Val Leu
705                 710                 715                 720
Ala Gly Gly Ala Asn Val Leu Thr Lys Leu Gly Ala Gly Asp Leu Asp
                725                 730                 735
Ala Gly Met Leu Gly Gly Ala Asn Ile Ile Thr His Leu Asn Asp Gly
            740                 745                 750
```

-continued

Glu Ile Ser Gly Thr Thr Ala Val Ala Leu Gly Gly Ala Asn Ile Leu
    755                 760                 765

Thr Lys Lys Gly Arg Gly Lys Ala Ile Ala Leu Met Gly Gly Gly Ala
770                 775                 780

Asn Val Leu Thr His Ile Gly Asn Gly Ser Thr Thr Gly Met Met Leu
785                 790                 795                 800

Gly Gly Ala Asn Ile Leu Thr Lys Val Gly Asn Gly Asp Ala Thr Gly
            805                 810                 815

Ile Met Leu Gly Leu Gly Asn Val Leu Thr His Val Gly Ser Gly Gln
        820                 825                 830

Thr Leu Gly Val Met Gly Ala Ala Gly Asn Val Phe Thr Lys Val Gly
            835                 840                 845

Ser Gly Thr Thr Ile Ala Ala Met Ile Gly Ala Gly Asn Ile Phe Thr
    850                 855                 860

His Val Gly Asn Gly Asp Ala Trp Gly Leu Met Gly Leu Gly Leu Gly Asn
865                 870                 875                 880

Val Phe Thr Lys Val Gly Asn Gly Lys Ala Leu Ala Leu Met Ile Ala
                885                 890                 895

Ala Gly Asn Val Phe Thr His Ile Gly Asp Glu Met Ser Val Ala Leu
            900                 905                 910

Met Leu Ala Lys Gly Asn Ile Ala Thr Lys Val Gly Asn Gly Met Met
        915                 920                 925

Leu Ala Ala Met Ile Gly Glu Ala Asn Val Met Thr His Ile Gly Asn
930                 935                 940

Gly Ser Thr Phe Ala Ala Met Ile Gly Gln Gly Asn Ile Leu Thr Lys
945                 950                 955                 960

Val Gly Asn Asp Leu Ala Leu Gly Leu Met Val Gly Glu Ala Asn Ile
            965                 970                 975

Tyr Ser His Val Gly Asn Gly Thr Ser Ile Gly Leu Phe Ala Gly Glu
        980                 985                 990

Leu Asn Val Met Thr Arg Val Gly Asp Gly Thr Thr Leu Ala Ala Met
            995                 1000                1005

Phe Gly Gln Ala Asn Ile Met Thr His Ser Gly Asn Gly Leu Thr
    1010                1015                1020

Gly Val Leu Ala Leu Gly Glu Ala Asn Ile Val Thr Lys Val Gly
    1025                1030                1035

Asp Asp Phe Met Gly Val Val Ala Ala Ala Glu Ala Asn Val Ile
    1040                1045                1050

Thr His Lys Gly Ser Ser Thr Thr Ala Ala Val Leu Phe Gly Lys
    1055                1060                1065

Gly Asn Ile Leu Thr Lys Val Gly Asp Gly Thr Thr Val Gly Leu
    1070                1075                1080

Leu Ile Ser Asp Val Gly Asn Ile Met Thr His Val Gly Asp Gly
    1085                1090                1095

Thr Thr Val Gly Phe Ala Lys Gly Lys Ala Asn Ile Ile Thr Lys
    1100                1105                1110

Val Gly Asn Gly Thr Gly Val Asn Ala Val Trp Gly Asp Ala Asn
    1115                1120                1125

Ile Leu Thr Gln Val Gly Asp Gly Asp Arg Tyr Asn Phe Ala Lys
    1130                1135                1140

Gly Lys Ala Asn Ile Ile Thr Lys Val Gly Asn Asn Gln Glu Ile
    1145                1150                1155

Thr Val Val Gln Gly Asp Ala Asn Ile Ile Thr His Val Gly Gln
    1160                1165                1170

-continued

```
Gly Asp Asp Tyr Thr Gly Ala Trp Gly Lys Ala Asn Val Ile Thr
1175                1180                1185

Lys Val Gly Asp Gly Arg Asn Val Val Leu Ala Lys Ala Asp Ala
1190                1195                1200

Asn Ile Val Thr Gln Val Gly Asn Gly Asp Ser Phe Asn Ala Leu
1205                1210                1215

Trp Ser Arg Gly Asn Ile Val Thr Lys Val Gly Asp Gly Met Gln
1220                1225                1230

Val Thr Ala Ala Lys Gly Glu Ala Asn Ile Thr Thr Lys Val Gly
1235                1240                1245

Asn Gly Leu Ser Val Thr Ala Thr His Gly Asp Phe Asn Ile Asn
1250                1255                1260

Thr Asn Val Gly Asp Gly Ile Ser Ile Asn Ala Ala Trp Gly Glu
1265                1270                1275

Tyr Asn Val Asn Thr Lys Val Gly Gln Gly Leu Asn Val Ala Ile
1280                1285                1290

Met Lys Gly Lys Gly Asn Ala Asn Ile His Ile Gly Asp Gly Leu
1295                1300                1305

Gly Ile Asn Ala Ser Tyr Ala Arg Asn Asn Leu Ala Ile Lys Val
1310                1315                1320

Gly Asn Gly Asp Phe Tyr Thr Leu Ser Ile Ala Glu Ser Asn Thr
1325                1330                1335

Gln Ser Asn Asn Leu Pro Phe Leu Phe Lys Ser Ile Lys Arg Thr
1340                1345                1350

Val Leu Ser Val Glu Gly Ser Gln Ala Ile Asn Tyr Leu Ile His
1355                1360                1365

Gly Asn Glu Ala Asn Ser Ser Gly Thr Tyr Arg Ser Arg Gly Ala
1370                1375                1380

Ile Asn Leu Thr Glu Val Ser Ala Ile Asp Gly Phe Gln Met Asn
1385                1390                1395

Ala Ile Asp Asp Val Gly Ser Asp Leu Arg Asp Lys Leu Ser Gly
1400                1405                1410

Thr Val Thr Gln Val Glu Ile Pro Asp Thr Glu Ala Ile Gln Asn
1415                1420                1425

Ala Leu His Ile Gly Asp Lys Val Asp Ser Thr Gln Ser Glu Ser
1430                1435                1440

Ser Ser Gln Ala Asp Ala Val Ile Lys Gln Ala Lys Gln Asp Ser
1445                1450                1455

Ala Glu Gln Asn Ala Leu Asn Asp Lys Glu Lys Ala Glu Glu Asn
1460                1465                1470

Tyr Arg Ile Leu Glu Gln Arg Asp Asn Gln Leu Lys Glu Ile
1475                1480                1485

Ser Lys Pro Gln Phe Gln Leu Glu Ser Thr Asp Gln Asn Val Leu
1490                1495                1500

Asn Thr Asn Gly Gln Val Gln Arg Asp Ala Ile Ser Gly Glu Ser
1505                1510                1515

Arg Ala Val Thr Lys Glu Leu Leu Ser Met Thr Gln Arg Leu Asn
1520                1525                1530

Ala Leu Asn Asp Asp Gly Asn Tyr Ala Gly Glu Leu Gly Asp Glu
1535                1540                1545

Trp Arg Asn Arg Phe Ala Val Gly Tyr Leu Asp Arg Ile Gln Glu
1550                1555                1560

Lys Leu Asp Asp Thr Lys Leu Ile Ser Gln Lys Lys Leu Ala Asp
```

```
                            1565                1570                1575

Leu Ser Pro Arg Phe Ile Asp Asn Gln Gln Val Lys Asn Ala
    1580                1585                1590

Val Gly Lys Ser Glu Thr Gly Leu Glu Gln Ser Tyr His Asn Ile
    1595                1600                1605

Lys Asn Ala Asp Asp Asn Ile Glu Asp Ala His Thr Lys Ala Lys
    1610                1615                1620

Ser Arg Gln Lys Glu Ala Asp Leu Gln Arg Leu Arg Ala Thr Lys
    1625                1630                1635

Ala Glu Ser Asp Ala Tyr Ala Val Tyr Glu Glu Ala Lys Gln Arg
    1640                1645                1650

Gly Glu His Asp Ser Ser Val Ala Lys Asn Lys Ala Ala Gln Val
    1655                1660                1665

Gln Ala Asp Ala Lys Gly Ala Lys Gln Thr Gly Asp Val Lys Pro
    1670                1675                1680

Glu Arg Ser Gly Ala Thr Gly Ser Gly Leu Ser Gly Lys Ala Tyr
    1685                1690                1695

Thr Pro Ile Asp Val Ala Lys Pro Lys Ser His Ile Asn Pro Glu
    1700                1705                1710

Ala Lys Met Glu Ala Asn Gly Trp Asn Ser Glu Asp Leu Thr Leu
    1715                1720                1725

Thr Ala Ala Asp Leu Ala Gly Leu Asn Ser Ala Gln Arg Ala Ile
    1730                1735                1740

Asn Arg Leu Gln Ile Asn Arg Ser Ser Arg Pro Glu Asn Val Gly
    1745                1750                1755

Ala Ser Ile Ile Ser Leu Leu Thr Gly Thr Pro Ser Asp Arg Val
    1760                1765                1770

Val Glu Pro Ile Ser Asn Gln Thr Arg Lys Leu Ile Thr Thr Ala
    1775                1780                1785

Pro Val Met Ser Gly Ile Asn Leu Gln Gly Leu Gly Gln Val Ile
    1790                1795                1800

Gly Gly Asp Ser Phe Lys Ser His Ser Ser Ile Leu Arg Glu Phe
    1805                1810                1815

Glu Pro Phe Leu Leu Ser Gln Gly Asp Lys Arg Phe Ile Ala Ser
    1820                1825                1830

Thr Lys Arg Tyr Leu Gly Gln Ile Asn Thr Asp Arg Pro Ser Lys
    1835                1840                1845

Ala Leu Val Ala Val Arg Glu Ala Phe Asn Asn Ala Ala Glu Gln
    1850                1855                1860

Pro Asp Glu Gln His Val Leu Gln Leu Glu Gln Ala Leu Ala His
    1865                1870                1875

Trp Gln Gln His Asp Pro Asn Glu Phe Ala Lys Arg Gly Arg Leu
    1880                1885                1890

Val Lys Ser Leu Arg Phe Glu Met Gly Glu Leu Val Ala Tyr Leu
    1895                1900                1905

Gln Ala Lys Arg Ala Glu Ser Ala Gly Ile Leu Gly Val Ser Leu
    1910                1915                1920

Ala Pro Asp His Val Ala Gln Phe Asp Gln Gln Val Ser Phe Asp
    1925                1930                1935

Gly Phe Gly Arg Val Val Gly Leu Lys Gly Asp Ile Ala Gln Ser
    1940                1945                1950

Asp Ile His Arg Leu Thr Asp Leu Gln Ile Lys Pro Leu Thr Gln
    1955                1960                1965
```

-continued

Ile Asn Ser Ala Ala Glu Arg Glu Ala Pro Lys Thr Glu Ser Glu
1970                1975                1980

Ser Leu Ile Val Phe Val Ser Arg Leu Gln Gln Glu Ala Ile Pro
    1985                1990                1995

Glu Gly Met Pro Leu Ile Glu Arg Ala Lys Asn Leu Trp Leu Ser
2000                2005                2010

Gly Gln Val Thr Arg Gln Glu Thr Ile Lys Leu Phe Glu Asp Ala
    2015                2020                2025

Val Ser Gln Leu Gln Thr His Pro Glu Leu His Thr Leu Ala Gln
2030                2035                2040

Gln Leu Leu Ala Asp Ala Arg Lys Glu Lys Thr Thr Gly Gln Tyr
    2045                2050                2055

Ile Asp Asn Leu Phe Gly Arg His Phe Asp Ser Glu Leu Ala Asp
2060                2065                2070

Glu Leu Val Lys Thr Ala Pro Gln Asp Ala Met Thr Thr Ala Arg
    2075                2080                2085

Gln Thr Gly Gln Phe Leu Val Glu Arg Phe Glu Gln Trp Ile Gly
2090                2095                2100

Gly Phe Tyr Pro Asp Val Ala Glu Arg Glu Lys Ile Ile Ala Lys
    2105                2110                2115

Lys Met Ala Gly Phe Ala Arg Ala Ile Asn Lys Asp Phe Arg Pro
2120                2125                2130

Trp Phe Ser Arg Val Pro Glu Leu Thr Thr Phe Leu Asp Glu Pro
    2135                2140                2145

Thr Phe Ala Asn Phe Lys Ile Met Met Thr Gln Val Asp Asp Gly
2150                2155                2160

Phe Ala Val Ile Lys Ile Pro Phe Leu Ala Val Lys Met Ala Ile
    2165                2170                2175

Thr Ser Gly Met Gly Met Gly Arg Ala Gln Trp Lys Val Ala Gly
2180                2185                2190

Asp Arg Phe Tyr Glu Glu Val Ile Thr Lys Ala Arg Ser Thr Ser
    2195                2200                2205

Ser Gln Leu Thr Ser Gly Ala Asp Val Thr Tyr Asn Val Glu Ile
2210                2215                2220

Thr Glu Lys Gln Thr Asn Asp Tyr Gly Thr Ala Leu Pro Tyr Gln
    2225                2230                2235

Pro Ala Asn Asn Lys His Asp Asp Phe Leu Tyr Gly Arg Lys Val
2240                2245                2250

Ala Ala Gly Arg Ile Leu Val Pro Gly Trp Glu Thr Arg Phe Glu
    2255                2260                2265

His Asn Ala Leu Ala Gln Gly His Ser Val Val Thr Gly Ala Ser
2270                2275                2280

Gly Ser Thr Asn Ile Met Val His Leu Asn Asn Tyr Ile Ala Ser
    2285                2290                2295

Glu Gln Ile Ala Ser Glu Gln Pro Thr Phe Ser Val Arg Gln Ser
2300                2305                2310

Tyr Leu Asn Thr Leu Val Phe Leu Val Phe Asp Gly Gly His Ser
    2315                2320                2325

Val Asn Glu Ser Leu Ala Val Tyr Arg Ala Leu Gln Val Thr Asp
2330                2335                2340

Asp Glu Gln Arg Lys Gln Leu Leu Asn Ser Tyr Thr Ala Asn Tyr
    2345                2350                2355

Arg Glu Leu Val Asp Ile Ala Gly Glu Glu Gly Lys Val Trp Val
2360                2365                2370

```
Ser Gln Ala Leu Asp Asn Ala Phe Arg Glu Thr Gly Glu Phe Tyr
    2375            2380                2385
Gln Lys His Ala Lys Val Lys Pro Gln Ser Arg Pro Ala Val Glu
    2390            2395                2400
Ala Leu Asp Trp Leu Ser Gly Lys Asn Lys Arg Pro Glu Pro Thr
    2405            2410                2415
Ile Ile Asp Asp Thr His Gln Asp Lys Lys Ile Ser Arg Leu Leu
    2420            2425                2430
Gly Asp Trp Gln Met Glu Gln Val Thr Pro Gln Ala Asp Gly Arg
    2435            2440                2445
Glu Thr Arg Phe Asp Gly Gln Ile Ile Ile Gln Met Glu Asp Asp
    2450            2455                2460
Pro Ile Val Ala Lys Ala Ala Ala Asn Leu Ala Gly Lys His Ser
    2465            2470                2475
Asp Ser Ser Val Val Val Gln Leu Asp Ser Lys Gly Lys Tyr Arg
    2480            2485                2490
Val Val Tyr Gly Asp Leu Thr Arg Leu Ser Gly Lys Leu Arg Trp
    2495            2500                2505
Gln Val Val Gly His Gly Arg Asp Thr Ser Glu Gln Asn Asn Ile
    2510            2515                2520
Arg Leu Ser Gly Tyr Thr Ala Asp Glu Leu Ala Thr Arg Leu Thr
    2525            2530                2535
Arg Phe Tyr Gln Asp Val Asn Gln Gly Lys Ser Ile Thr His Lys
    2540            2545                2550
Pro Asp His Ile Ser Ile Val Gly Cys Ser Leu Ile Ser Asp Asp
    2555            2560                2565
Lys Arg Asp Gly Phe Ala Arg Arg Phe Ile Thr Val Leu Asp Lys
    2570            2575                2580
Gln Gly Ile Arg Ser Asp Val Ser Ala Arg Ser Glu Val Ala
    2585            2590                2595
Val Asp Val Ser Gly Arg Lys Phe Thr Arg Asp Gln Asn Asn Gln
    2600            2605                2610
Trp Val Asn Asn Leu Pro Asp Asn Lys Ile Val Leu Ser Trp Tyr
    2615            2620                2625
Asp Gln Asn Glu Leu Ile Thr His Thr Glu Leu Val Arg Arg Gly
    2630            2635                2640
Ile Ala Glu Ser Asp Ile Asn Phe Ser Lys Val Gly Tyr Thr Glu
    2645            2650                2655
Ala Asp Thr Val Ile Asn Gly Ala Ile Ser Gly Asn Val Glu Leu
    2660            2665                2670
Phe Val Lys Pro Asn Lys Arg Glu Asn Thr Ile Gln Ile Asp Ser
    2675            2680                2685
Asn Glu Lys Thr Asn Asn Gln Leu Ser Tyr Ser Gly Asn Ile Gln
    2690            2695                2700
Val Asn Val Gly Asp Gly Glu Phe Thr Ala Leu Asn Trp Gly Thr
    2705            2710                2715
Ser Asn Val Gly Ile Lys Val Gly Ser Gly Gly Phe Lys Ser Leu
    2720            2725                2730
Ala Phe Gly Asp Asn Asn Val Met Val His Ile Gly Asn Gly Asp
    2735            2740                2745
Ser Lys Gln Ser Phe Asp Ile Ala Gly Tyr Gln Ala Leu Glu Gly
    2750            2755                2760
Ala Gln Met Phe Ile Gly Asn Arg Asn Val Ser Phe Asn Gln Gly
```

```
            2765                2770                2775

Arg Ser Asn Asp Leu Ile Val Met Met Asp Lys Ser Ile Pro Thr
        2780                2785                2790

Pro Pro Leu Ile Asn Pro Phe Asp Gly Val Ala Arg Ile Ala Asp
        2795                2800                2805

Val Leu Gln Gly Val Ala Gly Ala Ser Glu Asp Gln Asp Trp Leu
        2810                2815                2820

Ala Ala Gln Asp Gln Gln Trp Thr Ile Ala Gly Ala Lys Lys Phe
        2825                2830                2835

Val Gln Asp Leu Ser Gly Leu Asp Gln Thr Ser Asn Val Asp Tyr
        2840                2845                2850

Asn Thr Leu Val Glu Leu Asp Ser Gln His Glu Arg Ser Ser Arg
        2855                2860                2865

Gly Leu Lys Tyr Asp Ala Glu Leu Thr Leu Asn Lys Lys Phe Asn
        2870                2875                2880

Gln Trp Leu Gly Glu His Gly Asn Gly Ala Asp Met Gly Lys Ile
        2885                2890                2895

Ser Arg Met Asp Lys Phe Arg Gln Ala Asn Gln Lys Leu Ala Phe
        2900                2905                2910

Asn Phe Ala Val Gly Gly Arg Gly Ala Asp Ile Gln Val Thr Thr
        2915                2920                2925

Gly Asn Trp Asn Leu Met Phe Gly Asp His Ile Gln Ser Ile Leu
        2930                2935                2940

Asp Thr Asn Leu Gly Ser Leu Phe Gly Leu Met Thr Gln Gln Tyr
        2945                2950                2955

Ser Ala Thr Gly Met Ala Lys Thr Thr Phe Thr Tyr Asn Pro Gln
        2960                2965                2970

Asp Leu Pro Arg Gln Leu Lys Asn Lys Leu Ile Gly Arg Leu Ala
        2975                2980                2985

Ser Val Asn Ala Asp Thr Thr Leu Ala Asp Ile Phe Gly Val Asn
        2990                2995                3000

Tyr Thr Ala Glu Gly Lys Ile Ile Ser Arg Thr Gly Glu Ser Val
        3005                3010                3015

Asp Gly Glu Ala Ile Leu Gln Glu Met Leu Glu Val Ile Gly Glu
        3020                3025                3030

Phe Ser Gly Asp Gln Leu Gln Ala Phe Ile Asn Pro Glu Thr Leu
        3035                3040                3045

Leu Asp Ser Leu Lys Ala Gly Ile Asp Met Gly Glu Glu Gly Val
        3050                3055                3060

Arg Ser Phe Ala Glu Ser His Gly Leu Lys Gln Lys Ala Pro Asp
        3065                3070                3075

Glu Arg Gln Glu Ser Gly Ser Ser Val Asn Ile Asn Gly Glu Asn
        3080                3085                3090

Val Gln Thr Asn Asn Lys Pro Lys Pro Ala Phe Gly Phe Asn Ser
        3095                3100                3105

Leu Asn Leu Pro Asn Leu Phe Ala Thr Met Phe Ser Glu Glu Lys
        3110                3115                3120

Gln Arg Glu Met Lys Ser Leu Val Ala Asn Leu Lys Glu Asn Leu
        3125                3130                3135

Thr Thr Asp Leu Leu Asn Met Glu Glu Lys Thr Phe Asp Phe Leu
        3140                3145                3150

Arg Asn Ser Gly His Leu Gln Gly Asp Gly Asp Ile His Val Ser
        3155                3160                3165
```

```
Leu Gly Asn Tyr Asn Phe Asn Trp Gly Gly Asp Gly Lys Asp Leu
    3170            3175                3180

Gly Thr Tyr Leu Gly Asp Asn Asn Phe Trp Gly Gly Arg Gly
    3185            3190                3195

Asp Asp Val Tyr Tyr Ser Leu Gly Thr Ser Asn Ile Phe Ser Gly
    3200            3205                3210

Gly Glu Gly Asn Asp Leu Gly Val Leu Met Gly Arg Glu Asn Trp
    3215            3220                3225

Met Phe Gly Gly Lys Gly Asp Asp Thr Ala Val Val Ala Gly Arg
    3230            3235                3240

Ile Asn His Val Phe Met Gly Glu Gly Asn Asp Gln Thr Phe Val
    3245            3250                3255

Phe Gly Glu Gly Gly Phe Ile Asp Ala Gly Asn Gly Gln Asp Tyr
    3260            3265                3270

Val Val Thr Ala Gly Asn Tyr Asn Arg Met Asp Thr Gly Lys Gly
    3275            3280                3285

Gln Asp Tyr Ala Val Ile Ile Gly Asn Asn Asn Gln Ala Glu Leu
    3290            3295                3300

Gly Gly Gly Asp Asp Phe Ala Arg Val Phe Gly Asn Asp Asn Arg
    3305            3310                3315

Leu Asp Gly Tyr Cys Gly Asn Asp Ala Ile Lys Leu Met Gly Tyr
    3320            3325                3330

His Ala Val Ile Asn Gly Gly Glu Gly Asp His Leu Ile Ala
    3335            3340                3345

Ala Ala Ile Ser Lys Phe Ser Gln Leu Asp Gly Gly Glu Gly Gln
    3350            3355                3360

Asp Leu Leu Val Leu Gly Gly Tyr Gln Asn His Phe Arg Gly Gly
    3365            3370                3375

Ala Gly Val Asp Ser Phe Val Ser Glu Glu Val Ile Asp Asn
    3380            3385                3390

Arg Val Ser Asp Ile Asn Ala Glu Asp Met Ile Leu Phe Asn Gly
    3395            3400                3405

Val Asp Trp Gln Asn Leu Trp Leu Gln Arg Ser Gly Tyr Asp Leu
    3410            3415                3420

Val Leu Ser Val Lys Arg His Thr Gln Asp Asn Thr Ala Gln Gly
    3425            3430                3435

Arg Phe Glu Ser Glu Gly Ser Val Ile Phe Asn Asp Tyr Phe Asn
    3440            3445                3450

Gly Asn Arg Ala Lys Leu Val Thr Arg Met Ser Asp Lys Asn Ala
    3455            3460                3465

Ser Gly Glu Arg Glu Phe Thr Ala Leu Ser Asp Asn Ala Val Asp
    3470            3475                3480

Ser Leu Ile Gln Ala Met Ser Gly Phe Ala Pro Ala Val Gly Asp
    3485            3490                3495

Asn Gly Phe Ile Ala Gly Leu Asp Ser Gln Ala Lys Thr Ala Ile
    3500            3505                3510

Ala Thr Ala Trp Thr Asp Val Thr Ile Gly Lys Gly Lys Phe Ala
    3515            3520                3525

<210> SEQ ID NO 7
<211> LENGTH: 3531
<212> TYPE: PRT
<213> ORGANISM: Photorhabdus luminescens

<400> SEQUENCE: 7
```

```
Met Gly Lys Ser Ser Asn Arg Ser Ala Glu Phe Phe Thr Gly Lys
1               5                   10                  15

Tyr Asp Asp Asp Gly Gly Asn Asn Ile Val Ala Ile Gly Leu Gly
            20                  25                  30

Gly Glu Ile Tyr Ala Lys Gly Gly Asn Asp His Ile Thr Val Gly Ser
            35                  40                  45

Leu Gly Ala Thr Ile Tyr Ala Ser Ser Gly Asp Lys Thr Val Asp Gly
50                  55                  60

Gly Ala Gly Tyr Leu Lys Ile Val Asn Ile Gly Asp Leu Lys Val
65                  70                  75                  80

His Gly Ala Ala Gly Tyr Ala Ser Ile Asp Lys Asn Gly Asn Gly Asn
                85                  90                  95

Ile Ser Phe Ile Gly Ala Ala Gly Val Ser Met Asp His Arg Gly
            100                 105                 110

Ser Ser Gly Asn Leu Asn Phe Ser Gly Ala Ala Tyr Asn Asn Leu
        115                 120                 125

Ser Arg Arg Gly Gln Ser Gly Asn Val Thr Phe Lys Gly Ile Gly Gly
        130                 135                 140

Tyr Asn Gly Leu Trp His Glu Thr His Gln Gly Asp Leu Asn Phe Asn
145                 150                 155                 160

Ala Ala Gly Ala Gly Asn Lys Ile Asp Arg Thr Trp His Asp Arg Tyr
                165                 170                 175

Glu Gly Ser Lys Gly Asn Val Ile Phe Val Gly Gly Ala Ala Asn
            180                 185                 190

Ser Ile Ser Ser Arg Val Glu Ser Gly Asn Ile Glu Phe Thr Gly Ala
        195                 200                 205

Gly Val Asp Asn His Ile Ile Arg Lys Gly Lys Glu Gly Asn Ile Ile
        210                 215                 220

Phe Gln Gly Ala Gly Ala Leu Asn Arg Ile Glu Arg Leu Arg Asp Ser
225                 230                 235                 240

Lys Asp Lys Tyr Glu Gln Thr Arg Gly Asn Ile Glu Phe Glu Gly Ala
            245                 250                 255

Gly Gly Tyr Asn Lys Val Tyr Ser Asp Ile Ala His Gly Asn Ile Arg
            260                 265                 270

Phe Ser Gly Ser Gly Gly Tyr Asn Glu Ile Ser Arg Ile Gly Glu Asp
        275                 280                 285

Ser Asp Ser Tyr Asn Lys Ala Leu Gly Tyr Ala Ser Ala Glu Lys Ile
        290                 295                 300

Val Leu Ile Thr Ala Lys Met Gly Ser Gln Lys Pro Gln Gln Val Thr
305                 310                 315                 320

Ala Ile Lys Ser Thr Thr Glu Ser Asn Thr Tyr Leu Phe Ala Phe Ala
            325                 330                 335

Asp Gly Lys Tyr Thr Lys Ile Ser Lys Val Gln Leu Lys Asn Asp Pro
            340                 345                 350

Lys Thr Asn Lys Leu Ser Tyr Tyr Ser Thr Ser Trp Arg Lys Asn Gly
        355                 360                 365

Asn Gln Leu Lys Asn Leu Ala Thr Glu Asn Ile Ser Leu Glu Asn Gly
        370                 375                 380

Tyr Asp Asp Ile Ser Asn Asp Gly Asp Tyr Arg Leu Ser Asn Leu Ile
385                 390                 395                 400

Phe Glu His His Gln Pro Val Thr Ile Gln His Thr Val Glu Glu Asp
            405                 410                 415

Leu Arg Glu Asn Gln Trp Val Thr Tyr Ala Ser Gly Thr Ala Lys
            420                 425                 430
```

```
Ala Glu Asp Ile Lys Leu Ile Asp Ala Lys Met His Gly Arg Ser Ile
        435                 440                 445
His Ser Asn Gly Ser Val Leu Asp Val Ser Ala Val Lys Ser Asn Arg
        450                 455                 460
Arg Ser Asn Ala Tyr Val Tyr Ala Lys Tyr Val Glu Ser Tyr Thr Lys
465                 470                 475                 480
Val Val Val Val Glu Leu Lys Asn Asp Lys Thr Gly Glu Leu Lys
                    485                 490                 495
Tyr Tyr Ala Ser Ala Trp Tyr Lys Ala Gly Asp His Thr Arg Asp Leu
                500                 505                 510
Ala Asn Glu Asp Phe Ser Arg Ala Asn Gly Tyr Ser Met Glu Val
        515                 520                 525
Gly Gly Tyr Ser Leu Thr Asn Leu Lys Tyr Gln Val Asp Thr Val Arg
        530                 535                 540
Arg Val Ser Glu His Leu Glu His Ile Glu Glu Asp Ser Leu Gln Glu
545                 550                 555                 560
Trp Val Lys Ser Ser Asn Ile Gly Asp Ser Ser Gly Asp Val Asn
                565                 570                 575
Phe Ser Gly Met Gly Gly Gly Asn Leu Ile Lys Ser Ser Val Ile Asn
            580                 585                 590
Gly Asn Val Asn Phe Glu Gly Asp Gly Ile Ala Asn Val Ile Leu His
            595                 600                 605
Ser Ser Arg Ser Gly Asn Thr His Phe Glu Gly Ala Gly Ala Ala Asn
        610                 615                 620
Ile Ile Glu Lys Ser Gly Ile Asp Gly Asn Leu Thr Phe Arg Gly Ala
625                 630                 635                 640
Gly Leu Ala Asn Val Leu Val His Gln Ser Arg Asn Gly Glu Met Asp
                645                 650                 655
Val Tyr Ala Gly Gly Ala Ala Asn Val Leu Val Arg Val Gly Asp Gly
            660                 665                 670
Arg Tyr Leu Ala Arg Leu Leu Ala Ile Gly Asn Ile Ser Ile His Gln
        675                 680                 685
Gly Asn Gly Asp Ser Arg Val Val Met Leu Gly Gly Tyr Asn Thr His
        690                 695                 700
Thr Gln Ile Gly Lys Gly Ser Ala Asn Trp Leu Gly Ala Gly Gly Phe
705                 710                 715                 720
Asn Val Met Thr Gln Lys Gly Lys Gly Ser Ile Ser Ser Leu Leu Leu
                725                 730                 735
Gly Gly Ala Asn Val Leu Thr Lys Leu Gly Gly Asp Asn Leu Val Ser
            740                 745                 750
Gly Met Leu Gly Gly Ala Asn Ile Ile Thr His Ile Ser Gly Asp Asn
        755                 760                 765
Glu Ile Ser Asp Thr Thr Ala Ile Ala Leu Gly Ala Asn Ile Leu
        770                 775                 780
Thr Lys Lys Gly Arg Gly Asp Ala Val Ala Leu Met Gly Gly Gly Ala
785                 790                 795                 800
Asn Val Leu Thr His Ile Gly Tyr Gly Ser Thr Gly Val Met Leu
                805                 810                 815
Gly Gly Ala Asn Ile Leu Thr Lys Val Gly Asn Gly Asp Thr Thr Gly
            820                 825                 830
Ile Met Leu Gly Ile Gly Asn Val Leu Thr His Val Gly Asp Asp Gln
        835                 840                 845
Thr Leu Gly Val Met Gly Ala Ala Gly Asn Ile Phe Thr Lys Val Gly
```

-continued

```
                850                 855                 860
Asp Gly Thr Ala Ile Ala Ala Met Ile Gly Ala Gly Asn Ile Phe Thr
865                 870                 875                 880
His Val Gly Lys Gly Asp Ala Trp Ala Leu Met Gly Gly Leu Gly Asn
                885                 890                 895
Ile Phe Thr Lys Val Gly Asp Gly Lys Ala Leu Ala Leu Met Ile Ala
                900                 905                 910
Ala Gly Asn Val Phe Thr His Val Gly Asn Gly Met Ser Val Ala Leu
                915                 920                 925
Met Leu Ala Lys Gly Asn Ile Ala Thr Lys Val Gly Asp Gly Thr Thr
930                 935                 940
Leu Ala Ala Met Ile Gly Glu Ala Asn Val Met Thr His Val Gly Asn
945                 950                 955                 960
Gly Ser Thr Phe Ala Ala Met Ile Gly Gln Gly Asn Ile Leu Thr Lys
                965                 970                 975
Ala Gly Asn Asp Leu Ala Leu Gly Leu Met Val Gly Glu Ala Asn Ile
                980                 985                 990
Tyr Ser His Val Gly Asp Gly Thr Ser Ile Gly Leu Leu Ala Gly Lys
                995                 1000                1005
Leu Asn Val Met Thr Lys Met Gly Asp Gly Thr Thr Leu Ala Ala
    1010                1015                1020
Met Phe Gly Glu Ala Asn Ile Met Thr His Tyr Gly Asp Gly Leu
    1025                1030                1035
Thr Gly Val Leu Ala Leu Gly Lys Ala Asn Ile Val Thr Lys Val
    1040                1045                1050
Gly Lys Gly Phe Met Gly Val Val Ala Ala Ala Glu Ala Asn Val
    1055                1060                1065
Val Thr His Met Gly Ala Ser Thr Thr Ala Ala Val Leu Leu Gly
    1070                1075                1080
Lys Gly Asn Ile Leu Thr Lys Glu Gly Ser Gly Thr Thr Val Gly
    1085                1090                1095
Leu Leu Ile Ser Asp Val Gly Asn Ile Met Thr His Ile Gly Asp
    1100                1105                1110
Gly Thr Thr Val Gly Phe Ala Lys Gly Lys Ala Asn Ile Ile Thr
    1115                1120                1125
Lys Val Gly Glu Gly Thr Gly Ile Asn Ala Val Trp Gly Glu Ala
    1130                1135                1140
Asn Ile Leu Thr His Val Gly Asn Gly Asp Arg Tyr Asn Phe Ala
    1145                1150                1155
Lys Gly Lys Ala Asn Ile Ile Thr Lys Val Gly Gly Met Arg Glu
    1160                1165                1170
Val Thr Val Val Gln Gly Asp Ala Asn Ile Ile Thr His Val Gly
    1175                1180                1185
Asn Gly Asp Asp Tyr Thr Gly Ala Trp Gly Lys Ala Asn Val Ile
    1190                1195                1200
Thr Lys Val Gly Asp Gly Asn Asn Val Val Leu Ala Lys Ala Asp
    1205                1210                1215
Ala Asn Ile Val Thr Gln Val Gly Asn Gly Asp Ser Phe Asn Ala
    1220                1225                1230
Leu Trp Ser Lys Gly Asn Ile Val Thr Lys Val Gly Asp Gly Met
    1235                1240                1245
Gln Val Thr Ala Ala Lys Gly Lys Ala Asn Ile Thr Thr Thr Val
    1250                1255                1260
```

-continued

```
Gly Asn Gly Leu Ser Val Thr Ala Thr His Gly Asp Leu Asn Val
1265                1270                1275

Asn Thr Lys Val Gly Asp Val Ser Val Asn Ala Val Trp Gly
1280                1285                1290

Glu Tyr Asn Val Asn Thr Lys Val Gly Asn Gly Leu Asn Val Ala
1295                1300                1305

Ile Met Lys Gly Lys Gly Asn Ala Asn Ile His Ile Gly Asp Gly
1310                1315                1320

Leu Gly Ile Asn Ala Ser Tyr Ala Arg Asn Asn Val Ala Ile Lys
1325                1330                1335

Val Gly Asn Gly Asp Phe Tyr Ser Leu Ser Ile Ala Glu Ser Asn
1340                1345                1350

Thr Gln Ser Ser His Leu Ser Ser Leu Phe Glu Asn Ile Lys Gln
1355                1360                1365

Thr Val Phe Asn Val Glu Gly Ser Gln Thr Ile Asn Tyr Leu Ile
1370                1375                1380

Arg Gly Asp Glu Ala Asn Thr Ser Gly Val Asn Lys Gly Arg Gly
1385                1390                1395

Ala Ile Asn Leu Thr Glu Val Ser Ala Ile Asp Gly Phe Gln Met
1400                1405                1410

Asp Lys Ile Asp Glu Val Ser Ser Asp Leu Ala Asn Asn Leu Ser
1415                1420                1425

Gly Ala Ile Thr Pro Val Glu Thr Pro Asp Ile Asn Val Ile Gln
1430                1435                1440

Asn Asp Leu Gln Ile Gly Asp Asn Val Gly Ser Ala Gln Asp Gln
1445                1450                1455

Ala Ser Pro His Ala Asp Ala Val Val Arg His Ala Lys Gln Asn
1460                1465                1470

Lys Ala Ala Gln Asn Ala Leu Ser Asp Lys Glu Lys Ala Glu Ile
1475                1480                1485

Asn His Gln Arg Leu Gln Gln Glu Lys Asp Lys Gln Leu Lys Thr
1490                1495                1500

Ile Ser Lys Ser Gln Gly Gln Leu Glu Ser Thr Asn Gln Ala Ala
1505                1510                1515

Leu Asn Thr Asn Gly Gln Val Gln Arg Asp Val Ile Ser Glu Glu
1520                1525                1530

Ser Arg Gly Val Thr Glu Glu Leu Phe Ser Leu Thr Gln Gly Met
1535                1540                1545

Gly Ala Leu Asn Asn Tyr Gly Asn Tyr Asp Gly Lys Ser Gly Asp
1550                1555                1560

Glu Trp Arg Asn Arg Phe Ala Gly Gly Tyr Leu Asp Asn Ile Gln
1565                1570                1575

Asn Lys Leu Asn Asp Ala Lys Leu Thr Ala Gln Lys Lys Leu Ala
1580                1585                1590

Asp Ala Gln Gln His Phe Ile Asp Lys Arg Glu Thr Val Ile Thr
1595                1600                1605

Ala Ile Lys Lys Ser Glu Val Gly Phe Thr Lys Ser Ala Glu Asn
1610                1615                1620

Leu Asp Ser Ala Asp Asp Ile Val Asp Ala Glu Lys Lys Ala
1625                1630                1635

Glu Gln Arg Lys Glu Glu Ala Leu Leu Gln Lys Gln Arg Ala Asp
1640                1645                1650

Lys Ala Val Ser Asp Ala Asn Thr Ala Tyr Asp Lys Ala Lys Gln
1655                1660                1665
```

```
Arg Gly Glu Ser Asp Ser Thr Ala Ala Glu Asn Lys Thr Ile Gln
    1670            1675                1680

Ala Gln Lys Asn Ala Lys Ser Val Lys Gln Ala Asp Asn Ala Lys
    1685            1690                1695

Pro Asp Arg Thr Gly Ala Ala Gly Ser Gly Leu Ser Gly Asn Ala
    1700            1705                1710

Tyr Ile Pro Ile Glu Val Glu Lys Ser Lys Ser His Ile Asp Pro
    1715            1720                1725

Ala Ser Lys Ala Glu Pro Asp Gly Trp Leu Ser Glu Asp Leu Ala
    1730            1735                1740

Leu Thr Ala Glu Asp Leu Ala Ala Leu Asn Asn Ala Gln Gln Ala
    1745            1750                1755

Val Asn Arg Leu Gln Leu Asn Lys Gly Met Arg Ser Glu Asn Thr
    1760            1765                1770

Gly Ala Ser Ile Met Ser Met Phe Thr Glu Thr Ser Ser Asp Gly
    1775            1780                1785

Ala Val Lys Ser Thr Leu Asn Lys Ser Arg Glu Leu Ile Arg Lys
    1790            1795                1800

Ala Pro Thr Ile Ser Gly Ile Asp Leu Gln Gly Leu Gly Gly Asn
    1805            1810                1815

Asn Pro Arg Ser His Ser Ser Val Leu Lys Lys Leu Glu Leu Ile
    1820            1825                1830

Leu Leu Lys Lys Asp Asn Lys Arg Phe Ile Asp Ser Thr Lys Arg
    1835            1840                1845

Arg Leu Gly Ser Ile Asn Thr Asp Leu Pro Ser Lys Ala Leu Val
    1850            1855                1860

Ala Val Arg Glu Ala Phe Asn Arg Thr Val Glu Gln Pro Asp Glu
    1865            1870                1875

Gln His Val Leu Gln Leu Glu Gln Thr Leu Ala His Trp Gln Gln
    1880            1885                1890

His Asp Pro Lys Glu Phe Thr Gln Arg Ser Lys Leu Val Lys Ser
    1895            1900                1905

Leu Arg Phe Glu Met Gly Glu Leu Val Ala His Ile Gln Ala Gln
    1910            1915                1920

Arg Ala Glu Ser Ala Gly Ile Leu Gly Ile Ala Val Ala Pro Glu
    1925            1930                1935

Gln Val Thr Gln Phe Gly Gln Val Ser Phe Asp Gly Ile Gly
    1940            1945                1950

Arg Val Val Gly Leu Lys Gly Asp Ile Ala Gln Ser Glu Ile Asn
    1955            1960                1965

Arg Leu Thr Asp Leu Gln Ile Lys Pro Leu Thr Gln Thr Asn Ser
    1970            1975                1980

Val Ala Glu Arg Glu Ala Pro Lys Thr Glu Asn Glu Ser Leu Ile
    1985            1990                1995

Val Phe Val Ser Arg Leu Gln Gln Glu Ala Ile Pro Glu Gly Lys
    2000            2005                2010

Pro Leu Ile Glu Arg Ala Arg Lys Leu Trp Leu Thr Gly Gln Val
    2015            2020                2025

Thr Asn Glu Lys Thr Lys Glu Leu Phe Lys Asp Ala Val Ala Gln
    2030            2035                2040

Leu Gln Thr Tyr Pro Glu Leu His Thr Leu Ala Gln Gln Leu Leu
    2045            2050                2055

Thr Asp Ala Asn Lys Glu Lys Ala Thr Gly Gln Tyr Ile Asp Asn
```

-continued

```
            2060                2065                2070
Leu Phe Gly Arg His Phe Asp Ser Glu Leu Ala Tyr Glu Leu Val
    2075                2080                2085
Lys Thr Ala Ser Pro Glu Ala Lys Asn Thr Ala Glu Arg Thr Gly
    2090                2095                2100
Asn Phe Leu Val Glu Asp Phe Glu Arg Trp Ile Gly Asp Leu Tyr
    2105                2110                2115
Pro Glu Gly Glu Lys Arg Asn Gly Ala Ile Asp Lys Lys Met Lys
    2120                2125                2130
Ser Phe Ala Glu Ala Ile Asp Lys Asp Phe Arg Pro Trp Phe Ser
    2135                2140                2145
Arg Val Pro Glu Val Thr Thr Phe Leu Asp Asp Pro Thr Phe Ala
    2150                2155                2160
Asn Phe Lys Thr Met Met Thr Lys Val Asp Asp Gly Phe Ser Val
    2165                2170                2175
Ile Lys Val Pro Phe Leu Ala Val Lys Met Ala Thr Thr Ser Gly
    2180                2185                2190
Met Gly Met Asp Val Ala Asp Trp Lys Arg Lys Gly Asp Ser Phe
    2195                2200                2205
Tyr Leu Asn Val Ile Thr Lys Ala Arg Ser Thr Ser Thr Glu Leu
    2210                2215                2220
Thr Ala Gly Thr Asn Ala Glu Asp Val Lys Tyr Lys Val Lys Ile
    2225                2230                2235
Thr Glu Lys Gln Thr Asn Asp Tyr Gly Thr Ala Leu Pro Tyr Gln
    2240                2245                2250
Pro Ala Asn Asn Lys His Asp Asp Phe Leu Tyr Gly Arg Lys Val
    2255                2260                2265
Ala Ala Gly Arg Ile Leu Thr Pro Gly Arg Glu Thr Ala Phe Glu
    2270                2275                2280
Ser Asn Ala Leu Glu Arg Gly Gln Ser Val Val Thr Gly Ala Ser
    2285                2290                2295
Gly Ser Thr Asn Ile Met Val His Leu Asn Asp Tyr Ile Ala Ser
    2300                2305                2310
Lys Gln Pro Asp Phe Ser Thr Gly Gln Ser Tyr Leu Asn Thr Leu
    2315                2320                2325
Ser Phe Leu Val Phe Asp Gly Gly His Ser Val Asn Glu Ser Leu
    2330                2335                2340
Val Val Tyr Gln Ala Leu Gln Ala Thr Asp Glu Ile Lys Arg Lys
    2345                2350                2355
Gln Ile Leu Asn Ser Tyr Thr Ala Asn Tyr Gln Asp Leu Ala Asp
    2360                2365                2370
Ile Ala Gly Glu Ser Gly Lys Val Trp Val Asn Gln Ala Leu Asp
    2375                2380                2385
Asn Ala Phe Lys Glu Thr Gln Glu Phe Tyr Gln Lys Tyr Ala Val
    2390                2395                2400
Val Lys Pro Gln Ser Arg Pro Ala Val Glu Asp Leu Glu Gly Leu
    2405                2410                2415
Ser Gly Thr Asn Lys Gly Val Glu Pro Thr Ile Ile Gly Asp Ser
    2420                2425                2430
His Leu Lys Lys Pro Val Asp Gly Trp Gln Lys Val Asp Val Thr
    2435                2440                2445
Pro Gln Thr Asp Gly Arg Glu Thr Arg Phe Asp Gly Gln Ile Ile
    2450                2455                2460
```

-continued

Leu Gln Met Glu Asp Asp Pro Ile Ala Ala Arg Ala Ala Ala Asn
2465                2470                2475

Leu Ala Gly Lys His Pro Asp Ser Ser Val Val Ile Gln Leu Asp
2480                2485                2490

Ala Asn Gly Lys Tyr Arg Val Val Tyr Gly Asp Leu Ala Lys Leu
2495                2500                2505

Ser Asn Lys Leu Arg Trp Gln Val Val Gly His Gly Arg Asp Thr
2510                2515                2520

Ser Glu Gln Asn Asn Ile Arg Leu Ser Gly Tyr Ser Ala Asp Glu
2525                2530                2535

Leu Ala Thr Lys Leu Lys Gln Phe Tyr Gln Ala Ala Lys Leu Gly
2540                2545                2550

Lys Gln Ala Ile Ser Lys Pro Asp His Ile Ser Leu Val Gly Cys
2555                2560                2565

Ser Leu Ile Ser Asp Asn Lys Arg Asp Gly Phe Ala Arg Arg Phe
2570                2575                2580

Ile Thr Glu Leu Asp Lys Gln Gly Ile Arg Ser Asp Val Ser Ala
2585                2590                2595

Arg Ser Ser Glu Val Ala Val Asp Ala Thr Gly Arg Lys Phe Thr
2600                2605                2610

Arg Asp Glu Asn Asn Gln Trp Val Asn Asn Ser Pro Asp Asn Lys
2615                2620                2625

Ile Val Leu Ser Leu Asn Ala Glu Asn Lys Leu Ile Thr His Thr
2630                2635                2640

Glu Gln Val Arg Arg Gly Ile Ala Glu Ser Asp Ile Asp Phe Ala
2645                2650                2655

Lys Val Gly Tyr Thr Gln Ala Asp Ser Val Thr Lys Gly Glu Ile
2660                2665                2670

Ala Asp Asn Thr Glu Ile Phe Ile Lys Pro Gln Lys Arg Glu Lys
2675                2680                2685

Val Asn Thr Ser Asp Asn Ser His Arg Gln Leu Ser Tyr Ser Gly
2690                2695                2700

Asn Ile Gln Val Asp Val Gly Glu Gly Glu Phe Thr Ala Leu Asn
2705                2710                2715

Trp Gly Thr Ser Asn Val Gly Ile Lys Val Gly Thr Gly Gly Phe
2720                2725                2730

Lys Ser Leu Ala Phe Gly Asp Asn Asn Val Met Val His Ile Gly
2735                2740                2745

His Gly Asp Ser Lys His Ser Val Asp Ile Gly Gly Tyr Gln Ala
2750                2755                2760

Leu Glu Gly Ala Gln Met Phe Ile Gly Asn Arg Asn Val Ser Phe
2765                2770                2775

Asn Gln Gly Arg Ser Asn Asp Leu Ile Val Met Met Asp Lys Ser
2780                2785                2790

Ile Pro Thr Pro Pro Leu Val Asn Pro Phe Asp Asp Thr Ala Arg
2795                2800                2805

Ile Ala Glu Val Leu Lys Gly Ile Ala Arg Ser Gly Glu Thr Gln
2810                2815                2820

Asp Trp Leu Ala Ala Gln Asp Gln Gln Trp Thr Ile Ala Gly Ala
2825                2830                2835

Arg Lys Phe Val Arg Asp Met Ser Gly Leu Asp Gln Thr Ser Ser
2840                2845                2850

Val Asp Tyr Lys Thr Leu Leu Asp Leu Asp Ser Gln His Glu Arg
2855                2860                2865

```
Ser Ser Arg Gly Leu Gln Asn Asp Ala Glu Ser Ala Leu Asn Lys
    2870            2875            2880

Lys Phe Asn Gln Trp Leu Gly Glu Asn Gly Asn Ser Ile Glu Met
    2885            2890            2895

Gly Lys Met Ser Arg Ala Asp Lys Phe Arg Gln Ala Asn Gln Lys
    2900            2905            2910

Leu Ala Phe Asn Phe Ala Val Gly Gly Arg Gly Ala Asp Ile Gln
    2915            2920            2925

Val Thr Thr Gly Asn Trp Asn Phe Thr Phe Gly Asp Asn Ile Gln
    2930            2935            2940

Ser Ile Leu Asp Thr Asn Leu Gly Ser Leu Phe Gly Leu Met Thr
    2945            2950            2955

Gln Gln Tyr Ser Ala Thr Gly Met Ala Lys Thr Thr Phe Thr Tyr
    2960            2965            2970

Thr Pro Gln Asp Leu Pro Arg Gln Leu Gln Asn Lys Leu Leu Gly
    2975            2980            2985

Arg Leu Ser Glu Val Gly Ala Asp Thr Thr Leu Ala Asp Ile Phe
    2990            2995            3000

Gly Val Asp Tyr Thr Ala Asp Gly Arg Ile Val Ser Arg Thr Gly
    3005            3010            3015

Lys Pro Val Asp Gly Glu Ala Met Leu Lys Glu Met Leu Glu Val
    3020            3025            3030

Ile Lys Glu Phe Ser Gly Asp Gln Leu Ala Ala Phe Thr Asn Pro
    3035            3040            3045

Gly Lys Leu Leu Asp Ser Leu Glu Ala Gly Ile Lys Ala Gly Glu
    3050            3055            3060

Asp Gly Val Arg Thr Phe Ala Glu Ser His Gly Leu Lys Glu Lys
    3065            3070            3075

Ala Pro Asp Lys Asn Gln Glu Gln Gly Ala Val Val Ser Thr Asn
    3080            3085            3090

Gly Asp Ser Ala Gln Ala Asn Asn Lys Ala Glu Arg Ala Phe Gly
    3095            3100            3105

Phe Asn Ser Leu Asn Leu Pro Asn Leu Phe Ala Thr Met Phe Ser
    3110            3115            3120

Lys Asp Lys Gln Ala Glu Met Gln Ser Leu Val Thr Asn Leu Lys
    3125            3130            3135

Glu Asn Leu Thr Ala Asp Leu Leu Asn Met Lys Gln Lys Thr Phe
    3140            3145            3150

Asp Phe Leu Arg Asn Ser Gly His Leu Gln Gly Asp Gly Asp Ile
    3155            3160            3165

Asn Val Ser Leu Gly Asn Tyr Asn Phe Asn Trp Gly Gly Asp Gly
    3170            3175            3180

Lys Asp Leu Gly Ala Tyr Leu Gly Asp Asn Asn Phe Trp Gly
    3185            3190            3195

Gly Arg Gly Asp Asp Val Tyr Tyr Ser Leu Gly Thr Ser Asn Ile
    3200            3205            3210

Phe Thr Gly Gly Glu Gly Asn Asp Met Gly Val Leu Met Gly Arg
    3215            3220            3225

Glu Asn Trp Met Phe Gly Gly Asp Gly Asp Thr Ala Val Val
    3230            3235            3240

Ala Gly Arg Ile Asn His Val Phe Met Gly Glu Gly Asn Asp Gln
    3245            3250            3255

Thr Phe Val Phe Gly Glu Gly Gly Leu Ile Asp Ala Gly Asn Gly
```

```
                    3260               3265               3270

Gln Asp Tyr Val Val Thr Ser Gly Asn Tyr Asn Arg Val Asp Thr
    3275                3280                3285

Gly Ala Gly Gln Asp Tyr Ala Val Thr Ile Gly Asn Asn Asn Arg
    3290                3295                3300

Val Asp Leu Gly Glu Gly Asp Asp Phe Ala Arg Val Phe Gly Asn
    3305                3310                3315

Asp Asn Arg Ile Asp Gly Tyr Ser Gly Asn Asp Thr Ile Lys Leu
    3320                3325                3330

Met Gly Tyr His Ala Met Ile Asn Gly Gly Glu Gly Asp Asp His
    3335                3340                3345

Leu Ile Ala Ala Ala Ile Ser Lys Phe Ser Gln Phe Asn Gly Gly
    3350                3355                3360

Asp Gly Gln Asp Leu Leu Val Leu Gly Gly Tyr Gln Asn Ser Phe
    3365                3370                3375

Gln Gly Gly Ala Gly Val Asp Ser Phe Val Val Ser Ala Glu Val
    3380                3385                3390

Ile Asp Asn Arg Val Asn Asp Ile Asn Ala Glu Asp Met Ile Leu
    3395                3400                3405

Phe Asn Gly Val Asp Trp Lys Asp Leu Trp Phe Gln Arg Ser Gly
    3410                3415                3420

Tyr Asp Leu Val Leu Ser Val Asn Arg His Thr Gln Asp Asn Thr
    3425                3430                3435

Ala Gln Glu Ile Phe Glu Ser Val Gly Ser Val Thr Phe Asn Asp
    3440                3445                3450

Tyr Phe Asn Gly His Arg Ala Lys Leu Val Thr Gln Met Gly Asp
    3455                3460                3465

Lys Asp Lys Ser Gly Glu Tyr Glu Phe Thr Ala Leu Ser Asp Asn
    3470                3475                3480

Ala Val Asp Ser Leu Ile Gln Ala Met Ser Ser Phe Ser Pro Thr
    3485                3490                3495

Val Gly Asp Asn Gly Phe Ile Glu Ser Leu Gly Ser Lys Ala Arg
    3500                3505                3510

Ala Ala Val Ala Thr Ala Trp Ala Asp Val Thr Leu Gly Lys Gly
    3515                3520                3525

Lys Phe Ala
    3530

<210> SEQ ID NO 8
<211> LENGTH: 201
<212> TYPE: PRT
<213> ORGANISM: Xenorhabdus nematophila

<400> SEQUENCE: 8

Ser Pro Glu Ser His Ile Arg Val Asn Asn His Asp Val Gly Ser Trp
1               5                   10                  15

Glu Asn Ile Thr Val Lys Pro Gln Pro Glu Ser Gly Asp Ser Arg Phe
            20                  25                  30

Ser Gly Gln Ile Ile Ile Gln Thr Glu Asn Asp Pro Val Ala Ala Lys
        35                  40                  45

Ala Ala Ala Asn Leu Ala Gly Lys His Pro Asp Ser Ser Val Ile Val
    50                  55                  60

Gln Leu Asp Ala Asn Gly Gln Tyr Arg Val Val Tyr Gly Asp Pro Ala
65                  70                  75                  80

Asp Leu Ser Asn Lys Leu Gln Ser Gly Lys Leu Arg Trp Gln Ile Val
```

```
                    85                  90                  95
Gly His Gly Arg Glu Glu Ser Ala Gln Asn His Thr Arg Ile Ser Gly
                100                 105                 110
Tyr Ser Ala Asp Glu Leu Ala Leu Arg Leu Lys Gln Phe Ser Ile Asp
                115                 120                 125
Phe Lys Gln Ala Gly Lys Pro Asp His Ile Ser Leu Val Gly Cys Ser
            130                 135                 140
Leu Ile Ser Asp Asp Lys Arg Asn Gly Phe Ala Arg Arg Phe Ile Ser
145                 150                 155                 160
Ala Leu Asn Glu Gln Gly Val Arg Thr Thr Val Ser Ala Arg Ser Ser
                165                 170                 175
Glu Val Ala Val Asp Ser Ile Gly Arg Lys Tyr Thr Lys Asp Ala Gln
                180                 185                 190
Asp Gln Trp Val His Lys Leu Thr Asp
                195                 200

<210> SEQ ID NO 9
<211> LENGTH: 196
<212> TYPE: PRT
<213> ORGANISM: Xenorhabdus bovienii

<400> SEQUENCE: 9

Leu Pro Glu Gly Val Asp Arg Val Val Asn Asn Glu Asn Val Glu His
1               5                   10                  15
Trp Glu Pro Ala Phe Val Lys Pro Gln Ala Glu Gly Gly Asp Ser Arg
                20                  25                  30
Phe Asn Ser Gln Val Ile Ile Gln Thr Glu Asn Asp Pro Val Ala Ala
            35                  40                  45
Lys Ala Ala Ala Arg Leu Ala Gly Lys His Pro Asp Ser Val Ile Val
        50                  55                  60
Gln Leu Asp Ala Asn Gly Arg Tyr Arg Val Val Tyr Gly Asp Pro Ala
65                  70                  75                  80
Thr Leu Ser Gly Lys Leu Arg Trp Gln Ile Val Gly His Gly Arg Asp
                85                  90                  95
Glu Ser Val Gln His His Thr Arg Met Ser Gly Tyr Ser Ala Asp Glu
                100                 105                 110
Leu Ala Leu Lys Leu Lys Gln Phe Arg Thr Asp Phe Lys Gln Ala Gly
            115                 120                 125
Ser Pro Asp His Ile Ser Leu Val Gly Cys Ser Leu Ile Ser Asp Asp
        130                 135                 140
Lys Arg Asp Gly Phe Ala Arg His Phe Ile Ser Glu Leu Asp Lys Gln
145                 150                 155                 160
Gly Ile Arg Thr Ile Val Ser Ala Arg Ser Ser Glu Val Ala Val Asp
                165                 170                 175
Ser Ile Gly Arg Lys Phe Thr Arg Asn Ala Glu Glu Gln Trp Val His
                180                 185                 190
Lys Leu Met Asp
        195

<210> SEQ ID NO 10
<211> LENGTH: 3103
<212> TYPE: PRT
<213> ORGANISM: Yersinia pseudotuberculosis

<400> SEQUENCE: 10

Met Pro Asn Gly Asn Glu Met Ala Gly Phe Tyr Ile Asn Lys Leu Ser
1               5                   10                  15
```

Leu Ser Gln Arg Leu Ser Ile Leu Ser Glu Thr Tyr Asp Arg Ile Asn
            20                  25                  30
Lys Asn Asn Lys Lys Glu Lys Phe Lys Tyr Ser Tyr Ala Asp Ile Glu
            35                  40                  45
Met Ile Lys Lys Arg Phe Ile Lys Tyr Ile Asp Ala Gln Leu Tyr Ser
 50                  55                  60
Leu Ile Arg Glu Gly Phe Ser Val Pro Thr Thr Leu Thr Gln Glu Glu
 65                  70                  75                  80
Lys Ile Lys Ile Ala Asp Leu Ala Ile Asp Ala Ala Leu Tyr Asn Asp
                 85                  90                  95
Tyr Gly Arg Phe Asn Glu Leu Ile Ile Tyr Ile Ser Ser Leu Gly Ile
                100                 105                 110
Ser Val Thr Pro Pro Leu Pro Gln Glu Glu Gly Gly Ser Arg Leu Tyr
                115                 120                 125
Ile Tyr Phe Ser Gly Asp Ile His Thr Tyr Met Asp Val Trp Arg Gly
                130                 135                 140
Asp Leu Leu Val Gly Ser Gly Thr Glu Leu Ser Asp Ile Gln Ser Ile
145                 150                 155                 160
Thr Gly Leu Arg Phe Met Ile Asp Met Ala Glu Ser Leu Lys Leu Asn
                165                 170                 175
Ile Ile Asn Pro Ser Asp Lys Ala Met Val Asp Leu Ile Asn His Leu
                180                 185                 190
Arg Tyr Lys Met Ile Ser Tyr Ala Ser Ser Phe Tyr Ala Thr Tyr Ser
                195                 200                 205
Ala Glu Arg Gly Gly Thr Val Tyr Leu Ser Ser Pro Gly Gly Leu Arg
                210                 215                 220
Ile Asn Asn Tyr Phe Trp Asn Ser Glu Leu Pro Val Leu Arg Ala Leu
225                 230                 235                 240
Gln Lys Gln Gly Leu Ile Gly Asp Ile Arg Ile Leu His Lys Pro Leu
                245                 250                 255
Glu Phe Tyr Lys Asp Thr Pro Leu Asp Glu Leu Gly Asp Leu Leu Thr
                260                 265                 270
Ala Lys Asp Leu Ser Met Thr Ala Glu Tyr Gln Phe Leu Pro Val Trp
                275                 280                 285
Leu Gln Glu Lys Leu Leu Val Asp Ile Tyr Gln Trp Leu Asp Glu
                290                 295                 300
Glu Phe Gln Pro Ser Leu Phe Thr Val Arg Lys Glu Ile Ile Asn Thr
305                 310                 315                 320
Ile Asp Ile Asp Arg Asn Ala Pro Glu Val Glu Leu Leu Arg Tyr Phe
                325                 330                 335
Leu Ser Lys Ile His Glu Gln Leu Asp Glu Ile Thr Glu Tyr Lys Val
                340                 345                 350
Leu Ile Glu Ala Glu Arg Ile Asp Phe Ile Lys Lys Ile Ala Val
                355                 360                 365
Gly Ser Glu Ile Glu Ser Trp Leu Asp Asn Val Pro Ala Ile Asp Val
                370                 375                 380
Asn Glu Arg Lys Val Ile Leu Glu Asn Leu Leu Gln Lys Glu Ser Leu
385                 390                 395                 400
Leu Phe Ser Asn Val Arg Asp Ile Lys Lys Phe Pro Ile Pro Leu Asp
                405                 410                 415
Phe Asn Ser Asp Val Ile Asn Val Asn Thr Ser Lys Leu Lys Asn Thr
                420                 425                 430
Phe Ile Pro Phe Asn Leu Leu Arg Glu Lys Trp Asp Ile Ile Ile Ser

```
                435                 440                 445
Asp Arg Ser Leu Val Asp Gly Thr Leu Thr Ile His Phe Ser Ala Gly
450                 455                 460

Arg Lys Ile Met Ile Lys Val Asp Ala Asn Arg Asn Gln Leu Lys Gln
465                 470                 475                 480

Met Ala Thr Leu Glu Arg Phe Leu Leu Ala Asn Phe Thr Pro Lys Asn
                485                 490                 495

Ala Pro Gln Asp Leu Gln Leu Ile Glu Asn Val Ile Met Ser Gly Asp
                500                 505                 510

Ala Val Leu Ala Glu Arg Lys Gly Asp Lys Gly Trp His Asn Asp Gln
                515                 520                 525

Gln Met Ile Glu Lys Val Lys Leu Ser Glu Phe Asp Tyr Phe Leu Lys
530                 535                 540

Ser Asn Asp Leu Gly Ile Lys Ile Asn Asp Asn Gly Phe Val Leu Tyr
545                 550                 555                 560

Leu Ile Ser Asp Pro Glu Asp Ser Arg Asp Val Ile Ile Asn Pro Asn
                565                 570                 575

Asn Asp Tyr Asn Leu Lys Ser Ile Lys Asp Phe Ile Glu Asn Asn Tyr
                580                 585                 590

Leu Phe Phe Asp Asp Val Pro Glu Tyr Leu Ile Val Lys Lys Asn Ala
                595                 600                 605

Glu Asn Lys Glu Cys Ile Phe Ala His Asn Glu Arg Glu Thr Tyr Gln
610                 615                 620

Val Ala Tyr Arg Asp Glu Gly Thr Trp Val Leu Leu Tyr Lys Lys Asp
625                 630                 635                 640

Leu Ser Asp Gln Ile Lys Ile Ile Asn Glu Ile Thr Thr Ser Val Asn
                645                 650                 655

Met Asn Asn Ala Glu Ser Arg Ser Val Ala Leu Ile Leu Cys Leu Leu
                660                 665                 670

Asn Lys His Val Arg Leu Val Ser Ile Leu Pro Asp Thr His Pro Lys
                675                 680                 685

Val Met Glu Asn Leu Leu Asp Ile Asp Ser Leu Leu Lys Asn Ser Lys
690                 695                 700

His Pro Phe Ser His Pro His Tyr Asn Lys Ile Leu Asp Ser Leu Ser
705                 710                 715                 720

Asn Asp Ile Asn Asp Asn Val Asn Ser Leu Gln Glu Ile Lys Asp Phe
                725                 730                 735

Thr Arg Phe Phe Ser Tyr Asp Ile Lys Pro Gly Met Tyr Met Asn Thr
                740                 745                 750

Trp Asp Lys Ile Asp Lys Asn Val Val Leu Glu Tyr Ala Val Lys Gln
                755                 760                 765

Asn Asn Lys Asn Gln Tyr Pro Gln Phe Ile Val Leu Leu Gln Asp Asp
770                 775                 780

Ser Leu Ser Lys Arg Val Gly Glu Val Leu Ser Ser Tyr His His Asp
785                 790                 795                 800

Lys Ser Val Val Leu Gln Phe Asp Ala Arg Ser Ser Glu Ala Arg Ile
                805                 810                 815

Ala Tyr Gly Val Pro Ser Asn Ile Ala Glu Met Gly Gly Phe Glu Leu
                820                 825                 830

Ser Phe Val Thr His Gly Ala Pro Asp Gly Leu Tyr Ser Phe Ser Ile
                835                 840                 845

Ala Asn Ile Ile Asp Ile Tyr Lys Leu Thr Thr Asn Ser Phe Ala Leu
850                 855                 860
```

```
Pro Pro Pro Val Lys Ile Arg Leu Val Ile Cys Ser Ile Ala Asp Asn
865                 870                 875                 880

Gly Gln Gly Ala Gln Gly Phe Asn Gly Thr His Pro Ala Leu Gly Ile
            885                 890                 895

Val Asn Met Met His Gln Glu Gly Phe Asp Ile Pro Ile Leu Ala Tyr
                900                 905                 910

Thr Thr Lys Val Gly Val Ser Val Glu Tyr Pro Gly Glu Leu Val Val
                915                 920                 925

Phe Asn Ser Glu Asn Gln Gly Gly Val Leu Glu Asn Ile Asp Asp Tyr
930                 935                 940

Gln Val Leu Tyr His Tyr Lys Asn Asn Ile Leu Leu Ile Asp Gly Ile
945                 950                 955                 960

Pro Ala Val Glu Leu Leu Leu Lys Asp Val Arg Asp Lys Ile Lys Ser
                965                 970                 975

Val Asp Gln Leu Ile Glu Ser Tyr Ser Gln Tyr Leu Val Pro Phe Phe
                980                 985                 990

Ser Asp Asn Asn Gly Val Ile Asp Arg Asn Leu Leu Glu Leu Thr Ile
            995                 1000                1005

Asn Asp Ser Asn Thr His Ser Lys Phe Glu Asn Phe Leu Asp Ile
    1010                1015                1020

Ile Arg Gln Arg Pro Glu Leu Arg Asn Ser Asp Asn Trp Gln Leu
    1025                1030                1035

Val Val Ala Asn Asn Ala Thr Gly Phe Leu Ile Thr Thr Leu Asp
    1040                1045                1050

Glu Pro Val Val Lys Tyr Pro Asp Ile Val Lys Val Asn Glu Trp
    1055                1060                1065

Asp Leu Pro Ala Ile Ala Asn Ile Asp Lys Thr Ala Thr Ala Ser
    1070                1075                1080

Gln Tyr Asp Met Gln Ile Val Phe Gln Cys Glu Asn Asn Pro Thr
    1085                1090                1095

Val Asn Arg Ala Ala Thr Arg Leu Ala Gly Lys His Ala Lys Asn
    1100                1105                1110

Ser Ile Ile Ile Gln Leu Asp Val Asp Asn Asn His Arg Ala Phe
    1115                1120                1125

Ile Ile Asp Asp Asn Ile His Ala Glu Trp Arg Glu Ile Ser His
    1130                1135                1140

Asn Glu Leu Val Thr Lys Leu Lys Ile Gln Pro Glu Asn Gly Lys
    1145                1150                1155

Ile Arg Trp Gln Val Val Gly His Gly Arg Ser Glu Gly Gly Asn
    1160                1165                1170

Asp Lys His Pro Thr Leu Ala Gly Gln Arg Pro Glu Gln Leu Thr
    1175                1180                1185

Ala Arg Leu Asn Gln Phe Ser Asp Tyr Leu Gln Thr Glu His Gln
    1190                1195                1200

Ile Asn Ile Ser Pro Gln Gln Val Ser Leu Val Gly Cys Ala Met
    1205                1210                1215

Ser Ser Ser Asp Arg Tyr Thr Ser Phe Ala His Lys Phe Met Ser
    1220                1225                1230

His Leu Asn Glu Asn Gly Ile Arg Thr Asn Val Ser Ala Ser Thr
    1235                1240                1245

Lys Ala Ile Glu Val Asp Pro Leu Gly His Lys His Asp Val Asp
    1250                1255                1260

Thr Pro Asp Ile Asp Ser Tyr Asn Asn Lys Tyr Leu Ser Ser Ile
    1265                1270                1275
```

```
Lys Gly Thr Glu Lys Leu Tyr Trp Asn Arg Trp Gly Glu Ile Thr
    1280            1285                1290

Thr Glu Arg Lys Lys Asp Ile Asn Gly Arg Leu Asn Asn Ile Asp
    1295            1300                1305

Ser Leu Leu Asp Asn Leu Ile Thr Arg Gln Leu Ser Val Asn Gln
    1310            1315                1320

Ile Asn Lys Lys Gln Gln Arg Lys Leu Ala Glu Ile Phe Pro Gln
    1325            1330                1335

Leu Thr Asp Lys Lys Leu Asn Lys Gly Glu Leu Leu Leu Thr Leu
    1340            1345                1350

His Asp Ser Trp Arg Met Gln Thr Leu Lys Tyr Asp Leu Leu Phe
    1355            1360                1365

Leu Gln Lys Ile Ser Asp Arg Pro Asp Phe Asp Thr Glu Leu Trp
    1370            1375                1380

Arg Val Thr Asp Arg Trp Arg Ile Thr Glu Thr Asp Gly Asn Thr
    1385            1390                1395

Leu Gln Asp Val Arg Ile Lys Ser Gly Ser Gln His Lys Thr Asp
    1400            1405                1410

Leu Ala Thr Tyr Pro His Ser Ile Thr Ser Asp Pro Asp Leu Lys
    1415            1420                1425

Thr Ser Asn Pro Lys Ala Arg Thr Ala Ile Phe Gly Arg Phe Gly
    1430            1435                1440

Tyr Gly Met Gln Gly Tyr Gly Phe Ile Ser Ala Leu Arg Leu Ser
    1445            1450                1455

Ala Asp Tyr Gln Arg Trp Met Ser Asn Gly Asp Leu Thr Glu Lys
    1460            1465                1470

Gln Glu Glu Glu Ile Gln Leu Gln Leu Ala Met Ala Trp Gly Gly
    1475            1480                1485

Ile Gly Ala Asn Leu Ala Thr Asp Gly Leu Gln Tyr Ala Phe Gly
    1490            1495                1500

Lys Trp Gly Ile Gly Tyr Leu Gln Lys Leu Val Ser Lys Gly Gly
    1505            1510                1515

Arg Leu Ser Pro Ala Leu Leu Ser Gln Leu Thr Leu Leu Lys Arg
    1520            1525                1530

Asn Pro Ala Leu Leu Leu Ala Pro Gly Phe Leu Lys Asp Leu Arg
    1535            1540                1545

Lys Leu Ala Leu Asn Gln Phe Ala His Gly Ala Ala Arg Phe Ser
    1550            1555                1560

Met Pro Leu Leu Ser Ala Leu Thr Ser Gly Ile Asp Ile Tyr Gln
    1565            1570                1575

Ala Tyr His Ala Phe Ser Gln Leu Ala Thr Glu Thr Asp Pro His
    1580            1585                1590

Val Arg Arg Asp Leu Ile Ala Ser Gly Val Phe Ser Thr Ile Asn
    1595            1600                1605

Ala Thr Ile Gly Leu Gly Val Ala Phe Ala Met Ala Met Gly Gly
    1610            1615                1620

Thr Ala Ala Thr Ala Ala Gly Pro Ala Gly Ile Ala Leu Ala Phe
    1625            1630                1635

Thr Met Ile Ile Val Gly Asp Ile Tyr Ser Ala Val Ser Gln Ile
    1640            1645                1650

Glu Arg Ile Arg Asp Ile Val Pro Asp Met Thr Gly Ser Gln Arg
    1655            1660                1665

Phe Glu Asn Gly Leu Arg Leu Phe Leu Lys Phe Gly Leu Thr Pro
```

```
                 1670                1675                1680

Gly  Leu  Asp  Asn  Gln  Ile  Arg  Tyr  Asn  Gln  Thr  Met  Glu  Ser  Val
     1685                1690                1695

Tyr  Gln  Arg  Gln  Arg  Asp  Tyr  Tyr  Glu  Ala  Leu  Leu  Ala  Ser  Lys
     1700                1705                1710

Gln  Gly  Val  Asp  Thr  Leu  Phe  Tyr  Ser  Arg  Gly  Glu  Ala  Val  Leu
     1715                1720                1725

Lys  Ala  Ile  Pro  Phe  Ile  Lys  Arg  Asp  Glu  Arg  Ser  Gln  Thr  Glu
     1730                1735                1740

Arg  Asp  Leu  Glu  Lys  Ile  Ser  Ile  Phe  Ser  Gly  Asp  Pro  Phe  Thr
     1745                1750                1755

Asn  Ala  Lys  Ile  Tyr  Thr  Thr  Tyr  Ala  Glu  Met  Gly  Lys  His  Glu
     1760                1765                1770

Tyr  Tyr  Glu  Leu  Asp  Lys  Ile  Asn  Asp  Val  Asp  Asp  Tyr  Val  Ile
     1775                1780                1785

Ala  Asp  Phe  Phe  Glu  Asp  Asn  Asn  Arg  Ser  Val  Val  Lys  Leu  Gln
     1790                1795                1800

Asn  Lys  Asn  Leu  His  Gln  Ala  Phe  Ser  Glu  Leu  Asp  Ile  Asp  Ser
     1805                1810                1815

Thr  Tyr  Ser  Pro  Phe  Ile  Leu  Ser  Ala  Asp  Val  Asp  Arg  Asn  Gly
     1820                1825                1830

Leu  Asn  Asp  Phe  Ile  Val  Ile  Asn  Glu  Lys  Tyr  Asn  Thr  Thr  Ile
     1835                1840                1845

Ala  Ser  Arg  Lys  Asn  Ser  Val  Gly  Met  Thr  Val  Ile  Asp  Asp  Tyr
     1850                1855                1860

Val  Ser  Arg  Trp  His  Tyr  Glu  Leu  Tyr  Thr  Trp  Leu  Ala  Gln  Pro
     1865                1870                1875

Asp  Gly  Ser  Tyr  Leu  Lys  Ile  Asp  Thr  Arg  Leu  Glu  Trp  Glu  Lys
     1880                1885                1890

Leu  Phe  His  Ala  Ile  Glu  Val  Asp  Lys  Phe  Asn  Glu  Val  Val  Phe
     1895                1900                1905

Pro  Val  Leu  Gly  Asp  Phe  Asn  Gly  Asp  Asn  Val  Phe  Glu  Leu  Val
     1910                1915                1920

Ile  Phe  His  Asp  Asp  Lys  Met  Thr  Thr  Tyr  His  Tyr  Asp  Ser  Leu
     1925                1930                1935

Asp  Phe  Asn  Gln  Ser  Gly  Lys  Asp  Asn  His  Asn  Val  Ile  Asn  Ile
     1940                1945                1950

Gly  Asp  Phe  Ile  Glu  Pro  Val  Arg  Leu  Ala  Phe  Glu  Gly  Glu  Lys
     1955                1960                1965

Ser  Lys  Asn  Tyr  Pro  Tyr  Ser  Leu  Val  Gly  Asp  Ile  Asn  Asn  Asp
     1970                1975                1980

Gly  Phe  Asp  Asp  Ile  Leu  Leu  Leu  Asn  Lys  Ser  Gly  Asp  Met  Leu
     1985                1990                1995

His  Leu  Met  Gly  Asn  Ser  Ser  Gly  Val  Phe  Arg  Gln  His  Lys  Thr
     2000                2005                2010

Lys  Leu  Ser  Ser  Glu  Leu  Thr  Ser  Leu  Leu  Ser  Ser  Asn  Leu
     2015                2020                2025

His  Arg  Ser  Gln  Leu  Gln  Leu  Thr  Asp  Leu  Asn  Lys  Asp  Gly  Gly
     2030                2035                2040

Leu  Asp  Leu  Val  Ile  Ile  Leu  Asn  Asp  Gly  Ile  Tyr  Tyr  Gln  Ala
     2045                2050                2055

Leu  Gly  Asp  Lys  Ile  Asp  Gly  Glu  Tyr  His  Phe  Asp  Thr  Pro  Ser
     2060                2065                2070
```

-continued

Met Val Asn Lys Ile Thr Ile Lys Thr Glu Gly Gly Asp Ser Val
2075              2080                 2085

Arg Tyr Gln Gln Asn Arg Leu Ser Gln Ile Asn Lys Asn Lys Ile
2090              2095                 2100

Ile Ala Ile Ser Pro Ser Asp Gln Gly Glu Asn Arg Leu Ile Ser
2105              2110                 2115

Leu Ser Asp Ser Gly Glu Leu Leu Ala His Pro Leu Arg Glu Ile
2120              2125                 2130

Lys Glu Asn Asp Val Ala Ala Leu Phe Asp Leu Gly Gly Gly Asp
2135              2140                 2145

Asp Val Ala Lys Gly Tyr His Lys Lys Lys Asn Ile Phe Thr Ile
2150              2155                 2160

Gly Ser Gly Phe Lys Gln Tyr Gln Gly Gly Glu Asn Ala Asp Thr
2165              2170                 2175

Phe Ile Leu Thr Ser Ala Ala Ala Ser Lys Ser His Ile Leu Ser
2180              2185                 2190

Gly Gly Glu Gly Asn Asp Thr Val Ala Leu Gly Glu Val Leu Gly
2195              2200                 2205

Asn Glu Ile Asp Ser Ile Ile Asp Ile Ser Lys Gly Tyr Tyr Ser
2210              2215                 2220

Gln Val Asn Gly Gly Val Glu Lys Gln Val Ala Leu Leu Tyr Asp
2225              2230                 2235

Phe Glu Asn Ile Leu Gly His Glu Asn Val Asn Asp Thr Ile Ile
2240              2245                 2250

Gly Asn Asp Val Asp Asn Tyr Leu Asn Gly Met Gly Gly Asp Asp
2255              2260                 2265

Lys Ile Trp Gly Asn Gly Gly Asn Asp Leu Leu Ala Leu Gln Ser
2270              2275                 2280

Gly Leu Ala Gln Gly Gly Thr Gly Leu Asp Ser Tyr His Ile Leu
2285              2290                 2295

Lys Ser Thr His Glu Lys Ser Leu Gln Ile Arg Ile Glu Glu Val
2300              2305                 2310

Ser Glu Asn Asn Asn Thr Asp Met Gln Ile Ser Asn Ile Phe Leu
2315              2320                 2325

Glu His Lys Leu Asn Gln Ile Lys Ser Ile Glu Leu Asp Asn Ile
2330              2335                 2340

Asp Val Leu Ile Asn Ile Asn Asn Asp Asn Gly Phe Met Thr Gln
2345              2350                 2355

Ile Arg Leu Val Gly Val Tyr Asn Ile Asn Asn Asn Gln Lys Gln
2360              2365                 2370

Gln Val Leu Asn Phe Thr Ile Gln Thr Val Asp Gly Phe Thr Met
2375              2380                 2385

Val Pro Leu Trp Pro Ser Tyr Leu Asn Glu Ile Thr Glu Phe Ser
2390              2395                 2400

Pro Asn Met Val Ala Tyr Tyr Ser Ser Leu Val Asp Arg Asn Tyr
2405              2410                 2415

Lys Glu Leu Val Gly Lys Gly Asp Pro Asp Asp Ile Val Val Arg
2420              2425                 2430

Phe Ser Leu Asp Asn Gly Tyr Gln Gln Gln Gln Val Thr His Leu
2435              2440                 2445

Gln Arg Val Glu Gly Glu Lys Asp Ile Val Leu Arg Gln Ala Ile
2450              2455                 2460

Leu Pro Asp Phe Ile Arg Leu Ser Pro Gln Glu His Ser Met Leu
2465              2470                 2475

```
Met Gly Phe Leu Pro Arg Tyr Glu Leu Leu Gly Asp Asn Lys Asp
    2480                2485                2490

Asn Leu Leu Gln Val Leu Ser Gly Glu Gly Leu Leu Glu Gly Arg
    2495                2500                2505

Gly Gly Gln Asp Thr Tyr Leu Ile Gln Glu Lys Glu Gly Ser Pro
    2510                2515                2520

Thr Asp Ile Ile Ile Asn Asn Phe Asp Asp Ser Leu Ala Ser Asp
    2525                2530                2535

Asn Leu Val Leu Ser Ser Trp Leu Leu Cys Asp Val Ile Val Glu
    2540                2545                2550

Arg Ser Asp Asp Asp Leu Leu Leu Arg Tyr Arg Asp Gln Pro Glu
    2555                2560                2565

Lys His Gln Ser Ile Arg Leu Val Asn Tyr Met Asn Asp Glu Arg
    2570                2575                2580

Tyr Arg His Leu Lys Ile Thr Asp Lys Ser Gly Gln Ser Gln Tyr
    2585                2590                2595

Arg Asp Pro Val Thr Gly Thr Phe Ile Asp Tyr Gln Ile Asn Leu
    2600                2605                2610

Asp Lys Asn Gly His Pro Phe Ile Ala Ala Gln Gln Ala Pro Val
    2615                2620                2625

Val Ser Ser Gly Asn Asp Glu Val Val Ile Asn Ser Ala Thr Phe
    2630                2635                2640

Leu Pro Gly Asn Tyr Ile Asp Thr Gly Asp Gly Asn Asp Ala Ile
    2645                2650                2655

Ile Tyr Ile Arg Gly His Glu Gly Thr Met Leu Lys Gly Gly Gly
    2660                2665                2670

Gly Asp Asp Thr Tyr Tyr Tyr Ser Ala Gly Ser Gly Ala Ile Asn
    2675                2680                2685

Ile Ala Asp Thr Ser Gly Leu Asp His Leu Tyr Leu Asp Lys His
    2690                2695                2700

Ile Leu Leu His Thr Leu Ser Ala Glu Arg Arg Glu Asn Asn Leu
    2705                2710                2715

Val Leu Asn Ile Ala Asp Asn Thr Ser Gly Arg Ile Ile Phe Val
    2720                2725                2730

Asp Trp Tyr Leu Ala Asp Glu Asn Lys Val Asp Phe Ile Trp Val
    2735                2740                2745

Glu Gly Ser Gln Ile Thr Phe Asp Glu Leu Phe Ser Leu Cys Pro
    2750                2755                2760

Tyr Ser Asp Glu Tyr Tyr Gln Leu Cys Gln Gln Leu Lys Ser Met
    2765                2770                2775

Gly Leu Ser Leu Thr Val Arg Gln Leu Ala Asp Leu Asp Ser Gln
    2780                2785                2790

Asp Gly Tyr Asn Thr Leu Asn Gln Leu Arg Thr Ile Lys Ala Trp
    2795                2800                2805

Ala Thr Lys Asn Pro Ile Tyr Asp Val Ala Asp Leu Asp Tyr Leu
    2810                2815                2820

Val Ala Met Ser Ser Ile Ala Trp Arg Gly Asn Ala Arg Asn Thr
    2825                2830                2835

Asp Pro Leu Pro Leu Ile Glu Gln Lys Ile Asp Ala Phe Phe Gln
    2840                2845                2850

Pro Leu Ile Ala Glu Arg Ile Ser Leu Thr Glu Glu His Val Thr
    2855                2860                2865

Trp Ile Gln Arg Glu Glu Phe Asp Thr Val Asp Ile Ala Lys Trp
```

```
                    2870                2875                2880
Val Lys Asn Tyr His Leu Arg  Ser Gln Asn Glu Ile  Asn Tyr Leu
    2885                2890                2895

Leu Glu Gln Leu Gly Leu Leu  Lys Glu Ser Pro Leu  Ser Asp Lys
    2900                2905                2910

Ala Leu Asp Phe Thr Phe Lys  Asn Arg Ile Asp Leu  Ala Gln Ala
    2915                2920                2925

Asp Ile Glu Leu Cys Gln Gln  Glu Cys Gly Ile Asn  Arg Gln Ser
    2930                2935                2940

Leu Ile Asn Leu Ala Met Lys  Tyr His Val Thr Gly  Arg Gly His
    2945                2950                2955

Phe Glu Leu Leu Ile Ser Asn  Ile Gln Val Leu Lys  Glu Tyr Gly
    2960                2965                2970

Val Val Val Ser Glu Ser Glu  Gln Pro Leu Val Leu  Arg Lys Pro
    2975                2980                2985

Ile Asp Leu Arg Gln Tyr Phe  Asn Gln Lys Asn Leu  Thr Lys Asp
    2990                2995                3000

His Val Gly Arg Leu Ala Glu  His Asp Met Ser Phe  Asp Glu Leu
    3005                3010                3015

Thr Leu Leu Leu Asp Lys Asn  Ile Pro Ile Glu Gln  Ala Phe Thr
    3020                3025                3030

Gln Arg Leu Gln Thr Gln Leu  Gly Pro Leu Lys Leu  Phe Asn Asp
    3035                3040                3045

Glu Arg Val Leu Asn Gln Gly  Asp Ile Phe Asp Gln  Asp Ile Ser
    3050                3055                3060

Gln Leu Ala Glu Ala Met Gly  Gly Leu Glu Ser Thr  Glu Ser Tyr
    3065                3070                3075

Ser Leu Pro Leu Glu Arg Gln  Thr Ala Met Ala Ile  Thr Thr His
    3080                3085                3090

Gln Phe Val Ser Asp Ser Ile  Ala Ala Tyr
    3095                3100

<210> SEQ ID NO 11
<211> LENGTH: 1449
<212> TYPE: PRT
<213> ORGANISM: Yersinia mollaretti

<400> SEQUENCE: 11

Met Gly Glu Thr Ile Asp Phe  Ser Val Trp Glu Ser  Pro Asp Gln Ala
1               5                   10                  15

Tyr Phe Thr Ser Leu Pro Asn  Thr Pro Leu Glu Pro  Glu Gly Thr His
            20                  25                  30

Tyr Glu Lys Thr Leu Ile Phe  Gln Leu Gln Gly Asp  Asp Thr Cys Phe
        35                  40                  45

Glu Ala Ser Arg Ala Leu Phe  Asn Lys His Arg Tyr  Thr Ser Glu Trp
    50                  55                  60

Leu Gln Leu Gly Asp Gly Lys  Pro Ala Glu Val Phe  Thr Trp Gly Glu
65                  70                  75                  80

Thr Tyr Lys Lys Phe Val Tyr  Thr Ser Pro Leu Lys  Leu Asp Lys Glu
                85                  90                  95

Gly Lys Ile Arg Ile Thr Leu  Val Gly His Gly Glu  Thr Glu Gly Asp
            100                 105                 110

Thr Thr Thr Phe Gly Gly Met  Asn Ala Glu Thr Leu  Lys Gly His Leu
        115                 120                 125

Ser Ser Leu Phe Ala Arg Leu  Gly Ser Ser Ser Val  Leu Ile Lys Gly
```

```
                130              135              140
Ile Thr Leu Asn Leu Thr Gly Cys Ser Leu Leu Asn Pro Lys Gln Pro
145              150              155              160

Leu Ala Asp Thr Leu Pro Gly Gln Leu Ala Ile Trp Leu Lys Gln Gln
                165              170              175

Ala Glu Ile Leu Gly Leu Asp Asp Ser Asn Trp Ser Val Asn Ala Arg
                180              185              190

Glu Asn Asp Leu Leu Val Leu Glu Asn Gly Lys Lys Glu Ile Arg Ile
                195              200              205

Asn Asp His Trp Ile Asn Lys Glu Val Ala Asp Ile His Gly Leu Val
210              215              220

Tyr Lys Thr Lys Leu Val Trp Asn Lys Glu Thr Gln Ser Leu Tyr Lys
225              230              235              240

Leu Pro Leu Ser Ile Glu Glu Leu Gln Gln Val Thr Pro Tyr Ile Asp
                245              250              255

Asp Ala Ile Ala Thr His Asn Gln Leu Asp Ser Gln Ser Ala Thr Leu
                260              265              270

Leu Glu Glu Met His Arg Gln Val Ser Gln Arg Ile Ser Glu Leu Leu
                275              280              285

Leu Leu Asn Glu Lys His Glu Ser His Arg Asn Glu Ile Glu Gln Arg
                290              295              300

Val Ser Glu Leu Leu Glu Leu Val Asn Leu Gly Asn Glu Trp Asn Asp
305              310              315              320

Ala Ala Ser Gln Leu His Leu Asp Asn His Leu Asp Glu His Trp His
                325              330              335

Ala Thr Phe Thr Val Gln Ala Gly Glu Asn Gly Gly His Gln Val Ala
                340              345              350

Phe Val Asn Ser Leu Thr Asp Lys Ile Gln Tyr Ile Ser Thr Arg Glu
                355              360              365

Ser Ile Phe Ser Glu Phe Ser Gln Arg Tyr Gln Leu Leu Gly His
                370              375              380

Phe Ser Ser Gly Leu Met Leu Asp Lys Gln Ser Gly Lys Ile Ile Ala
385              390              395              400

Lys Pro Asn Val Leu Glu Gly Glu Ala Ala His Thr Leu Asn Ala Ala
                405              410              415

Phe Met Leu Gln Thr Leu Met Asn Ile Asn Pro Ser Asn Gly Gly Ile
                420              425              430

Asn Ala Leu Ser Trp Pro Leu Gln Leu Gln Thr Tyr Thr Gln Leu Ala
                435              440              445

Gln Asn Thr Leu Gly Leu Val His Asp Val Ser Ala Val Ala Asn Leu
450              455              460

Val Lys Leu Ala Ser Ala Thr Glu Leu Lys Pro Leu Ser Ala Ala Thr
465              470              475              480

Ser Leu Leu Gly Thr Val Ala Pro Gly Val Val Gly Leu Leu Leu Asp
                485              490              495

Ala Ala Asn Ile Leu Gly Met Ser Phe Gln Leu Ser Ala Ser Thr Asp
                500              505              510

Pro Val Glu Ile Asn Thr Thr Ile Ala Asn Leu Thr Leu Ser Ser Leu
                515              520              525

Met Val Gly Thr Asn Ile Ala Ala Leu Leu Thr Ser Leu Ser Ala Ala
                530              535              540

Ser Ala Ala Val Ser Gly Leu Leu Gly Met Val Ala Val Pro Leu Ala
545              550              555              560
```

```
Gly Ile Ala Ala Gly Leu Pro Ala Leu Val Gly Asn Tyr Thr Thr Leu
                565                 570                 575

Ala Glu Gln Asn Lys Ser Ala Leu Thr Ala Phe Asp Ala Ile Gln Thr
            580                 585                 590

Ser Val Ser Gln Pro Asn Gln Leu Arg Lys Ile Ser Asp Ala Gly Gln
        595                 600                 605

Ser Pro Ile Val Trp Gly Leu Ala Met Gly Ala Val Val Asp Ser Ile
    610                 615                 620

Asn Phe Arg Asp Asn His Val His Phe Gly Ser Val Thr Ser Val Gly
625                 630                 635                 640

Ser Lys Gly Gly Ser Trp His Thr His Ser Gly His Trp Asp His Tyr
                645                 650                 655

Leu Ser Gly Pro Ser Ile Asp Tyr Gly Leu Lys Leu Asp Leu Tyr Leu
            660                 665                 670

Gly Leu Gly Leu Lys Glu His Thr Gln Glu Leu Asp Leu Thr Asp Ala
        675                 680                 685

Gln Ile Phe Leu Leu Pro Ala Ser Ala Gln Arg His Tyr Thr Phe Gly
    690                 695                 700

Tyr Asp Glu Ala Pro Gly Ile Arg Tyr Lys Asn Pro Ser Ala Leu Met
705                 710                 715                 720

Ala Leu Gly Gln Tyr Tyr Gly Ala Gln Phe Lys Trp Gly Phe Tyr Ala
                725                 730                 735

Leu Pro Thr Asp Trp Ala Ile Thr Arg Leu Thr Ala Glu Leu Phe Ser
            740                 745                 750

Thr Pro Ile Asn Val Gln Leu Asp Ser Arg Ala Arg Thr Leu Ile Val
        755                 760                 765

Pro Thr Leu Leu Asp Asp Thr Glu Arg Gly Lys Leu Phe Tyr Gln Leu
    770                 775                 780

Ile Gly Asn Gly Gly Glu Tyr Thr Leu Ile Met Pro Ser Lys Thr Val
785                 790                 795                 800

Ala Ile Thr Ile Thr Cys Ala Asp Ala Asp Lys Glu His Trp Ile Phe
                805                 810                 815

Asp Ile Glu Ala Leu Ile Lys Gln Ser Ser Val Val Asp Asn Lys Ile
            820                 825                 830

Val Leu Gly Ala Leu Leu Pro Glu Arg Ile Lys Ala Ile Thr Leu His
        835                 840                 845

Asn Asn Ile Leu Ser Val Gly Asp Gln Arg Ile Gln Phe Asn Gly Lys
    850                 855                 860

Pro Pro Val His Leu Leu Glu Ser Arg Leu Thr Leu Thr Gly Val
865                 870                 875                 880

Thr Lys Gln Asn Asn Ser Leu Pro Thr Leu Thr Leu Ala Leu Ser Val
                885                 890                 895

Gly Glu Gln Asn Ser Pro Pro Arg Pro Val Leu Met Phe Ser Asp Asp
            900                 905                 910

Thr Leu Glu Gln Tyr Ala Ala Gln Ile Leu Gln Ala Val Arg Pro
        915                 920                 925

Leu Ala Ser Leu Val Ala Lys Ile Pro Phe Val Ala Gly Lys Ser Asn
    930                 935                 940

Gly Val Ile Asp Ile Ala Asn Asn Trp Leu Trp Leu Ala Gln Ser Gln
945                 950                 955                 960

Gly Gln Leu Leu Leu Cys Asp Gly Asn Arg Leu Ser Lys Ser Leu Phe
                965                 970                 975

Pro Lys Ser Ala Gln Val Leu Ile Gly Pro Asn Asp Lys Ile Met Ala
            980                 985                 990
```

-continued

```
Thr Gly Lys Met Gly Asp Leu Ser  Phe Asn Ala Ile Leu  Glu Gln Gln
        995              1000                1005

Ser Gly  Asn Ile Ala Val Ser  Leu Ile Tyr Leu Glu  Ile Val Ile
    1010              1015              1020

Ala Asp  Ala Thr Ser Phe Ser  Gln Ala Pro Phe Gln  Glu Phe Ala
    1025              1030              1035

Asp His  Ser Leu Gly Gly Val  Ile Asp Ser Leu Leu  Ala Arg Tyr
    1040              1045              1050

Pro Gly  Ser Phe Ala Arg Glu  Asn Leu Ser Phe Asn  Pro Gln Gly
    1055              1060              1065

Val Trp  Arg Phe Ala Ser Gln  Gln Gly Glu Gly Phe  Ser Phe Ala
    1070              1075              1080

Leu Ser  Glu Arg Asp Leu Leu  Ser Val Ser Asn Ala  Asn Trp Ser
    1085              1090              1095

Asn Ser  Gln Ala Glu Phe Ile  Tyr Asn Asn Leu Tyr  Ser Ser Thr
    1100              1105              1110

Thr Lys  Thr Leu Glu Val Lys  Ala Lys Ala Thr Thr  Val Glu Leu
    1115              1120              1125

Asn Leu  Ser Lys Gln Gln Leu  Glu Leu Asn Trp Leu  Asp Lys Asn
    1130              1135              1140

Thr Gln  Ile Ile Ile Phe Tyr  Gln Asp Asn Leu Ser  Cys Ile Gly
    1145              1150              1155

Leu Ala  Leu Asn Asp Ile Pro  Val Ala Asn Leu Tyr  Ile Ala Gly
    1160              1165              1170

Leu Ser  Arg Lys Asn Arg Phe  Thr Val Asn Ile Leu  Asp His Thr
    1175              1180              1185

Gln Gln  Ser Met Leu Leu Asn  Ile Thr Asp Asn Asp  Phe Val Met
    1190              1195              1200

Arg Ser  Asn Leu Gly His Ser  Ile Lys Val Ala Asn  Ala Leu Asn
    1205              1210              1215

Met Glu  Glu Ile Leu Phe Phe  Ser Phe Leu Asn Ser  Gln Gln Met
    1220              1225              1230

Ser Phe  Gln Lys Ile Lys Ala  Asn Ile Leu Phe Ser  Leu Asn Lys
    1235              1240              1245

Pro Ile  Thr Gln Val Met Thr  Tyr Phe Asn Leu Glu  Ser Ile Pro
    1250              1255              1260

Asn Ala  Glu Leu Ile Asp Gly  Tyr Tyr His Phe Met  Gly Lys Ser
    1265              1270              1275

Gly Leu  Tyr Tyr Gln Ala Pro  Met Asp Ile Ala Ala  Ala Asn Lys
    1280              1285              1290

Ala Ala  Asp Ile Ala Asp Ala  Ala Asp Ile Thr His  Ala Gln Ile
    1295              1300              1305

Gln Val  Gln Gln Leu Ala Ser  Ile Val Pro Phe Phe  Asp Met
    1310              1315              1320

Glu Pro  Glu Pro Thr Leu Ser  Asn Gly Arg Ala Phe  Thr Val Val
    1325              1330              1335

Gly Tyr  Lys Gly Pro Gln Ala  Tyr Arg Ile Pro Pro  Asn Ile Arg
    1340              1345              1350

Ser Ile  Ser Ile Leu Leu Gln  Ile Ile Gln Gly Gly  Thr Ile Phe
    1355              1360              1365

Asn Gly  Val Lys Phe Gln Asn  Ile Asn Leu Asp Thr  Phe Phe Pro
    1370              1375              1380

Glu Thr  Gly Gln Glu Ala Ile  Ile Trp Leu Gln Lys  Ile Glu Met
```

```
                    1385              1390              1395

Leu Val  Thr His Ser Gly Gln  Asn Gln Phe Ile Gln  Arg Leu Met
         1400              1405              1410

Phe Gly  Ser Gln Pro Asn Thr  Ser Ile Glu Ile Asn  Ile Arg Asp
         1415              1420              1425

Val Lys  Lys Phe Ile Asn Asp  Tyr Leu Asn Lys Ala  Ile Lys Gln
         1430              1435              1440

Gly Gly  Trp Val Ser Asn
         1445

<210> SEQ ID NO 12
<211> LENGTH: 2710
<212> TYPE: PRT
<213> ORGANISM: Clostridium difficile

<400> SEQUENCE: 12

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
                20                  25                  30

Tyr Asn Lys Leu Thr Thr Asn Asn Glu Asn Lys Tyr Leu Gln Leu
            35                  40                  45

Lys Lys Leu Asn Glu Ser Ile Asp Val Phe Met Asn Lys Tyr Lys Thr
50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
                100                 105                 110

Tyr Ile Lys Gln Trp Ala Asp Ile Asn Ala Glu Tyr Asn Ile Lys Leu
            115                 120                 125

Trp Tyr Asp Ser Glu Ala Phe Leu Val Asn Thr Leu Lys Lys Ala Ile
        130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
                180                 185                 190

Ile Asn Lys Pro Thr Val Pro Thr Ile Asp Asp Ile Ile Lys Ser His
            195                 200                 205

Leu Val Ser Glu Tyr Asn Arg Asp Glu Thr Val Leu Glu Ser Tyr Arg
        210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
                260                 265                 270

Leu Leu Ala Leu Lys Asn Phe Gly Gly Val Tyr Leu Asp Val Asp Met
            275                 280                 285

Leu Pro Gly Ile His Ser Asp Leu Phe Lys Thr Ile Ser Arg Pro Ser
        290                 295                 300

Ser Ile Gly Leu Asp Arg Trp Glu Met Ile Lys Leu Glu Ala Ile Met
```

```
            305                 310                 315                 320
Lys Tyr Lys Lys Tyr Ile Asn Asn Tyr Thr Ser Glu Asn Phe Asp Lys
                    325                 330                 335

Leu Asp Gln Gln Leu Lys Asp Asn Phe Lys Leu Ile Ile Glu Ser Lys
                    340                 345                 350

Ser Glu Lys Ser Glu Ile Phe Ser Lys Leu Glu Asn Leu Asn Val Ser
                    355                 360                 365

Asp Leu Glu Ile Lys Ile Ala Phe Ala Leu Gly Ser Val Ile Asn Gln
                370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                    405                 410                 415

Ile Glu Ser Asp Asn Asn Phe Thr Asp Thr Thr Lys Ile Phe His Asp
                    420                 425                 430

Ser Leu Phe Asn Ser Ala Thr Ala Glu Asn Ser Met Phe Leu Thr Lys
                    435                 440                 445

Ile Ala Pro Tyr Leu Gln Val Gly Phe Met Pro Glu Ala Arg Ser Thr
                    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                    485                 490                 495

Leu Ile Glu Phe Lys Phe Pro Glu Asn Asn Leu Ser Gln Leu Thr Glu
                500                 505                 510

Gln Glu Ile Asn Ser Leu Trp Ser Phe Asp Gln Ala Ser Ala Lys Tyr
                515                 520                 525

Gln Phe Glu Lys Tyr Val Arg Asp Tyr Thr Gly Gly Ser Leu Ser Glu
                530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                    565                 570                 575

Lys Asn Tyr Val His Tyr Ile Ile Gln Leu Gln Gly Asp Asp Ile Ser
                    580                 585                 590

Tyr Glu Ala Thr Cys Asn Leu Phe Ser Lys Asn Pro Lys Asn Ser Ile
                595                 600                 605

Ile Ile Gln Arg Asn Met Asn Glu Ser Ala Lys Ser Tyr Phe Leu Ser
                610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                    645                 650                 655

Lys Asp Glu Phe Asn Thr Ser Phe Ala Arg Leu Ser Val Asp Ser
                    660                 665                 670

Leu Ser Asn Glu Ile Ser Ser Phe Leu Asp Thr Ile Lys Leu Asp Ile
                    675                 680                 685

Ser Pro Lys Asn Val Glu Val Asn Leu Leu Gly Cys Asn Met Phe Ser
                690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                    725                 730                 735
```

-continued

Ile Thr Ile Gly Ala Asn Gln Tyr Glu Val Arg Ile Asn Ser Gly
            740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
            805                 810                 815

Pro Asp Thr Lys Phe Ile Leu Asn Asn Leu Lys Leu Asn Ile Glu Ser
        820                 825                 830

Ser Ile Gly Asp Tyr Ile Tyr Tyr Glu Lys Leu Glu Pro Val Lys Asn
    835                 840                 845

Ile Ile His Asn Ser Ile Asp Asp Leu Ile Asp Glu Phe Asn Leu Leu
850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
            885                 890                 895

Thr Tyr Ser Val Arg Phe Ile Asn Lys Ser Asn Gly Glu Ser Val Tyr
        900                 905                 910

Val Glu Thr Glu Lys Glu Ile Phe Ser Lys Tyr Ser Glu His Ile Thr
    915                 920                 925

Lys Glu Ile Ser Thr Ile Lys Asn Ser Ile Ile Thr Asp Val Asn Gly
930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
            965                 970                 975

Lys Asp Val Leu Asn Asp Leu Ser Thr Ser Val Lys Val Gln Leu Tyr
        980                 985                 990

Ala Gln Leu Phe Ser Thr Gly Leu Asn Thr Ile Tyr Asp Ser Ile Gln
    995                 1000                1005

Leu Val Asn Leu Ile Ser Asn Ala Val Asn Asp Thr Ile Asn Val
    1010                1015                1020

Leu Pro Thr Ile Thr Glu Gly Ile Pro Ile Val Ser Thr Ile Leu
    1025                1030                1035

Asp Gly Ile Asn Leu Gly Ala Ala Ile Lys Glu Leu Leu Asp Glu
    1040                1045                1050

His Asp Pro Leu Leu Lys Lys Glu Leu Glu Ala Lys Val Gly Val
    1055                1060                1065

Leu Ala Ile Asn Met Ser Leu Ser Ile Ala Ala Thr Val Ala Ser
    1070                1075                1080

Ile Val Gly Ile Gly Ala Glu Val Thr Ile Phe Leu Leu Pro Ile
    1085                1090                1095

Ala Gly Ile Ser Ala Gly Ile Pro Ser Leu Val Asn Asn Glu Leu
    1100                1105                1110

Ile Leu His Asp Lys Ala Thr Ser Val Val Asn Tyr Phe Asn His
    1115                1120                1125

Leu Ser Glu Ser Lys Lys Tyr Gly Pro Leu Lys Thr Glu Asp Asp
    1130                1135                1140

Lys Ile Leu Val Pro Ile Asp Asp Leu Val Ile Ser Glu Ile Asp
    1145                1150                1155

-continued

```
Phe Asn Asn Asn Ser Ile Lys Leu Gly Thr Cys Asn Ile Leu Ala
    1160                1165                1170

Met Glu Gly Gly Ser Gly His Thr Val Thr Gly Asn Ile Asp His
    1175                1180                1185

Phe Phe Ser Ser Pro Ser Ile Ser Ser His Ile Pro Ser Leu Ser
    1190                1195                1200

Ile Tyr Ser Ala Ile Gly Ile Glu Thr Glu Asn Leu Asp Phe Ser
    1205                1210                1215

Lys Lys Ile Met Met Leu Pro Asn Ala Pro Ser Arg Val Phe Trp
    1220                1225                1230

Trp Glu Thr Gly Ala Val Pro Gly Leu Arg Ser Leu Glu Asn Asp
    1235                1240                1245

Gly Thr Arg Leu Leu Asp Ser Ile Arg Asp Leu Tyr Pro Gly Lys
    1250                1255                1260

Phe Tyr Trp Arg Phe Tyr Ala Phe Phe Asp Tyr Ala Ile Thr Thr
    1265                1270                1275

Leu Lys Pro Val Tyr Glu Asp Thr Asn Ile Lys Ile Lys Leu Asp
    1280                1285                1290

Lys Asp Thr Arg Asn Phe Ile Met Pro Thr Ile Thr Thr Asn Glu
    1295                1300                1305

Ile Arg Asn Lys Leu Ser Tyr Ser Phe Asp Gly Ala Gly Gly Thr
    1310                1315                1320

Tyr Ser Leu Leu Leu Ser Ser Tyr Pro Ile Ser Thr Asn Ile Asn
    1325                1330                1335

Leu Ser Lys Asp Asp Leu Trp Ile Phe Asn Ile Asp Asn Glu Val
    1340                1345                1350

Arg Glu Ile Ser Ile Glu Asn Gly Thr Ile Lys Lys Gly Lys Leu
    1355                1360                1365

Ile Lys Asp Val Leu Ser Lys Ile Asp Ile Asn Lys Asn Lys Leu
    1370                1375                1380

Ile Ile Gly Asn Gln Thr Ile Asp Phe Ser Gly Asp Ile Asp Asn
    1385                1390                1395

Lys Asp Arg Tyr Ile Phe Leu Thr Cys Glu Leu Asp Asp Lys Ile
    1400                1405                1410

Ser Leu Ile Ile Glu Ile Asn Leu Val Ala Lys Ser Tyr Ser Leu
    1415                1420                1425

Leu Leu Ser Gly Asp Lys Asn Tyr Leu Ile Ser Asn Leu Ser Asn
    1430                1435                1440

Thr Ile Glu Lys Ile Asn Thr Leu Gly Leu Asp Ser Lys Asn Ile
    1445                1450                1455

Ala Tyr Asn Tyr Thr Asp Glu Ser Asn Asn Lys Tyr Phe Gly Ala
    1460                1465                1470

Ile Ser Lys Thr Ser Gln Lys Ser Ile Ile His Tyr Lys Lys Asp
    1475                1480                1485

Ser Lys Asn Ile Leu Glu Phe Tyr Asn Asp Ser Thr Leu Glu Phe
    1490                1495                1500

Asn Ser Lys Asp Phe Ile Ala Glu Asp Ile Asn Val Phe Met Lys
    1505                1510                1515

Asp Asp Ile Asn Thr Ile Thr Gly Lys Tyr Tyr Val Asp Asn Asn
    1520                1525                1530

Thr Asp Lys Ser Ile Asp Phe Ser Ile Ser Leu Val Ser Lys Asn
    1535                1540                1545

Gln Val Lys Val Asn Gly Leu Tyr Leu Asn Glu Ser Val Tyr Ser
```

```
                    1550                1555                1560

Ser Tyr Leu Asp Phe Val Lys Asn Ser Asp Gly His His Asn Thr
    1565            1570                1575

Ser Asn Phe Met Asn Leu Phe Leu Asp Asn Ile Ser Phe Trp Lys
    1580            1585                1590

Leu Phe Gly Phe Glu Asn Ile Asn Phe Val Ile Asp Lys Tyr Phe
    1595            1600                1605

Thr Leu Val Gly Lys Thr Asn Leu Gly Tyr Val Glu Phe Ile Cys
    1610            1615                1620

Asp Asn Asn Lys Asn Ile Asp Ile Tyr Phe Gly Glu Trp Lys Thr
    1625            1630                1635

Ser Ser Ser Lys Ser Thr Ile Phe Ser Gly Asn Gly Arg Asn Val
    1640            1645                1650

Val Val Glu Pro Ile Tyr Asn Pro Asp Thr Gly Glu Asp Ile Ser
    1655            1660                1665

Thr Ser Leu Asp Phe Ser Tyr Glu Pro Leu Tyr Gly Ile Asp Arg
    1670            1675                1680

Tyr Ile Asn Lys Val Leu Ile Ala Pro Asp Leu Tyr Thr Ser Leu
    1685            1690                1695

Ile Asn Ile Asn Thr Asn Tyr Tyr Ser Asn Glu Tyr Tyr Pro Glu
    1700            1705                1710

Ile Ile Val Leu Asn Pro Asn Thr Phe His Lys Lys Val Asn Ile
    1715            1720                1725

Asn Leu Asp Ser Ser Ser Phe Glu Tyr Lys Trp Ser Thr Glu Gly
    1730            1735                1740

Ser Asp Phe Ile Leu Val Arg Tyr Leu Glu Glu Ser Asn Lys Lys
    1745            1750                1755

Ile Leu Gln Lys Ile Arg Ile Lys Gly Ile Leu Ser Asn Thr Gln
    1760            1765                1770

Ser Phe Asn Lys Met Ser Ile Asp Phe Lys Asp Ile Lys Lys Leu
    1775            1780                1785

Ser Leu Gly Tyr Ile Met Ser Asn Phe Lys Ser Phe Asn Ser Glu
    1790            1795                1800

Asn Glu Leu Asp Arg Asp His Leu Gly Phe Lys Ile Ile Asp Asn
    1805            1810                1815

Lys Thr Tyr Tyr Tyr Asp Glu Asp Ser Lys Leu Val Lys Gly Leu
    1820            1825                1830

Ile Asn Ile Asn Asn Ser Leu Phe Tyr Phe Asp Pro Ile Glu Phe
    1835            1840                1845

Asn Leu Val Thr Gly Trp Gln Thr Ile Asn Gly Lys Lys Tyr Tyr
    1850            1855                1860

Phe Asp Ile Asn Thr Gly Ala Ala Leu Thr Ser Tyr Lys Ile Ile
    1865            1870                1875

Asn Gly Lys His Phe Tyr Phe Asn Asn Asp Gly Val Met Gln Leu
    1880            1885                1890

Gly Val Phe Lys Gly Pro Asp Gly Phe Glu Tyr Phe Ala Pro Ala
    1895            1900                1905

Asn Thr Gln Asn Asn Asn Ile Glu Gly Gln Ala Ile Val Tyr Gln
    1910            1915                1920

Ser Lys Phe Leu Thr Leu Asn Gly Lys Lys Tyr Tyr Phe Asp Asn
    1925            1930                1935

Asn Ser Lys Ala Val Thr Gly Trp Arg Ile Ile Asn Asn Glu Lys
    1940            1945                1950
```

```
Tyr Tyr Phe Asn Pro Asn Asn Ala Ile Ala Val Gly Leu Gln
1955                 1960            1965

Val Ile Asp Asn Asn Lys Tyr Tyr Phe Asn Pro Asp Thr Ala Ile
    1970            1975            1980

Ile Ser Lys Gly Trp Gln Thr Val Asn Gly Ser Arg Tyr Tyr Phe
1985                 1990            1995

Asp Thr Asp Thr Ala Ile Ala Phe Asn Gly Tyr Lys Thr Ile Asp
    2000            2005            2010

Gly Lys His Phe Tyr Phe Asp Ser Asp Cys Val Val Lys Ile Gly
    2015            2020            2025

Val Phe Ser Thr Ser Asn Gly Phe Glu Tyr Phe Ala Pro Ala Asn
    2030            2035            2040

Thr Tyr Asn Asn Asn Ile Glu Gly Gln Ala Ile Val Tyr Gln Ser
    2045            2050            2055

Lys Phe Leu Thr Leu Asn Gly Lys Lys Tyr Tyr Phe Asp Asn Asn
    2060            2065            2070

Ser Lys Ala Val Thr Gly Trp Gln Thr Ile Asp Ser Lys Lys Tyr
    2075            2080            2085

Tyr Phe Asn Thr Asn Thr Ala Glu Ala Ala Thr Gly Trp Gln Thr
    2090            2095            2100

Ile Asp Gly Lys Lys Tyr Tyr Phe Asn Thr Asn Thr Ala Glu Ala
    2105            2110            2115

Ala Thr Gly Trp Gln Thr Ile Asp Gly Lys Lys Tyr Tyr Phe Asn
    2120            2125            2130

Thr Asn Thr Ala Ile Ala Ser Thr Gly Tyr Thr Ile Ile Asn Gly
    2135            2140            2145

Lys His Phe Tyr Phe Asn Thr Asp Gly Ile Met Gln Ile Gly Val
    2150            2155            2160

Phe Lys Gly Pro Asn Gly Phe Glu Tyr Phe Ala Pro Ala Asn Thr
    2165            2170            2175

Asp Ala Asn Asn Ile Glu Gly Gln Ala Ile Leu Tyr Gln Asn Glu
    2180            2185            2190

Phe Leu Thr Leu Asn Gly Lys Lys Tyr Tyr Phe Gly Ser Asp Ser
    2195            2200            2205

Lys Ala Val Thr Gly Trp Arg Ile Ile Asn Asn Lys Lys Tyr Tyr
    2210            2215            2220

Phe Asn Pro Asn Asn Ala Ile Ala Ala Ile His Leu Cys Thr Ile
    2225            2230            2235

Asn Asn Asp Lys Tyr Tyr Phe Ser Tyr Asp Gly Ile Leu Gln Asn
    2240            2245            2250

Gly Tyr Ile Thr Ile Glu Arg Asn Asn Phe Tyr Phe Asp Ala Asn
    2255            2260            2265

Asn Glu Ser Lys Met Val Thr Gly Val Phe Lys Gly Pro Asn Gly
    2270            2275            2280

Phe Glu Tyr Phe Ala Pro Ala Asn Thr His Asn Asn Asn Ile Glu
    2285            2290            2295

Gly Gln Ala Ile Val Tyr Gln Asn Lys Phe Leu Thr Leu Asn Gly
    2300            2305            2310

Lys Lys Tyr Tyr Phe Asp Asn Asp Ser Lys Ala Val Thr Gly Trp
    2315            2320            2325

Gln Thr Ile Asp Gly Lys Lys Tyr Tyr Phe Asn Leu Asn Thr Ala
    2330            2335            2340

Glu Ala Ala Thr Gly Trp Gln Thr Ile Asp Gly Lys Lys Tyr Tyr
    2345            2350            2355
```

Phe Asn Leu Asn Thr Ala Glu Ala Ala Thr Gly Trp Gln Thr Ile
2360                2365                2370

Asp Gly Lys Lys Tyr Tyr Phe Asn Thr Asn Thr Phe Ile Ala Ser
2375                2380                2385

Thr Gly Tyr Thr Ser Ile Asn Gly Lys His Phe Tyr Phe Asn Thr
2390                2395                2400

Asp Gly Ile Met Gln Ile Gly Val Phe Lys Gly Pro Asn Gly Phe
2405                2410                2415

Glu Tyr Phe Ala Pro Ala Asn Thr Asp Ala Asn Asn Ile Glu Gly
2420                2425                2430

Gln Ala Ile Leu Tyr Gln Asn Lys Phe Leu Thr Leu Asn Gly Lys
2435                2440                2445

Lys Tyr Tyr Phe Gly Ser Asp Ser Lys Ala Val Thr Gly Leu Arg
2450                2455                2460

Thr Ile Asp Gly Lys Lys Tyr Tyr Phe Asn Thr Asn Thr Ala Val
2465                2470                2475

Ala Val Thr Gly Trp Gln Thr Ile Asn Gly Lys Lys Tyr Tyr Phe
2480                2485                2490

Asn Thr Asn Thr Ser Ile Ala Ser Thr Gly Tyr Thr Ile Ile Ser
2495                2500                2505

Gly Lys His Phe Tyr Phe Asn Thr Asp Gly Ile Met Gln Ile Gly
2510                2515                2520

Val Phe Lys Gly Pro Asp Gly Phe Glu Tyr Phe Ala Pro Ala Asn
2525                2530                2535

Thr Asp Ala Asn Asn Ile Glu Gly Gln Ala Ile Arg Tyr Gln Asn
2540                2545                2550

Arg Phe Leu Tyr Leu His Asp Asn Ile Tyr Tyr Phe Gly Asn Asn
2555                2560                2565

Ser Lys Ala Ala Thr Gly Trp Val Thr Ile Asp Gly Asn Arg Tyr
2570                2575                2580

Tyr Phe Glu Pro Asn Thr Ala Met Gly Ala Asn Gly Tyr Lys Thr
2585                2590                2595

Ile Asp Asn Lys Asn Phe Tyr Phe Arg Asn Gly Leu Pro Gln Ile
2600                2605                2610

Gly Val Phe Lys Gly Ser Asn Gly Phe Glu Tyr Phe Ala Pro Ala
2615                2620                2625

Asn Thr Asp Ala Asn Asn Ile Glu Gly Gln Ala Ile Arg Tyr Gln
2630                2635                2640

Asn Arg Phe Leu His Leu Leu Gly Lys Ile Tyr Tyr Phe Gly Asn
2645                2650                2655

Asn Ser Lys Ala Val Thr Gly Trp Gln Thr Ile Asn Gly Lys Val
2660                2665                2670

Tyr Tyr Phe Met Pro Asp Thr Ala Met Ala Ala Ala Gly Gly Leu
2675                2680                2685

Phe Glu Ile Asp Gly Val Ile Tyr Phe Phe Gly Val Asp Gly Val
2690                2695                2700

Lys Ala Pro Gly Ile Tyr Gly
2705                2710

<210> SEQ ID NO 13
<211> LENGTH: 2367
<212> TYPE: PRT
<213> ORGANISM: Clostridium difficile

<400> SEQUENCE: 13

```
Met Ser Leu Val Asn Arg Lys Gln Leu Glu Lys Met Ala Asn Val Arg
1               5                   10                  15

Phe Arg Val Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Thr Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Ile Glu Ile Leu Glu Leu Lys Asn Ser Asn Leu Thr Pro Val Glu Lys
                85                  90                  95

Asn Leu His Phe Ile Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
            115                 120                 125

Val Phe Tyr Asp Ser Asn Ala Phe Leu Ile Asn Thr Leu Lys Lys Thr
        130                 135                 140

Ile Ile Glu Ser Ala Ser Asn Asp Thr Leu Glu Ser Phe Arg Glu Asn
145                 150                 155                 160

Leu Asn Asp Pro Glu Phe Asn His Thr Ala Phe Phe Arg Lys Arg Met
                165                 170                 175

Gln Ile Ile Tyr Asp Lys Gln Gln Asn Phe Ile Asn Tyr Tyr Lys Ala
            180                 185                 190

Gln Lys Glu Glu Asn Pro Asp Leu Ile Ile Asp Asp Ile Val Lys Thr
        195                 200                 205

Tyr Leu Ser Asn Glu Tyr Ser Lys Asp Ile Asp Glu Leu Asn Ala Tyr
210                 215                 220

Ile Glu Glu Ser Leu Asn Lys Val Thr Glu Asn Ser Gly Asn Asp Val
225                 230                 235                 240

Arg Asn Phe Glu Glu Phe Lys Thr Gly Glu Val Phe Asn Leu Tyr Glu
            245                 250                 255

Gln Glu Ser Val Glu Arg Trp Asn Leu Ala Gly Ala Ser Asp Ile Leu
            260                 265                 270

Arg Val Ala Ile Leu Lys Asn Ile Gly Gly Val Tyr Leu Asp Val Asp
        275                 280                 285

Met Leu Pro Gly Ile His Pro Asp Leu Phe Lys Asp Ile Asn Lys Pro
290                 295                 300

Asp Ser Val Lys Thr Ala Val Asp Trp Glu Glu Met Gln Leu Glu Ala
305                 310                 315                 320

Ile Met Lys His Lys Glu Tyr Ile Pro Glu Tyr Thr Ser Lys His Phe
            325                 330                 335

Asp Thr Leu Asp Glu Glu Val Gln Ser Ser Phe Glu Ser Val Leu Ala
            340                 345                 350

Ser Lys Ser Asp Lys Ser Glu Ile Phe Leu Pro Leu Gly Asp Ile Glu
        355                 360                 365

Val Ser Pro Leu Glu Val Lys Ile Ala Phe Ala Lys Gly Ser Ile Ile
        370                 375                 380

Asn Gln Ala Leu Ile Ser Ala Lys Asp Ser Tyr Cys Ser Asp Leu Leu
385                 390                 395                 400

Ile Lys Gln Ile Gln Asn Arg Tyr Lys Ile Leu Asn Asp Thr Leu Gly
            405                 410                 415

Pro Ile Ile Ser Gln Gly Asn Asp Phe Asn Thr Thr Met Asn Asn Phe
```

```
                    420             425             430
Gly Glu Ser Leu Gly Ala Ile Ala Asn Glu Asn Ile Ser Phe Ile
                435             440             445
Ala Lys Ile Gly Ser Tyr Leu Arg Val Gly Phe Tyr Pro Glu Ala Asn
    450                 455                 460
Thr Thr Ile Thr Leu Ser Gly Pro Thr Ile Tyr Ala Gly Ala Tyr Lys
465                 470                 475                 480
Asp Leu Leu Thr Phe Lys Glu Met Ser Ile Asp Thr Ser Ile Leu Ser
                485                 490                 495
Ser Glu Leu Arg Asn Phe Glu Phe Pro Lys Val Asn Ile Ser Gln Ala
            500                 505                 510
Thr Glu Gln Glu Lys Asn Ser Leu Trp Gln Phe Asn Glu Glu Arg Ala
        515                 520                 525
Lys Ile Gln Phe Glu Glu Tyr Lys Lys Asn Tyr Phe Glu Gly Ala Leu
    530                 535                 540
Gly Glu Asp Asp Asn Leu Asp Phe Ser Gln Asn Thr Val Thr Asp Lys
545                 550                 555                 560
Glu Tyr Leu Leu Glu Lys Ile Ser Ser Thr Lys Ser Ser Glu Gly
                565                 570                 575
Gly Tyr Val His Tyr Ile Val Gln Leu Gln Gly Asp Lys Ile Ser Tyr
            580                 585                 590
Glu Ala Ala Cys Asn Leu Phe Ala Lys Asn Pro Tyr Asp Ser Ile Leu
        595                 600                 605
Phe Gln Arg Asn Ile Glu Asp Ser Glu Val Ala Tyr Tyr Tyr Asn Pro
    610                 615                 620
Thr Asp Ser Glu Ile Gln Glu Ile Asp Lys Tyr Arg Ile Pro Asp Arg
625                 630                 635                 640
Ile Ser Asp Arg Pro Lys Ile Lys Leu Thr Phe Ile Gly His Gly Lys
                645                 650                 655
Ala Glu Phe Asn Thr Asp Ile Phe Ala Gly Leu Asp Val Asp Ser Leu
            660                 665                 670
Ser Ser Glu Ile Glu Thr Ala Ile Gly Leu Ala Lys Glu Asp Ile Ser
        675                 680                 685
Pro Lys Ser Ile Glu Ile Asn Leu Leu Gly Cys Asn Met Phe Ser Tyr
    690                 695                 700
Ser Val Asn Val Glu Glu Thr Tyr Pro Gly Lys Leu Leu Leu Arg Val
705                 710                 715                 720
Lys Asp Lys Val Ser Glu Leu Met Pro Ser Met Ser Gln Asp Ser Ile
                725                 730                 735
Ile Val Ser Ala Asn Gln Tyr Glu Val Arg Ile Asn Ser Glu Gly Arg
            740                 745                 750
Arg Glu Leu Leu Asp His Ser Gly Glu Trp Ile Asn Lys Glu Glu Ser
        755                 760                 765
Ile Ile Lys Asp Ile Ser Ser Lys Glu Tyr Ile Ser Phe Asn Pro Lys
    770                 775                 780
Glu Asn Lys Ile Ile Val Lys Ser Lys Asn Leu Pro Glu Leu Ser Thr
785                 790                 795                 800
Leu Leu Gln Glu Ile Arg Asn Asn Ser Asn Ser Ser Asp Ile Glu Leu
                805                 810                 815
Glu Glu Lys Val Met Leu Ala Glu Cys Glu Ile Asn Val Ile Ser Asn
            820                 825                 830
Ile Glu Thr Gln Val Val Glu Glu Arg Ile Glu Glu Ala Lys Ser Leu
        835                 840                 845
```

-continued

Thr Ser Asp Ser Ile Asn Tyr Ile Lys Asn Glu Phe Lys Leu Ile Glu
850                 855                 860

Ser Ile Ser Glu Ala Leu Cys Asp Leu Lys Gln Gln Asn Glu Leu Glu
865                 870                 875                 880

Asp Ser His Phe Ile Ser Phe Glu Asp Ile Ser Glu Thr Asp Glu Gly
                885                 890                 895

Phe Ser Ile Arg Phe Ile Asn Lys Glu Thr Gly Glu Ser Ile Phe Val
                900                 905                 910

Glu Thr Glu Lys Thr Ile Phe Ser Gly Tyr Ala Asn His Ile Thr Glu
            915                 920                 925

Glu Ile Ser Lys Ile Lys Gly Thr Ile Phe Asp Thr Val Asn Gly Lys
        930                 935                 940

Leu Val Lys Lys Val Asn Leu Asp Thr Thr His Glu Val Asn Thr Leu
945                 950                 955                 960

Asn Ala Ala Phe Phe Ile Gln Ser Leu Ile Glu Tyr Asn Ser Ser Lys
                965                 970                 975

Glu Ser Leu Ser Asn Leu Ser Val Ala Met Lys Val Gln Val Tyr Ala
            980                 985                 990

Gln Leu Phe Ser Thr Gly Leu Asn Thr Ile Thr Asp Ala Ala Lys Val
        995                 1000                1005

Val Glu Leu Val Ser Thr Ala Leu Asp Glu Thr Ile Asp Leu Leu
    1010                1015                1020

Pro Thr Leu Ser Glu Gly Leu Pro Ile Ile Ala Thr Ile Ile Asp
    1025                1030                1035

Gly Val Ser Leu Gly Ala Ala Ile Lys Glu Leu Ser Glu Thr Ser
    1040                1045                1050

Asp Pro Leu Leu Arg Gln Glu Ile Glu Ala Lys Ile Gly Ile Met
    1055                1060                1065

Ala Val Asn Leu Thr Thr Ala Thr Thr Ala Ile Ile Thr Ser Ser
    1070                1075                1080

Leu Gly Ile Ala Ser Gly Phe Ser Ile Leu Leu Val Pro Leu Ala
    1085                1090                1095

Gly Ile Ser Ala Gly Ile Pro Ser Leu Val Asn Asn Glu Leu Val
    1100                1105                1110

Leu Arg Asp Lys Ala Thr Lys Val Val Asp Tyr Phe Lys His Val
    1115                1120                1125

Ser Leu Val Glu Thr Glu Gly Val Phe Thr Leu Leu Asp Asp Lys
    1130                1135                1140

Val Met Met Gln Gln Asp Asp Leu Val Ile Ser Glu Ile Asp Phe
    1145                1150                1155

Asn Asn Asn Ser Ile Val Leu Gly Lys Cys Glu Ile Trp Arg Met
    1160                1165                1170

Glu Gly Gly Ser Gly His Thr Val Thr Asp Asp Ile Asp His Phe
    1175                1180                1185

Phe Ser Ala Pro Ser Ile Thr Tyr Arg Glu Pro His Leu Ser Ile
    1190                1195                1200

Tyr Asp Val Leu Glu Val Gln Lys Glu Glu Leu Asp Leu Ser Lys
    1205                1210                1215

Asp Leu Met Val Leu Pro Asn Ala Pro Asn Arg Val Phe Ala Trp
    1220                1225                1230

Glu Thr Gly Trp Thr Pro Gly Leu Arg Ser Leu Glu Asn Asp Gly
    1235                1240                1245

Thr Lys Leu Leu Asp Arg Ile Arg Asp Asn Tyr Glu Gly Glu Phe
    1250                1255                1260

```
Tyr Trp Arg Tyr Phe Ala Phe Ile Ala Asp Ala Leu Ile Thr Thr
1265                1270                1275

Leu Lys Pro Arg Tyr Glu Asp Thr Asn Ile Arg Ile Asn Leu Asp
1280                1285                1290

Ser Asn Thr Arg Ser Phe Ile Val Pro Ile Ile Thr Thr Glu Tyr
1295                1300                1305

Ile Arg Glu Lys Leu Ser Tyr Ser Phe Tyr Gly Ser Gly Gly Thr
1310                1315                1320

Tyr Ala Leu Pro Leu Ser Gln Tyr Asn Met Gly Ile Asn Ile Glu
1325                1330                1335

Leu Ser Glu Ser Asp Val Trp Ile Ile Asp Val Asp Asn Val Val
1340                1345                1350

Arg Asp Val Thr Ile Glu Ser Asp Lys Ile Lys Lys Gly Asp Leu
1355                1360                1365

Ile Glu Gly Ile Leu Ser Thr Leu Ser Ile Glu Glu Asn Lys Ile
1370                1375                1380

Ile Leu Asn Ser His Glu Ile Asn Phe Ser Gly Glu Val Asn Gly
1385                1390                1395

Ser Asn Gly Phe Val Ser Leu Thr Phe Ser Ile Leu Glu Gly Ile
1400                1405                1410

Asn Ala Ile Ile Glu Val Asp Leu Leu Ser Lys Ser Tyr Lys Leu
1415                1420                1425

Leu Ile Ser Gly Glu Leu Lys Ile Leu Met Leu Asn Ser Asn His
1430                1435                1440

Ile Gln Gln Lys Ile Asp Tyr Ile Gly Phe Asn Ser Glu Leu Gln
1445                1450                1455

Lys Asn Ile Pro Tyr Ser Phe Val Asp Ser Glu Gly Lys Glu Asn
1460                1465                1470

Gly Phe Ile Asn Gly Ser Thr Lys Glu Gly Leu Phe Val Ser Glu
1475                1480                1485

Leu Pro Asp Val Val Leu Ile Ser Lys Val Tyr Met Asp Asp Ser
1490                1495                1500

Lys Pro Ser Phe Gly Tyr Tyr Ser Asn Asn Leu Lys Asp Val Lys
1505                1510                1515

Val Ile Thr Lys Asp Asn Val Asn Ile Leu Thr Gly Tyr Tyr Leu
1520                1525                1530

Lys Asp Asp Ile Lys Ile Ser Leu Ser Leu Thr Leu Gln Asp Glu
1535                1540                1545

Lys Thr Ile Lys Leu Asn Ser Val His Leu Asp Glu Ser Gly Val
1550                1555                1560

Ala Glu Ile Leu Lys Phe Met Asn Arg Lys Gly Ser Thr Asn Thr
1565                1570                1575

Ser Asp Ser Leu Met Ser Phe Leu Glu Ser Met Asn Ile Lys Ser
1580                1585                1590

Ile Phe Val Asn Phe Leu Gln Ser Asn Ile Lys Phe Ile Leu Asp
1595                1600                1605

Ala Asn Phe Ile Ile Ser Gly Thr Thr Ser Ile Gly Gln Phe Glu
1610                1615                1620

Phe Ile Cys Asp Glu Asn Asn Asn Ile Gln Pro Tyr Phe Ile Lys
1625                1630                1635

Phe Asn Thr Leu Glu Thr Asn Tyr Thr Leu Tyr Val Gly Asn Arg
1640                1645                1650

Gln Asn Met Ile Val Glu Pro Asn Tyr Asp Leu Asp Asp Ser Gly
```

```
                1655                1660                1665

Asp Ile Ser Ser Thr Val Ile Asn Phe Ser Gln Lys Tyr Leu Tyr
    1670                1675                1680

Gly Ile Asp Ser Cys Val Asn Lys Val Val Ile Ser Pro Asn Ile
    1685                1690                1695

Tyr Thr Asp Glu Ile Asn Ile Thr Pro Val Tyr Glu Thr Asn Asn
    1700                1705                1710

Thr Tyr Pro Glu Val Ile Val Leu Asp Ala Asn Tyr Ile Asn Glu
    1715                1720                1725

Lys Ile Asn Val Asn Ile Asn Asp Leu Ser Ile Arg Tyr Val Trp
    1730                1735                1740

Ser Asn Asp Gly Asn Asp Phe Ile Leu Met Ser Thr Ser Glu Glu
    1745                1750                1755

Asn Lys Val Ser Gln Val Lys Ile Arg Phe Val Asn Val Phe Lys
    1760                1765                1770

Asp Lys Thr Leu Ala Asn Lys Leu Ser Phe Asn Phe Ser Asp Lys
    1775                1780                1785

Gln Asp Val Pro Val Ser Glu Ile Ile Leu Ser Phe Thr Pro Ser
    1790                1795                1800

Tyr Tyr Glu Asp Gly Leu Ile Gly Tyr Asp Leu Gly Leu Val Ser
    1805                1810                1815

Leu Tyr Asn Glu Lys Phe Tyr Ile Asn Asn Phe Gly Met Met Val
    1820                1825                1830

Ser Gly Leu Ile Tyr Ile Asn Asp Ser Leu Tyr Tyr Phe Lys Pro
    1835                1840                1845

Pro Val Asn Asn Leu Ile Thr Gly Phe Val Thr Val Gly Asp Asp
    1850                1855                1860

Lys Tyr Tyr Phe Asn Pro Ile Asn Gly Gly Ala Ala Ser Ile Gly
    1865                1870                1875

Glu Thr Ile Ile Asp Asp Lys Asn Tyr Tyr Phe Asn Gln Ser Gly
    1880                1885                1890

Val Leu Gln Thr Gly Val Phe Ser Thr Glu Asp Gly Phe Lys Tyr
    1895                1900                1905

Phe Ala Pro Ala Asn Thr Leu Asp Glu Asn Leu Glu Gly Glu Ala
    1910                1915                1920

Ile Asp Phe Thr Gly Lys Leu Ile Ile Asp Glu Asn Ile Tyr Tyr
    1925                1930                1935

Phe Glu Asp Asn Tyr Arg Gly Ala Val Glu Trp Lys Glu Leu Asp
    1940                1945                1950

Gly Glu Met His Tyr Phe Ser Pro Glu Thr Gly Lys Ala Phe Lys
    1955                1960                1965

Gly Leu Asn Gln Ile Gly Asp Asp Lys Tyr Tyr Phe Asn Ser Asp
    1970                1975                1980

Gly Val Met Gln Lys Gly Phe Val Ser Ile Asn Asp Asn Lys His
    1985                1990                1995

Tyr Phe Asp Asp Ser Gly Val Met Lys Val Gly Tyr Thr Glu Ile
    2000                2005                2010

Asp Gly Lys His Phe Tyr Phe Ala Glu Asn Gly Glu Met Gln Ile
    2015                2020                2025

Gly Val Phe Asn Thr Glu Asp Gly Phe Lys Tyr Phe Ala His His
    2030                2035                2040

Asn Glu Asp Leu Gly Asn Glu Glu Gly Glu Glu Ile Ser Tyr Ser
    2045                2050                2055
```

```
Gly Ile Leu Asn Phe Asn Asn Lys Ile Tyr Tyr Phe Asp Asp Ser
            2060                2065                2070

Phe Thr Ala Val Val Gly Trp Lys Asp Leu Glu Asp Gly Ser Lys
    2075                2080                2085

Tyr Tyr Phe Asp Glu Asp Thr Ala Glu Ala Tyr Ile Gly Leu Ser
    2090                2095                2100

Leu Ile Asn Asp Gly Gln Tyr Tyr Phe Asn Asp Asp Gly Ile Met
    2105                2110                2115

Gln Val Gly Phe Val Thr Ile Asn Asp Lys Val Phe Tyr Phe Ser
    2120                2125                2130

Asp Ser Gly Ile Ile Glu Ser Gly Val Gln Asn Ile Asp Asp Asn
    2135                2140                2145

Tyr Phe Tyr Ile Asp Asp Asn Gly Ile Val Gln Ile Gly Val Phe
    2150                2155                2160

Asp Thr Ser Asp Gly Tyr Lys Tyr Phe Ala Pro Ala Asn Thr Val
    2165                2170                2175

Asn Asp Asn Ile Tyr Gly Gln Ala Val Glu Tyr Ser Gly Leu Val
    2180                2185                2190

Arg Val Gly Glu Asp Val Tyr Tyr Phe Gly Glu Thr Tyr Thr Ile
    2195                2200                2205

Glu Thr Gly Trp Ile Tyr Asp Met Glu Asn Glu Ser Asp Lys Tyr
    2210                2215                2220

Tyr Phe Val Pro Glu Thr Lys Lys Ala Cys Lys Gly Ile Asn Leu
    2225                2230                2235

Ile Asp Asp Ile Lys Tyr Tyr Phe Asp Glu Lys Gly Ile Met Arg
    2240                2245                2250

Thr Gly Leu Ile Ser Phe Glu Asn Asn Asn Tyr Tyr Phe Asn Glu
    2255                2260                2265

Asn Gly Glu Ile Gln Phe Gly Tyr Ile Asn Ile Glu Asp Lys Met
    2270                2275                2280

Phe Tyr Phe Gly Glu Asp Gly Val Met Gln Ile Gly Val Phe Asn
    2285                2290                2295

Thr Pro Asp Gly Phe Lys Tyr Phe Ala His Gln Asn Thr Leu Asp
    2300                2305                2310

Glu Asn Phe Glu Gly Glu Ser Ile Asn Tyr Thr Gly Trp Leu Gly
    2315                2320                2325

Leu Asp Glu Lys Arg Tyr Tyr Phe Thr Asp Glu Tyr Ile Ala Ala
    2330                2335                2340

Thr Gly Ser Val Ile Ile Asp Gly Glu Glu Tyr Tyr Phe Asp Pro
    2345                2350                2355

Asp Thr Ala Gln Leu Val Ile Ser Glu
    2360                2365

<210> SEQ ID NO 14
<211> LENGTH: 2178
<212> TYPE: PRT
<213> ORGANISM: Clostridium noveyi

<400> SEQUENCE: 14

Met Leu Ile Thr Arg Glu Gln Leu Met Lys Ile Ala Ser Ile Pro Leu
1               5                   10                  15

Lys Arg Lys Glu Pro Glu Tyr Asn Leu Ile Leu Asp Ala Leu Glu Asn
                20                  25                  30

Phe Asn Arg Asp Ile Glu Gly Thr Ser Val Lys Glu Ile Tyr Ser Lys
        35                  40                  45
```

-continued

```
Leu Ser Lys Leu Asn Glu Leu Val Asp Asn Tyr Gln Thr Lys Tyr Pro
 50                  55                  60

Ser Ser Gly Arg Asn Leu Ala Leu Glu Asn Phe Arg Asp Ser Leu Tyr
 65                  70                  75                  80

Ser Glu Leu Arg Glu Leu Ile Lys Asn Ser Arg Thr Ser Thr Ile Ala
                 85                  90                  95

Ser Lys Asn Leu Ser Phe Ile Trp Ile Gly Pro Ile Ser Asp Gln
            100                 105                 110

Ser Leu Glu Tyr Tyr Asn Met Trp Lys Met Phe Asn Lys Asp Tyr Asn
                115                 120                 125

Ile Arg Leu Phe Tyr Asp Lys Asn Ser Leu Leu Val Asn Thr Leu Lys
        130                 135                 140

Thr Ala Ile Ile Gln Glu Ser Ser Lys Val Ile Ile Glu Gln Asn Gln
145                 150                 155                 160

Ser Asn Ile Leu Asp Gly Thr Tyr Gly His Asn Lys Phe Tyr Ser Asp
                165                 170                 175

Arg Met Lys Leu Ile Tyr Arg Tyr Lys Arg Glu Leu Lys Met Leu Tyr
            180                 185                 190

Glu Asn Met Lys Gln Asn Asn Ser Val Asp Asp Ile Ile Ile Asn Phe
                195                 200                 205

Leu Ser Asn Tyr Phe Lys Tyr Asp Ile Gly Lys Leu Asn Asn Gln Lys
        210                 215                 220

Glu Asn Asn Asn Asn Lys Met Ile Ala Ile Gly Ala Thr Asp Ile Asn
225                 230                 235                 240

Thr Glu Asn Ile Leu Thr Asn Lys Leu Lys Ser Tyr Tyr Tyr Gln Glu
                245                 250                 255

Leu Ile Gln Thr Asn Asn Leu Ala Ala Ala Ser Asp Ile Leu Arg Ile
            260                 265                 270

Ala Ile Leu Lys Lys Tyr Gly Gly Val Tyr Cys Asp Leu Asp Phe Leu
        275                 280                 285

Pro Gly Val Asn Leu Ser Leu Phe Asn Asp Ile Ser Lys Pro Asn Gly
    290                 295                 300

Met Asp Ser Asn Tyr Trp Glu Ala Ala Ile Phe Glu Ala Ile Ala Asn
305                 310                 315                 320

Glu Lys Lys Leu Met Asn Asn Tyr Pro Tyr Lys Tyr Met Glu Gln Val
                325                 330                 335

Pro Ser Glu Ile Lys Glu Arg Ile Leu Ser Phe Val Arg Asn His Asp
            340                 345                 350

Ile Asn Asp Leu Ile Leu Pro Leu Gly Asp Ile Lys Ile Ser Gln Leu
        355                 360                 365

Glu Ile Leu Leu Ser Arg Leu Lys Ala Ala Thr Gly Lys Lys Thr Phe
    370                 375                 380

Ser Asn Ala Phe Ile Ile Ser Asn Asn Asp Ser Leu Thr Leu Asn Asn
385                 390                 395                 400

Leu Ile Ser Gln Leu Glu Asn Arg Tyr Glu Ile Leu Asn Ser Ile Ile
                405                 410                 415

Gln Glu Lys Phe Lys Ile Cys Glu Thr Tyr Asp Ser Tyr Ile Asn Ser
            420                 425                 430

Val Ser Glu Leu Val Leu Glu Thr Thr Pro Lys Asn Leu Ser Met Asp
        435                 440                 445

Gly Ser Ser Phe Tyr Gln Gln Ile Ile Gly Tyr Leu Ser Ser Gly Phe
    450                 455                 460

Lys Pro Glu Val Asn Ser Thr Val Phe Phe Ser Gly Pro Asn Ile Tyr
465                 470                 475                 480
```

```
Ser Ser Ala Thr Cys Asp Thr Tyr His Phe Ile Lys Asn Thr Phe Asp
                485                 490                 495
Met Leu Ser Ser Gln Asn Gln Glu Ile Phe Glu Ala Ser Asn Asn Leu
            500                 505                 510
Tyr Phe Ser Lys Thr His Asp Glu Phe Lys Ser Ser Trp Leu Leu Arg
        515                 520                 525
Ser Asn Ile Ala Glu Lys Glu Phe Gln Lys Leu Ile Lys Thr Tyr Ile
    530                 535                 540
Gly Arg Thr Leu Asn Tyr Glu Asp Gly Leu Asn Phe Asn Lys Trp Lys
545                 550                 555                 560
Arg Val Thr Thr Ser Glu Leu Leu Lys Val Ile Glu Val Asn Ser
                565                 570                 575
Thr Lys Ile Tyr Glu Asn Tyr Asp Leu Asn Met Ile Leu Gln Ile Gln
                580                 585                 590
Gly Asp Asp Ile Ser Tyr Glu Ser Ala Val Asn Val Phe Gly Lys Asn
            595                 600                 605
Pro Asn Lys Ser Ile Leu Ile Gln Gly Val Asp Phe Ala Asn Val
        610                 615                 620
Phe Tyr Phe Glu Asn Gly Ile Val Gln Ser Asp Asn Ile Asn Asn Ile
625                 630                 635                 640
Leu Ser Arg Phe Asn Asp Ile Lys Lys Ile Lys Leu Thr Leu Ile Gly
                645                 650                 655
His Gly Glu Asn Val Phe Asn Pro Lys Leu Phe Gly Gly Lys Thr Val
                660                 665                 670
Asn Asp Leu Tyr Thr Asn Ile Ile Lys Pro Lys Leu Gln His Leu Leu
            675                 680                 685
Glu Arg Glu Gly Val Ile Leu Lys Asn Lys Tyr Leu Lys Ile Asn Ile
        690                 695                 700
Leu Gly Cys Tyr Met Phe Thr Pro Lys Val Asp Ile Asn Ser Thr Phe
705                 710                 715                 720
Val Gly Lys Leu Phe Asn Lys Ile Ser Arg Asp Leu Gln Pro Lys Gly
                725                 730                 735
Phe Ser Lys Asn Gln Leu Glu Ile Ser Ala Asn Lys Tyr Ala Ile Arg
                740                 745                 750
Ile Asn Arg Glu Gly Lys Arg Glu Val Leu Asp Tyr Phe Gly Lys Trp
            755                 760                 765
Val Ser Asn Thr Asp Leu Ile Ala Glu Gln Ile Ser Asn Lys Tyr Val
        770                 775                 780
Val Tyr Trp Asn Glu Val Glu Asn Thr Leu Ser Ala Arg Val Glu Gln
785                 790                 795                 800
Leu Asn Lys Val Ala Glu Phe Ala Lys Asp Ile Asn Ser Ile Ile Gln
                805                 810                 815
Thr Thr Asn Asn Gln Glu Leu Lys Gln Ser Leu Val Asn Thr Tyr Ala
            820                 825                 830
Asp Leu Ile Thr Thr Leu Tyr Ser Glu Leu Leu Lys Glu Asp Ile Pro
        835                 840                 845
Phe Glu Leu Asp Asn Ile Gln Ile Lys Glu Arg Ile Ile Leu Asn Glu
    850                 855                 860
Ile Ser Arg Leu His Asp Phe Ser Asn Ile Ile Leu Asp Phe Tyr Gln
865                 870                 875                 880
Lys Asn Asn Ile Ser Asn Asn Met Ile Ile Leu Phe Asp Ser Ile Ile
                885                 890                 895
Lys Glu Lys Asp Tyr Tyr Asn Val Lys Leu Ala Asn Lys Ile Thr Gly
```

-continued

```
                900             905             910
Glu Thr Ser Val Ile Lys Thr Tyr Ser Asp Ser Leu Trp Asn Phe Thr
        915                 920                 925
Asn Lys Tyr Lys Lys Ile Val Asp Asp Ile Lys Gly Ile Ile Val Lys
        930                 935                 940
Asp Ile Asn Gly Glu Phe Ile Lys Lys Ala Asp Phe Glu Ile Glu Gln
945                 950                 955                 960
Asn Pro Ser Leu Leu Asn Ser Ala Met Leu Met Gln Leu Leu Ile Asp
                965                 970                 975
Tyr Lys Pro Tyr Thr Glu Ile Leu Thr Asn Met Asn Thr Ser Leu Lys
        980                 985                 990
Val Gln Ala Tyr Ala Gln Ile Phe Gln Leu Ser Ile Gly Ala Ile Gln
        995                 1000                1005
Glu Ala Thr Glu Ile Val Thr Ile Ile Ser Asp Ala Leu Asn Ala
        1010                1015                1020
Asn Phe Asn Ile Leu Ser Lys Leu Lys Val Gly Ser Ser Val Ala
        1025                1030                1035
Ser Val Ile Ile Asp Gly Ile Asn Leu Ile Ala Ala Leu Thr Glu
        1040                1045                1050
Leu Lys Asn Val Lys Thr Asn Phe Glu Arg Lys Leu Ile Glu Ala
        1055                1060                1065
Lys Val Gly Met Tyr Ser Ile Gly Phe Ile Leu Glu Ser Ser Ser
        1070                1075                1080
Leu Ile Ser Gly Leu Leu Gly Ala Thr Ala Val Ser Glu Ile Leu
        1085                1090                1095
Gly Val Ile Ser Val Pro Val Ala Gly Ile Leu Val Gly Leu Pro
        1100                1105                1110
Ser Leu Val Asn Asn Ile Leu Val Leu Gly Glu Lys Tyr Asn Gln
        1115                1120                1125
Ile Leu Asp Tyr Phe Ser Lys Phe Tyr Pro Ile Val Gly Lys Asn
        1130                1135                1140
Pro Phe Ser Ile Gln Asp Asn Ile Ile Ile Pro Tyr Asp Asp Ile
        1145                1150                1155
Ala Ile Thr Glu Leu Asn Phe Lys Tyr Asn Lys Phe Lys Tyr Gly
        1160                1165                1170
Tyr Ala Lys Ile Ser Gly Leu Lys Val Gly Leu Val Thr His Ile
        1175                1180                1185
Gly Glu Asn Ile Asp His Tyr Phe Ser Ala Pro Ser Leu Asp His
        1190                1195                1200
Tyr Ile Glu Leu Ser Ile Tyr Pro Ala Leu Lys Leu Asn Asp Thr
        1205                1210                1215
Asn Leu Pro Lys Gly Asn Val Val Leu Leu Pro Ser Gly Leu Asn
        1220                1225                1230
Lys Val Tyr Lys Pro Glu Ile Ser Ala Ile Ala Gly Ala Asn Ser
        1235                1240                1245
Gln Glu Gly Asn Gly Val Glu Val Leu Asn Leu Ile Arg Asn Tyr
        1250                1255                1260
Tyr Val Asp Ser Asn Gly Asn Thr Lys Phe Pro Trp Lys Tyr Glu
        1265                1270                1275
Ala Pro Phe Glu Tyr Ser Phe Ser Tyr Met Arg Val Glu Tyr Phe
        1280                1285                1290
Asp Thr Lys Val Asn Val Ile Leu Asp Asn Glu Asn Lys Thr Leu
        1295                1300                1305
```

```
Ile Ile Pro Val Leu Thr Ile Asp Glu Met Arg Asn Lys Ile Ser
1310                1315                1320

Tyr Glu Ile Leu Gly Asp Gly Gln Tyr Asn Val Ile Leu Pro
1325                1330                1335

Val Asn Gln Thr Asn Ile Asn Ile Val Ser Asn Lys Asn Asp Ile
1340                1345                1350

Trp Asn Phe Asp Val Ser Tyr Ile Val Lys Glu Ser Lys Ile Glu
1355                1360                1365

Asp Asn Lys Phe Val Leu Asp Gly Phe Ile Asn Asn Ile Phe Ser
1370                1375                1380

Thr Leu Lys Val Ser Asn Asp Gly Phe Lys Ile Gly Lys Gln Phe
1385                1390                1395

Ile Ser Ile Lys Asn Thr Pro Arg Ala Ile Asn Leu Ser Phe Lys
1400                1405                1410

Ile Asn Asn Asn Ile Val Ile Val Ser Ile Tyr Leu Asn His Glu
1415                1420                1425

Lys Ser Asn Ser Ile Thr Ile Ile Ser Ser Asp Leu Asn Asp Ile
1430                1435                1440

Lys Asn Asn Phe Asp Asn Leu Leu Asp Asn Ile Asn Tyr Ile Gly
1445                1450                1455

Leu Gly Ser Ile Ser Asp Asn Thr Ile Asn Cys Ile Val Arg Asn
1460                1465                1470

Asp Glu Val Tyr Met Glu Gly Lys Ile Phe Leu Asn Glu Lys Lys
1475                1480                1485

Leu Val Phe Ile Gln Asn Glu Leu Glu Leu His Leu Tyr Asp Ser
1490                1495                1500

Val Asn Lys Asp Ser Gln Tyr Leu Ile Asn Asn Pro Ile Asn Asn
1505                1510                1515

Val Val Lys Tyr Lys Asp Gly Tyr Ile Val Glu Gly Thr Phe Leu
1520                1525                1530

Ile Asn Ser Thr Glu Asn Lys Tyr Ser Leu Tyr Ile Glu Asn Asn
1535                1540                1545

Lys Ile Met Leu Lys Gly Leu Tyr Leu Glu Ser Ser Val Phe Lys
1550                1555                1560

Thr Ile Gln Asp Lys Ile Tyr Ser Lys Glu Lys Val Asn Asp Tyr
1565                1570                1575

Ile Leu Ser Leu Ile Lys Lys Phe Phe Thr Val Asn Ile Gln Leu
1580                1585                1590

Cys Pro Phe Met Ile Val Ser Gly Val Asp Glu Asn Asn Arg Tyr
1595                1600                1605

Leu Glu Tyr Met Leu Ser Thr Asn Asn Lys Trp Ile Ile Asn Gly
1610                1615                1620

Gly Tyr Trp Glu Asn Asp Phe Asn Asn Tyr Lys Ile Val Asp Phe
1625                1630                1635

Glu Lys Cys Asn Val Ile Val Ser Gly Ser Asn Lys Leu Asn Ser
1640                1645                1650

Glu Gly Asp Leu Ala Asp Thr Ile Asp Val Leu Asp Lys Asp Leu
1655                1660                1665

Glu Asn Leu Tyr Ile Asp Ser Val Ile Ile Pro Lys Val Tyr
1670                1675                1680

Thr Lys Lys Ile Ile Ile His Pro Ile Pro Asn Asn Pro Gln Ile
1685                1690                1695

Asn Ile Ile Asn Thr Gln Ser Ile His Asp Lys Cys His Leu Ile
1700                1705                1710
```

-continued

```
Ile Asp Ser Val Leu Thr Asn Asn Tyr His Trp Glu Ser Asp Gly
1715                1720                1725
Asp Asp Leu Ile Ile Thr Asn Gly Leu Asp Ile Asn Ile Arg Ile
1730                1735                1740
Leu Gln Gly Leu Ser Phe Gly Phe Lys Tyr Lys Asn Ile Tyr Leu
1745                1750                1755
Lys Phe Ser Asn Tyr Asp Glu Leu Ser Leu Asn Asp Phe Leu Leu
1760                1765                1770
Gln Asn Tyr Asn Val Lys Gly Leu Tyr Tyr Ile Asn Gly Glu Leu
1775                1780                1785
His Tyr Lys Asn Ile Pro Gly Asp Thr Phe Glu Tyr Gly Trp Ile
1790                1795                1800
Asn Ile Asp Ser Arg Trp Tyr Phe Phe Asp Ser Ile Asn Leu Ile
1805                1810                1815
Ala Lys Lys Gly Tyr Gln Glu Ile Glu Gly Glu Arg Tyr Tyr Phe
1820                1825                1830
Asn Pro Asn Thr Gly Val Gln Glu Ser Gly Val Phe Leu Thr Pro
1835                1840                1845
Asn Gly Leu Glu Tyr Phe Thr Asn Lys His Ala Ser Ser Lys Arg
1850                1855                1860
Trp Gly Arg Ala Ile Asn Tyr Thr Gly Trp Leu Thr Leu Asp Gly
1865                1870                1875
Asn Lys Tyr Tyr Phe Gln Ser Asn Ser Lys Ala Val Thr Gly Leu
1880                1885                1890
Gln Lys Ile Ser Asp Lys Tyr Tyr Tyr Phe Asn Asp Asn Gly Gln
1895                1900                1905
Met Gln Ile Lys Trp Gln Ile Ile Asn Asn Asn Lys Tyr Tyr Phe
1910                1915                1920
Asp Gly Asn Thr Gly Glu Ala Ile Ile Gly Trp Phe Asn Asn Asn
1925                1930                1935
Lys Glu Arg Tyr Tyr Phe Asp Ser Glu Gly Arg Leu Leu Thr Gly
1940                1945                1950
Tyr Gln Val Ile Gly Asp Lys Ser Tyr Tyr Phe Ser Asp Asn Ile
1955                1960                1965
Asn Gly Asn Trp Glu Glu Gly Ser Gly Val Leu Lys Ser Gly Ile
1970                1975                1980
Phe Lys Thr Pro Ser Gly Phe Lys Leu Phe Ser Ser Glu Gly Asp
1985                1990                1995
Lys Ser Ala Ile Asn Tyr Lys Gly Trp Leu Asp Leu Asn Gly Asn
2000                2005                2010
Lys Tyr Tyr Phe Asn Ser Asp Ser Ile Ala Val Thr Gly Ser Tyr
2015                2020                2025
Asn Ile Lys Gly Ile Gln Tyr Tyr Phe Asn Pro Lys Thr Ala Val
2030                2035                2040
Leu Thr Asn Gly Trp Tyr Thr Leu Asp Asn Asn Asn Tyr Tyr Val
2045                2050                2055
Ser Asn Gly His Asn Val Leu Gly Tyr Gln Asp Ile Asp Gly Lys
2060                2065                2070
Gly Tyr Tyr Phe Asp Pro Ser Thr Gly Ile Gln Lys Ala Gly Val
2075                2080                2085
Phe Pro Thr Pro Asn Gly Leu Arg Tyr Phe Thr Met Lys Pro Ile
2090                2095                2100
Asp Gly Gln Arg Trp Gly Gln Cys Ile Asp Tyr Thr Gly Trp Leu
```

-continued

```
                2105                2110                2115

His Leu Asn Gly Asn Lys Tyr Tyr Phe Gly Tyr Tyr Asn Ser Ala
        2120                2125                2130

Val Thr Gly Trp Arg Val Leu Gly Gly Lys Arg Tyr Phe Phe Asn
        2135                2140                2145

Ile Lys Thr Gly Ala Ala Thr Thr Gly Leu Leu Thr Leu Ser Gly
        2150                2155                2160

Lys Arg Tyr Tyr Phe Asn Glu Lys Gly Glu Gln Leu Thr Leu Val
        2165                2170                2175

<210> SEQ ID NO 15
<211> LENGTH: 2364
<212> TYPE: PRT
<213> ORGANISM: Clostridium sordellii

<400> SEQUENCE: 15

Met Asn Leu Val Asn Lys Ala Gln Leu Gln Lys Met Val Tyr Val Lys
1               5                   10                  15

Phe Arg Ile Gln Glu Asp Glu Tyr Val Ala Ile Leu Asn Ala Leu Glu
                20                  25                  30

Glu Tyr His Asn Met Ser Glu Ser Ser Val Val Glu Lys Tyr Leu Lys
            35                  40                  45

Leu Lys Asp Ile Asn Asn Leu Thr Asp Asn Tyr Leu Asn Thr Tyr Lys
        50                  55                  60

Lys Ser Gly Arg Asn Lys Ala Leu Lys Lys Phe Lys Glu Tyr Leu Thr
65                  70                  75                  80

Met Glu Val Leu Glu Leu Lys Asn Asn Ser Leu Thr Pro Val Glu Lys
                85                  90                  95

Asn Leu His Phe Ile Trp Ile Gly Gly Gln Ile Asn Asp Thr Ala Ile
            100                 105                 110

Asn Tyr Ile Asn Gln Trp Lys Asp Val Asn Ser Asp Tyr Thr Val Lys
        115                 120                 125

Val Phe Tyr Asp Ser Asn Ala Phe Leu Ile Asn Thr Leu Lys Lys Thr
    130                 135                 140

Ile Val Glu Ser Ala Thr Asn Asn Thr Leu Glu Ser Phe Arg Glu Asn
145                 150                 155                 160

Leu Asn Asp Pro Glu Phe Asp Tyr Asn Lys Phe Tyr Arg Lys Arg Met
                165                 170                 175

Glu Ile Ile Tyr Asp Lys Gln Lys His Phe Ile Asp Tyr Tyr Lys Ser
            180                 185                 190

Gln Ile Glu Glu Asn Pro Glu Phe Ile Ile Asp Asn Ile Ile Lys Thr
        195                 200                 205

Tyr Leu Ser Asn Glu Tyr Ser Lys Asp Leu Glu Ala Leu Asn Lys Tyr
    210                 215                 220

Ile Glu Glu Ser Leu Asn Lys Ile Thr Ala Asn Asn Gly Asn Asp Ile
225                 230                 235                 240

Arg Asn Leu Glu Lys Phe Ala Asp Glu Asp Leu Val Arg Leu Tyr Asn
                245                 250                 255

Gln Glu Leu Val Glu Arg Trp Asn Leu Ala Ala Ala Ser Asp Ile Leu
            260                 265                 270

Arg Ile Ser Met Leu Lys Glu Asp Gly Gly Val Tyr Leu Asp Val Asp
        275                 280                 285

Ile Leu Pro Gly Ile Gln Pro Asp Leu Phe Lys Ser Ile Asn Lys Pro
    290                 295                 300

Asp Ser Ile Thr Asn Thr Ser Trp Glu Met Ile Lys Leu Glu Ala Ile
```

```
            305                 310                 315                 320
Met Lys Tyr Lys Glu Tyr Ile Pro Gly Tyr Thr Ser Lys Asn Phe Asp
                325                 330                 335

Met Leu Asp Glu Glu Val Gln Arg Ser Phe Glu Ser Ala Leu Ser Ser
                340                 345                 350

Lys Ser Asp Lys Ser Glu Ile Phe Leu Pro Leu Asp Asp Ile Lys Val
                355                 360                 365

Ser Pro Leu Glu Val Lys Ile Ala Phe Ala Asn Asn Ser Val Ile Asn
            370                 375                 380

Gln Ala Leu Ile Ser Leu Lys Asp Ser Tyr Cys Ser Asp Leu Val Ile
385                 390                 395                 400

Asn Gln Ile Lys Asn Arg Tyr Lys Ile Leu Asn Asp Asn Leu Asn Pro
                405                 410                 415

Ser Ile Asn Glu Gly Thr Asp Phe Asn Thr Thr Met Lys Ile Phe Ser
            420                 425                 430

Asp Lys Leu Ala Ser Ile Ser Asn Glu Asp Asn Met Met Phe Met Ile
            435                 440                 445

Lys Ile Thr Asn Tyr Leu Lys Val Gly Phe Ala Pro Asp Val Arg Ser
            450                 455                 460

Thr Ile Asn Leu Ser Gly Pro Gly Val Tyr Thr Gly Ala Tyr Gln Asp
465                 470                 475                 480

Leu Leu Met Phe Lys Asp Asn Ser Thr Asn Ile His Leu Leu Glu Pro
                485                 490                 495

Glu Leu Arg Asn Phe Glu Phe Pro Lys Thr Lys Ile Ser Gln Leu Thr
                500                 505                 510

Glu Gln Glu Ile Thr Ser Leu Trp Ser Phe Asn Gln Ala Arg Ala Lys
            515                 520                 525

Ser Gln Phe Glu Glu Tyr Lys Lys Gly Tyr Phe Glu Gly Ala Leu Gly
            530                 535                 540

Glu Asp Asp Asn Leu Asp Phe Ala Gln Asn Thr Val Leu Asp Lys Asp
545                 550                 555                 560

Tyr Val Ser Lys Lys Ile Leu Ser Ser Met Lys Thr Arg Asn Lys Glu
                565                 570                 575

Tyr Ile His Tyr Ile Val Gln Leu Gln Gly Asp Lys Ile Ser Tyr Glu
            580                 585                 590

Ala Ser Cys Asn Leu Phe Ser Lys Asp Pro Tyr Ser Ser Ile Leu Tyr
            595                 600                 605

Gln Lys Asn Ile Glu Gly Ser Glu Thr Ala Tyr Tyr Tyr Val Ala
            610                 615                 620

Asp Ala Glu Ile Lys Glu Ile Asp Lys Tyr Arg Ile Pro Tyr Gln Ile
625                 630                 635                 640

Ser Asn Lys Arg Asn Ile Lys Leu Thr Phe Ile Gly His Gly Lys Ser
                645                 650                 655

Glu Phe Asn Thr Asp Thr Phe Ala Asn Leu Asp Val Asp Ser Leu Ser
                660                 665                 670

Ser Glu Ile Glu Thr Ile Leu Asn Leu Ala Lys Ala Asp Ile Ser Pro
            675                 680                 685

Lys Tyr Ile Glu Ile Asn Leu Leu Gly Cys Asn Met Phe Ser Tyr Ser
            690                 695                 700

Ile Ser Ala Glu Glu Thr Tyr Pro Gly Lys Leu Leu Leu Lys Ile Lys
705                 710                 715                 720

Asp Arg Val Ser Glu Leu Met Pro Ser Ile Ser Gln Asp Ser Ile Thr
                725                 730                 735
```

-continued

```
Val Ser Ala Asn Gln Tyr Glu Val Arg Ile Asn Glu Gly Lys Arg
                740                 745                 750

Glu Ile Leu Asp His Ser Gly Lys Trp Ile Asn Lys Glu Ser Ile
                755                 760                 765

Ile Lys Asp Ile Ser Ser Lys Glu Tyr Ile Ser Phe Asn Pro Lys Glu
                770                 775                 780

Asn Lys Ile Ile Val Lys Ser Lys Tyr Leu His Glu Leu Ser Thr Leu
785                 790                 795                 800

Leu Gln Glu Ile Arg Asn Asn Ala Asn Ser Ser Asp Ile Asp Leu Glu
                805                 810                 815

Lys Lys Val Met Leu Thr Glu Cys Glu Ile Asn Val Ala Ser Asn Ile
                820                 825                 830

Asp Arg Gln Ile Val Glu Gly Arg Ile Glu Glu Ala Lys Asn Leu Thr
                835                 840                 845

Ser Asp Ser Ile Asn Tyr Ile Lys Asn Glu Phe Lys Leu Ile Glu Ser
                850                 855                 860

Ile Ser Asp Ser Leu Tyr Asp Leu Lys His Gln Asn Gly Leu Asp Asp
865                 870                 875                 880

Ser His Phe Ile Ser Phe Glu Asp Ile Ser Lys Thr Glu Asn Gly Phe
                885                 890                 895

Arg Ile Arg Phe Ile Asn Lys Glu Thr Gly Asn Ser Ile Phe Ile Glu
                900                 905                 910

Thr Glu Lys Glu Ile Phe Ser Glu Tyr Ala Thr His Ile Ser Lys Glu
                915                 920                 925

Ile Ser Asn Ile Lys Asp Thr Ile Phe Asp Asn Val Asn Gly Lys Leu
                930                 935                 940

Val Lys Lys Val Asn Leu Asp Ala Ala His Glu Val Asn Thr Leu Asn
945                 950                 955                 960

Ser Ala Phe Phe Ile Gln Ser Leu Ile Glu Tyr Asn Thr Thr Lys Glu
                965                 970                 975

Ser Leu Ser Asn Leu Ser Val Ala Met Lys Val Gln Val Tyr Ala Gln
                980                 985                 990

Leu Phe Ser Thr Gly Leu Asn Thr Ile Thr Asp Ala Ser Lys Val Val
                995                1000                1005

Glu Leu Val Ser Thr Ala Leu Asp Glu Thr Ile Asp Leu Leu Pro
                1010                1015                1020

Thr Leu Ser Glu Gly Leu Pro Ile Ile Ala Thr Ile Ile Asp Gly
                1025                1030                1035

Val Ser Leu Gly Ala Ala Ile Lys Glu Leu Ser Glu Thr Asn Asp
                1040                1045                1050

Pro Leu Leu Arg Gln Glu Ile Glu Ala Lys Ile Gly Ile Met Ala
                1055                1060                1065

Val Asn Leu Thr Ala Ala Ser Thr Ala Ile Val Thr Ser Ala Leu
                1070                1075                1080

Gly Ile Ala Ser Gly Phe Ser Ile Leu Leu Val Pro Leu Ala Gly
                1085                1090                1095

Ile Ser Ala Gly Ile Pro Ser Leu Val Asn Asn Glu Leu Ile Leu
                1100                1105                1110

Gln Asp Lys Ala Thr Lys Val Ile Asp Tyr Phe Lys His Ile Ser
                1115                1120                1125

Leu Ala Glu Thr Glu Gly Ala Phe Thr Leu Leu Asp Asp Lys Ile
                1130                1135                1140

Ile Met Pro Gln Asp Asp Leu Val Leu Ser Glu Ile Asp Phe Asn
                1145                1150                1155
```

-continued

```
Asn Asn Ser Ile Thr Leu Gly Lys Cys Glu Ile Trp Arg Ala Glu
    1160            1165                1170

Gly Gly Ser Gly His Thr Leu Thr Asp Asp Ile Asp His Phe Phe
    1175            1180                1185

Ser Ser Pro Ser Ile Thr Tyr Arg Lys Pro Trp Leu Ser Ile Tyr
    1190            1195                1200

Asp Val Leu Asn Ile Lys Lys Glu Lys Ile Asp Phe Ser Lys Asp
    1205            1210                1215

Leu Met Val Leu Pro Asn Ala Pro Asn Arg Val Phe Gly Tyr Glu
    1220            1225                1230

Met Gly Trp Thr Pro Gly Phe Arg Ser Leu Asp Asn Asp Gly Thr
    1235            1240                1245

Lys Leu Leu Asp Arg Ile Arg Asp His Tyr Glu Gly Gln Phe Tyr
    1250            1255                1260

Trp Arg Tyr Phe Ala Phe Ile Ala Asp Ala Leu Ile Thr Lys Leu
    1265            1270                1275

Lys Pro Arg Tyr Glu Asp Thr Asn Val Arg Ile Asn Leu Asp Gly
    1280            1285                1290

Asn Thr Arg Ser Phe Ile Val Pro Val Ile Thr Thr Glu Gln Ile
    1295            1300                1305

Arg Lys Asn Leu Ser Tyr Ser Phe Tyr Gly Ser Gly Gly Ser Tyr
    1310            1315                1320

Ser Leu Ser Leu Ser Pro Tyr Asn Met Asn Ile Asp Leu Asn Leu
    1325            1330                1335

Val Glu Asn Asp Thr Trp Val Ile Asp Val Asp Asn Val Val Lys
    1340            1345                1350

Asn Ile Thr Ile Glu Ser Asp Glu Ile Gln Lys Gly Glu Leu Ile
    1355            1360                1365

Glu Asn Ile Leu Ser Lys Leu Asn Ile Glu Asp Asn Lys Ile Ile
    1370            1375                1380

Leu Asn Asn His Thr Ile Asn Phe Tyr Gly Asp Ile Asn Glu Ser
    1385            1390                1395

Asn Arg Phe Ile Ser Leu Thr Phe Ser Ile Leu Glu Asp Ile Asn
    1400            1405                1410

Ile Ile Ile Glu Ile Asp Leu Val Ser Lys Ser Tyr Lys Ile Leu
    1415            1420                1425

Leu Ser Gly Asn Cys Met Lys Leu Ile Glu Asn Ser Ser Asp Ile
    1430            1435                1440

Gln Gln Lys Ile Asp His Ile Gly Phe Asn Gly Glu His Gln Lys
    1445            1450                1455

Tyr Ile Pro Tyr Ser Tyr Ile Asp Asn Glu Thr Lys Tyr Asn Gly
    1460            1465                1470

Phe Ile Asp Tyr Ser Lys Lys Glu Gly Leu Phe Thr Ala Glu Phe
    1475            1480                1485

Ser Asn Glu Ser Ile Ile Arg Asn Ile Tyr Met Pro Asp Ser Asn
    1490            1495                1500

Asn Leu Phe Ile Tyr Ser Ser Lys Asp Leu Lys Asp Ile Arg Ile
    1505            1510                1515

Ile Asn Lys Gly Asp Val Lys Leu Leu Ile Gly Asn Tyr Phe Lys
    1520            1525                1530

Asp Asp Met Lys Val Ser Leu Ser Phe Thr Ile Glu Asp Thr Asn
    1535            1540                1545

Thr Ile Lys Leu Asn Gly Val Tyr Leu Asp Glu Asn Gly Val Ala
```

-continued

```
             1550                1555                1560

Gln Ile Leu Lys Phe Met Asn Asn Ala Lys Ser Ala Leu Asn Thr
    1565                1570                1575

Ser Asn Ser Leu Met Asn Phe Leu Glu Ser Ile Asn Ile Lys Asn
    1580                1585                1590

Ile Phe Tyr Asn Asn Leu Asp Pro Asn Ile Glu Phe Ile Leu Asp
    1595                1600                1605

Thr Asn Phe Ile Ile Ser Gly Ser Asn Ser Ile Gly Gln Phe Glu
    1610                1615                1620

Leu Ile Cys Asp Lys Asp Lys Asn Ile Gln Pro Tyr Phe Ile Asn
    1625                1630                1635

Phe Lys Ile Lys Glu Thr Ser Tyr Thr Leu Tyr Val Gly Asn Arg
    1640                1645                1650

Gln Asn Leu Ile Val Glu Pro Ser Tyr His Leu Asp Asp Ser Gly
    1655                1660                1665

Asn Ile Ser Ser Thr Val Ile Asn Phe Ser Gln Lys Tyr Leu Tyr
    1670                1675                1680

Gly Ile Asp Arg Tyr Val Asn Lys Val Ile Ala Pro Asn Leu
    1685                1690                1695

Tyr Thr Asp Glu Ile Asn Ile Thr Pro Val Tyr Lys Pro Asn Tyr
    1700                1705                1710

Ile Cys Pro Glu Val Ile Ile Leu Asp Ala Asn Tyr Ile Asn Glu
    1715                1720                1725

Lys Ile Asn Val Asn Ile Asn Asp Leu Ser Ile Arg Tyr Val Trp
    1730                1735                1740

Asp Asn Asp Gly Ser Asp Leu Ile Leu Ile Ala Asn Ser Glu Glu
    1745                1750                1755

Asp Asn Gln Pro Gln Val Lys Ile Arg Phe Val Asn Val Phe Lys
    1760                1765                1770

Ser Asp Thr Ala Ala Asp Lys Leu Ser Phe Asn Phe Ser Asp Lys
    1775                1780                1785

Gln Asp Val Ser Val Ser Lys Ile Ile Ser Thr Phe Ser Leu Ala
    1790                1795                1800

Ala Tyr Ser Asp Gly Phe Phe Asp Tyr Glu Phe Gly Leu Val Ser
    1805                1810                1815

Leu Asp Asn Asp Tyr Phe Tyr Ile Asn Ser Phe Gly Asn Met Val
    1820                1825                1830

Ser Gly Leu Ile Tyr Ile Asn Asp Ser Leu Tyr Tyr Phe Lys Pro
    1835                1840                1845

Pro Lys Asn Asn Leu Ile Thr Gly Phe Thr Thr Ile Asp Gly Asn
    1850                1855                1860

Lys Tyr Tyr Phe Asp Pro Thr Lys Ser Gly Ala Ala Ser Ile Gly
    1865                1870                1875

Glu Ile Thr Ile Asp Gly Lys Asp Tyr Tyr Phe Asn Lys Gln Gly
    1880                1885                1890

Ile Leu Gln Val Gly Val Ile Asn Thr Ser Asp Gly Leu Lys Tyr
    1895                1900                1905

Phe Ala Pro Ala Gly Thr Leu Asp Glu Asn Leu Glu Gly Glu Ser
    1910                1915                1920

Val Asn Phe Ile Gly Lys Leu Asn Ile Asp Gly Lys Ile Tyr Tyr
    1925                1930                1935

Phe Glu Asp Asn Tyr Arg Ala Ala Val Glu Trp Lys Leu Leu Asp
    1940                1945                1950
```

-continued

Asp Glu Thr Tyr Tyr Phe Asn Pro Lys Thr Gly Glu Ala Leu Lys
1955                1960               1965

Gly Leu His Gln Ile Gly Asp Asn Lys Tyr Tyr Phe Asp Asp Asn
1970                1975               1980

Gly Ile Met Gln Thr Gly Phe Ile Thr Ile Asn Asp Lys Val Phe
1985                1990               1995

Tyr Phe Asn Asn Asp Gly Val Met Gln Val Gly Tyr Ile Glu Val
2000                2005               2010

Asn Gly Lys Tyr Phe Tyr Phe Gly Lys Asn Gly Glu Arg Gln Leu
2015                2020               2025

Gly Val Phe Asn Thr Pro Asp Gly Phe Lys Phe Phe Gly Pro Lys
2030                2035               2040

Asp Asp Asp Leu Gly Thr Glu Glu Gly Glu Leu Thr Leu Tyr Asn
2045                2050               2055

Gly Ile Leu Asn Phe Asn Gly Lys Ile Tyr Phe Phe Asp Ile Ser
2060                2065               2070

Asn Thr Ala Val Val Gly Trp Gly Thr Leu Asp Asp Gly Ser Thr
2075                2080               2085

Tyr Tyr Phe Asp Asp Asn Arg Ala Glu Ala Cys Ile Gly Leu Thr
2090                2095               2100

Val Ile Asn Asp Cys Lys Tyr Tyr Phe Asp Asp Asn Gly Ile Arg
2105                2110               2115

Gln Leu Gly Phe Ile Thr Ile Asn Asp Asn Ile Phe Tyr Phe Ser
2120                2125               2130

Glu Ser Gly Lys Ile Glu Leu Gly Tyr Gln Asn Ile Asn Gly Asn
2135                2140               2145

Tyr Phe Tyr Ile Asp Glu Ser Gly Leu Val Leu Ile Gly Val Phe
2150                2155               2160

Asp Thr Pro Asp Gly Tyr Lys Tyr Phe Ala Pro Leu Asn Thr Val
2165                2170               2175

Asn Asp Asn Ile Tyr Gly Gln Ala Val Lys Tyr Ser Gly Leu Val
2180                2185               2190

Arg Val Asn Glu Asp Val Tyr Tyr Phe Gly Glu Thr Tyr Lys Ile
2195                2200               2205

Glu Thr Gly Trp Ile Glu Asn Glu Thr Asp Lys Tyr Tyr Phe Asp
2210                2215               2220

Pro Glu Thr Lys Lys Ala Tyr Lys Gly Ile Asn Val Val Asp Asp
2225                2230               2235

Ile Lys Tyr Tyr Phe Asp Glu Asn Gly Ile Met Arg Thr Gly Leu
2240                2245               2250

Ile Ser Phe Glu Asn Asn Asn Tyr Tyr Phe Asn Glu Asp Gly Lys
2255                2260               2265

Met Gln Phe Gly Tyr Leu Asn Ile Lys Asp Lys Met Phe Tyr Phe
2270                2275               2280

Gly Lys Asp Gly Lys Met Gln Ile Gly Val Phe Asn Thr Pro Asp
2285                2290               2295

Gly Phe Lys Tyr Phe Ala His Gln Asn Thr Leu Asp Glu Asn Phe
2300                2305               2310

Glu Gly Glu Ser Ile Asn Tyr Thr Gly Trp Leu Asp Leu Asp Gly
2315                2320               2325

Lys Arg Tyr Tyr Phe Thr Asp Glu Tyr Ile Ala Ala Thr Gly Ser
2330                2335               2340

Leu Thr Ile Asp Gly Tyr Asn Tyr Tyr Phe Asp Pro Asp Thr Ala
2345                2350               2355

```
Glu Leu  Val Val Ser Glu
    2360

<210> SEQ ID NO 16
<211> LENGTH: 4196
<212> TYPE: PRT
<213> ORGANISM: Bordetella pertussis

<400> SEQUENCE: 16

Met Asn Lys His Cys Phe Lys Leu Val His Ser Pro Ala Leu Gly Met
1               5                   10                  15

Leu Val Pro Val His Glu His Arg Thr Gly Arg Pro Leu Arg Gly Ala
            20                  25                  30

Arg Arg Ala Met Ala Val Thr Leu Ala Val Leu Ala Pro Ala Gly Ala
        35                  40                  45

Ala Ala Ala Gly Gly Ile Ala Pro Gln Gly Ala Thr Gln Val Ala Pro
    50                  55                  60

Ala Arg Asn Gly Val Pro Val Ile Gln Ile Ala Ala Pro Asp Ala Thr
65                  70                  75                  80

Gly Ile Ser His Asn Arg Tyr Thr Glu Phe Asn Val Arg Gln Pro Gly
                85                  90                  95

Val Val Leu Asn Asn Ser Thr Ala Glu Gly Val Ser Ala Leu Ala Gly
            100                 105                 110

Arg Ile Ser Gly Asn Pro Gly Leu Arg Gly Pro Ala Arg Ala Ile Leu
        115                 120                 125

Asn Glu Val Thr Gly Val Ser Pro Thr Thr Leu Glu Gly Ala Leu Glu
    130                 135                 140

Val Phe Gly Pro Ala Ala Asp Val Leu Val Ala Asn Pro Asn Gly Leu
145                 150                 155                 160

Thr Ala Asn Gly Leu Ser Thr Ile Asn Ile Arg Gly Leu Thr Leu Ser
                165                 170                 175

Thr Gly Arg Pro Gly Ala Gly Gly Val Leu Asp Val Ala Arg Gly Arg
            180                 185                 190

Leu Glu Ile Gly Pro His Gly Val Asn Thr Ala Gly Leu Ser Tyr Phe
        195                 200                 205

Asp Leu Val Ala Arg Thr Val Ala Leu His Gly Pro Val Gly Ala Gly
    210                 215                 220

Asp Gly Gln Pro Pro Ala Asp Ile Asn Val Val Ala Gly Ala Asn Arg
225                 230                 235                 240

Tyr Asp Tyr Gly Arg Arg Thr Arg Leu Gln Pro Thr Gly Arg Pro Ala
                245                 250                 255

Ala Ala Pro Asp Ala Ser Ala Gly His Ala Ile Asp Gly Ser Ala Ala
            260                 265                 270

Gly Ala Met Tyr Gly Arg His Ile Thr Leu Val Ser Ser Asp Ala Gly
        275                 280                 285

Leu Gly Ala Arg His Arg Gly Leu Val Ser Ala Ala Gly His Ile Ala
    290                 295                 300

Ile Asp Ala Ala Gly Gly Val Ser Val Gln Ala Leu Ala Ala His Ala
305                 310                 315                 320

Ala Ser Asp Gly Thr Ala Gly Ser Ala Thr Ile Arg Ala Gly Gly Asp
                325                 330                 335

Ala Leu Ile Gly Ser Val Ile Ala Phe Gly Gly Asp Ile Glu Val Arg
            340                 345                 350

Ala Ala Ala Gly Arg Ile Ala Thr His Gly Ala Leu Asn Ala Pro Arg
        355                 360                 365
```

```
Gly Arg Val Arg Leu Gln Ala Gly Asp Ala Leu Ala Val His Gly Pro
        370                 375                 380

Val Gln Ala Ala Arg Val Ala Leu Ala Thr Arg Gly Asp Ala Ser Ile
385                 390                 395                 400

Ala Ala Asp Leu His Ala Thr Arg Asp Gly Val Ser Leu Ala Ala Arg
                405                 410                 415

Asn Ala Thr Leu Ala His Ala Arg Val Ile Ala Thr Pro Pro Ala Ala
                420                 425                 430

Gln Ala Arg Pro Ser Thr Pro Ala Ile Asp Ile Ala Leu Ser Gly Thr
            435                 440                 445

Leu Thr Leu Arg Gly Thr Leu His Asp Ala Asp Gly Asp Gly Arg Arg
            450                 455                 460

Ile Glu Gly Thr Ser Val Ala Leu Ala Asn Gly Met Pro Val Ile Val
465                 470                 475                 480

Asp Thr Arg Gln Pro Gln Arg Ala Val Pro Asn Ala Leu Leu Ala Ser
                485                 490                 495

Asp Ala Gly Leu Tyr Ala Ala Ser Gln Pro Ile Ser Ile Arg Ala Ala
                500                 505                 510

Gly Leu Arg Asn Glu Gly Gly Ala Ile Asp Ser Thr Gly Thr Gly Gln
            515                 520                 525

Gly His Ile Gly Leu Arg Ile Gly Gly Pro Ala Val Asn Leu Gly Tyr
            530                 535                 540

Ile Ala Thr His Gly Thr Leu Glu Ala Thr Val Asp Gly Thr Leu Glu
545                 550                 555                 560

Asn Arg Met Leu Leu Ser Ala Ala Leu Arg Val Ala Thr His Asp
                565                 570                 575

Leu Ser Asn His Ala Ala Met Thr Ala Ser Gly Pro Asp Thr Gly Thr
                580                 585                 590

Pro Ala Leu Asp Leu Ser Val Gln His Arg Val Glu Asn Ala Gly Ser
            595                 600                 605

Leu Leu Ala Ala Arg Gly Ala Leu Arg Leu Arg Gly Gly Ala Glu Leu
            610                 615                 620

Ser Ile Val Asn Gln Pro Ala Gly Phe Met Leu Ala His Gly Gln Asp
625                 630                 635                 640

Ile Ala Ala Ala Arg Leu Ala Asn Ala Gly Thr Leu Ser Ser Thr Ala
                645                 650                 655

Ala Gly Thr Leu Thr Leu Ala Gly Asp Leu Glu Asn Ser Gly Val Leu
                660                 665                 670

Gln Ser Ala His Ala Leu Arg Val Gln Ala Arg Ile Ala Ser Arg
            675                 680                 685

Gly Arg Leu Ala Thr Ala Thr Asp Gly Ala Gly Leu Thr Leu Ala Ala
            690                 695                 700

Asp Glu Asn Leu Thr Leu Ala Gly Arg Thr Ser Ser Ala Gly Ala Leu
705                 710                 715                 720

Leu Ala Arg Ala Gly Ala Ala Leu Val Asn Glu Gly Ile Val Thr Ala
                725                 730                 735

Arg Gln Asp Leu Ser Trp Arg Ala Arg Asp Ile Val Asn Asp Ala Ala
                740                 745                 750

Gly Asn Val Val Ala Arg Ser Val Asp Met Arg Ala Gly Gln Gly Phe
            755                 760                 765

Asp His Arg Gly Ala Ile Gly Ser Val Thr Asp Leu Val Leu Lys Ala
            770                 775                 780

Ala Arg Ile Asp Ser Ala Gly Val Leu Arg Ala Asn Gln Asp Ile Asp
```

```
                785                 790                 795                 800
Met His Ala Asp Asp Ala Met Arg Leu Lys Ala Gly Ala Arg Thr Leu
                    805                 810                 815
Ala Gly Arg Asp Leu Ala Leu Ala Ala Asp Gln Leu Glu Gln Ser Gly
                820                 825                 830
Met Ala Gln Ala Gly Arg Thr Leu Thr Ala Thr Ala Gly Ala Leu Glu
            835                 840                 845
Asn Asp Gly Leu Leu Asp Ala Asp Ala Lys Leu Arg Thr Thr Arg
        850                 855                 860
Ala Phe Val Asn Arg Gly Gln Ile Gln Ala Asp Met Leu Gln Ala Gln
865                 870                 875                 880
Gly Pro Gln Ile Arg Asn Ala Gly Val Leu Arg Thr Gly Ala Leu Leu
                885                 890                 895
Ala Leu Gln Ala Ala Gly Arg Leu Glu Asn Thr Gly Gly Met Ala Ala
                900                 905                 910
Ser Gly Ser Leu Ser Ile Ala Ala Ala Gly Pro Phe Ala Asn Ser Gly
                915                 920                 925
Thr Met Gly Ala Asn Gly Asp Ala Ser Phe Ala Leu Ser Ser Phe Ala
    930                 935                 940
Asn Thr Gly Ser Ile Ser Val Gly Gly Asp Leu Ala Leu Arg Leu Pro
945                 950                 955                 960
Asp Val Glu Leu Thr Leu Asp Ala Asp His Arg Leu Pro Val Ser Gln
                965                 970                 975
Gly Thr Thr Leu Leu Gln Val Ala Ser Leu Asp Asn Arg Ala Arg Ser
            980                 985                 990
Glu Thr Pro Gly Arg Leu Ser Val  Gln Ala Arg Gly Ala  Ile Arg Asn
            995                 1000                1005
Gln Asp  Thr Leu Ala Ala Gly  Gln Gly Leu Trp Leu  Glu Ser Ala
    1010                1015                1020
Ala Asn  Asp Ile Glu Asn Gly  Ala Gly Ala Leu Leu  Trp Ser Gly
    1025                1030                1035
Ala Asp  Leu Arg Leu Arg Gly  Thr Arg Ile Ile Asn  Arg Glu Ala
    1040                1045                1050
Ala Ile  Ile Glu Ser Ala Ala  Gly Met Val Leu Asp  Ala Arg Ala
    1055                1060                1065
Glu Ile  Asp Asn Gly Leu Gly  Ile Ile Arg Ala Gly  Gly Asp Leu
    1070                1075                1080
Trp Ala  Asp Ala Pro Leu Leu  Arg Asn Ser Gly Arg  Leu Gly Gly
    1085                1090                1095
Arg Ile  Val Pro Ala Gly Asp  Ala Ala Ile Gly Gly  Gly Thr Tyr
    1100                1105                1110
Asp His  Tyr His Ser Ala Ala  Val Val Trp His Glu  Leu Phe Thr
    1115                1120                1125
Ala Gly  Ala Ala Gly Ile Arg  Val Pro Arg Tyr Asp  Gly Lys Asp
    1130                1135                1140
Val Arg  Val Ala Gln Ser Val  Val Gln Ala Gly Gly  Asn Leu His
    1145                1150                1155
Leu Asn  Gln Gly Glu Gln Lys  Gly Arg Gln Ala Arg  Val Ser Asn
    1160                1165                1170
Gln Gly  Arg Ile Glu Ala Ala  Gly Met Ala Leu Val  Asp Gly Asn
    1175                1180                1185
Val Asp  Asn Ala Ser Leu His  Leu Ser Leu Ser Val  Asp Glu Tyr
    1190                1195                1200
```

```
Leu Arg Arg Pro Leu Ala Ala Pro Ile Val Leu Arg Ala Thr Asp
1205                1210                1215

Ser Arg Ala Gln His Val Ile Pro Ala Phe Trp Lys Phe His Thr
1220                1225                1230

Leu Tyr Glu Phe Leu Asp Phe Leu Leu Ser Asn Asn Glu Pro Arg
1235                1240                1245

Tyr Ile Trp Gly Tyr Tyr Arg Thr Trp Pro Glu Trp Ala Phe Gln
1250                1255                1260

Thr Leu Arg Asn Leu Asp Leu Gly Tyr Ala Gly Ala Pro Asp Pro
1265                1270                1275

Thr Ala Pro Pro Val Pro Arg Pro Pro Val Leu Asp Pro Gln Ala
1280                1285                1290

Lys Ala Ser Thr Thr Pro Ala Ala Gln Ala Leu Val Ala Gln Tyr
1295                1300                1305

His Lys Asp Leu Ala Glu Tyr Ala Thr Ala Leu Glu Ala Ala Gln
1310                1315                1320

Arg Ala Glu Ala Ile Arg Thr Ala Arg Gln Arg Val Asp Gly Ala
1325                1330                1335

Leu Arg Ala Arg Tyr Gly Glu Lys Leu Ala Gln Leu Lys Thr Arg
1340                1345                1350

Thr Pro Glu Val Asp Ala Ala Val Ala Ala Leu Ala Gln Thr Ile
1355                1360                1365

Phe Asp Ala Arg Ala Lys Pro Ala Ala Glu Val Glu Lys Leu Ile
1370                1375                1380

Ala Ala Ala Leu Cys Ser Pro Arg Ala Gln Ala Cys Ala Ala Gly
1385                1390                1395

Thr Ala Arg Ile Ala Gln Leu Leu Asp Gln Ala Ser Leu Pro Pro
1400                1405                1410

Arg Arg Pro Ala Val Ala Leu Phe Ala Gln Ala Met Ala Ala Val
1415                1420                1425

Leu Gly Pro Asp Trp His Gly Pro Val Gly His Ala Thr Leu Met
1430                1435                1440

Ala Arg Tyr Ala Asp Phe Lys Arg Arg Val Ala Thr Gln Gly Arg
1445                1450                1455

Ala Ala Gly Gly Glu Leu Ala Phe Tyr Pro Ala Gln Gln Thr Val
1460                1465                1470

Leu Ala Gly Gly Ala Gly Leu Val Leu Ser Gly Gly Arg Val Thr
1475                1480                1485

Asn Gly Glu Asn Val Ala Gly Leu Leu Ala Arg Asn Met Thr Val
1490                1495                1500

His Ile Gly Glu Gln Arg Ile Glu Thr Pro Arg Gly Ser Ile Asp
1505                1510                1515

Ala Ile Arg His Pro Asp Ala Gly Pro Ala Val Thr Val Lys Asp
1520                1525                1530

Ser Ile His Ala Leu Leu Glu Asn Arg Arg Leu Phe Ala Arg Thr
1535                1540                1545

Ala Pro Ala Arg Ala Ala Ala Gly Pro Gly Gly Pro Asp Val Pro
1550                1555                1560

Ala Thr Pro Pro Gly Leu Pro Gln Pro Leu Tyr Glu Thr Arg Leu
1565                1570                1575

Ser Tyr Leu Asp Gln Ser His Tyr Tyr Gly Ser Gln Tyr Phe Phe
1580                1585                1590

Asp Leu Ile Arg Tyr Arg Pro Asp Arg Pro Leu Arg Thr Ile Gly
1595                1600                1605
```

```
Asp Asn Tyr Phe Glu Thr Arg Leu Ile Arg Glu Gln Ile Ala Arg
    1610            1615                1620

Ala Met Gly Gly His Glu Tyr Arg Asn Ala Val Arg Gly Leu Ala
    1625            1630                1635

Leu Val Gln Ser Leu Met Asp Ala Ala Pro Leu Ala Ala Ala Glu
    1640            1645                1650

Leu Gly Leu Arg Val Gly Gln Ala Pro Thr Ala Glu Gln Leu Ala
    1655            1660                1665

Arg Ala Thr Arg Asp Phe Val Trp Tyr Val Arg Glu Thr Val Asp
    1670            1675                1680

Gly Gln Glu Val Leu Val Pro Arg Val Tyr Leu Thr Arg Ala Thr
    1685            1690                1695

Arg Thr Ala Ala Ser Ala Thr Arg Glu Ala Gly Gly Ala Leu Met
    1700            1705                1710

Ala Ser Ala Gly Thr Val Leu Ala Asp Thr Gly Gly Ala Ala Ile
    1715            1720                1725

Glu Ser Gly Asn Ala Ala Phe Leu Gly Lys Asp Val Ile Leu Asp
    1730            1735                1740

Ala Ala Gly Gly Ala Val Arg Leu Ile Asn Asp Lys Gly Ile Ala
    1745            1750                1755

Gly Gly Ala Arg Ala Leu Gly Thr Leu Ala Ile Arg Gly Gly Asp
    1760            1765                1770

Ile Ala Ile Gln Gly Gly Leu Leu Asp Ala Ala Gln Ala Tyr Leu
    1775            1780                1785

Thr Gly Glu Arg Val Ser Leu Ala Ala Ser Ala Arg Tyr Asp Ala
    1790            1795                1800

His Gly Arg Leu Val Ser Arg His Asp Ala Arg Leu Asn Gly Arg
    1805            1810                1815

Ala Asp Ala Ala Gly Leu Leu Tyr Ile Ala Ala Lys Arg Leu Asp
    1820            1825                1830

Ser Ala Gly Ala Thr Leu Ser Gly Asp His Val Arg Leu Glu Ala
    1835            1840                1845

Asp Lys Val Arg Leu Gly Gly Leu Tyr Asp Val Asp Ser Ser Tyr
    1850            1855                1860

Ser Gln Thr Ser Arg Tyr Gly Leu Gly Lys Ala Trp Trp Leu Leu
    1865            1870                1875

Ser Ser Gln Thr Glu Thr Ala Thr Ala Ser His Ala Arg Phe Gln
    1880            1885                1890

Gly Thr Thr Leu Glu Gly Ala Ile Leu Ser Gly Arg Ala Thr Asp
    1895            1900                1905

Met Asp Ile Glu Gly Ser Ser Ala Arg Phe Gln Gln Thr Asp Leu
    1910            1915                1920

Gln Val Ala His Asp Phe Lys Ala Arg Ala Ala Ala Asp Tyr Ala
    1925            1930                1935

Tyr Ala Glu Arg Ala Lys Arg Val Asp Gln Leu Phe Leu Arg Leu
    1940            1945                1950

Ser Ala Gly Ala Gly Gly Tyr Glu Ala Gly Ile Asp Leu Ser Ala
    1955            1960                1965

Gln Gly Gly Leu Gln Ala His Ala Gly Arg Gly Gln Thr Ala Gly
    1970            1975                1980

Ala His Ala Ser Ala Gly Phe Glu Ser Thr Arg Glu Tyr Glu Arg
    1985            1990                1995

Ser Arg Met Thr His Tyr Arg Asn Ala Asp Leu Asn Phe Gly Ala
```

```
                2000                2005                 2010

Gly Leu  Leu Ala Val Gly Asn  Thr Ala Asp Leu  Gly Gly Ala Asp
    2015                 2020                 2025

Ile Asn  Arg Asp Arg Tyr Gly  Gln Gly Ala Ser  Thr Ala Ser Asp
    2030                 2035                 2040

Ala Ile  Pro Gly Asp Leu Leu  Arg Ile Arg Ala  Ala Arg Val Ala
    2045                 2050                 2055

Ala Thr  Lys Tyr Leu Asp Val  Thr Asp Ser Leu  Thr Ala Ser Ser
    2060                 2065                 2070

Tyr Leu  Arg Ala Ser Ile Asp  Gly Ala Leu Thr  Ser Ser Val Ala
    2075                 2080                 2085

Thr Ala  Ala Thr Arg Leu Gly  Asp Thr Leu Ala  Glu Ala Arg Gln
    2090                 2095                 2100

Glu Asn  Ser Gln Val His Ala  Gly Gln Met Ala  Leu Gln Met Ala
    2105                 2110                 2115

Gly Glu  Ala Thr Gln Leu Ala  Thr Thr Asp Thr  Ala Ala Leu Ser
    2120                 2125                 2130

Ile Ser  Ala Thr Phe Ala Ala  Gly Tyr Ala Asp  Ser His Arg Asn
    2135                 2140                 2145

Thr Gln  Thr Glu Asn Thr Asn  Tyr Phe Gly Gly  Asn Leu Asp Ile
    2150                 2155                 2160

Arg Ala  Thr Glu Gln Asp Ile  Asp Leu Ala Gly  Thr Lys Phe Ser
    2165                 2170                 2175

Gly Ala  Asp Trp Leu Ala Leu  Ser Ala Arg Arg  Asp Ile Asn Val
    2180                 2185                 2190

Arg Ala  Ala Ala Ser Arg Tyr  Gln Glu Ser Gly  Glu Gln His Asp
    2195                 2200                 2205

Leu Gln  Leu His Gln Thr Ile  Asn Ala Gly Ala  Asn Ala Met Gln
    2210                 2215                 2220

Ala Ala  Ala Gly Val Gly Val  Thr Ala Gly Leu  Ser Gly Ser His
    2225                 2230                 2235

Met Val  Arg His Gly Ala Gly  Gln Thr Tyr Glu  Gly Ser Ala Leu
    2240                 2245                 2250

Arg Ala  Thr Gln Leu His Leu  Gln Ala Arg Asp  Leu Asn Leu Asp
    2255                 2260                 2265

Ala Ser  Met Ala Gln Ala Thr  Arg Met Asp Leu  His Val Ala Arg
    2270                 2275                 2280

Asp Leu  Asn Ala Ile Ser Arg  Gln Asp Glu Gln  Arg Phe Ala Gln
    2285                 2290                 2295

Thr Gly  Gly Asn Trp Glu Val  Ser Leu Gly Ala  Ala Ile Gln Asn
    2300                 2305                 2310

Arg Thr  Leu Val Ala Pro Val  Gly Thr Ile Gly  Ala Gly Val Arg
    2315                 2320                 2325

His Glu  His Asp Tyr Gln Ala  Leu Thr Gln Asn  Gly Gln Ala Gly
    2330                 2335                 2340

Leu Leu  Ala Ser Gln Gly Leu  Arg Ala Thr Val  Gly Arg Asp Ala
    2345                 2350                 2355

Arg Leu  Arg Gly Ala Ile Ile  Ala Asp Ala Ser  Asn Gln Gly Gly
    2360                 2365                 2370

Met Asp  Ile Ala Gly Arg Ile  His Ala Glu Ala  Leu His Asp Tyr
    2375                 2380                 2385

Arg Asp  Lys Asp Gly Phe Glu  Thr Gly Ala Ser  Val Gly Ile Ser
    2390                 2395                 2400
```

-continued

Ser Thr Thr Leu Asn Pro Thr Leu Ser Leu Thr Leu Gly Arg Pro
2405                2410                2415

Ala Val Glu Gln Tyr Arg Ala Val Arg Gln Ala Thr Ile Ala Met
2420                2425                2430

Gly Ala Ala Pro Gly Ala Pro Arg Tyr Thr Ala Arg Gly Gly Val
2435                2440                2445

Ser Gly Arg Leu Asn Thr Asp Ser Gly Gln Ala Val Val Val Gln
2450                2455                2460

Arg Ala Glu Arg Trp Ala Ser Ala Arg Thr Glu Phe Ser Phe Asp
2465                2470                2475

Gln Pro Ser Arg Arg Asp Lys Ala Asp Ser Gly Ser Pro Gly Ala
2480                2485                2490

Arg Pro Ala His Pro Gly Ala Ala Lys Ala Pro Ala Leu Pro Leu
2495                2500                2505

Ala Arg Pro Leu Thr Ser Val Leu Ala Gly Pro Ser Ser Thr Ser
2510                2515                2520

Pro Thr Ala Asn Pro Ala Ala Ala Pro Gly Ile Ala Ala Gln Pro
2525                2530                2535

Ala Pro Ala Ser Pro Gly Arg Asp Ala Pro Lys Pro Asp Pro Tyr
2540                2545                2550

Ala Asn Arg Val Ile Val Gln Leu Ala Gln Asp Val Ala Thr
2555                2560                2565

Gln Ala Ala Gln Ala Leu Phe His Lys His Ala Glu Gln Ser Asp
2570                2575                2580

Trp Tyr Arg Gln Ala Asp Asp Gly Ser Leu His Pro Val His Pro
2585                2590                2595

Leu Arg Ala Ala Ala Gly Pro Thr Lys Ile Gln Leu Val Gly
2600                2605                2610

His Gly Ser Ala Asp Arg Gln Ala Leu Ser Gly His Asp Gly His
2615                2620                2625

Ala Val Ala Gly Ile Val Gln Gln Leu Arg Glu Arg Leu Pro Pro
2630                2635                2640

Ala Ala Ala Leu Ala Lys Val Ala Leu Val Gly Cys Asp Thr Asp
2645                2650                2655

Cys Ala Ser Gly Ala Ser Leu Arg Gly Asp Val Ala Gln Arg Leu
2660                2665                2670

Ala Ala Asp Gly Ala Gln Pro Ala Pro Ala Val Ser Gly Tyr Ile
2675                2680                2685

Gly Arg Leu Glu Val Asp Ala Ala Gly Arg Lys His Ala Val Ala
2690                2695                2700

Gln Gly Gly Leu Gly Asp Val Asp Pro Glu Ala Arg Ala Gln Gly
2705                2710                2715

Thr Gln Pro Val Pro Arg Val Phe Ser His Gly Pro Val Asn Ile
2720                2725                2730

Ala Gln Ser Gly Gln Ala Arg Gln Leu Val Ile Asp Gly His Gly
2735                2740                2745

Ser Trp Val Arg Pro Asp Arg Ala Val Ala Pro Ser Tyr Ser Gly
2750                2755                2760

Thr Val Arg Leu Pro Ala Gly Thr Arg Met His Phe Tyr Ser Asp
2765                2770                2775

Asp Gly Gln Met Val Ser Ala Ile Pro Leu Arg Asn Ile Pro Asp
2780                2785                2790

Asn Pro Glu Arg Ala Trp Arg Ala Gln Pro Phe Ser Glu Arg Ile
2795                2800                2805

```
Ser Ser Glu Arg Ile Arg Arg Val Ala Asn Ala Ala Lys Val Pro
    2810            2815                2820

Phe Asp Val Ala Arg Gln Gly Phe Glu Thr Ser Thr Gln Val Arg
    2825            2830                2835

Glu Ile Ala Ala Pro Gly Thr Ala Val Lys Asn Tyr Leu Leu Thr
    2840            2845                2850

Pro Ile Asp Pro Gln Arg Asp Ala Ala Leu Ala Phe His Gln Ser
    2855            2860                2865

Arg Ser Gln Ala Asp Val Asp Leu Ala Ser Ala Ala Pro Gly Lys
    2870            2875                2880

Gly Ala Leu Leu Ser Asp Leu Leu Leu Ala Val Ala Ala Ser Gly
    2885            2890                2895

His Ser Tyr Pro Leu Ile His Tyr Thr Cys Cys Arg Gly Glu Phe
    2900            2905                2910

Gln Arg Pro Gly Ser Asp Thr Pro Ser Pro Gln Leu Pro Pro His
    2915            2920                2925

Glu Leu Leu Ile Arg Ser Trp Leu Ala Ser Ser Ala Pro Val His
    2930            2935                2940

Ala Leu Pro Leu Pro Pro Ser Ser Arg Gly Thr Leu Pro Gly Ala
    2945            2950                2955

Asp Pro Tyr Ala Leu Arg Ser Ile Val Gln Leu Gly Thr Asp Ala
    2960            2965                2970

Ala Thr Ala Arg Ala Ala Ala Ala Leu His Gly Lys His Pro Ala
    2975            2980                2985

Asn Ser Asn Trp Tyr Leu Gln Thr Arg Asp Gly Gly Leu Glu Pro
    2990            2995                3000

Val Arg Gln Ala Ala Gly Pro Ala Ala Gly Pro His Lys Val Gln
    3005            3010                3015

Phe Val Gly His Gly Asp Val Tyr His Gly Val Pro Leu Leu Gly
    3020            3025                3030

Gly Asn Ala Ala Ala Thr Leu Ala Asp Leu Leu Asn Gln Val Glu
    3035            3040                3045

Gln His Ser Pro Ala Gly Ala Arg Leu Asp Lys Ile Ala Leu Val
    3050            3055                3060

Gly Cys Asp Thr Asp Cys Thr Gly Arg Pro Ser Leu Arg Glu Pro
    3065            3070                3075

Phe Arg Gln Ser Leu Ala Ala Arg Pro Asp Ala Pro Ala Leu Thr
    3080            3085                3090

Val Thr Gly Tyr Ile Gly Arg Ile Asp Val Asp Ser Ala Gly Arg
    3095            3100                3105

Lys Arg Arg Val Ala Thr Gly Gly Leu Gly Asp Arg Pro Pro Ala
    3110            3115                3120

Asp Glu Pro Ala Ser Pro Arg Pro Pro Ala Gln Pro Ala Ala Pro
    3125            3130                3135

Gly Pro Gly Ala Ala Thr Pro Ser Ser Ala Pro Ser Ala Pro Val
    3140            3145                3150

Ala Ala Arg Leu Phe Thr His Gly Pro Ile Thr Leu Ser Gln Ser
    3155            3160                3165

Glu Asn Ala Arg Gln Leu Leu Ile Gln Gly His Ser Gly Trp Thr
    3170            3175                3180

Arg Pro Pro Ala Gly Thr Ser Gly Ala Gly Glu Ile Pro Ala Gly
    3185            3190                3195

Trp Leu Arg Leu Pro Ser Gly Thr Arg Met His Phe Tyr Ser Val
```

-continued

```
             3200                3205                3210
Asp Asn Gln Gln Thr Ser Gly Val Pro Val Gln Ala Ile Pro Arg
    3215                3220                3225
Asn Pro Glu Leu Ala Trp Leu Gly Arg Pro Phe Val Arg Glu Phe
    3230                3235                3240
Pro Ala Ser Val Ile Arg Gln Phe Ala His Ala Arg Gln Ala Pro
    3245                3250                3255
Phe Asp Val Ala Arg Ala Ala Leu Val Glu Ser Thr Arg Val Gln
    3260                3265                3270
Glu Val Ala Ala Ala Gly Ala Leu Val Lys Asn Tyr Arg Leu Ala
    3275                3280                3285
Pro Ala Ile Asp Pro Leu Val Thr Gly Val Glu Gln Phe His Ala
    3290                3295                3300
Gln Arg Arg Gln Gly Asp Val Asp Met Ala Val Ala Arg Glu Arg
    3305                3310                3315
Ala Ser Leu Ser Asp Val Leu Ala Ala Val Glu Ala Ser Gly His
    3320                3325                3330
His Tyr Pro Leu Leu His Phe Thr Cys Cys Arg Gly Glu Thr Thr
    3335                3340                3345
Pro Pro Gly Ala Pro Pro Asp Ala Val Ala Pro Leu Ala Pro
    3350                3355                3360
Val Ser Ala Arg Tyr Leu Gln Gln Trp Arg Glu Arg Ser Gly Val
    3365                3370                3375
Ala Gln Pro Arg Pro Pro Thr Pro Leu Gly Ala Glu Pro Pro Val
    3380                3385                3390
His Gly Pro Asp Arg Tyr Gly His Arg Thr Ile Val Gln Leu Gly
    3395                3400                3405
Ser Asp Ala Leu Thr Glu Thr Ala Ala Arg Arg Leu Phe Arg Lys
    3410                3415                3420
His Ala Gly Asn Ala Ser Trp Tyr Ser Gln Asp Ala Ser Gly Gln
    3425                3430                3435
Leu Thr Gln Val Arg Ala Pro Ala Ala Pro Ala Thr Gly Pro Gln
    3440                3445                3450
Lys Ile Gln Phe Val Gly His Gly Ser Ile Leu Glu Gly Met Pro
    3455                3460                3465
Leu Leu Gly Gly Asn Asn Ala Ala Gln Leu Ala Arg Met Leu Pro
    3470                3475                3480
Ala Ile Arg Gln Gly Leu Pro Ala Thr Ala Arg Val Glu Lys Ile
    3485                3490                3495
Thr Leu Val Gly Cys Asn Thr Gly Cys Ala Ser Arg Ala Ser Leu
    3500                3505                3510
Arg Asn Leu Leu Asn His Tyr Leu Ile Thr Thr Ala Gly Leu Ser
    3515                3520                3525
Ala Glu Val Lys Gly Tyr Ala Gly Arg Val Asp Val Asp Ala Ala
    3530                3535                3540
Gly His Lys Gln Ile Val Glu Gln Gly Gly Leu Gly Asn Thr Pro
    3545                3550                3555
Pro Pro Glu Ala Ala Pro Ala Pro Arg Val Phe Arg His Gly Asn
    3560                3565                3570
Val Thr Leu Ser Gln Ser Gly Glu Ala Arg Gln Leu Thr Ile Val
    3575                3580                3585
Gly His Gly Phe Trp Pro Arg Pro Gly Pro Ala Asp Gln Pro Asp
    3590                3595                3600
```

-continued

Gly Ala Ser Pro Pro Gly Trp Val Arg Leu Pro Ala Asn Thr Ser
3605                3610                3615

Met Tyr Phe Tyr Ser Arg Glu Asn Gln Leu Val Gly Gly Leu Pro
3620                3625                3630

Ser Gln Ala Ala Leu Arg Ala Pro Met Leu Ala Ala Gln Gly Gln
3635                3640                3645

Gly Ala Ala Glu Leu Phe Ser Arg Ala Val Ile Arg Gly Phe Ala
3650                3655                3660

His Arg His Gln Leu Pro Phe Asp Val Ala Arg His Thr Leu Val
3665                3670                3675

Gly Ala Thr Arg Pro Gln Asp Ile Gly Glu Pro Gly Ala Leu Ile
3680                3685                3690

Lys Asp Tyr Val Val Ser Pro Ala Pro Glu Thr Gly Leu Gly Ala
3695                3700                3705

Ile Glu Asp Phe His Ala Ala Arg Gln Gln Pro Asp Met Asp Leu
3710                3715                3720

Ala Gln Ala Ala Pro Gly Ser Glu Ile Arg Leu Ser Glu Ile Leu
3725                3730                3735

Gln Ala Val Ala Gln Ser Gly Val Arg Tyr Asp Leu Ile His Tyr
3740                3745                3750

Ala Cys Cys Arg Ala Glu Ile Pro Ala Thr Asp Thr Pro Thr Gln
3755                3760                3765

Gln Val Ala Thr Pro Val Pro Ala Pro Asp Lys Leu Val Ile Gln
3770                3775                3780

Gln Trp His Ser Gly Ala Gly Ala Ala Arg Pro Pro Ser Pro Gln
3785                3790                3795

Ala Gln Ala Gln Ala Pro Tyr Gly Pro Asp Arg Tyr Ala His Arg
3800                3805                3810

Val Ile Val Gln Leu Gly Ser Asp Thr Val Thr Glu Ser Ala Ala
3815                3820                3825

Arg Arg Leu Phe Arg Lys His Ala Ala Thr Ser Leu Trp Tyr Gly
3830                3835                3840

Gln Thr Leu Glu Gly Thr Leu Met Leu Lys Gln Gly Gly Asp Thr
3845                3850                3855

Pro Ala Ala Gly Pro Leu Lys Ile Gln Phe Val Gly His Gly Gly
3860                3865                3870

Pro Arg Tyr Ser Met Pro Leu Leu Gly Gly Asn Thr Pro Ala Glu
3875                3880                3885

Leu Ala Gln Met Ala Ser Thr Ile Gln His Ala Gly Pro Pro Ser
3890                3895                3900

Gln Leu Glu Lys Val Thr Leu Val Gly Cys Gln Thr Asp Cys Val
3905                3910                3915

Ala Arg Pro Ser Leu Arg Lys Leu Phe Ser Thr Ala Leu Ala Thr
3920                3925                3930

Glu His Gly Leu Thr Pro Ala Val Thr Gly Tyr Ala Gly Arg Val
3935                3940                3945

Asp Val Asp Ala Ala Gly Arg Lys Arg Ile Val Glu Gln Gly Gly
3950                3955                3960

Leu Asn Glu Pro Arg Ala Gln Ala Gly Ala Ser Thr Ala Ala Pro
3965                3970                3975

Asn Arg Ile Val Gln Ser Val Ala His Gly Val Ala Leu Ser Gln
3980                3985                3990

Ser Gly Gln Ala Arg Gln Leu Val Val Leu Ala His Gly Gly Trp
3995                4000                4005

```
Lys Asp Lys Thr Thr Ser Arg Tyr Leu Arg Arg Val Arg Gly Asp
    4010                4015                4020

Gly Tyr Thr Glu Leu Pro Ala Asn Thr Arg Ile Asp Tyr Tyr Thr
    4025                4030                4035

Glu Asp Gly Ile Pro Thr Lys Gly Phe Ala Val Tyr Gln Glu Val
    4040                4045                4050

Thr Ala Arg Ala Asn Asp Thr Tyr Thr Gly Leu Gln Pro Thr Leu
    4055                4060                4065

Ala Ile Ser Pro Ala Asp Leu Glu Ala Leu Ala Arg Met His Asn
    4070                4075                4080

Thr Ser Pro Gln Ala Leu Thr Asp Ala Met Leu Ala Ser Ala Val
    4085                4090                4095

Gly Arg Arg Glu Ser Ile Ile Gly Ala Ala Thr Met Lys Asp Tyr
    4100                4105                4110

Ala Leu Tyr Tyr His Glu Gln Phe Ala Leu Asn Phe Leu Arg Arg
    4115                4120                4125

His Asn Ala Asp Gly Ser Ser Ala Asp Val Asp Leu Ala Ile Ile
    4130                4135                4140

Thr Glu Pro Thr His Lys Arg His Leu Ser Asp Val Leu Lys Ala
    4145                4150                4155

Ala Gly Glu Ser Gly Ala His Tyr Asp Val Val His Phe Gly Ala
    4160                4165                4170

Cys Arg Val Gly Arg Cys Arg Asn Ala Ala Ala Glu Met Gly Ala
    4175                4180                4185

Ser Ala Thr Ser Arg Leu Pro Pro
    4190                4195

<210> SEQ ID NO 17
<211> LENGTH: 211
<212> TYPE: PRT
<213> ORGANISM: Vibrio cholerae

<400> SEQUENCE: 17

Ala Leu Ala Asp Gly Lys Ile Leu His Asn Gln Asn Val Asn Ser Trp
1               5                   10                  15

Gly Pro Ile Thr Val Thr Pro Thr Thr Asp Gly Gly Glu Thr Arg Phe
            20                  25                  30

Asp Gly Gln Ile Ile Val Gln Met Glu Asn Asp Pro Val Val Ala Lys
        35                  40                  45

Ala Ala Ala Asn Leu Ala Gly Lys His Ala Glu Ser Ser Val Val Val
    50                  55                  60

Gln Leu Asp Ser Asp Gly Asn Tyr Arg Val Val Tyr Gly Asp Pro Ser
65                  70                  75                  80

Lys Leu Asp Gly Lys Leu Arg Trp Gln Leu Val Gly His Gly Arg Asp
                85                  90                  95

His Ser Glu Thr Asn Asn Thr Arg Leu Ser Gly Tyr Ser Ala Asp Glu
            100                 105                 110

Leu Ala Val Lys Leu Ala Lys Phe Gln Gln Ser Phe Asn Gln Ala Glu
        115                 120                 125

Asn Ile Asn Asn Lys Pro Asp His Ile Ser Ile Val Gly Cys Ser Leu
    130                 135                 140

Val Ser Asp Asp Lys Gln Lys Gly Phe Gly His Gln Phe Ile Asn Ala
145                 150                 155                 160

Met Asp Ala Asn Gly Leu Arg Val Asp Val Ser Val Arg Ser Ser Glu
                165                 170                 175
```

```
Leu Ala Val Asp Glu Ala Gly Arg Lys His Thr Lys Asp Ala Asn Gly
            180                 185                 190

Asp Trp Val Gln Lys Ala Glu Asn Asn Lys Val Ser Leu Ser Trp Asp
            195                 200                 205

Ala Gln Gly
    210

<210> SEQ ID NO 18
<211> LENGTH: 5
<212> TYPE: PRT
<213> ORGANISM: Artificial
<220> FEATURE:
<223> OTHER INFORMATION: Peptide linker utilized for fusing first
      polypeptide and second polypeptide in fusion protein

<400> SEQUENCE: 18

Gly Gly Gly Gly Ser
1               5
```

KITS FOR PRODUCING RECOMBINANT POLYPEPTIDES VIA CYSTEINE PROTEASE AUTOPROCESSING OF FUSION PROTEINS

CROSS-REFERENCE TO RELATED APPLICATIONS

The present application is a continuation of U.S. application Ser. No. 13/183,071, filed Jul. 14, 2011, which application was published on Dec. 1, 2011, as US2011/0294160, and which application is a continuation of U.S. application Ser. No. 12/630,603, filed on Dec. 3, 2009, which application was published on Jun. 3, 2010, as US2010/0137563, and claims the benefit under 35 U.S.C. §119(e) to U.S. Provisional Patent Application No. 61/119,489, filed on Dec. 3, 2008, the contents of which are incorporated herein by reference in their entireties.

STATEMENT REGARDING FEDERALLY SPONSORED RESEARCH OR DEVELOPMENT

This invention was made with U.S. Government Support from the following agency: NIH/NIAID, Grant No. R01AI051490. The U.S. Government has certain rights in the invention.

BACKGROUND

Purification of recombinant proteins from *Escherichia coli* and other model organisms is an essential component of biochemical and structural biology research. Over the past few decades, numerous strategies have been developed to allow easy purification of recombinant proteins by addition of a fusion protein or protein tag that allows rapid affinity purification. For some proteins, the fusion or tag poses a problem as the additional peptide sequences can interfere with function of the protein in biochemical assays or prevent the protein from forming compact crystals. If this occurs, the tag must often be removed after purification. This process of tag removal can be a cumbersome process.

Recently, a cysteine protease domain (CPD) embedded in a large protein toxin of *Vibrio cholerae* and other bacterial organisms was discovered that is inactive until induced by addition of the chemical compound inositol hexakisphosphate, also known as inositol-6-phosphate, InsP6, IP6, or phytic acid. Here, it is shown that a target protein can be purified as part of a fusion protein that includes the target protein fused to the CPD and a C-terminal peptide tag of 6-histidine residues. After purification of the fusion protein, the inducer molecule InsP6 is added and the protease and the peptide tag are removed from the fusion protein via autoproteolysis. The remaining portion of the fusion protein includes the target protein and an additional alanine and leucine residue added to the C-terminus of the target protein.

These disclosed strategies for purification of recombinant proteins followed by removal of a peptide tag may be adapted into any available cloning or purification systems. The molecule InsP6 is not produced by bacteria, hence, this strategy may be desirable for any recombinant protein produced in *E. coli* or other bacterial expression systems. This strategy also is desirable for any recombinant protein produced in plant, fungal, insect, or animal host cell expression systems in which the host cell is modified to block synthesis of InsP6.

SUMMARY

Disclosed are fusion proteins, polynucleotides that encode the disclosed fusion proteins, and methods for expressing and autoprocessing of the disclosed fusion proteins to obtain a target protein. The disclosed fusion proteins include an autoproteolytic cysteine protease fused to a heterologous polypeptide, which may be isolated as the target protein. In some embodiments, the protease activity of the cysteine protease is inducible. Suitable autoproteolytic cysteine proteases for the fusion proteins include the cysteine protease of the *Vibrio cholerae* RTX toxin. Examples of heterologous polypeptides may include target proteins, including but not limited to, industrial enzymes (process enzymes), enzymes targeted for use in consumer products, or proteins with pharmaceutical activity.

The fusion protein may include: (a) a first polypeptide; and (b) a second polypeptide fused to the C-terminus of the first peptide, where the first polypeptide is heterologous with respect to the second polypeptide and the second polypeptide has an amino acid sequence that includes the cysteine protease domain of the *Vibrio cholerae* RTX toxin or a cysteine proteases domain from a conserved or related toxin as contemplated herein. In some embodiments, the second polypeptide has an amino acid sequence that is at least 95% identical to any of SEQ ID NOs:1-17 (or at least 96%, 97%, 98%, or 99% identical to any of SEQ ID NOs:1-17), and the second polypeptide has cysteine protease activity when induced by inositol hexakisphosphate such that the second polypeptide is autocleaved (e.g., between amino acids 2 and 3 of the second polypeptide).

The fusion protein further may include a peptide tag fused at the C-terminus of the second polypeptide. Suitable peptide tags may include, but are not limited to a 6×His tag, a hemaglutinin tag, a FLAG tag, a glutathione-S-transferase tag, a green fluorescent protein tag, a maltose binding protein tag, a chitin binding protein tag, or another functional sequence of amino acids.

In the fusion protein, the first polypeptide and the second polypeptide may be directly fused. Alternatively, the first polypeptide and second polypeptide may be fused indirectly via a peptide linker (e.g., a linker which optionally is flexible and which optionally has one or more glycine or serine residues or any other compatible amino acid sequence).

Also disclosed are polynucleotides coding for the disclosed fusion proteins. For example, contemplated polynucleotides may include DNA or RNA molecules. The disclosed polynucleotides may be recombinant and may include one or more heterologous polynucleotide sequences fused to the polynucleotide sequence coding for the fusion protein. In some embodiments, contemplated recombinant polynucleotides include a promoter sequence operably linked to a polynucleotide coding for the disclosed fusion protein.

Also disclosed are vectors that include the recombinant polynucleotides. The vectors further may include selectable markers and may be utilized to transform a host cell (e.g., an isolated bacterial, plant, fungal, insect, or animal cell).

Also disclosed are methods for producing the disclosed fusion proteins. The methods may include: (a) culturing or fermenting a cell under conditions suitable for expression of the fusion protein, where the cell is transformed with a recombinant polynucleotide, and the recombinant polynucleotide includes a promoter sequence operably linked to a polynucleotide encoding the fusion protein; and (b) recovering the fusion protein so expressed. The fusion protein further may include a peptide tag as contemplated herein and the method further may include contacting the peptide tag with a molecule or resin that binds the peptide tag (e.g., in order to activate, isolate, separate, or purify the fusion protein). In some embodiments, the method further may include: (c) contacting the recovered fusion protein and inositol hexakisphosphate, thereby inducing cleavage of the fusion protein within the second polypeptide to provide: (i) a cleaved fragment of the fusion protein including the first polypeptide; and (ii) a cleaved fragment of the fusion protein including at least a portion of the second polypeptide. In some embodiments, the recovered fusion protein and the inositol hexahisphosphate are contacted in a reaction mixture comprising a protease inhibitor (e.g., a protease inhibitor that inhibits non-specific protease activity in the reaction mixture). Suitable proteases may include but are not limited to chloromethyl ketones and N-ethylmaleimide. In further embodiments, the method may include: (d) separating the cleaved fragment of the fusion protein that includes the first polypeptide and the cleaved fragment of the fusion protein that includes at least a portion of the second polypeptide. For example, where the fusion protein includes a peptide tag fused at the C-terminus of the second polypeptide, the peptide tag may be contacted with a molecule or resin that binds the peptide tag to remove the cleaved fragment of the fusion protein that includes at least a portion of the second polypeptide.

Also disclosed are kits for preparing and using the fusion proteins contemplated herein. In some embodiments, the kit includes: (1) an expression vector as contemplated herein for expressing the fusion protein; optionally (2) reagents for activating, isolating, separating, or purifying the fusion protein or cleavage products thereof (e.g., resins or columns that bind to the peptide tag present on the fusion protein); and optionally (3) an inducer compound (e.g., inositol hexakisphosphate).

DETAILED DESCRIPTION

Figure 1:
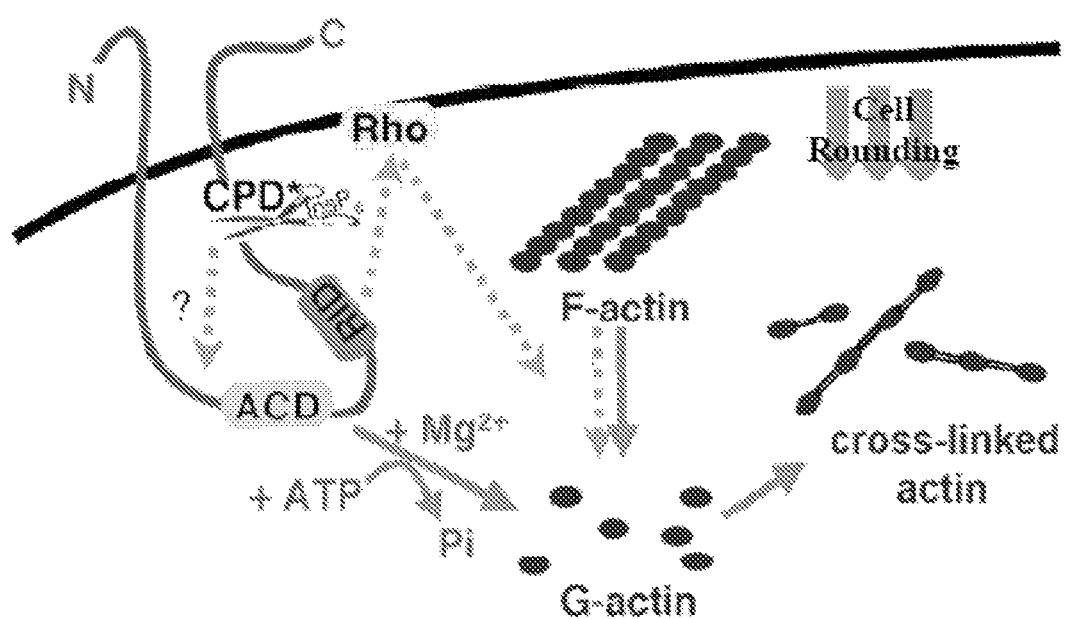
FIG. 1. Model for mechanism of MARTX-Vc-mediated cell rounding.
Figure 2:
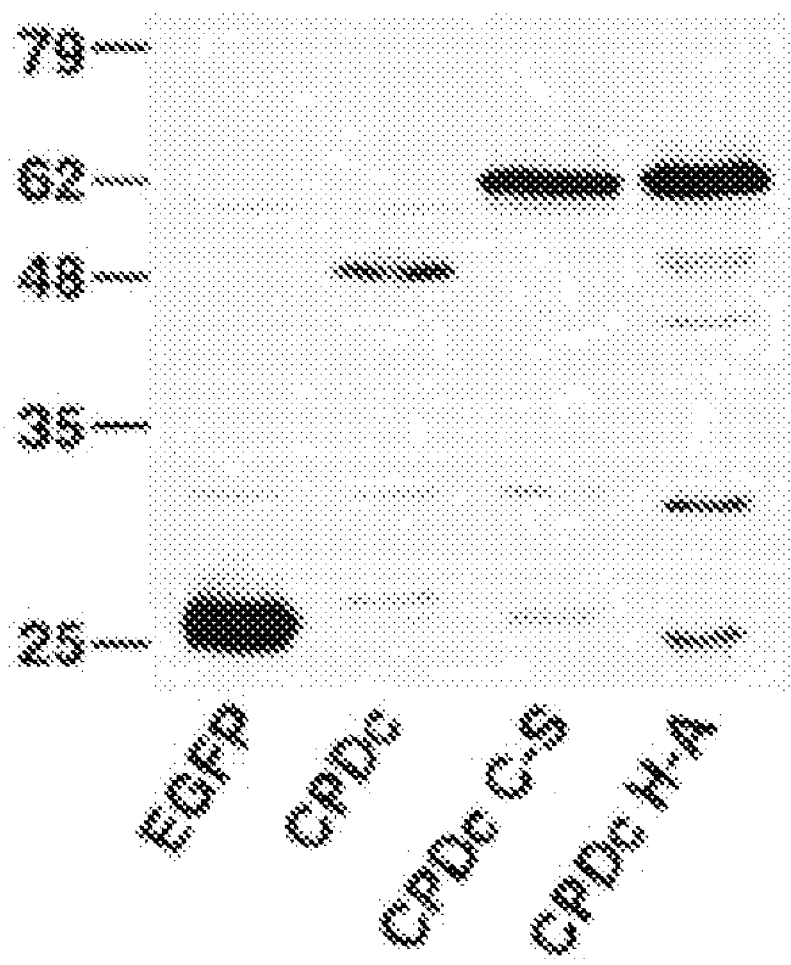
FIG. 2. HEp-2 cells transfected with CPD fused to EGFP (CPDc) do not have full-length CPD:EGFP as detected by Western blotting with anti-EGFP antibody. Mutagenesis of C3568 (CPDc C-S) or H3519 (CPDc H-A) resulted in proteins at the expected mol. wt.
Figure 3:
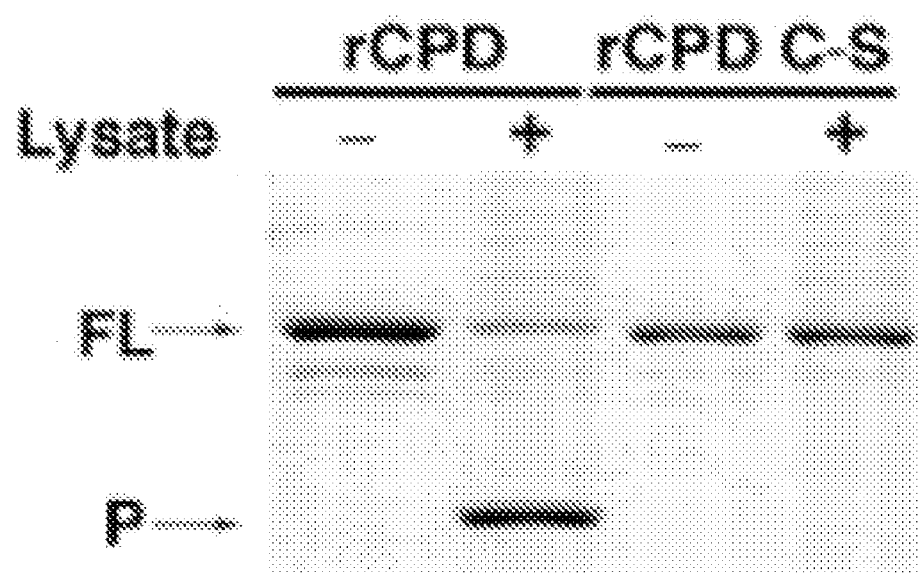
FIG. 3. Purified recombinant CPD (rCPD) or the C3568S mutant (rCPD C-S) were incubated at 37° C. for 2 hr in the (+) presence or (−) absence of a nuclear-free cell lysate. Arrows indicated full-length (FL) and processed (P) forms of rCPD.
Figure 4:
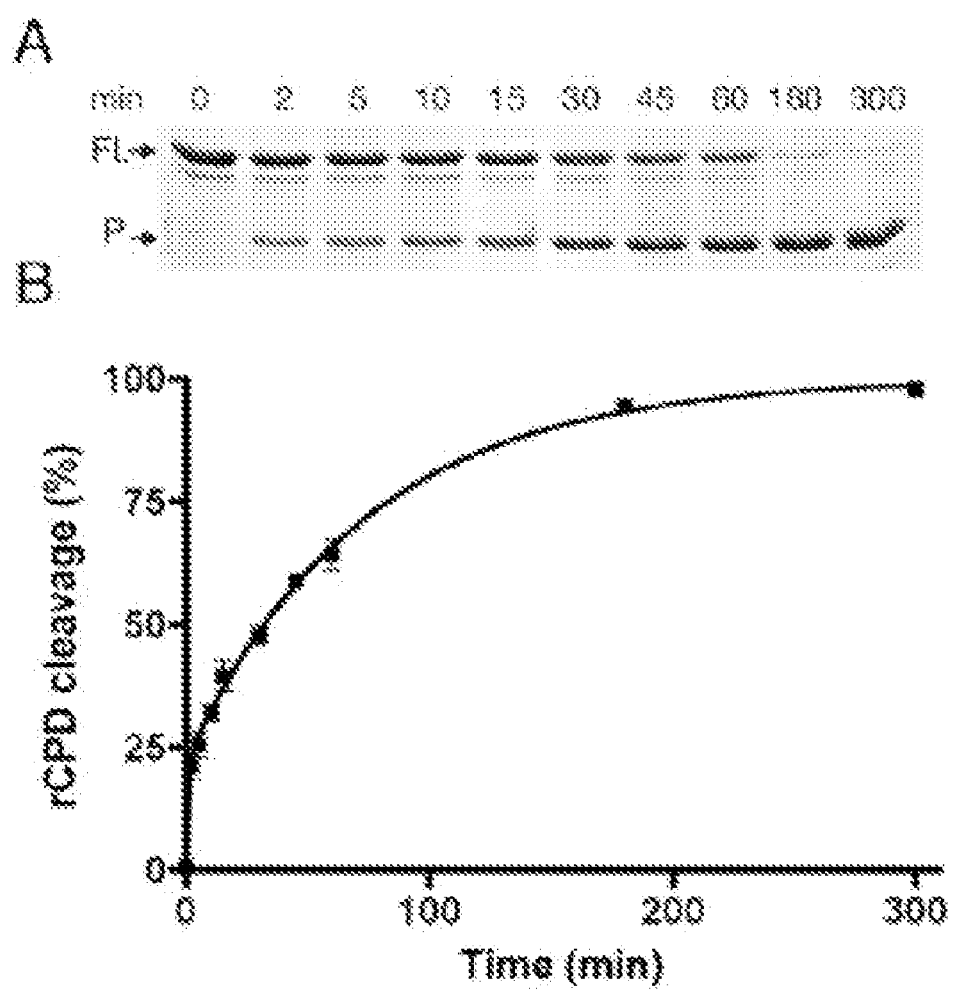
FIG. 4. Demonstrates autoprocessing of rCPD at its N-terminus after addition of 100 μM InsP6.
Figure 5:
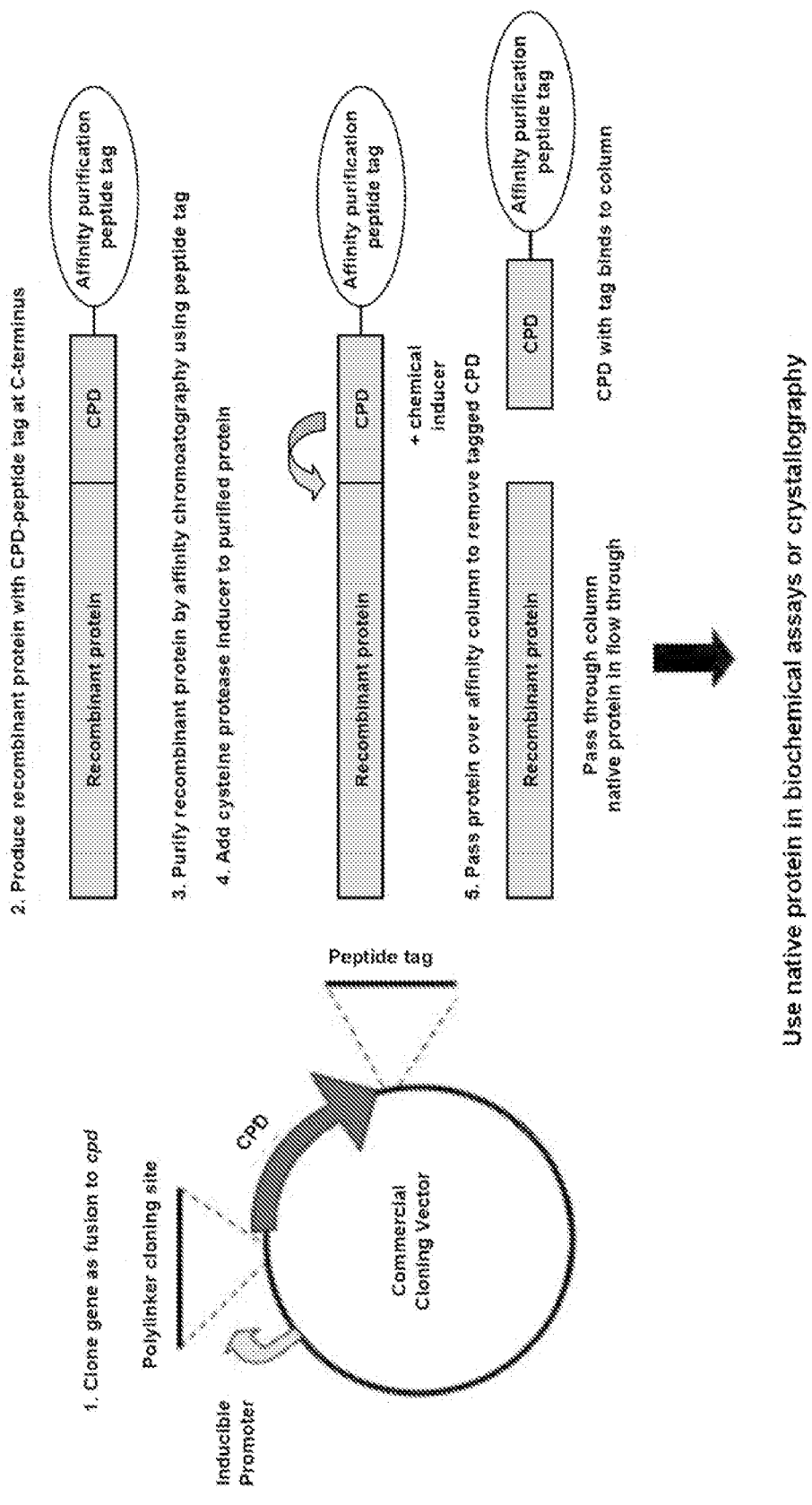
FIG. 5. Production of recombinant protein as part of a fusion protein and subsequent cleavage at CPD.
Figure 6:
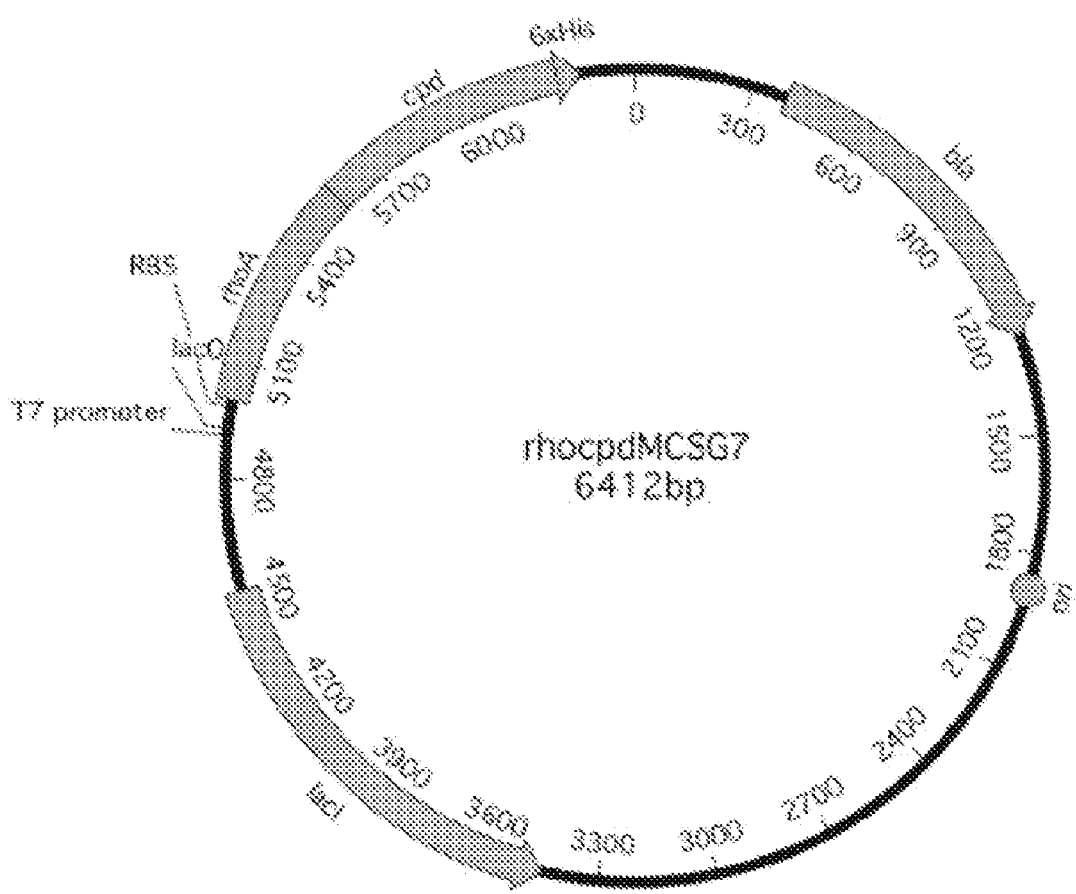
FIG. 6. Diagram of overexpression plasmid created to generate a fusion of RhoA to CPD:6×His.
Figure 7:
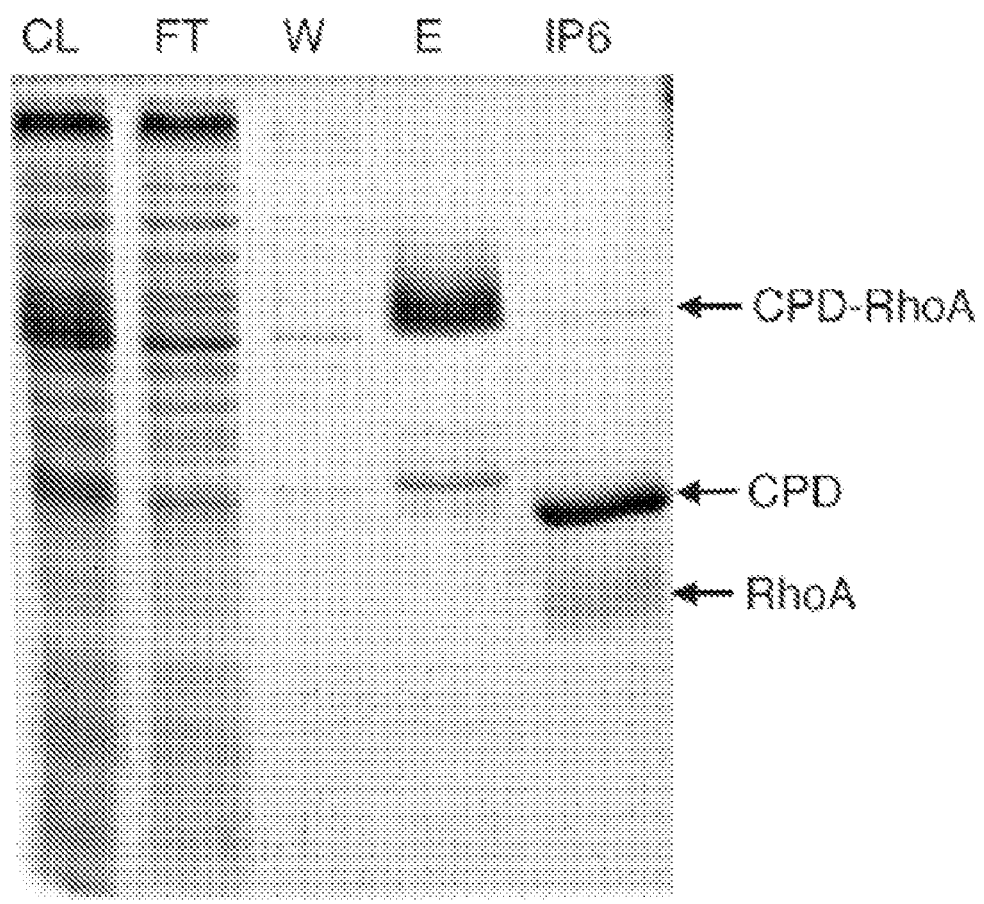
FIG. 7. Clarified lysate (CL) was loaded onto nickel column and Flow through (FT) and wash (W) fractions were collected. Protein was eluted in 250 mM imidazole and Rho was cleaved from CPD:6×His by addition of Inositol 6 phosphate (IP6).

The subject matter disclosed herein is described using several definitions and description, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a", "an", and "the" can mean one or more, depending upon the context in which it is used.

As used herein, "about," "approximately," "substantially," and "significantly" are terms that will be understood by persons of ordinary skill in the art and will vary to some extent on the context in which they are used. If there are uses of the term which are not clear to persons of ordinary skill in the art given the context in which the term is used or that are not clear in the context of the present disclosure, "about" or "approximately" will mean up to plus or minus 10% of the particular term and "substantially" and "significantly" will mean more than plus or minus 10% of the particular term.

Disclosed herein are fusion proteins that include an autoproteolytic cysteine protease fused to a heterologous polypeptide. As used herein, a "heterologous polypeptide" is a polypeptide that is not naturally cleaved by the autoproteolytic cysteine protease (e.g., a non-*Vibrio cholerae* RTX polypeptide). Preferably, the enzyme activity of the autoproteolytic cysteine protease is inducible. Suitable autoproteolytic cysteine proteases for the fusion proteins include the cysteine protease domain (CPD) of the *Vibrio cholerae* RTX toxin or cysteine protease domains from conserved or related toxins (e.g., the conserved toxin in large clostridial glucosylating toxins TcdB, TcdA, TcnA, and TcsL; putative toxins from *V. vulnificus, Yersinia* sp., *Photorhabdus* sp., and *Xenorhabdus* sp.; and a filamentous/hemagglutinin-like protein FhaL from *Bordetella* sp.). Examples of heterologous polypeptides may include, target proteins, including but not limited to, industrial enzymes (process enzymes), enzymes targeted for use in consumer products, or proteins with pharmaceutical activity. Fusion proteins and methods of making and using fusion proteins are disclosed in U.S. Pat. Nos. 7,378,512; 7,276,355; 7,176,287; and 7,045,677; the contents of which are incorporated herein by reference in their entireties.

Typically, the protease of the disclosed fusion proteins is fused in frame to the C-terminus of the heterologous polypeptide. The heterologous protein and the protease may be directly fused or indirectly fused via a linking peptide. For example, a linking peptide may comprise at least 1, 2, 3, 4, 5, 10, 15, or 20 amino acids. Suitable linkers may comprise any sequence of amino acids. Preferred linkers have neutral structural properties. For example, a linker preferably has a neutral pH and comprises relatively small-sized amino acids (e.g., glycine and serine). A preferred linker may comprise the sequence (GGGGS) (SEQ ID NO:18) or 1, 2, or 3 tandem repeats thereof.

In some embodiments, the enzyme activity of the autoproteolytic cysteine protease of the fusion protein is inducible (e.g., where the proteolytic activity of the protease is induced by contacting the protease with a chemical reagent such as inositol hexakisphosphate in a processing reaction). For example, the fusion protein may be expressed and subsequently the autoproteolytic activity of the protease may be induced in a processing reaction mixture such that the protease cleaves itself. The portion of the fusion protein comprising the heterologous polypeptide may be separated from the other cleaved portion of the fusion protein (i.e., the portion comprising the protease or the majority of the protease). Preferably, the fusion protein further comprises a peptide tag at the C-terminus of the protease, which may be utilized to isolate, separate, or purify the fusion protein or to isolate, separate, or purify the C-terminal portion of the fusion protein. In some embodiments, non-specific protease activity of the fusion protein may be inhibited by including in the processing reaction a protease inhibitor, including but not limited to chloromethyl ketones and N-ethylmaleimide. As contemplated herein, "non-specific protease activity" means cleavage by the autoprotease at a position other than between amino acids 2 and 3 of the autoprotease (or cleavage by another protease in the processing reaction mixture a position other than between amino acids 2 and 3 of the autoprotease). Preferably, the protease inhibitor does not inhibit or does not substantially inhibit specific protease activity of the autoprotease (i.e., cleavage by the autoprotease at the position between amino acids 2 and 3 of the autoprotease). As contemplated herein, a protease inhibitor that does not substantially inhibit the specific protease activity of the autoprotease is a protease inhibitor that does not inhibit the specific protease activity of the autoprotease by more than 50% (preferably that does not inhibit the specific protease activity of the autoprotease by more than 40%, 30%, 20%, or 10%).

Also disclosed are nucleic acid molecules that encode the disclosed fusion proteins. For example, contemplated are nucleic add molecules (e.g., DNA or RNA) which code for a fusion protein in which the fusion protein comprises a first polypeptide fused at its C-terminus to a second polypeptide as disclosed herein.

A preferred nucleic acid molecule is one that encodes the fusion protein contemplated herein in which the encoded second polypeptide of the fusion protein comprises the amino acid sequence of any of SEQ ID NOs:1-17 or the amino acid sequence of a variant, mutant, or derivative thereof with autoproteolytic cysteine protease activity. Variants or derivatives with autoproteolytic cysteine protease activity may include variants or derivative having one or more amino acid substitutions, deletions, additions and/or amino acid insertions, provided that autoproteolytic activity is retained.

The autoproteolytic cysteine protease activity of the disclosed fusion protein or polypeptides can be assayed by methods shown herein or by methods known in the art (e.g., by an in vitro system). For example, a DNA construct encoding a fusion protein or polypeptide may be transcribed into RNA and translated into protein with the aid of an in vitro translation kit. The resulting protein may be labeled by incorporating a detectable amino acid (e.g., a radioactive amino acid). Protease activity may be induced by adding inositol hexakisphosphate to the protein. If a fusion protein or polypeptide exhibits autoproteolysis, the resulting cleavage products can be detected using methods known in the art. For example, the protein can be loaded onto a protein gel (for example SDS-PAGE) and subjected to electrophoresis. The gel may be subsequently stained with suitable dyes or subjected to autoradiography. Alternatively, a Western blot and immunostaining may be performed. Cleavage of the protein can be assessed on the basis of the intensity of the resulting protein bands.

Also contemplated are bacterial, plant, fungal, insect, or animal host cell expression vectors that express the disclosed fusion proteins. Vectors may be used to transform appropriate host cells (e.g., *E. coli*). The transformed host cell may be cultivated or fermented such that the fusion protein is expressed constitutively or after adding a reagent that induces expression (e.g., via an inducible promoter). The fusion protein may exhibit autoproteolysis after expression. To assess the efficiency of autoproteolytic cleavage, a sample comprising the fusion protein may be taken after the end of the cultivation or induction phase and analyzed by SDS-PAGE or other methods.

Expression vectors as contemplated herein may include control sequences that modulate expression of the fusion protein. Expression control sequences may include constitutive or inducible promoters (e.g., T3, T7, Lac, trp, or phoA), ribosome binding sites, or transcription terminators.

The vectors disclosed herein may be utilized to transform host cells. Suitable host cells include bacterial, plant, fungal, insect, or animal host cell. Suitable bacteria include, but are not limited to: Gram-negative bacteria such as *Escherichia* species (e.g., *E. coli*), other Gram-negative bacteria, (e.g., *Pseudomonas* sp., such as *Pseudomonas aeruginosa*, or *Caulobacter* sp., such as *Caulobacter crescentus*), or Gram-positive bacteria (e.g., *Bacillus* sp., in particular *Bacillus subtlis*).

Also disclosed are methods for expressing, preparing, isolating, separating, or purifying fusion protein or polypeptides. In some embodiments, the methods may be utilized to produce the heterologous polypeptide of the fusion protein as disclosed herein. The steps of the methods may include: (i) cultivating or fermenting a transformed host cell (e.g., a bacterial host cell as contemplated herein) which comprises an expression vector (as contemplated herein) which in turn comprises a nucleic acid molecule encoding a fusion protein (as contemplated herein), wherein cultivation occurs under conditions which cause expression of the fusion protein and further autoproteolytic cleavage of the fusion protein; and (ii) isolating, separating, or purifying the cleaved heterologous polypeptide portion of the fusion protein. The transformed bacteria may be cultivated or fermented using methods known in the art in order to express the fusion protein. The cleaved heterologous polypeptide portion of the fusion protein may be isolated, separated, or purified by methods known in the art (see, e.g., M. P. Deutscher, in: Methods in Enzymology: Guide to Protein Purification, Academic Press Inc., (1990), 309-392). An exemplary isolation, separation, or purification method may include one or more of the following steps: a cell disruption step, a clarification step (e.g., via centrifugation or filtration), a chromatographic separation step, a dialysis step, and a precipitation step.

The terms "nucleic acid" and "nucleic acid sequence" refer to a nucleotide, oligonucleotide, polynucleotide (which terms may be used interchangeably), or any fragment thereof. These phrases also refer to DNA or RNA of genomic or synthetic origin (which may be single-stranded or double-stranded and may represent the sense or the antisense strand). These phrases also refer to peptide nucleic acid (PNA), or to any DNA-like or RNA-like material.

The terms "amino acid" and "amino acid sequence" refer to an oligopeptide, peptide, polypeptide, or protein sequence (which terms may be used interchangeably), or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

The amino acid sequences contemplated herein may include conservative amino acid substitutions relative to a reference amino acid sequence. For example, a variant, mutant, or derivative polypeptide may include conservative amino acid substitutions relative to a reference polypeptide. "Conservative amino acid substitutions" are those substitutions that are predicted to interfere least with the properties of the reference polypeptide. In other words, conservative amino acid substitutions substantially conserve the structure and the function of the reference protein. Table 1 provides a list of exemplary conservative amino acid substitutions.

TABLE 1

| Original Residue | Conservative Substitution |
|---|---|
| Ala | Gly, Ser |
| Arg | His, Lys |

TABLE 1-continued

| Original Residue | Conservative Substitution |
|---|---|
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

A "fragment" is a portion of an amino acid sequence or a polynucleotide which is identical in sequence to but shorter in length than a reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least 5, 10, 15, 20, 25, 30, 40, 50, 60, 70, 80, 90, 100, 150, 250, or 500 contiguous nucleotides or contiguous amino acid residues of a reference polynucleotide or reference polypeptide, respectively. Fragments may be preferentially selected from certain regions of a molecule. The term "at least a fragment" encompasses the full length polynucleotide or full length polypeptide.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences. Homology, sequence similarity, and percentage sequence identity may be determined using methods in the art and described herein.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed below).

Percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

A "variant," "mutant," or "derivative" of a particular nucleic acid sequence may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST)

(Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant," "mutant," or "derivative" of a particular polypeptide sequence is defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" or a "derivative" may have substantially the same functional activity as a reference polypeptide. For example, a variant or derivative of a cysteine protease may have cysteine protease activity (e.g., autoproteolytic cysteine protease activity).

The words "insertion" and "addition" refer to changes in an amino acid or nucleotide sequence resulting in the addition of one or more amino acid residues or nucleotides, respectively. An insertion or addition may refer to 1, 2, 3, 4, 5, 10, 20, 30, 40, 50, 60, 70, 80, 90, 100, 150, or 200 amino acid residues or nucleotides.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, J. et al. (1989) Molecular Cloning: A Laboratory Manual, 2$^{nd}$ ed., vol. 1 3, Cold Spring Harbor Press, Plainview N.Y. The term recombinant includes nucleic acids that have been altered solely by addition, substitution, or deletion of a portion of the nucleic acid. Frequently, a recombinant nucleic acid may include a nucleid acid sequence operably linked to a promoter sequence. Such a recombinant nucleic acid may be part of a vector that is used, for example, to transform a cell.

"Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "composition comprising a given amino acid sequence" and a "composition comprising a given polynucleotide sequence" refer broadly to any composition containing the given polynucleotide or amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components (e.g., Denhardt's solution, dry milk, salmon sperm DNA, and the like).

The contemplated fusion proteins may include at least a fragment of an amino acid sequence of a proven or putative cysteine protease. (See Sheahan K. L. et al., "Autoprocessing of the *Vibrio cholerae* RTX toxin by the cysteine protease domain," EMBO J. 2007 May 16; 26(10):2552-61, at page 2553, FIG. 1 and supplemental Table 1, the content of which is incorporated herein by reference in its entirety). Proven and putative cysteine protease domains for incorporation into the fusion proteins contemplated herein include, but are not limited to *Vibrio*-type RTX toxins such as toxins from *V. cholerae* (VcRtx); *V. vulnificus* (VvRtx), *V. splendidus* (VsRtx), *Xenorhabdus nematophila* (XnRtx), *X. bovienii* (XbRtx), and *Photorhabdus luminescens* (Plu1344, Plu1341, Plu3217, and Plu3324); clostridial-type toxins such as *Clostridium difficile* toxin A (TcdA), toxin B (TcdB), *C. sordellii* cytotoxin L (TcsL) and *C. noveyi* alpha toxin (TcnA); putative *Yersinia* toxins *Y. pseudotuberculosis* YPTB3219 (YpRtx) and *Y. mollaretti* Mfp2 (YmMfp2); and four domains arranged in tandem in *B. pertussis* putative adhesin FhaL (FhaL1-4). Contemplated fusion proteins may include at least a fragment of the proven and putative autoproteases disclosed in Table 2, in particular the listed amino acid fragment.

TABLE 2

| Protein | Abbreviation | Gen Bank Accession number | Amino Acid Fragment |
|---|---|---|---|
| Group 1: *Vibrio*-type RTX toxins | | | |
| *V. cholerae* RTX toxin | VcRtx | gi \| 4455065 | 3420-3619 |
| *V. vulnificus* RTX toxin | VvRtx | gi \| 37676690 | 4110-4288 |

TABLE 2-continued

| Protein | Abbreviation | Gen Bank Accession number | Amino Acid Fragment |
|---|---|---|---|
| V. splendidus putative RTX toxin | VsRtx | gi \| 84386478 | 3751-3975 |
| P. luminescens putative RTX toxins | Plu1341 | gi \| 37525303 | 2579-2764 |
|  | Plu1344 | gi \| 36784731 | 2965-3163 |
|  | Plu3217 | gi \| 36786533 | 2425-2620 |
|  | Plu3324 | gi \| 37686635 | 2440-2626 |
| Group 2: Putative toxins from Yersinia | | | |
| Y. pseudotuberculosis putative toxin | YpRtx | gi \| 51590811 | 1058-1271 |
| Y. mollaretti putative toxin | YmMfp2 | gi \| 77962640 | 1-224 |
| Group 3: Clostridial glucosylating toxins | | | |
| C. difficile Toxin A | TcdA | gi \| 98593 | 535-769 |
| C. difficile Toxin B | TcdB | gi \| 761714 | 536-768 |
| C. noveyi alpha toxin | TcnA | gi \| 755724 | 532-813 |
| C. sordellii cytotoxin L | TcsL | gi \| 1000695 | 526-825 |
| Group 4. Type V secreted adhesin | | | |
| Bordetella pertussis putative adhesin FhaL | cpd1 | gi \| 33563918 | 2551-2716 |
|  | cpd2 | gi \| 33563918 | 3079-3119 |
|  | cdp3 | gi \| 33563918 | 3375-3971 |
|  | cpd4 | gi \| 33563918 | 3397-3562 |

In some embodiments, the disclosed fusion proteins may include at least a fragment of the amino acid sequence of the MARTX toxin of V. cholerae as the second polypeptide of the fusion protein. (See, e.g., Satchell, K. J., "MARTX, Multifunctional Autoprocessing Repeats-in-Toxin Toxins," Infection and Immunity, November 2007, p. 5079-5084; Sheahan K. L. et al., "Autoprocessing of the Vibrio cholerase RTX toxin by the cysteine protease domain," EMBO J. 2007 May 16; 26(10):2552-61; Prochazkova K. et al., "Structure-function analysis of inositol hexakisphosphate-induced autoprocesssing of the *Vibrio cholerae* multifunctional autoprocessing RTX toxin," J. Biol. Chem. 2008 Aug. 29; 283 (35); Prochazkova et al., "Structural and molecular mechanism for autoprocessing of MARTX toxin of *Vibrio Cholerae* at multiple sites," J. Biol. Chem. 2009 2009 Sep. 25; 284(39):26557-68 Epub 2009 Jul. 20; the contents of which are incorporated by reference in their entireties). The entire MARTX toxin of *V. cholerae* is 4545 amino acids. (See Table 2 above where the MA RTX toxin is referred to as "VcRtx," and GenBank Accession No. gi |4455065, the content of which is incorporated herein by reference in its entirety). In some embodiments, the disclosed fusion proteins comprise amino acid sequence 3376-3637 of MARTX (e.g., as the contemplated protease domain or C-terminal second polypeptide of the presently disclosed fusion proteins), or a variant, mutant, or derivative thereof having cysteine protease activity. In other embodiments, the disclosed fusion proteins comprise amino acid sequence 3427-3637 of MARTX (SEQ ID NO:17) (e.g., as the contemplated protease domain or C-terminal second polypeptide of the presently disclosed fusion proteins), or a variant, mutant, or derivative thereof having cysteine protease activity. In other embodiments, the disclosed fusion proteins comprise amino acid sequence 3432-3637 of MARTX (e.g., as the contemplated protease domain or C-terminal second polypeptide of the presently disclosed fusion proteins), or a variant, mutant, or derivative thereof having cysteine protease activity. In even further embodiments, the disclosed fusion proteins comprise amino acid sequence 3441-3637 of MARTX (e.g., as the contemplated protease domain or C-terminal second polypeptide of the presently disclosed fusion proteins), or a variant, mutant, or derivative thereof having cysteine protease activity.

EXAMPLES

The following examples are illustrative and are not intended to limit the disclosed subject matter.

Example 1

Background

*Vibrio cholerae* MARTX Toxin.

The life-threatening diarrheal disease cholera is caused by toxigenic strains of the Gram-negative organism *Vibrio cholerae*. In addition to the well-characterized ADP-ribosylating cholera toxin (CT), *V. cholerae* secretes a novel cytotoxin that is the founding member of a new family of the RTX (repeats-in-toxin) family (Satchell, 2007). This toxin of *V. cholerae* contributes to virulence in mice and has been shown to be important for the bacterium to establish prolonged colonization of the small intestine (Olivier et al., 2007b; Olivier et al., 2007a). Hence, it has been proposed that this toxin is important for initiation of disease in cholera patients and is likely an important factor for prolonged colonization in asymptomatic carriers and thereby is important for dissemination of the pathogen.

Beyond its potential importance for pathogenesis, the Multifunctional-Autoprocessing RTX toxin of *V. cholerae* (MARTX-Vc) is of intrinsic interest due to its novel biochemical properties and mode of action. At 4545 aa and a predicted size of >480 kDa, MARTX-Vc is one of the largest single polypeptide toxins. However, unlike other RTX toxins, MARTX-Vc is not a pore-forming toxin, but rather induces actin depolymerization and cell rounding (Satchell, 2007).

Current knowledge about the process of cell rounding by MARTX-Vc is diagrammed in FIG. 1. Based on the mechanism of translocation of RTX toxin *Bordetella pertussis* adenylate cyclase (Osickova et al., 1999), it is predicted that MARTX-Vc self-inserts into the eukaryotic cytoplasmic membrane and then transfers activity domains to the cytoplasm. Thus far, at least three activities have been described for this toxin conferred by three discrete activity domains:

1. Cross-Linking Activity.

The toxin has been shown to covalently crosslink actin into oligomers (Fullner and Mekalanos, 2000). This activity is associated with the actin crosslinking domain (ACD) that is shared with a type 6 secretion effector of *V. cholerae* and with the putative MARTX toxin of *Aeromonas hydrophila* (MARTX-Ah) (Satchell, 2007; Sheahan et al., 2004). It has been shown that the substrate for crosslinking is free monomeric G-actin and crosslinking occurs dependent upon the hydrolysis of ATP. It has been hypothesized that cell rounding then occurs by depletion of the free G-actin pool leading to an equilibrium shift that drives the depolymerization of assembled actin fibers (Kudryashov et al., 2008; Cordero et al., 2006).

2. RhoGTPase Inactivation.

It also has been demonstrated that the toxin inactivates RhoGTPases, the master regulators of actin cytoskeletal assembly, by a mechanism that is distinct from all other known Rho-modulating toxins. This activity is associated with a Rho-inactivation domain (RID) that is shared with the MARTX toxin from *V. vulnificus* (MARTX-Vv) and the putative MARTX toxins from *Xenorhabdus* sp. (Satchell, 2007; Sheahan and Satchell, 2007).

3. Cysteine Protease Domain (CPD) Autoproteolysis.

It also has been shown that the toxin has an autoprocessing activity associated with it cysteine protease domain (CPD). This enzymatic region of the protein cleaves the toxin after binding cytosolic stimulatory factor inositol hexakisphosphate (InsP6), a molecule found exclusively in the eukaryotic cell cytosol. Thus, processing would be induced only after translocation to the eukaryotic cell cytosol to release the ACD and RID to access the substrates (Sheahan et al., 2007).

Identification of the CPD. Transient expression of aa 3376-3637 of the MARTX-Vc toxin in eukaryotic cells resulted in cells that appeared condensed and necrotic. A Western blot of cell lysates with anti-GFP antibody revealed the CPD:EGFP fusion protein expressed from plasmid pCPDc runs on SDS-PAGE at 48 kDa, approx. 9 kDa smaller than predicted (FIG. 2). Since one of only two Cys residues in the entire toxin is located within this region, it was hypothesized that Cys3568 was important for cytotoxicity. Indeed, cytotoxicity was not observed after transfection of a mutant plasmid carrying a C3568S mutation. The fusion protein expressed from pCPDc C-S ran on SDS-PAGE at the expected size of 57 kDa. A His3519A mutant also ran at the predicted mol. wt. (FIG. 2) These results showed this domain is an autoprotease with a His-Cys catalytic dyad in vivo (Sheahan et al., 2007).

Induced Autoprocessing of the CPD.

In order to demonstrate that the CPD is an autoprocessing cysteine protease, recombinant CPD and recombinant protein carrying the C3568S mutation were purified (rCPD and rCPD C-S, respectively). Both proteins purified from *E. coli* at the full length and were resolved on SDS-PAGE at the predicted m.w. of 34 kDa demonstrating that rCPD was not cleaved in *E. coli* or during purification. Cleavage occurred only after addition a nuclear-free eukaryotic cell lysate, which stimulated autoprocessing of rCPD, but not rCPD C-S (FIG. 3) (Sheahan et al., 2007).

Homologous CPDs have been identified in 18 large bacterial proteins including all MARTX toxins, four clostridial glucosylating toxins, 2 putative toxins from *Yersinia* sp., and an adhesin from *Bordetella* sp. (Sheahan et al., 2007). Of particular note is *Clostridum difficile* Toxin B (TcdB). This toxin has previously been demonstrated to undergo processing after translocation to release the glucosyl transferase catalytic domain (Rupnik et al., 2005; Pfeifer et al., 2003). A recent paper showed that autocatalytic processing of TcdB occurs after addition of inositol hexakisphosphate (InsP6), also known as inositol-6-phosphate, IP6, or phytic acid (Reineke et al., 2007). In a subsequent paper, InsP6-induced autoprocessing of both TcdA and TcdB was shown to be due to its cysteine protease domain, the same domain shared with MARTX-Vc (Egerer et al., 2007). Based on the TcdB results, InsP6 was assessed to determine whether it also induces autoprocessing of rCPD. Indeed, InsP6 induces autoprocessing of rCPD and has a binding constant for InsP6 of 0.6 μM. InsP6-induced autoprocessing of rCPD occurred in a time- and concentration-dependent manner (FIG. 4, Prochazkova K., and Satchell K. J., "Structure-function analysis of inositol hexakisphosphate-induced autoprocessing of the *Vibrio cholerae* multifunctional autoprocessing RTX toxin," J. Biol. Chem., 2008 Aug. 29; 283(35):23656-64).

Application of CPD to Recombinant Protein Purification.

The CPD of *V. cholerae* is not active in bacteria and is inducible only by adding the inducing compound inositol 6 phosphate in a processing reaction. As such, a recombinant protein fused at the N-terminus of the CPD was created and a peptide tag was added at the C-terminus of the CPD. It was hypothesized that the recombinant protein could be purified via the peptide tag which subsequently could be removed by inducing the CPD, allowing rapid production of native recombinant protein. The concept is diagrammed in FIG. 5 below. The recovered recombinant protein after cleavage includes two additional C-terminal amino acids from the CPD (i.e., an alanine-leucine dipeptide). CPD cleavage of the fusion protein could be induced on a column, after purification of the fusion protein, or during dialysis of the fusion protein. The peptide tag remains associated with the CPD and thus the tagged CPD may be removed from the recombinant protein by affinity chromatography. In some embodiments, protease inhibitors may be included in the processing reaction, including but not limited to chloromethyl ketones or N-ethylmaleimide. For example, protease inhibitors may be utilized to prevent cleavage at a site other than the specific site for CPD cleavage (e.g., at a position other than between amino acids 2 and 3 of the CPD).

In one example, a T7 overexpression plasmid was utilized to fuse the eukaryotic protein RhoA to CPD with a C-terminal 6×His Tag. A map of this vector is diagrammed in FIG. 6. This vector was created from pMCSG7 (Stols et al., 2002).

The vector was transformed to *E. coli* BL21(DE3) and bacteria were grown and induced with IPTG. RhoA:CPb:6×His fusion protein was purified from 100 ml cell lysate on an AKTA HisTrap column with elution in 250 mM imidazole. Eluted protein was incubated in 1 μM phytic acid (InsP6) from Sigma for 1 hr at 37° C. Result of cleavage is shown in FIG. 7.

REFERENCES

Cordero, C. L., Kudryashov, D. S., Reisler, E. and Satchell, K. J. (2006) The actin cross-linking domain of the *Vibrio cholerae* RTX toxin directly catalyzes the covalent cross-linking of actin. *J Biol. Chem.* 281: 32366-32374.

Egerer, M., Giesemann, T., Jank, T., Satchell, K. J. and Aktories, K. (2007) Auto-catalytic cleavage of *Clostridium difficile* toxins A and B depends on a cysteine protease activity. *J Biol Chem epub Jun.* 25, 2007.

Fullner, K. J. and Mekalanos, J. J. (2000) In vivo covalent crosslinking of actin by the RTX toxin of *Vibrio cholerae. EMBO J.* 19: 5315-5323.

Kudryashov, D. S., Cordero, C. L., Reisler, E. and Satchell, K. J. (2008) Characterization of the enzymatic activity of the actin cross-linking domain from the *Vibrio cholerae* MARTXVc toxin. *J Biol. Chem.* 283: 445-452.

Olivier, V., Salzman, N. H. and Satchell, K. J. (2007a) Prolonged colonization of mice by *Vibrio cholerae* El Tor O1 depends on accessory toxins. *Infect Immun.* 75: 5043-5051.

Olivier, V., Haines, G. K., 3rd, Tan, Y. and Satchell, K. J. (2007b) Hemolysin and the multifunctional autoprocessing RTX toxin are virulence factors during intestinal infection of mice with *Vibrio cholerae* El Tor O1 strains. *Infect Immun.* 75: 5035-5042.

Osickova, A., Osicka, R., Maier, E., Benz, R. and Sebo, P. (1999) An amphipathic alpha-helix including glutamates 509 and 516 is crucial for membrane translocation of adenylate cyclase toxin and modulates formation and cation selectivity of its membrane channels. *J. Biol. Chem.* 274: 37644-37650.

Pfeifer, G., Schirmer, J., Leemhuis, J., Busch, C., Meyer, D. K., Aktories, K. and Barth, H. (2003) Cellular uptake of *Clostridium difficile* toxin B. Translocation of the N-terminal catalytic domain into the cytosol of eukaryotic cells. *J Biol Chem.* 278: 44535-44541.

Reineke, J., Tenzer, S., Rupnik, M., Koschinski, A., Hasselmayer, O., Schrattenholz, A., et al (2007) Autocatalytic cleavage of *Clostridium difficile* toxin B. *Nature*. 446: 415-419.

Rupnik, M., Pabst, S., Rupnik, M., von Eichel-Streiber, C., Urlaub, H. and Soling, H. D. (2005) Characterization of the cleavage site and function of resulting cleavage fragments after limited proteolysis of *Clostridium difficile* toxin B (TcdB) by host cells. *Microbiology*. 151: 199-208.

Satchell, K. J. (2007) MARTX: Multifunctional-Autoprocessing RTX Toxins. *Infect Immun.* 75: 5079-5084.

Sheahan, K. L. and Satchell, K. J. (2007) Inactivation of small Rho GTPases by the multifunctional RTX toxin from *Vibrio cholerae. Cell Microbiol.* 9: 1324-1335.

Sheahan, K. L., Cordero, C. L. and Satchell, K. J. (2004) Identification of a domain within the multifunctional *Vibrio cholerae* RTX toxin that covalently cross-links actin. *Proc. Natl. Acad. Sci. USA.* 101: 9798-9803.

Sheahan, K. L., Cordero, C. L. and Satchell, K. J. (2007) Autoprocessing of the *Vibrio cholerae* RTX toxin by the cysteine protease domain. *EMBO J.* 26: 2552-2561.

Stols, L., Gu, M., Dieckman, L., Raffen, R., Collart, F. R. and Donnelly, M. I. (2002) A new vector for high-throughput, ligation-independent cloning encoding a tobacco etch virus protease cleavage site. *Protein Expr Purif.* 25: 8-15.

Example 2

Reference is made to the article Prochazkova K., and Satchell K. J., "Structure-function analysis of inositol hexakisphosphate-induced autoprocessing of the *Vibrio cholerae* multifunctional autoprocessing RTX toxin," published in the Journal of Biological Chemistry, volume 283(35), pages 23656-64, on Aug. 29, 2008, the content of which was disclosed and incorporated by reference in U.S. Provisional Patent Application No. 61/119,489, filed on Dec. 3, 2008.

The invention claimed is:

1. A kit for producing a recombinant polypeptide, the kit comprising:
   (a) an expression vector for expressing the polypeptide as a fusion protein, the fusion protein comprising:
      (i) the recombinant polypeptide; and
      (ii) an inducible autoproteolytic cysteine protease fused to the C-terminus of the recombinant polypeptide; and
   (b) an isolated inositol hexakisphosphate that induces the autoproteolytic cysteine protease.

2. The kit of claim 1, wherein the inducible autoproteolytic cysteine protease comprises an amino acid sequence that is at least 95% identical to SEQ ID NO:17.

3. The kit of claim 1, wherein the inducible autoproteolytic cysteine protease comprises SEQ ID NO:17.

4. The kit of claim 1, wherein the fusion protein comprises a fragment of *V. cholerae* RTX toxin (SEQ ID NO:1), *V. vulnificus* RTX toxin (SEQ ID NO:2), *V. splendidus* putative RTX toxin (SEQ ID NO:3), *P. luminescens* putative RTX toxin (SEQ ID NO:4-7), *Xenorhabdus nematophila* (XnRtx) (SEQ ID NO:8), *X. bovienii* (XbRtx) (SEQ ID NO:9), *Y. pseudotuberculosis* putative toxin (SEQ ID NO:10), *Y. mollaretti* putative toxin (SEQ ID NO:11), *C. difficile* Toxin A (SEQ ID NO:12), *C. difficile* Toxin B (SEQ ID NO:13), *C. noveyi* alpha toxin (SEQ ID NO:14), *C. sordellii* cytotoxin L (SEQ ID NO:15), or *Bordetella pertussis* putative adhesin FhaL (SEQ ID NO:16), and the fragment has inducible autoproteolytic cysteine protease activity.

5. The kit of claim 1, wherein the inducible autoproteolytic cysteine protease is cleaved between amino acids 2 and 3 of the inducible autoproteolytic cysteine protease.

6. The kit of claim 1, wherein the recombinant polypeptide and the inducible autoproteolytic cysteine protease are directly fused.

7. The kit of claim 1, wherein the recombinant polypeptide and the inducible autoproteolytic cysteine protease are fused indirectly via a peptide linker.

8. The kit of claim 1, wherein the fusion protein further comprises a peptide tag fused at the C-terminus of the inducible autoproteolytic cysteine protease.

9. The kit of claim 8, wherein the peptide tag is a 6×His tag, a hemaglutinin tag, a FLAG tag, a glutathione-S-transferase tag, a green fluorescent protein tag, a maltose binding protein tag, or a chitin binding protein tag.

10. The kit of claim 8 further comprising a resin that binds the peptide tag.

11. The kit of claim 1 further comprising a protease inhibitor that does not inhibit the autoproteolytic cysteine protease.

12. The kit of claim 1 further comprising competent prokaryotic cells for transforming with the expression vector.

* * * * *

UNITED STATES PATENT AND TRADEMARK OFFICE
CERTIFICATE OF CORRECTION

| | | |
|---|---|---|
| PATENT NO. | : 8,383,400 B2 | Page 1 of 1 |
| APPLICATION NO. | : 13/563171 | |
| DATED | : February 26, 2013 | |
| INVENTOR(S) | : Karla J. Fuller-Satchell | |

It is certified that error appears in the above-identified patent and that said Letters Patent is hereby corrected as shown below:

In the Specification:

Col. 1, Lines 18-25, please remove the government support clause as government funding does not apply to this invention.

Signed and Sealed this
Twenty-third Day of April, 2013

Teresa Stanek Rea
*Acting Director of the United States Patent and Trademark Office*